(12) United States Patent
Ringerike et al.

(10) Patent No.: US 8,361,711 B2
(45) Date of Patent: Jan. 29, 2013

(54) TOOLS AND METHODS USEFUL IN CHARACTERISING THE IMMUNOTOXIC ACTIVITY OF XENOBIOTIC SUBSTANCES

(75) Inventors: Tove Ringerike, Oslo (NO); Robert Jan Vandehriel, Bilthoven (NL); Aurelia Walczak-Drzewiecka, Lodz (PL); Khalid Al-Nedawi, Lodz (PL); Janina Wyczolkowska, Lodz (PL); Maciej Stepnik, Lodz (PL); Joanna Arkusz, Lodz (PL); Konrad Rydzynski, Lodz (PL); Violetta Adamczewska, Warsaw (PL); Dominka Trzaska, Warsaw (PL); Maciej Olszewski, Warsaw (PL); Urszula Bialek-Wyrzykowska, Warsaw (PL); Jaroslaw Dastych, Warsaw (PL); Martinus Lovik, Oslo (NO); Nilsson Gunnar, Uppsala (SE); Ulleras Erik, Uppsala (SE)

(73) Assignees: National Institute of Public Health and the Environment, Laboratory For Pathology and Immunobiology, Bilthoven (NL); Norwegian Institute of Public Health, Division of Environmental Medicine, Oslo (NO); Nofer Institute of Ocupational Medicine and Who/Collaborating Centre, Lodz (PL); Department of Biogenic Amines, Polish Academy of Sciences, Lodz (PL); International Institute of Molecular And Cell Biology In Warsaw, Warsaw (PL)

( * ) Notice: Subject to any disclaimer, the term of this patent is extended or adjusted under 35 U.S.C. 154(b) by 1576 days.

(21) Appl. No.: 10/577,268

(22) PCT Filed: Sep. 26, 2004

(86) PCT No.: PCT/PL2004/000075
§ 371 (c)(1),
(2), (4) Date: Dec. 18, 2006

(87) PCT Pub. No.: WO2005/030970
PCT Pub. Date: Apr. 7, 2005

(65) Prior Publication Data
US 2007/0117187 A1  May 24, 2007

(51) Int. Cl.
*C12N 5/02* (2006.01)
*C12N 15/74* (2006.01)
*C12P 21/06* (2006.01)
*C07H 21/04* (2006.01)
*C12Q 1/68* (2006.01)

(52) U.S. Cl. .................. 435/6.1; 435/69.1; 435/320.1; 435/325; 435/7.1; 536/23.5; 536/23.1

(58) Field of Classification Search .................. None
See application file for complete search history.

(56) References Cited

U.S. PATENT DOCUMENTS

| 7,393,944 B2 * | 7/2008 | Glimcher et al. | 536/23.5 |
| 2002/0132290 A1 * | 9/2002 | Frazer et al. | 435/69.1 |
| 2003/0149254 A1 | 8/2003 | Anderson et al. | |
| 2004/0029109 A1 | 2/2004 | Lai | |

FOREIGN PATENT DOCUMENTS

| WO | 9531722 | 11/1995 |
| WO | 9739722 | 10/1997 |

* cited by examiner

*Primary Examiner* — Jim Ketter
*Assistant Examiner* — Catherine Hibbert
(74) *Attorney, Agent, or Firm* — Gary J. Gershik; Cooper & Dunham LLP

(57) ABSTRACT

A method is described for the characterization of a tested substance, particularly useful in the study of its toxicity, and in particular immunotoxicity. Also described are cell lines and nucleic acids useful in its procurement, which may be used to embody said method, particularly in obtaining cell-chip collections destined for immunotoxicity assays.

15 Claims, 26 Drawing Sheets

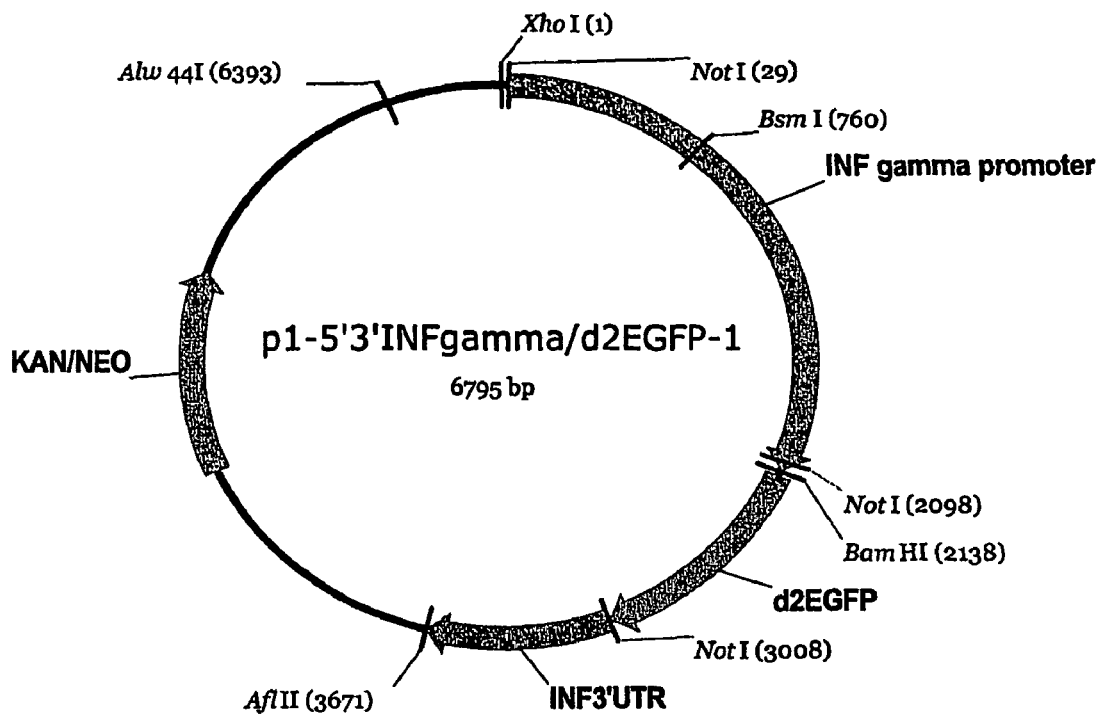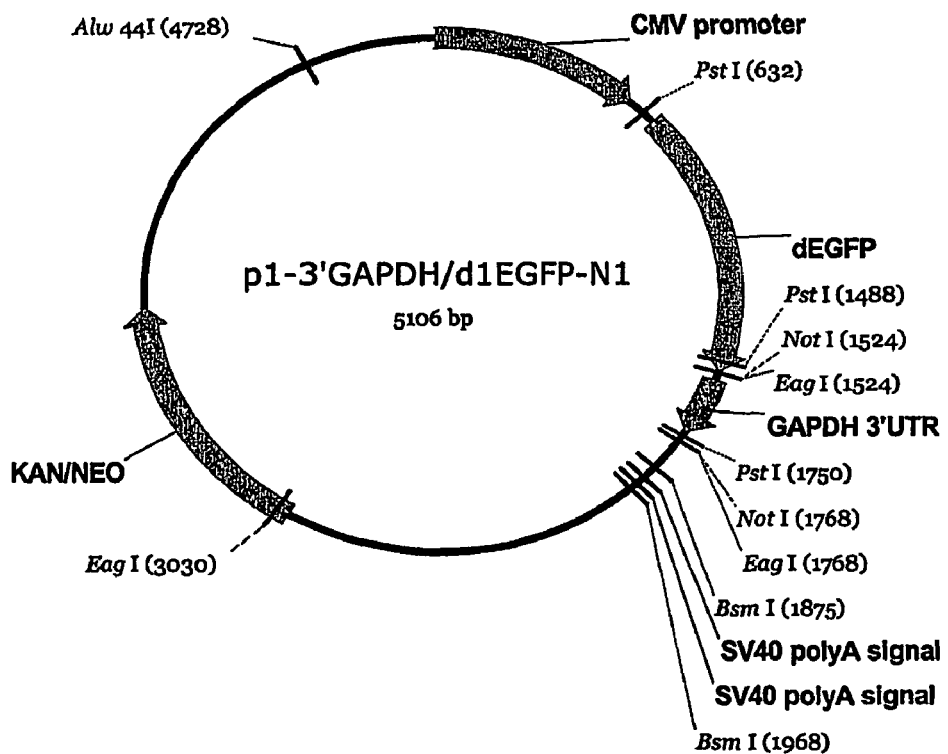
Fig. 18

Fig. 20

Cell viability testing.
Cell lines employed in the project were exposed to incresing concentrations of chemicals listed in Table II. LDH relase was determined using test (Roche) according to the manufacturer protocol. All concentrations are expresed in [µM].

| Chemical | solvent | Hel 30<br>Karcinocyte | 3T3-L1+pEGFFP-F<br>Fibroblast | EL-4<br>T-cell leukemia | J774A1<br>Macrophage-monocyte |
|---|---|---|---|---|---|
| Benzocaine<br>CAS Nr: 94-09-7 | Ethanol | A: -<br>B: 3000, 1000, 100<br>C: 10<br>D: - | A: -<br>B: 3000, 1000<br>C: 100, 10<br>D: - | A: -<br>B: -<br>C: 1500<br>D: 1000, 100 | A: 3000<br>B: 1000<br>C: -<br>D:100, 10 |
| Cyclosporin | Ethanol | A: -<br>B: 10<br>C: 1, 0.1, 0.01<br>D: - | A: -<br>B: 30, 10<br>C: 1, 0.1<br>D: - | A: 15, 10<br>B: 1<br>C: -<br>D: - | A: 30, 10<br>B: -<br>C: -<br>D: 1, 0.1 |
| DNCB,<br>dinitrochlorobenzene<br>CAS Nr: 9700-7 | Ethanol | A: 100, 33, 10<br>B: -<br>C: 3,3<br>D: - | A: 100, 10, 3.3<br>B: -<br>C: 1<br>D: - | A: 10<br>B: -<br>C: -<br>D: 1, 0.33, 0.033 | A: 10, 5<br>B: -<br>C: -<br>D: 0.5, 0.05 |
| MDI,diphenylmethane-<br>4,4-diisocyanate<br>CAS Nr: 101-68-8 | DMSO | A: -<br>B: -<br>C: 1000, 100, 10, 1<br>D: - | | A: 1500<br>B: -<br>C: -<br>D: 150, 15, 1.5 | |
| HgCl2, mercuric chloride<br>Cas nr: 7487-94-7 | ethanol | A: -<br>B: -<br>C: 1, 0.1, 0.01, 0.001<br>D: - | X: 10<br>A: -<br>B: -<br>C: 1, 0.1, 0.01<br>D: - | X: 10<br>A: 30<br>B: -<br>C: -<br>D: 1, 0.01 | |

Fig. 20 (continuation)

| Chemical | solvent | Hel 30<br>Karcinocyte | 3T3-L1+pEGFFP-F<br>Fibroblast | EL-4<br>T-cell leukemia | J774A1<br>Macrophage-monocyte |
|---|---|---|---|---|---|
| Penicillin G<br>Cas nr: 140-64-7 | medium | A: -<br>B: -<br>C: 1000, 100, 10, 1<br>D: - | A: -<br>B: -<br>C: 1000, 100, 10, 1<br>D: - | A: -<br>B: -<br>C: -<br>D: 1000, 100, 10, 1 | |
| SDS, sodium dodecyl sulphate | DMSO | A: 500<br>B: -<br>C: 50, 5, 0.5<br>D: - | A: 500<br>B: -<br>C: 50, 5, 0.5<br>D: - | A: 250<br>B: -<br>C: -<br>D: 50, 5, 0.5 | |
| TBTO, bis-tributyltin oxide<br>Cas nr: 584-3-9 | ethanol | A: 100, 10, 1<br>B: 0.1<br>C: -<br>D: - | A: 100, 10, 1<br>B: -<br>C: 0.1<br>D: - | A: 10, 1, 0.5, 0.1, 0.05<br>B: 0.1<br>C: -<br>D: - | |
| TDI, toluene-2,4-diisocyanate<br>Cas nr: 584-84-9 | ethanol | A: 1500<br>B: 150<br>C: 15, 1.5<br>D: - | | A:<br>B: 1000<br>C:<br>D: 100, 10, 1 | |
| K2PtCl4, tetrachloroplatinate (platinum salt)<br>Cas nr: 10025-99-7 | medium | A: -<br>B: -<br>C: 8.6, 0.86, 0.086, 0.0086<br>D: - | A: 300, 100<br>B: -<br>C: 10, 1<br>D: - | A:<br>B: 150, 50<br>C:<br>D: 5, 0.5 | |
| Thalidomide,<br>cas nr: 50-35-1 | DMSO | C: 1000, 100, 10, 1 | C: 1000, 100, 10, 1 | D: 1000, 100, 10, 1 | |

A: toxic-concentration, B: concentration inhibits cell growth, no toxicity, C: no toxic effect or growth inhibition, X: lower amount of LDH, but no toxic effect or cell growth inhibition

Fig. 21

Comparision of data obtained in cytotoxicity tests in two participating laboratories

Direct cytotoxicity assciated with chemicals listed in Table II was determined for EL-4 cell line using LDH relase assay in two laboratories according to the same experimental protocol. All concentrations are expresed in [µM].

| Chemical | solvent | NIPH solv. | EL-4<br>T-cell leukemia | in NIPH |
|---|---|---|---|---|
| Cyclosporin | Ethanol | Ethanol | A: 15, 10<br>B: 1<br>C:-<br>D:- | 20ug/mL and above is Toxic<br>below 10ug/mL OK |
| Penicillin G<br>Cas nr: 140-64-7 | medium | | A: -<br>B: -<br>C: -<br>D: 1000, 100, 10 | 2500 U = 15 mg/mL and below not toxic |
| Pentamidine<br>cas nr: 140-64-7 | medium | DMSO | | 30ug/mL and below=OK, 60ug/mL usure, 80ug/mL and above toxic |
| Rapamycin<br>cas nr 53123-88-9 | | DMSO | | Think 25000ng/mL toxic, below 1000 ng/mL OK |
| SDS, sodium dodecyl sulphate | DMSO | water | A: 1500<br>B: -<br>C: -<br>D: 150, 15, 1.5 | 50ug/mL and below not toxic, 2,5 mg/mL toxic |
| HgCl2, mercuric chloride<br>Cas nr: 7487-94-7 | ethanol | | X: 10<br>A: 30<br>B:-<br>C: -<br>D: 1, 0.01 | |
| TBTO, bis-tributyltin oxide<br>Cas nr: 584-3-9 | ethanol | | | |
| TDI, toluene-2,4-diisocyanate<br>Cas nr: 584-84-9 | ethanol | | | |
| K2PtCl4, tetrachloroplatinate (platinum salt)<br>Cas nr: 10025-99-7 | medium | water | | 150uM = -20 % toxicity |
| Thalidomide,<br>cas nr 50-35-1 | DMSO | | | |

Fig. 22

Expression of IL-1β and GFP in J.1.5.4 stimulated with tetrachloroplatinate TCP

A. The EC₅₀ values for selected chemicals from the list of model immunotoxicants (concentration causing death of 50% of cells in the population) obtained with MTT assay with macrophages J774A.1 and clone J 1.5.4

B. J 1.5.4, reporter cells were incubated with these chemicals and observed under fluorescence microscope. In the case of tetrachloroplatinate upregulation of green fluorescence was observed. The expression of GFP and endogenous IL-1β was confirmed with RT-PCR and with RT-PCR and ELISA, respectively.

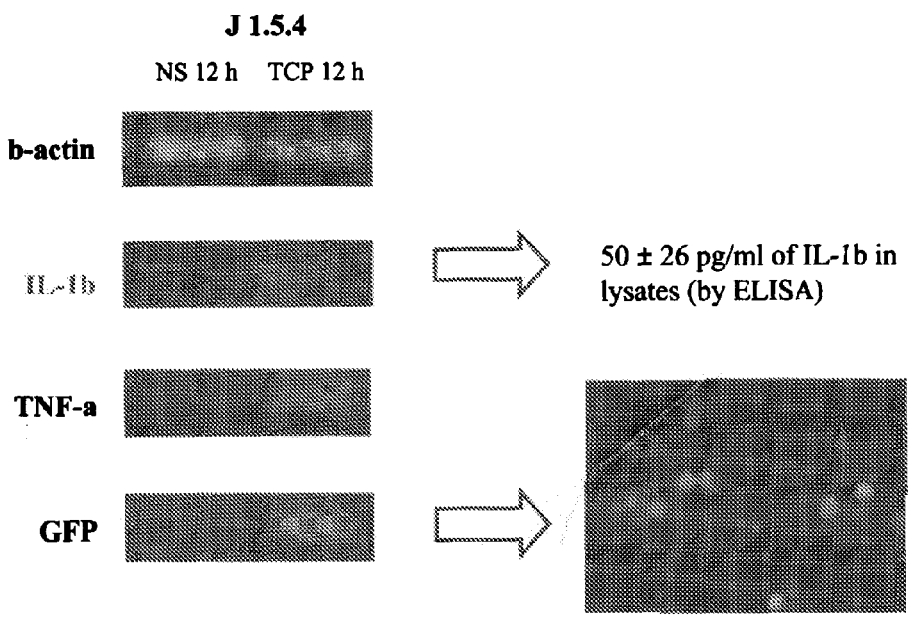

50 ± 26 pg/ml of IL-1b in lysates (by ELISA)

Response of reporter cell lines to model xenobiotics (I)

Two EL-4 derived IL-2 expression reporter cell lines were activated with TPA/ionomycine for 16 hr in the presence or absence of cyclosporin A or Rapamycin. The level of EGFP mediated fluorescence was determined by FACS

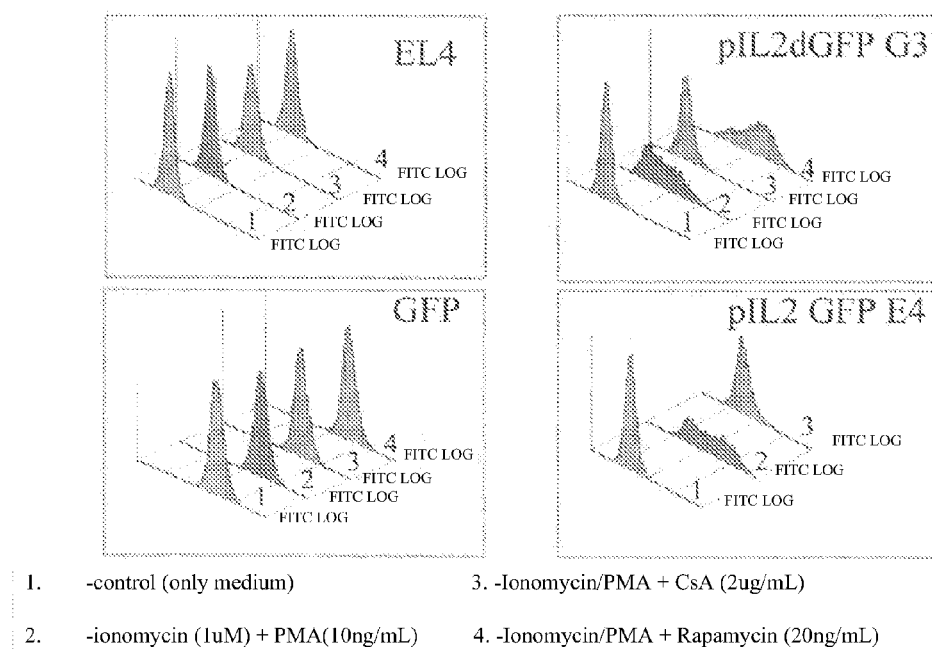

1. -control (only medium)
2. -ionomycin (1uM) + PMA(10ng/mL)
3. -Ionomycin/PMA + CsA (2ug/mL)
4. -Ionomycin/PMA + Rapamycin (20ng/mL)

Response of reporter cell lines to model xenobiotics (II)

A  Two EL-4 derived IL-2 expression reporter cell lines were activated with TPA/ionomycine for 16 hr in the presence or absence of Cyclosporin A or Rapamycin. The level of EGFP mediated fluorescence was determined with Fluorostar plate reader (A) and under fluorescence microscope (B)

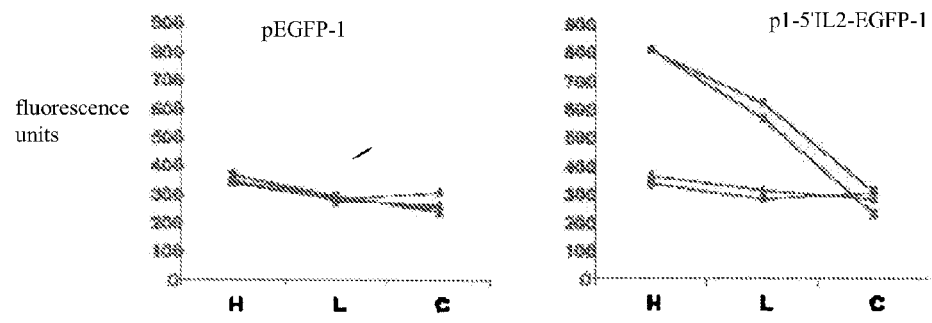

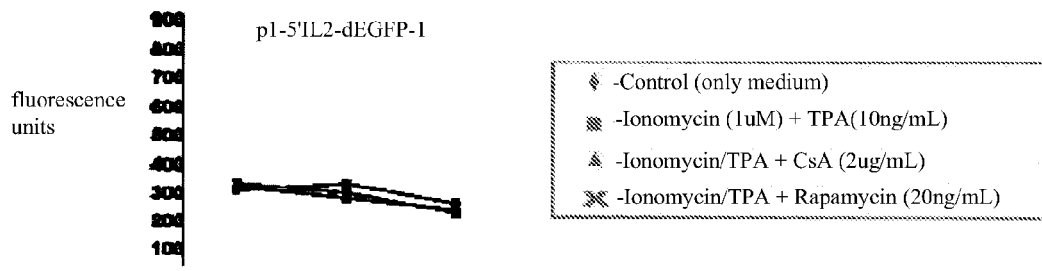

- Control (only medium)
- Ionomycin (1uM) + TPA(10ng/mL)
- Ionomycin/TPA + CsA (2ug/mL)
- Ionomycin/TPA + Rapamycin (20ng/mL)

B

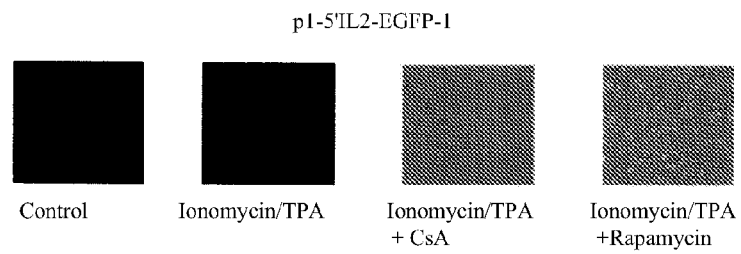

Fig. 25

Response of reporter cell lines to model xenobiotics (III)

A. EL-4 cells were incubated were activated with TPA/ionomycine for 16 hr in the presence or absence of Cyclosporin A or Rapamycin or TCDD. RNA was isolated using Tri reagent and RTPCR using primers specific for IL-2 and GAPDH (control) were performed. PCR products were analyzed on agarose gel B EL-4 derived reporter cells were incubated with media alone or activated with TPA/ionomycine for 16 hr in the presence or absence of Cyclosporin A or Rapamycin for 16 hr and the level of EGFP mediated fluorescence was determined by FACS.

A

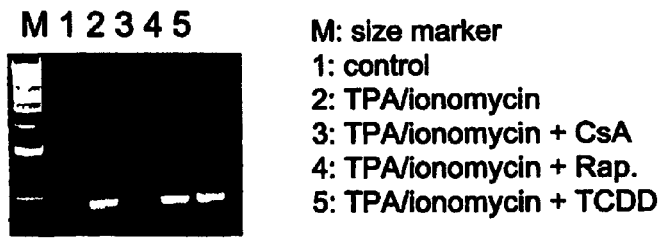

M: size marker
1: control
2: TPA/ionomycin
3: TPA/ionomycin + CsA
4: TPA/ionomycin + Rap.
5: TPA/ionomycin + TCDD

B

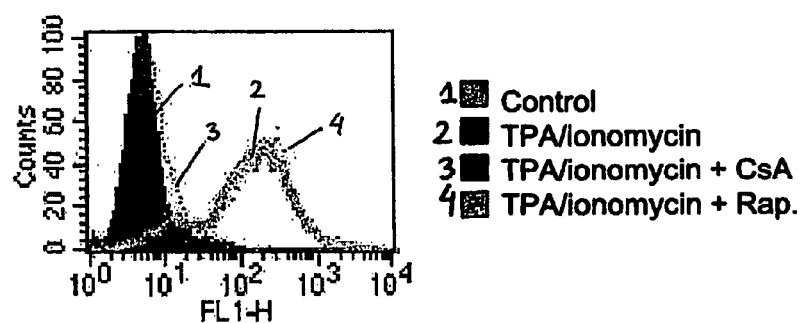

1 Control
2 TPA/ionomycin
3 TPA/ionomycin + CsA
4 TPA/ionomycin + Rap.

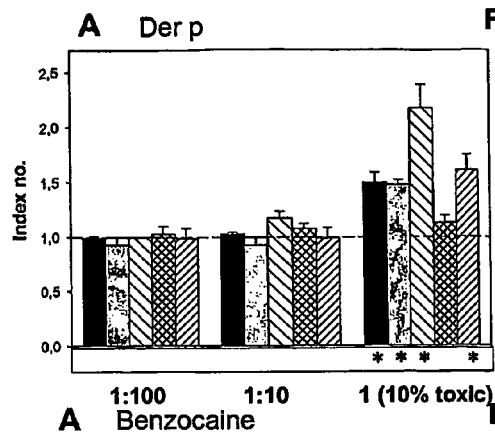
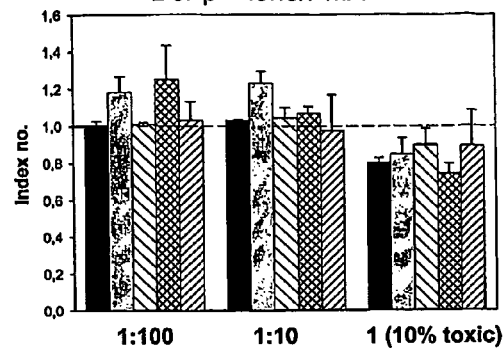
Fig. 29
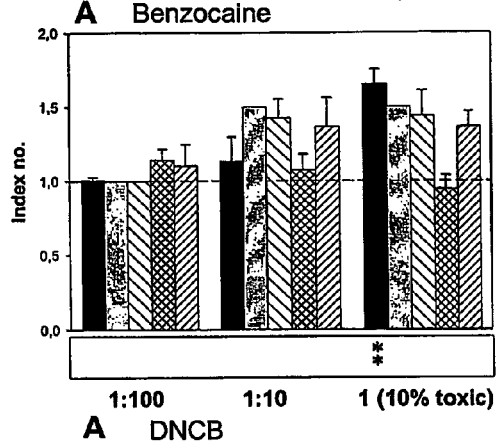
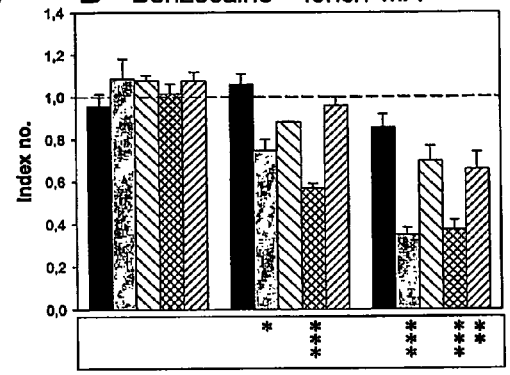
Fig. 30
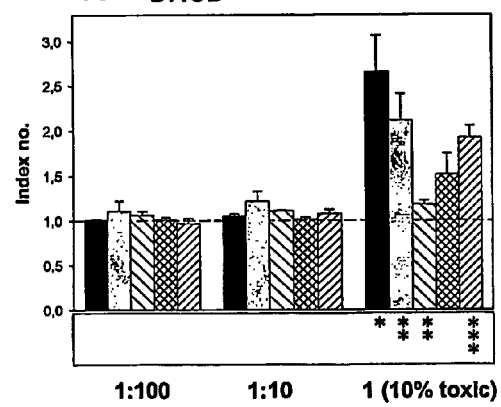
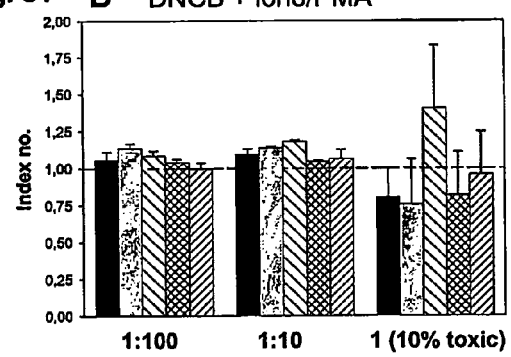
Fig. 31
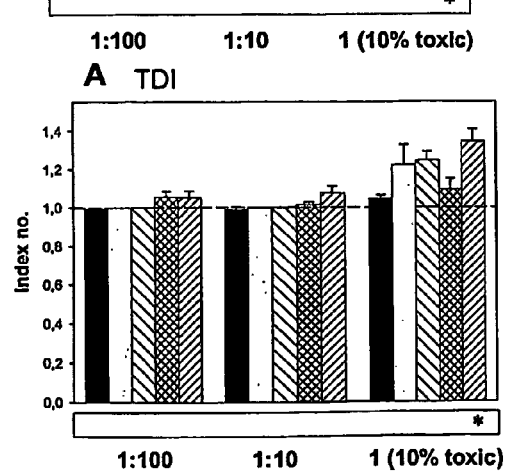
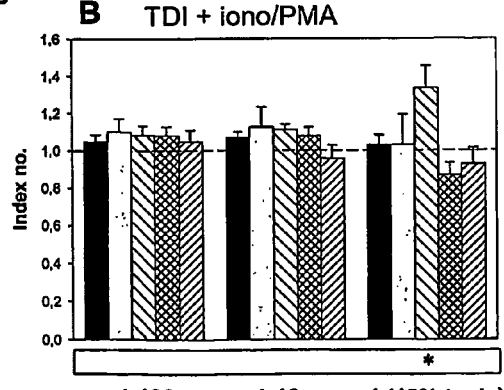
Fig. 32

TOOLS AND METHODS USEFUL IN CHARACTERISING THE IMMUNOTOXIC ACTIVITY OF XENOBIOTIC SUBSTANCES

This application is a §371 National Stage of PCT International Application No. PCT/PL2004/000075, filed Sep. 26, 2004, claiming priority of PCT International Application No. PCT/PL03/00098, filed Sep. 26, 2003, the contents of all of which are hereby incorporated by reference into this application.

FIELD OF THE INVENTION

The invention relates to methods of in-vitro characterisation of a tested substance in order to ascertain its biological activity, especially in reference to its potential toxicity, and particularly immunotoxicity. The invention further relates to products used in the embodiment of such a test, and in particular a collection of cell lines and nucleic acids useful in their procurement.

BACKGROUND OF THE INVENTION

Every year there are new chemicals introduced into the occupational and environmental settings, which together with those already present may increase the risk of different adverse health effects. Epidemiological data clearly shows an increase in the prevalence of immunological disorders, which in part can be related to xenobiotic exposure as for example is in the case of allergic diseases, including asthma, among populations of industrialized countries. The immune system consists of very sensitive and specific network of cellular and humoral interactions that, when deregulated, causes the general malfunction of physiological processes of the host. Immunotoxicity is understood as the ability of a given compound to alter function of immune system of human or animal in a deleterious way.

Immunotoxicity testing is difficult and it is rather generally accepted that it cannot be accomplished with a single test. Strategies for immunotoxicity testing that have been developed and underwent the process of validation are based on a battery of tests. Frequently a "two tier" approach is proposed for immunotoxicity testing. In such a system the first tier consists of several screening tests detecting general abnormalities in the immune system such as morphological changes, while the second tier represents a more in depth evaluation of immune function following contact with given compound. Most of the tests for immunotoxicity that have been developed and validated employed experimental animals. These tests use a combination of in vivo, ex vivo and in vitro assays of immune functions and frequently involve isolated immune cells, usually lymphocytes. The difficulties related to predictive testing for immunotoxicity are in part related to multiple molecular and cellular targets of immunotoxin actions that have to be taken into account.

WO99/37142 concerns the production of transgenic animals for the study of Insulin-dependent Diabetes Mellitus. The document describes a method for producing a transgenic non-human mammal carrying a transgene encoding an immuno-inducible autofluorescent protein, said method comprising chromosomally incorporating a first DNA sequence encoding a cytokin promoter operatively connected to a second DNA sequence encoding said autofluorescent protein, such as Green Fluorescent Protein (GFP) or its enhanced variants (EGFP) into the genome of a non-human mammalian animal. A somatic cell from the transgenic mammal has been claimed inter alia.

WO02/22786 describes a cell line comprising a human cell line capable of producing a selected cytokine associated with an inflammatory response in humans, and transfected with a vector containing DNA encoding a cytokine regulatory factor (CRF) under the control of a promoter, and a vector containing DNA encoding a detectable-marker protein, under the control of a promoter responsive to cytokine induction. Disclosed cell line is useful for screening test compounds for anti-inflammatory activity, by its culturing under conditions in which CRF is overproduced in the transfected cells, the selected cytokine is induced, and the detectable-marker protein is produced at detectable levels, adding a test compound to the cultured cells, and observing any diminution in the level of the detectable-marker protein. Furthermore, an amount of dsRNA effective in stimulating cytokine production in the cytokine overproducing cells is added to the culture, and a priming agent such as phorbol myristate acetate (PMA), calcium ionophores, sodium butyrate, endotoxin, and cytokines is also added. WO00/75660 provides methods of screening a test agent for the ability to reduce osteoclastic bone reabsorption. In a preferred embodiment, the methods involve screening the agent for the ability to inhibit tumor necrosis factor (TNF-alpha) expression through activity at an inhibitory TNF-alpha-responsive element (TNF-Re) in the tumor necrosis factor promoter or through activity at a complex formed by an estrogen receptor at TNF-Re. The document discloses screening a test agent for the ability to modulate osteoclastic bone reabsorption comprising: (a) contacting an estrogen receptor (ER) and a gene under the control of a tumor necrosis factor (TNF) modified promoter with a test agent; and (b) detecting a difference in the level of gene expression compared with a control cell. The method is useful for screening agents that reduce osteoclastic bone reabsorption, and for the identification of compounds that modulate TNF-alpha expression resulting in reduced osteoclastic bone reabsorption.

W00050872 provides systems, methods, screens, reagents and kits for an optical system analysis of cells to rapidly determine the distribution, environment, or activity of fluorescently labeled reporter molecules in cells for the purpose of screening large numbers of compounds for those that specifically affect particular biological functions.

WO0023615 discloses a method for extracting quantitative information relating to an influence on a cellular response in mechanically intact or permeabilized living cells, which method comprises recording variation in spatially distributed light emitted from a luminophore as a change in light intensity, measured by an instrument designed for the measurement of changes in fluorescence intensity. The luminophore, which is present in the cells, is capable of being redistributed in a manner which is related with the degree of the influence, and/or of being modulated by a component which is capable of being redistributed in a manner which is related to the degree of the influence.

There are attempts of in vitro immunotoxicity testing using isolated immune cells. In such tests immunosuppressive activity is expected when proliferative response or physiological functions like NK activity of immune cells are downregulated, and immunostimulation is expected when upregulation of these responses is detected. The possible immunomodulatory action is especially difficult to assess in vitro because of our limited understanding of molecular and cellular mechanisms mediating this effect. A specific problem for using in vitro tests lays in the fact that they generally do not take into account possible roles of metabolism in the xenobiotic's action.

Cytokines are generally defined as proteins secreted by cells that affect the behavior of other cells. They are produced by many cell types and through specific receptors affect activity of cells of different origin. It is believed that cytokines are critical regulators that orchestrate immune response by interconnecting dispersed elements of the immune system into one functional entity. They are grouped into families: the hematopoietins, the interferons, the chemokines, and the TNF family. T cells, among which one can distinguish function-related diversity, produce the greatest proportion of cytokines.

There is more and more evidence showing that at least certain types of immunotoxicity, such as those leading to hypersensitivity and autoimmunity are associated with modulation of the expression of particular cytokine genes in immune cells or non-immune cells. This effect seems to be important for immunotoxicity associated with heavy metals and amino acid derivatives linked to Eosinophilia-Myalgia Syndrome (USA in 1986). Derivatives of amino acids, which were putative ethiological agents in the epidemic mentioned above, were also shown to induce expression of a potent immunomodulatory cytokine, IL-5, in immune cells cultured in vitro. IL-4, the cytokine critical for development of allergic response, was secreted by lymphocytes and mast cells following contact with heavy metals, which represents a good correlation of xenobiotic action in vitro (upregulation of IL-4 in immune cells) and in vivo (upregulation of IgE in experimental animals). Certain cytokines expressed by non-immune cells are also important signals modulating immune response. For example, some chemical allergens were reported to stimulate keratinocytes to express particular cytokines such as IP-10, MIP-2, IL-1β, and IL-10. Some types of immunosuppression can also involve the modulation of cytokine expression like that observed with azathioprine or cyclosporin A, which inhibit IL-2 expression in lymphocytes.

In light of the presented current state of technology, it is desirable to develop new methods of (immuno)toxicity testing in vitro, which would not only indicate perturbations of the immune system but also allow the elucidation of the potential mechanism of immunomodulation. This approach would utilize the knowledge about pleiotropic activities of cytokines that regulate different processes of immune system.

Thus, the main objective of this invention is a development of a new system of characterising the biological activities of xenobiotics in vitro. A particular goal of the invention is to facilitate easy and reliable tests for their toxicity, particularly immunotoxicity.

SUMMARY OF THE INVENTION

The present invention relates to an isolated nucleic acid molecule coding an expression box with the formula $S_1$-$S_2$-$S_3$ where: $S_1$ is a promoter sequence, or it is absent, $S_2$ is a known reporter gene sequence, $S_3$ is a regulatory 3'UTR sequence, or it is absent, where the promoter sequence and the regulatory 3'UTR sequence originate from a known cytokine gene, and are the controlling sequences of said cytokine. In a preferential embodiment of the present invention, the reporter gene is a gene coding a Green Fluorescent Protein, preferentially selected from its variants: d1EGFP, d2EGFP, EGFP or EGFP-F. In a preferential embodiment of the present invention, the promoter sequence and regulatory 3'UTR sequence originate from a cytokine selected from among the following: IL-1β, IL-2, TNFα, IL-4, IL10 or INFγ. In particular, the nucleic acid molecule can be an expression box contained in a plasmid selected from among the following: p1-5'IL1β/d1EGFP-N1 (SEQ ID NO: 3), p2-5'IL1β/d1EGFP-N1 (SEQ ID NO: 4), p3-5'IL1β/d1EGFP-N1 (SEQ ID NO: 5), p4-5'IL1β/d1EGFP-N1 (SEQ ID NO: 6), p1-5'3'IL1β/d1EGFP-N1 (SEQ ID NO: 7), p2-5'3'IL1β/d1EGFP-N1 (SEQ ID NO: 8), p3-5'3'IL1β/d1EGFP-N1 (SEQ ID NO: 9), p4-5'3'IL1β/d1EGFP-N1 (SEQ ID NO: 10), p1-5'IL2/EGFP-1 (SEQ ID NO: 11), p1-5'IL2/d2EGFP-1 (SEQ ID NO: 12), p1-5'3'IL2/d2EGFP-1 (SEQ ID NO: 13), p1-3'TNFα/d1EGFP-N1 (SEQ ID NO: 14), p2-3'TNα/EGFP-F (SEQ ID NO: 15), p3-3'TNFα/EGFP-F (SEQ ID NO: 16), p1-5'TNFα/d1EGFP-N1 (SEQ ID NO: 17), p1-5'3'TNFα/d1EGFP-N1 (SEQ ID NO: 18), p1-3'IL4/d1EGFP-N1 (SEQ ID NO: 19), p2-3'IL4/EGFP-F (SEQ ID NO: 20), p3-3'IL4/EGFP-F (SEQ ID NO: 21), p4-3'IL4/CA-EGFP (SEQ ID NO: 22), p5-3'IL4/d1EGFP-N1 (SEQ ID NO 23), p1-5'IL4/EGFP-1 (SEQ ID NO: 24), p1-5'IL4/d1EGFP-N1 (SEQ ID NO: 26), p2-5'IL4/EGFP-1 (SEQ ID NO: 25), p2-5° IL4/d1EGFP-N1 (SEQ ID NO: 27), p1-5'3'IL4/EGFP-1 (SEQ ID NO: 30), p1-5'3'IL4/d1EGFP-N1 (SEQ ID NO: 28), p2-5'3'IL4/d1EGFP-N1 (SEQ ID NO: 29), p1-5'INFγ/EGFP-1 (SEQ ID NO: 31), p1-5'INFγ/d2EGFP-1 (SEQ ID NO: 32), p1-5'3'INFγ/d2EGFP-1 (SEQ ID NO: 33), p1-5'IL10/EGFP-1 (SEQ ID NO: 37), p1-5'3'IL10/EGFP-1 (SEQ ID NO: 39), p2-5'IL10/d2EGFP-1 (SEQ ID NO: 38), p2-5'3° IL10/d2EGFP-1 (SEQ ID NO: 40).

Another aspect of the present invention also relates to an expression vector, containing a nucleic acid molecule coding an expression box according to the present invention, as defined above. In a particular embodiment, the expression vector is a plasmid selected from among the following: p1-5'IL1β/d1EGFP-N1 (SEQ ID NO: 3), p2-5'IL1β/d1EGFP-N1 (SEQ ID NO: 4), p3-5' IL1β/d1EGFP-N1 (SEQ ID NO: 5), p4-5'IL1β/d1EGFP-N1 (SEQ ID No: 6), p1-5'3'IL1β/d1EGFP-N1 (SEQ ID NO: 7), p2-5'3'IL1β/d1EGFP-N1 (SEQ ID NO: 8), p3-5'3'IL1β/d1EGFP-N1 (SEQ ID NO: 9), p4-5'3'IL1β/d1EGFP-N1 (SEQ ID NO: 10), p1-5'IL2/EGFP-1 (SEQ ID NO: 11), p1-5'IL2/d2EGFP-1 (SEQ ID NO: 12), p1-5'3'IL2/d2EGFP-1 (SEQ ID NO: 13), p1-3'TNFα/d1EGFP-N1 (SEQ ID NO: 14), p2-3'TNFα/EGFP-F (SEQ ID NO: 15), p3-3'TNFα/EGFP-F (SEQ ID NO: 16), p1-5'TNFα/d1EGFP-N1 (SEQ ID NO: 17), p1-5'3'TNFα/d1EGFP-N1 (SEQ ID NO: 18), p1-3'IL4/d1EGFP-N1 (SEQ ID NO: 19), p2-3'IL4/EGFP-F (SEQ ID NO: 20), p3-3'IL4/EGFP-F (SEQ ID NO: 21), p4-3'IL4/CA-EGFP (SEQ ID NO: 22), p5-3'IL4/d1EGFP-N1 (SEQ ID NO: 23), p1-5'IL4/EGFP-1 (SEQ ID NO: 24), p1-5'IL4/d1EGFP-N1 (SEQ ID NO: 26), p2-5'IL4/EGFP-1 (SEQ ID NO: 25), p2-5'IL4/d1EGFP-N1 (SEQ ID NO: 27), p1-5'3'IL4/EGFP-1 (SEQ ID NO: 30), p1-5'3'IL4/d1EGFP-N1 (SEQ ID NO: 28), p2-5'3'IL4/d1EGFP-N1 (SEQ ID NO: 29), p1-5'INFγ/EGFP-1 (SEQ ID NO: 31), p1-5'INFγ/d2EGFP-1 (SEQ ID NO: 32) p1-5'3'INFγ/d2EGFP-1 (SEQ ID NO: 33), p1-5'IL10/EGFP-1 (SEQ ID NO: 37), p1-5'3'IL10/EGFP-1 (SEQ ID NO: 39), p2-5'IL10/d2EGFP-1 (SEQ ID NO: 38), p2-5'3'IL10/d2EGFP-1 (SEQ ID NO: 40).

Another aspect of the present invention also relates to a single-celled host transformed or transfected with a DNA molecule according to the present invention, as defined above. The initial cells used to obtain the single-celled host can be selected from among the group encompassing bacteria, yeast, mammalian cells, plant cells, insect cells, as well as eukaryotic cell lines. In a particular embodiment it is an immortal mammalian cell line, preferentially descendant from cells of the immune system, or for example it is a cell line selected from among T cell leukemia cells, thymoma, mast cells, macrophage-monocytes, fibroblasts and keratinocytes; for example, a cell line selected from among: EL4, BW5147.3, C57.1, J774A.1, 3T3 L1, MC/9 and HEL-30. In an embodiment, as a result of recombination, the natural cytokine gene extant in the host cell has been replaced by the DNA molecule according to the present invention, as defined above. In a particular embodiment, the single celled host is a cell line selected from among C/p1-5'3'TNFα-dEGFP/2 (deposited in ECACC, Accession No. 3091202), EL/p1-5'IL2-dEGFP/6 (deposited in ECACC, Accession No. 3091204), EL/p2-5'IL4-dEGFP/2 (deposited in ECACC, Accession No. 3091205), EL/p1-5'IFNγ-dEGFP/3 (deposited in ECACC, Accession No. 3091206), EL/p2-5'IL10-dEGFP/5 (deposited in ECACC, Accession No. 3091207), J/p4-5'IL1β-dEGFP/4 (deposited in ECACC, Accession No. 3091208).

Another aspect of the present invention also relates to a collection of cell lines recognizable in that it contains at least one cell line according to the present invention, as mentioned above, as well as at least one positive control cell line showing a constitutive expression of the reporter gene sequence. The positive control cell line originates from cells selected from the group encompassing bacteria, yeast, mammalian cells, plant cells, insect cells, as well as eukaryotic cell lines. In another embodiment, the positive control cell line is an immortal mammalian cell line. Preferentially, in the positive control cell line the reporter gene sequence is operationally bound to the regulatory sequence giving constitutive expression, where preferentially it contains at least one element from among the following: 3'UTR GAPDH, promoter/enhancer CMV, promoter-actin or derivatives thereof. In a particular embodiment, the positive control cell lines is transformed or transfected with a plasmid selected from among the following: p1-3'GAPHD/d1EGFP-N1 (SEQ ID NO: 34), p2-3'GAPHD/EGFP-F (SEQ ID NO: 35), p3-3'GAPDH/EGFP-F (SEQ ID NO: 36), pCA-EGFP-F (SEQ ID NO: 1), pCA-d1EGFP (SEQ ID NO: 2). In the example embodiment, the positive control cell line is the C/pCA-EGFP-F/2 line (deposited in ECACC, Accession No. 3091201) or EL/pCA-dEGFP/9 (deposited in ECACC, Accession No. 3091203). In a particularly preferential embodiment the collection of cell lines is a cell-chip.

Another aspect of the present invention also relates to a method of obtaining the characteristics of the tested substance characterised in that
a) the tested substance is put into contact with the cell line according to the present invention, or a cell line belonging to a collection of cell lines according to the present invention, as defined above,
b) it determines a change in the level of expression of a reporter gene caused by the tested substance,
c) the change in the level of expression described in (b) is accepted as characteristic of the tested substance.

In particular, GFP or one of its known variants is used as a reporter gene, and in stage (b) changes in the intensity of fluorescence are measured. In a particular embodiment of the method in stage (b), changes in th level of expression of the reporter gene is studied for each cell line in the collection. In stage (c) an expression profile characterizing the tested substance is obtained, based on results obtained from cell lines belonging to the collection. In a preferential embodiment of the method, stage (a) and/or (b) are performed simultaneously on all cells belonging to the collection. Stages (a) and (b) may be performed in an automated manner, and in stage (c), the results obtained may be computer analysed. In one of the possible embodiments the results obtained in stage (c) from the tested substance are compared to results obtained from substances of known properties. In a particular embodiment, stage (a) is performed in the presence of an expression modulator. The modulator of expression is an activator inducing the expression of the reporter gene, for example selected from among the following: PMA, ionomycin, calcium ionophore, LPS or a combination thereof. In a particular embodiment of the method, the characteristics obtained in stage (c) are used to ascertain the biological activity of the tested substance. In particular, in stage (c), the results of expression level measurements obtained from the tested substance are compared to results obtained from a reference substance of known biological activity. In a particular embodiment of this aspect, the studied biological activity is toxicity, particularly immunotoxicity.

Another aspect of the present invention relates to the use of a cell line according to the present invention, or a collection of cell lines according to the present invention, as defined above, to study the biological activity of the tested substance. In a particular embodiment of this aspect of the present invention, the studied biological activity is toxicity, particularly immunotoxicity.

Another aspect of the present invention relates to the use a cell line according to the present invention or a collection of cell lines according to the present invention, as defined above, to obtain the characteristics of the tested substance.

The presented system does not involve experimental animals, but instead is based on a number of immortalized cell lines representing different phenotypes of cells which regulate immune response in vivo. These cell lines have been tested in a uniform high throughput system for the expression of a number of cytokine genes. For this purpose, specialized reporter cell lines have been generated and used to detect signals, which upregulate and downregulate the expression of immunomodulatory cytokines upon contact of these cells with tested compounds e.g. a xenobiotic. Reporter cell lines have been prepared by genetic modification of cell lines in vitro. Each obtained cellular clone has been characterized and tested using a set of model immunotoxins, which have demonstrated adverse effects, in vivo. The entire panel of reporter cell lines was then pre-validated as a tool for testing immunotoxicity using data derived from already established tests as a reference.

The main achievement of this invention is the construction of a new tool for the detection of possible (immuno)toxicity associated with xenobiotics by performing an in vitro test. This tool consists of a series of reporter cell lines that regulate the expression of a transgene coding for fluorescent protein in the same way as they regulate the expression of cytokines. Expression of a fluorescent protein allows for the fast (near real time) detection of intracellular signals leading to changes in cytokine gene expression upon contact of the cells with the tested substance.

In a preferential embodiment of the invention, a single assay employing a cell chip allows the detection of possible interference of the tested xenobiotic with different tissue-specific molecular targets, such as signal transduction molecules and transcription factors, and to generate a compound specific pattern of response.

A pre-validation of a new testing system against data based on existing tests was performed. In particular this includes the standardization of the cell chip against several "model xenobiotics" (substances already known for their immunotoxic activities observed in vivo). This information suggests the conclusion that development of specialized genetically modified cell lines provides a useful biological marker for immunotoxicity testing and this technology might be expanded into other area of alternative toxicity testing.

The present method may also find an application as a facile method of characterising chemical substances, for example at the stage of screening a library of new chemical compounds, or in the search for new drugs.

DETAILED DESCRIPTION OF THE FIGURES

FIGS. 1-19 show schematics of plasmids obtained according to the procedure described in Example 1. The sequences of these plasmids have been disclosed in the Sequence Listing.

FIGS. 20 and 21 shows results of cell vialbility testing mentioned in Example 7.

Figure 1:
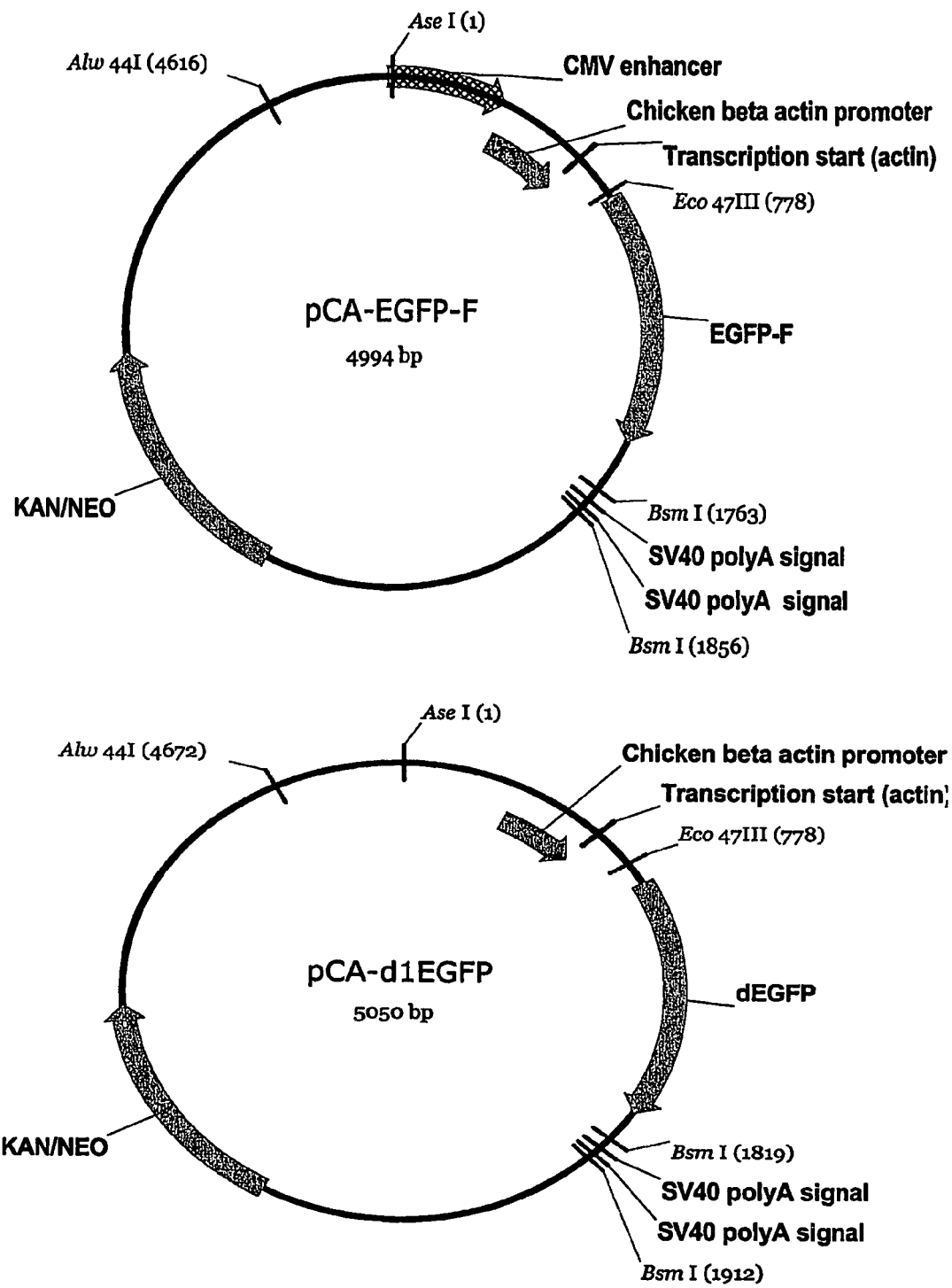
Figure 2:
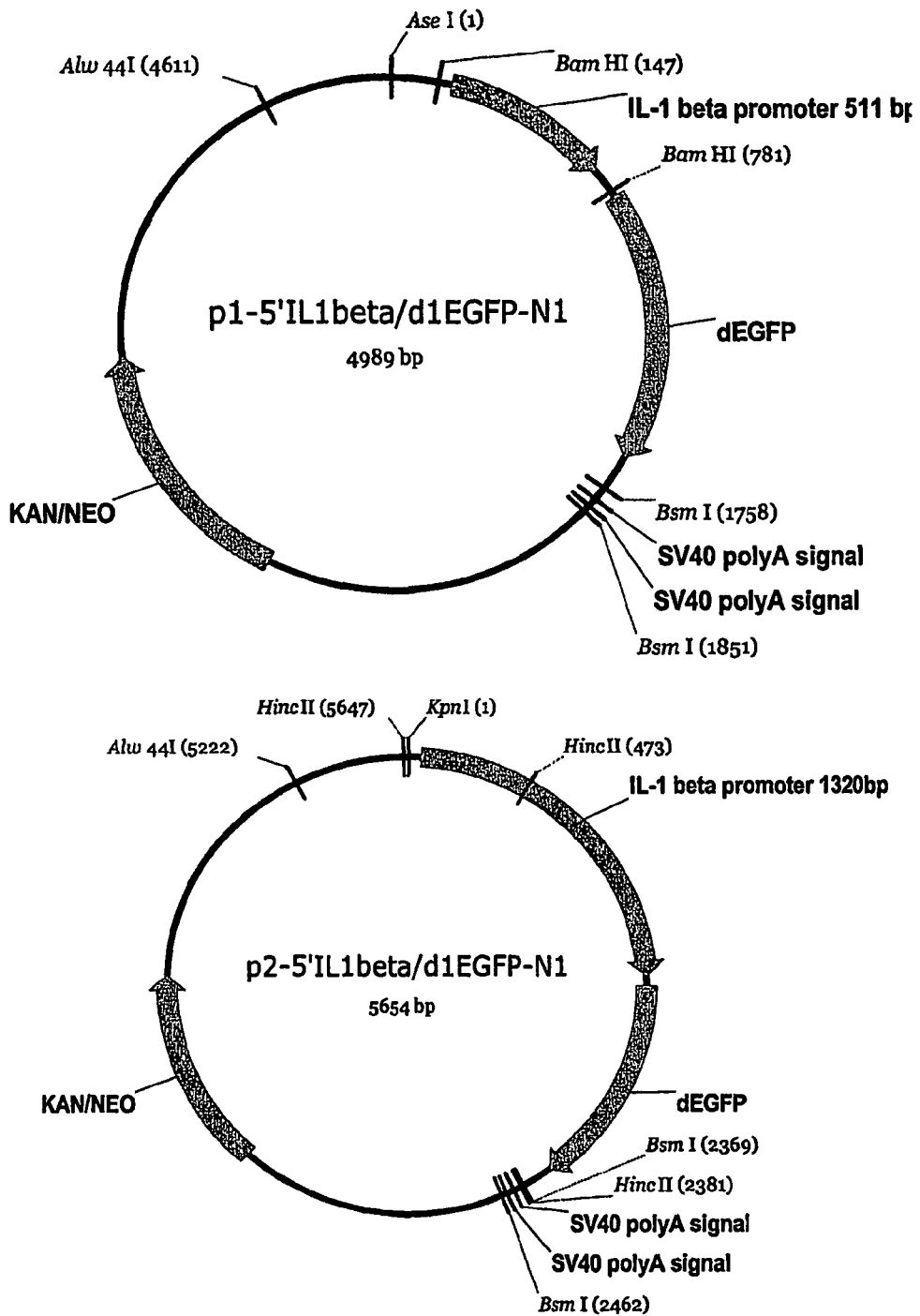
Figure 3:
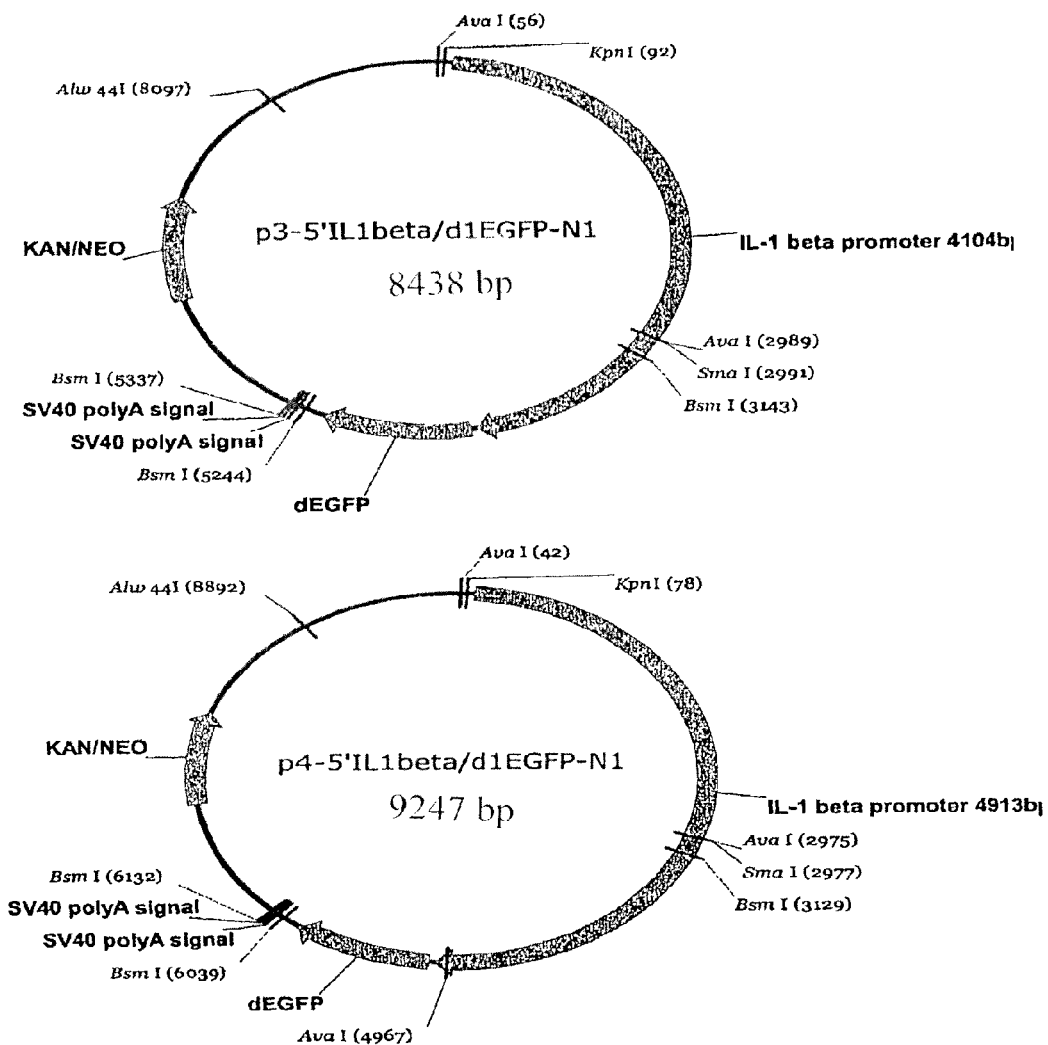
Figure 4:
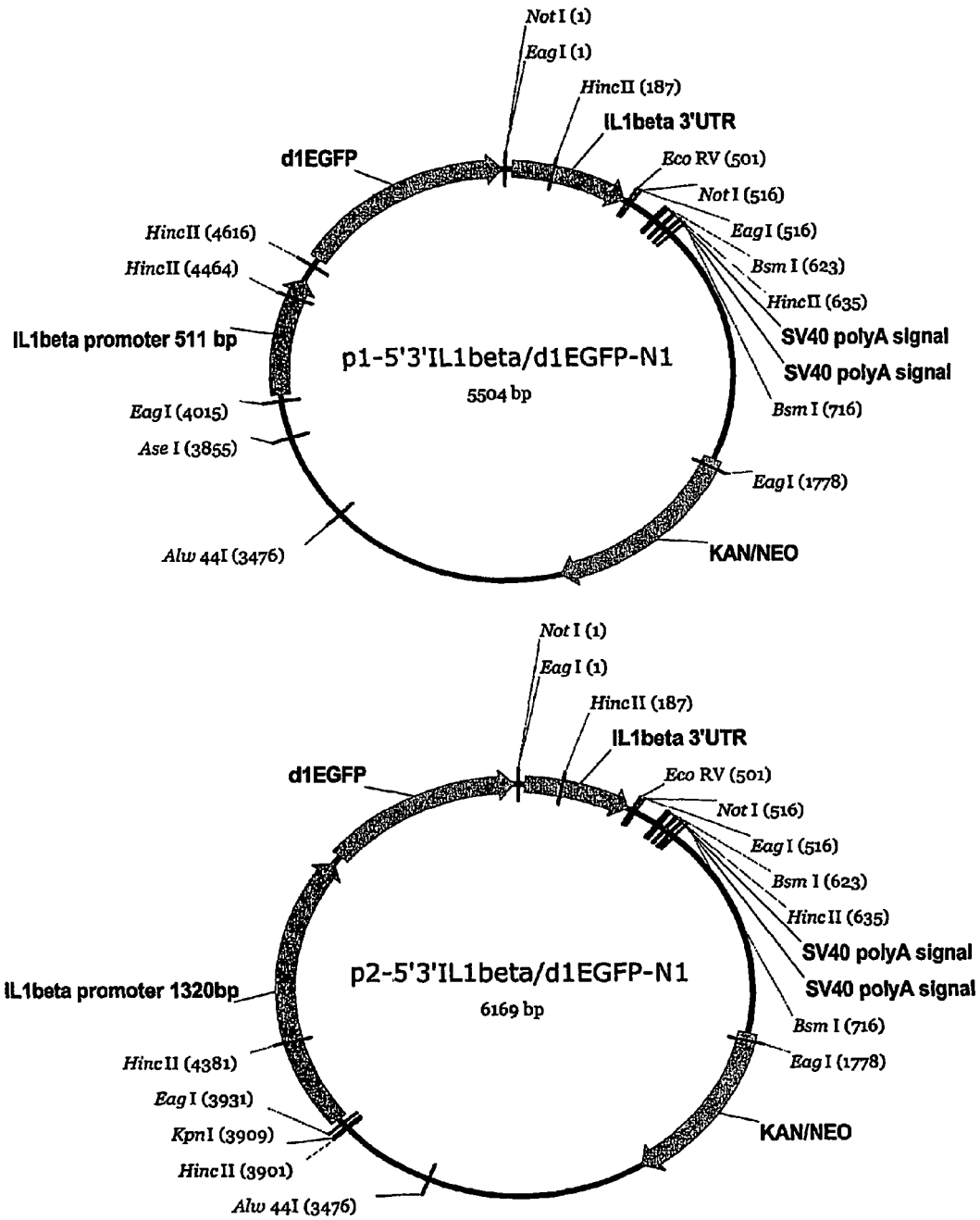
Figure 5:
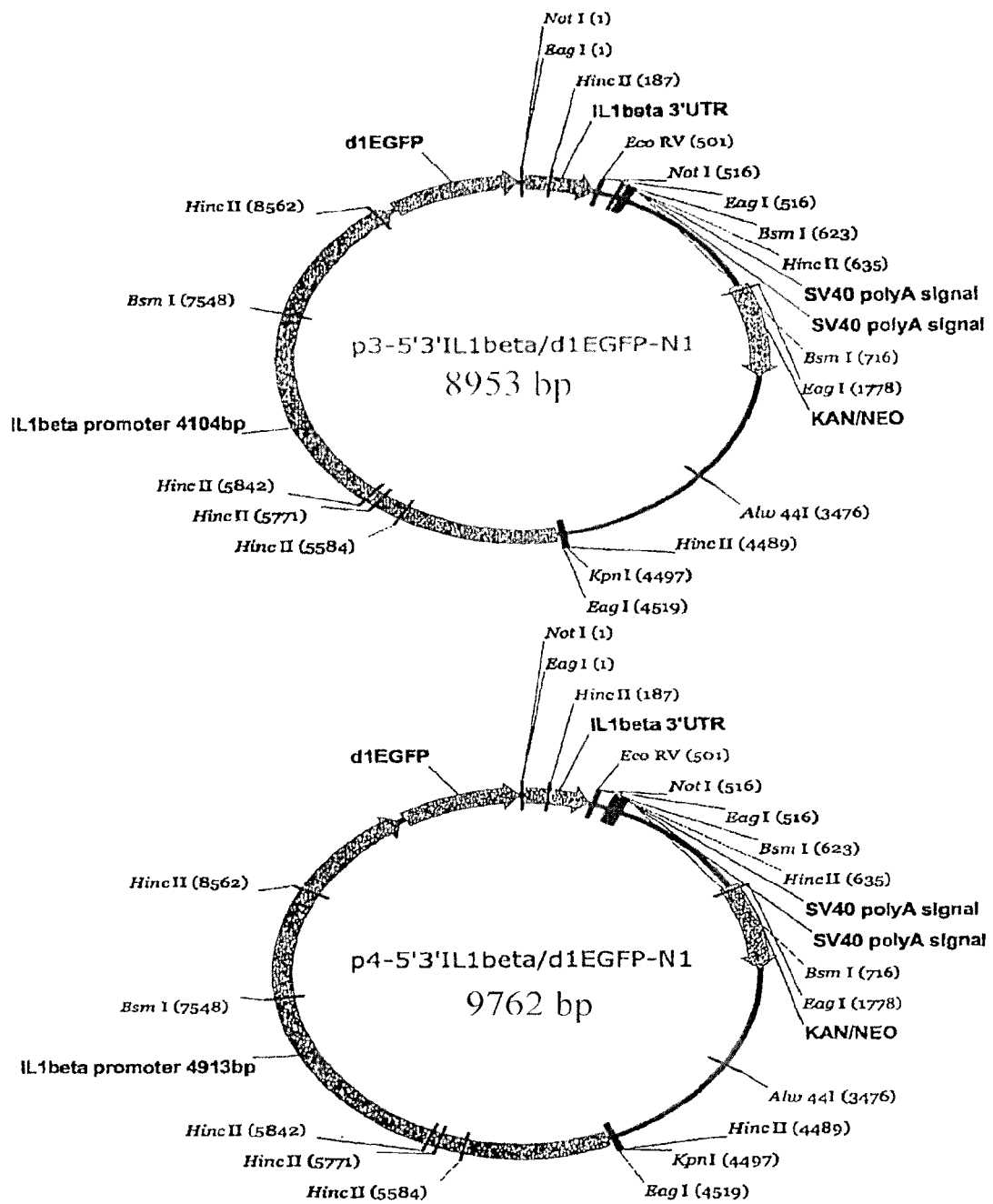
Figure 6:
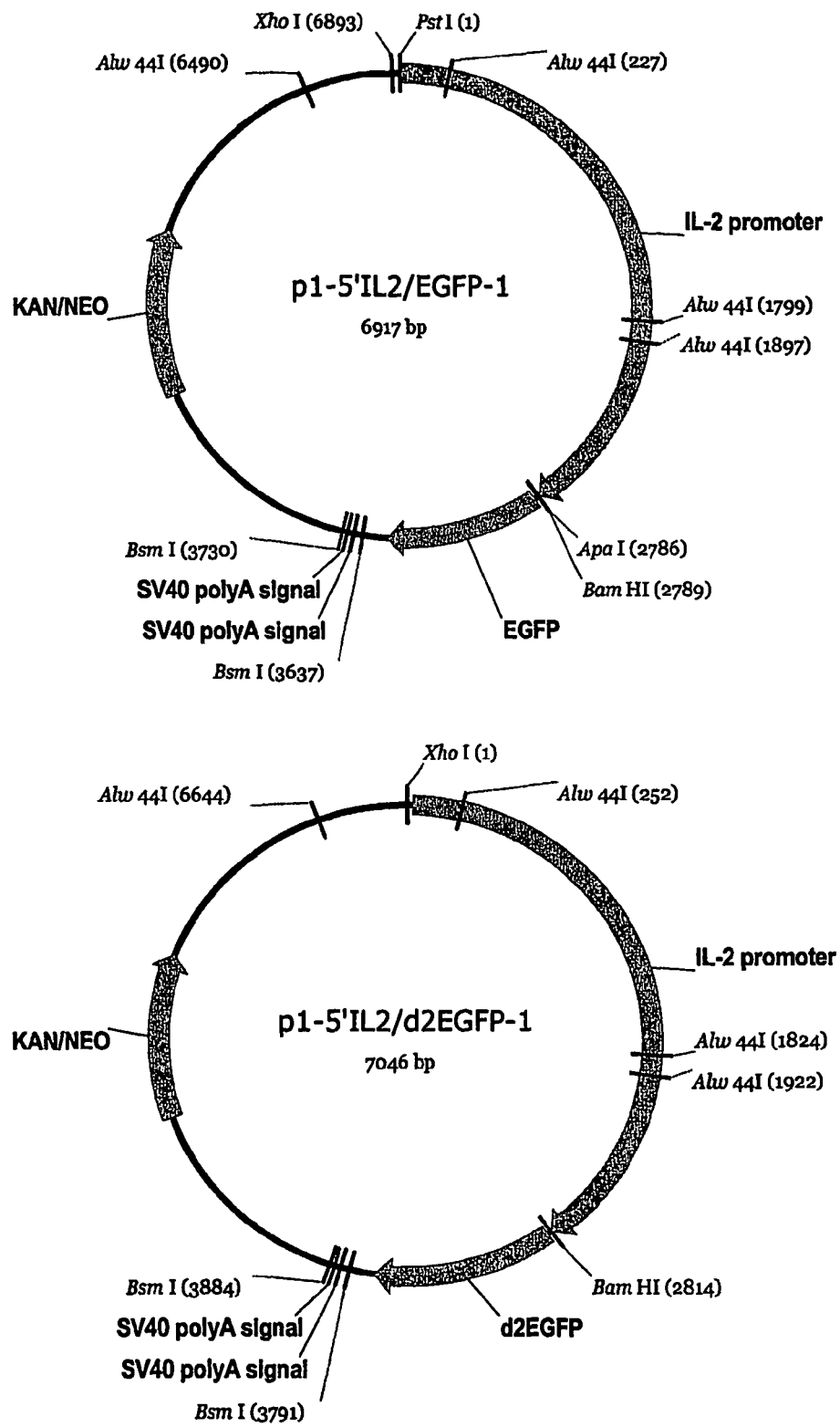
Figure 7:
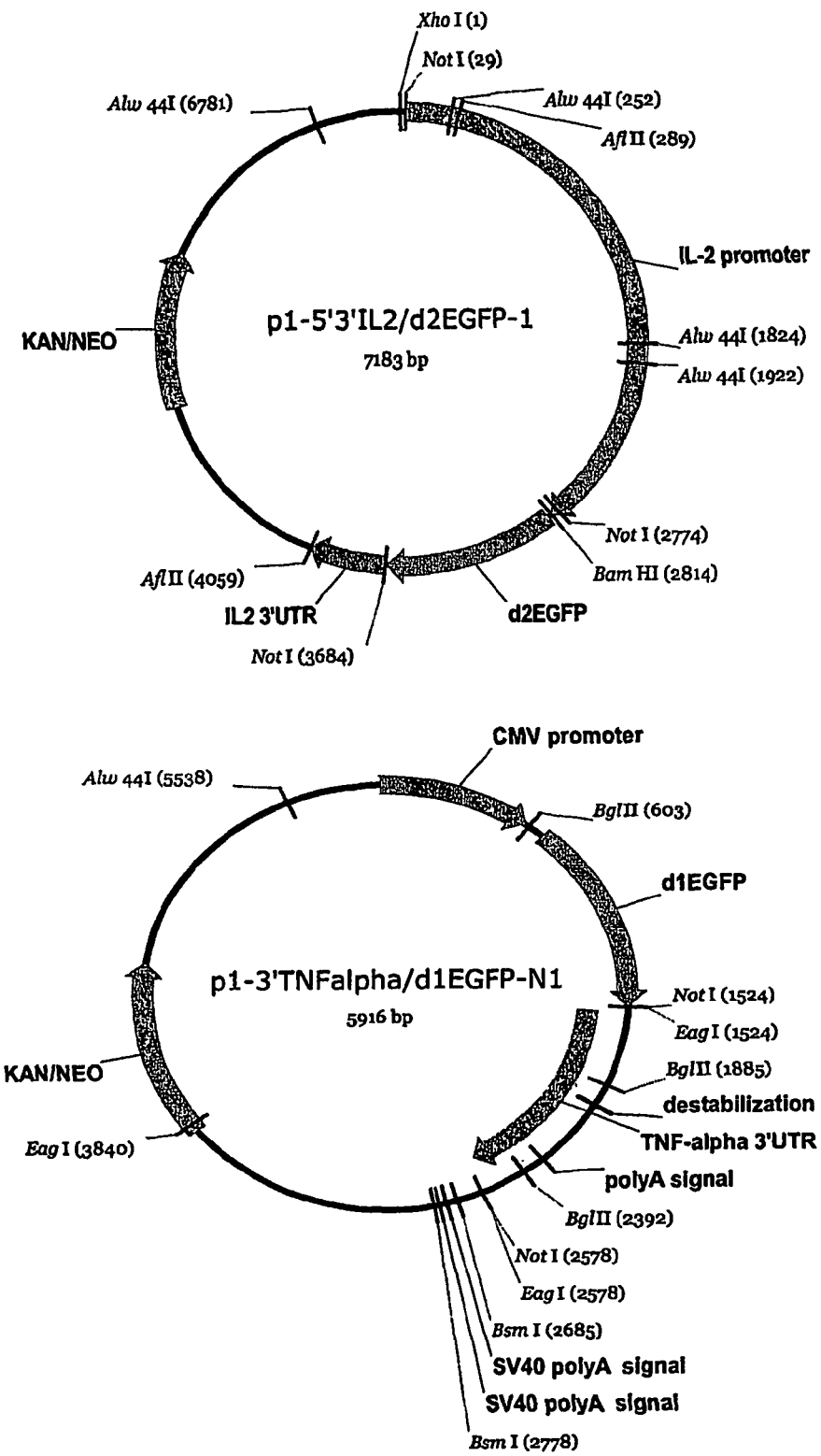
Figure 8:
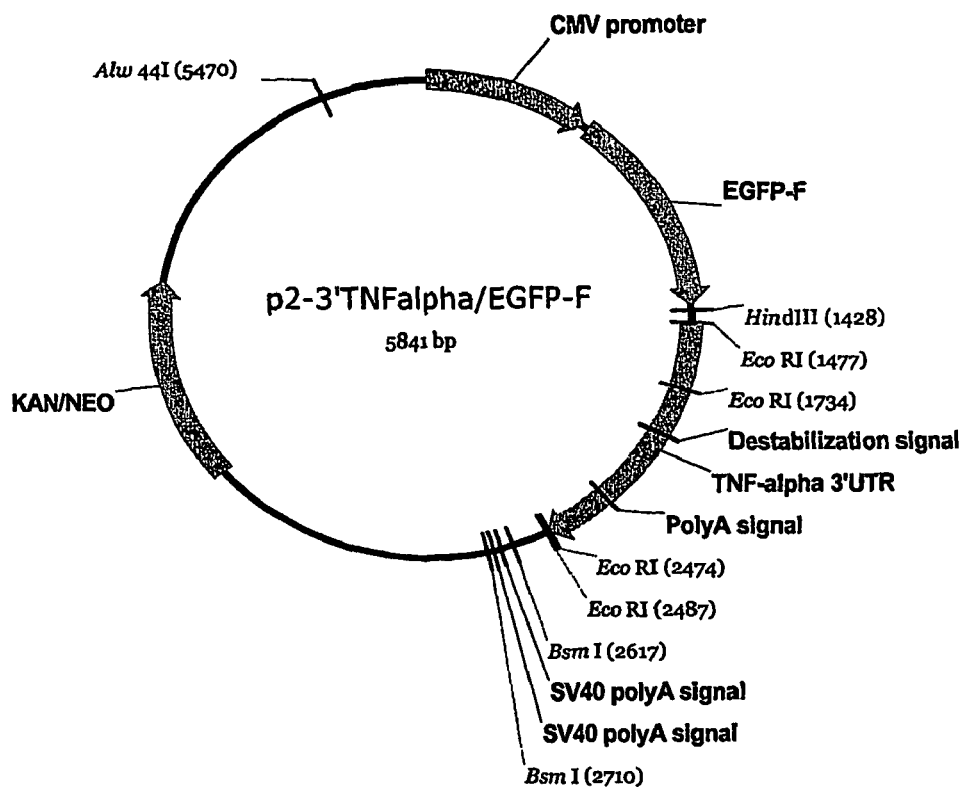
Figure 9:
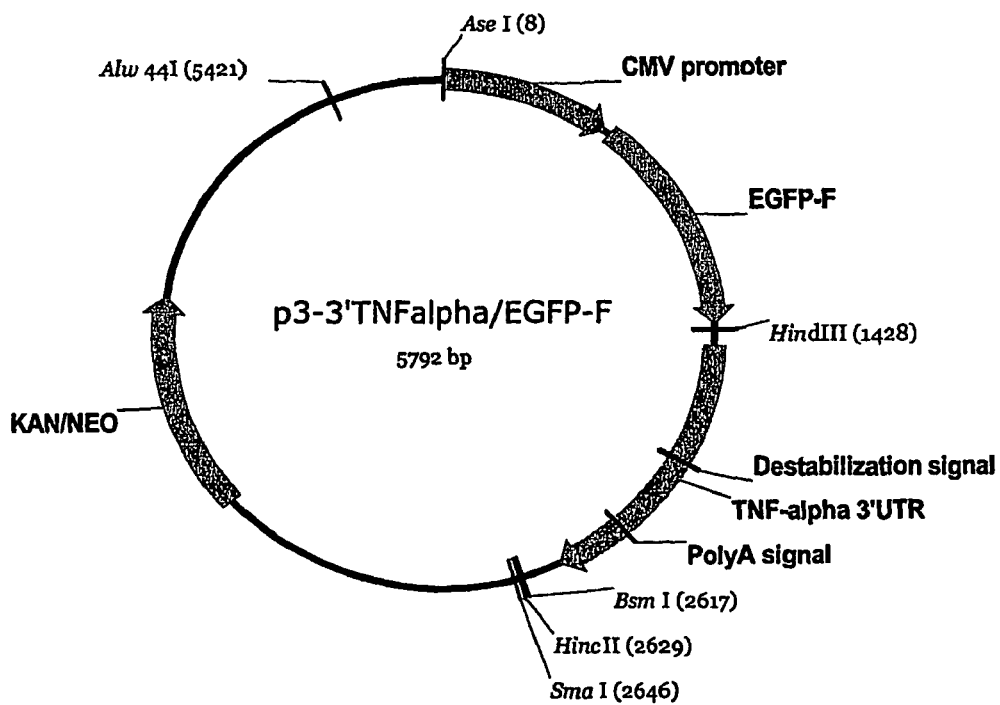
Figure 10:
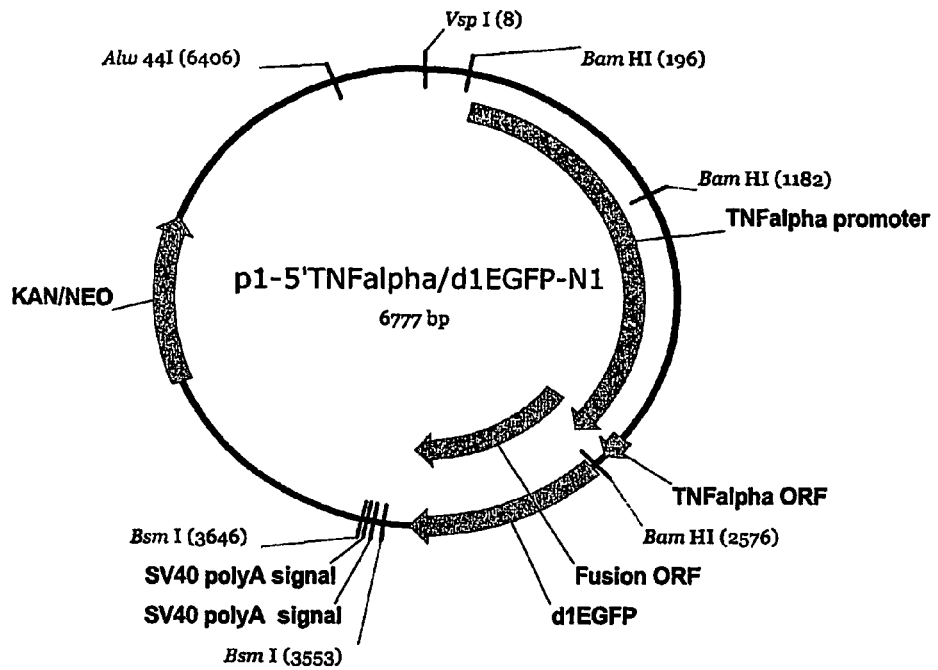
Figure 11:
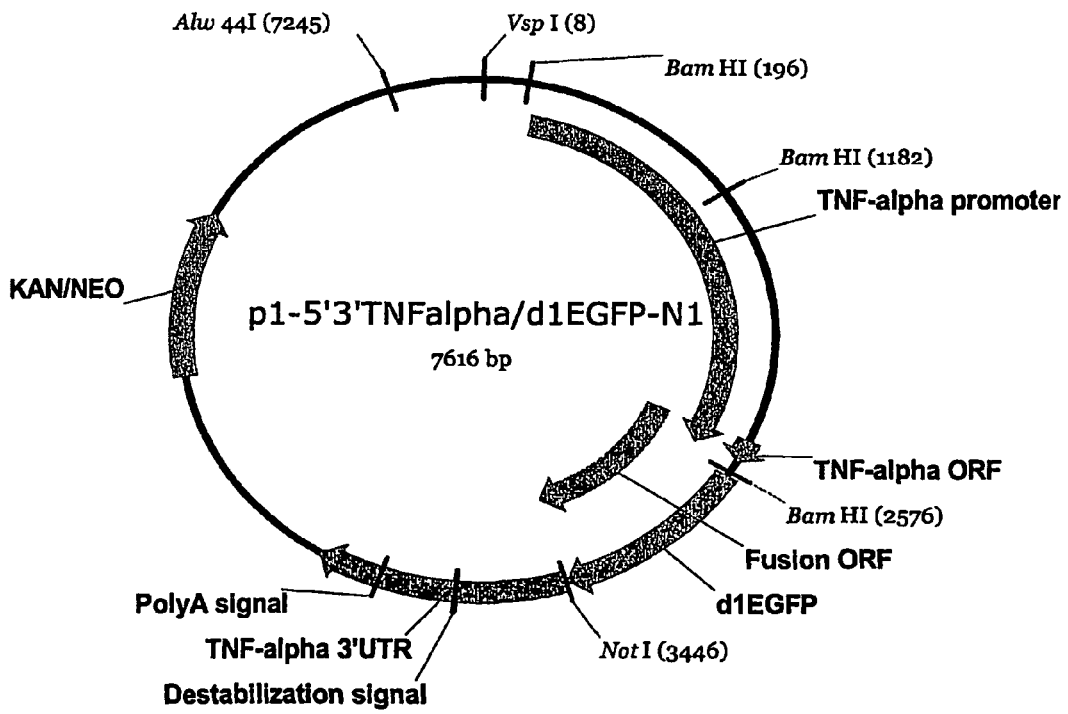
Figure 12:
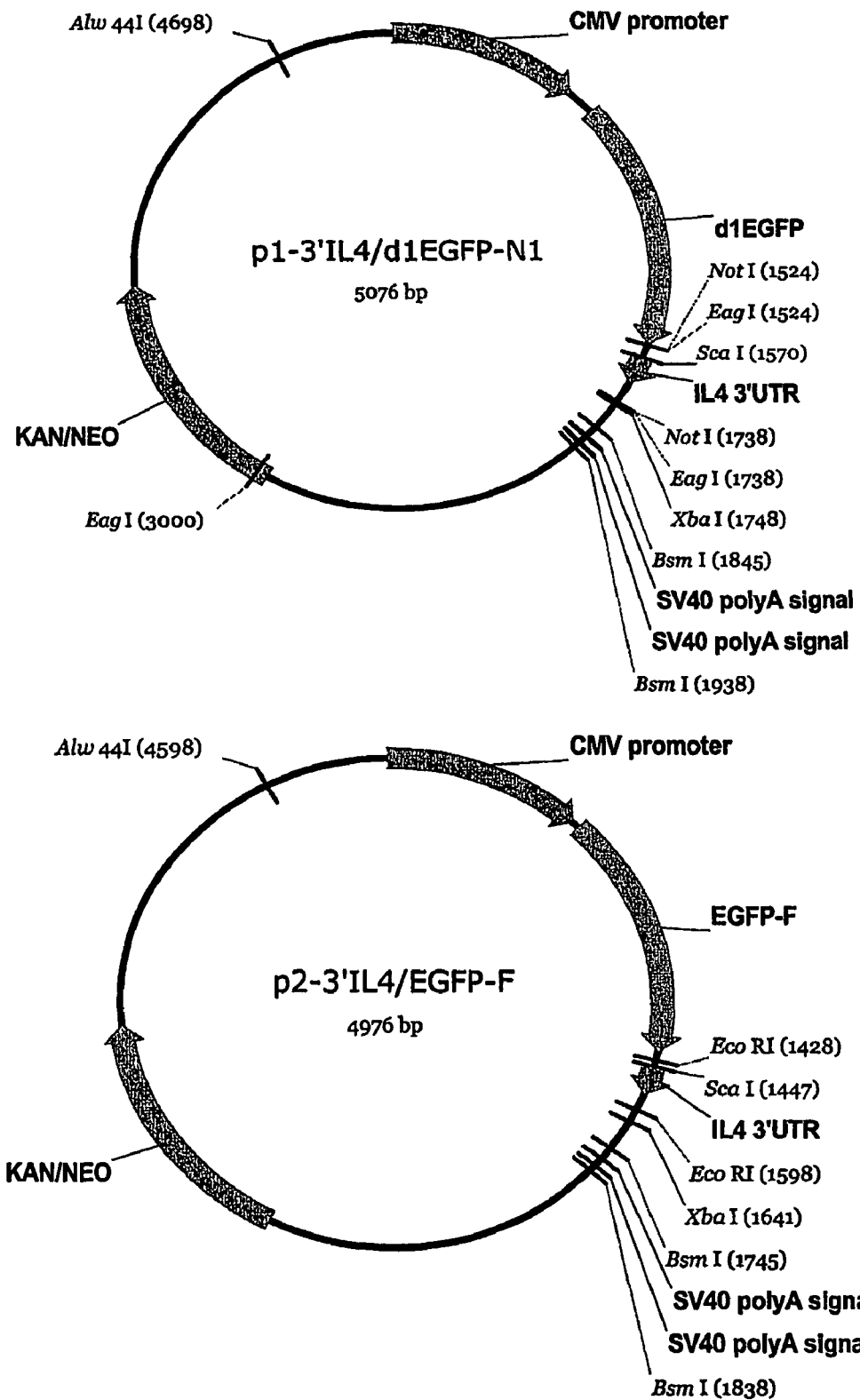
Figure 13:
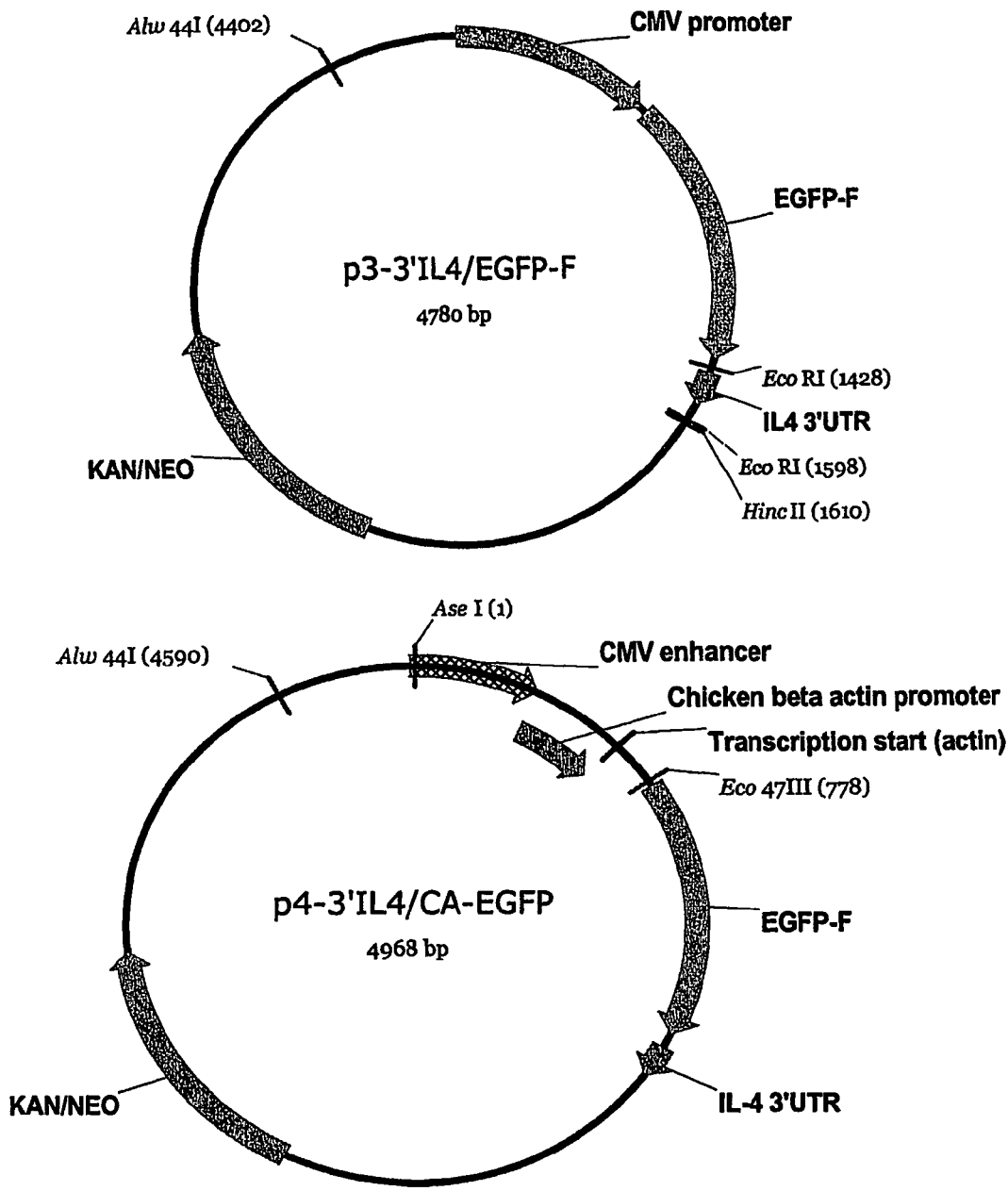
Figure 14:
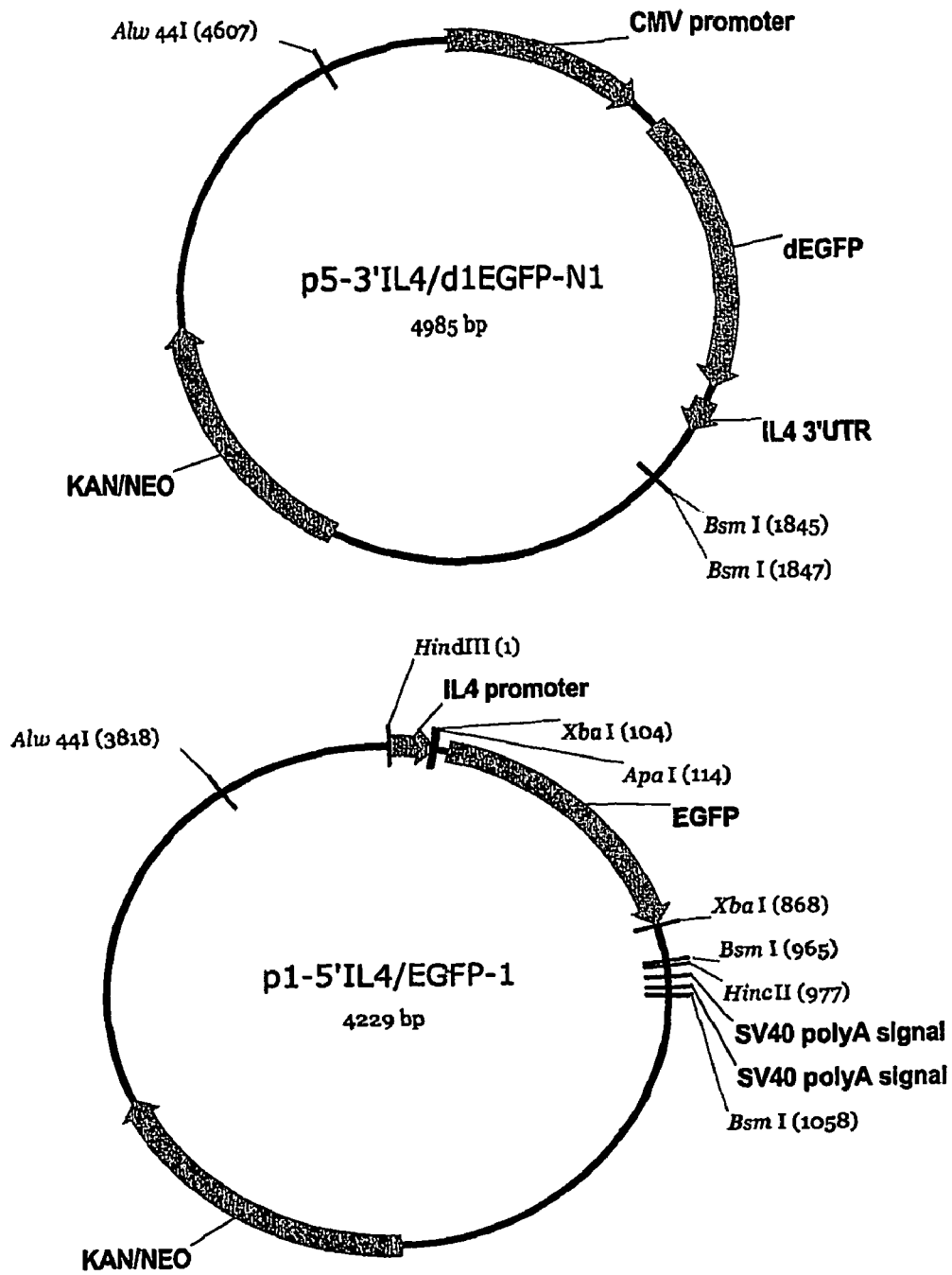
Figure 15:
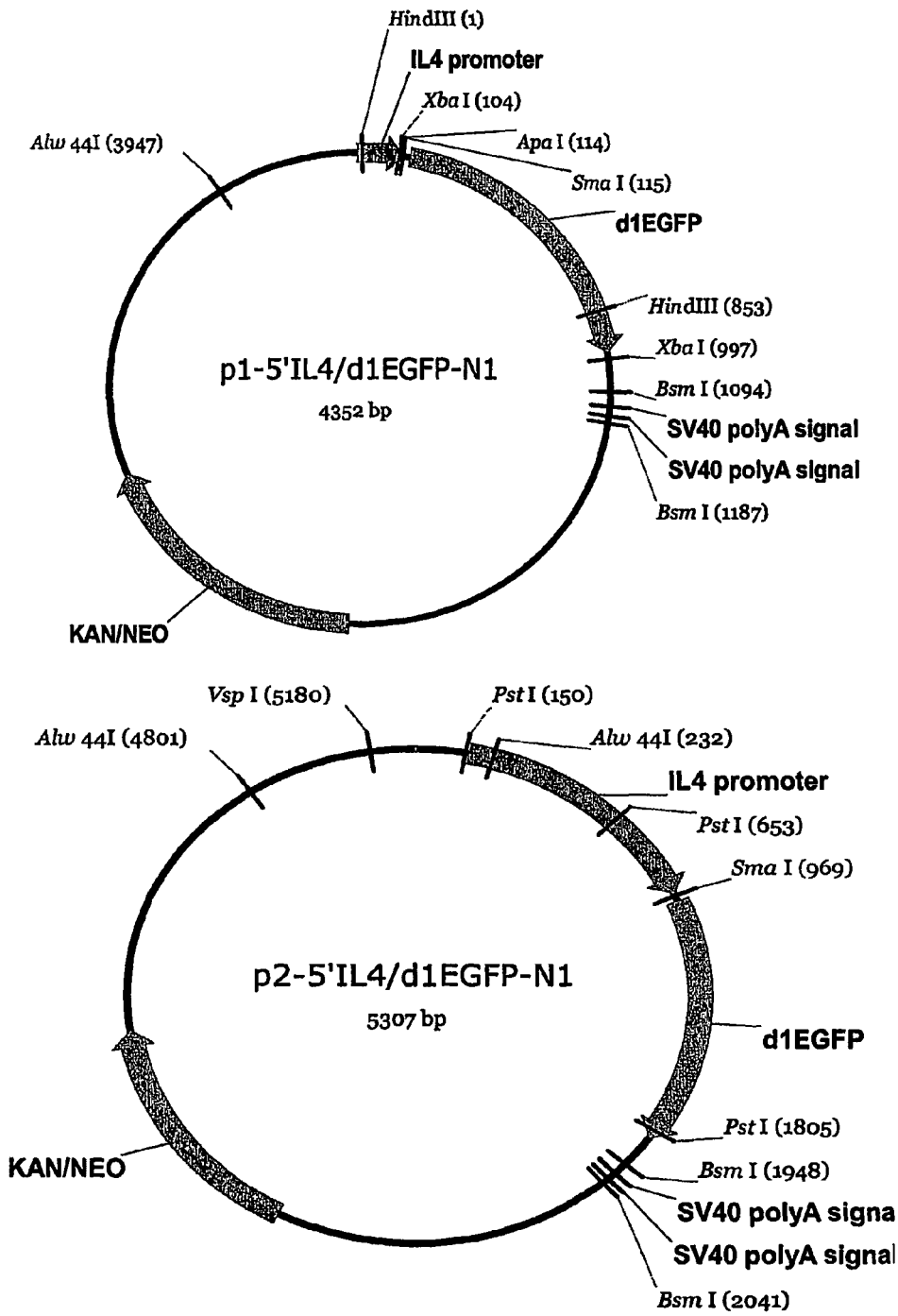
Figure 16:
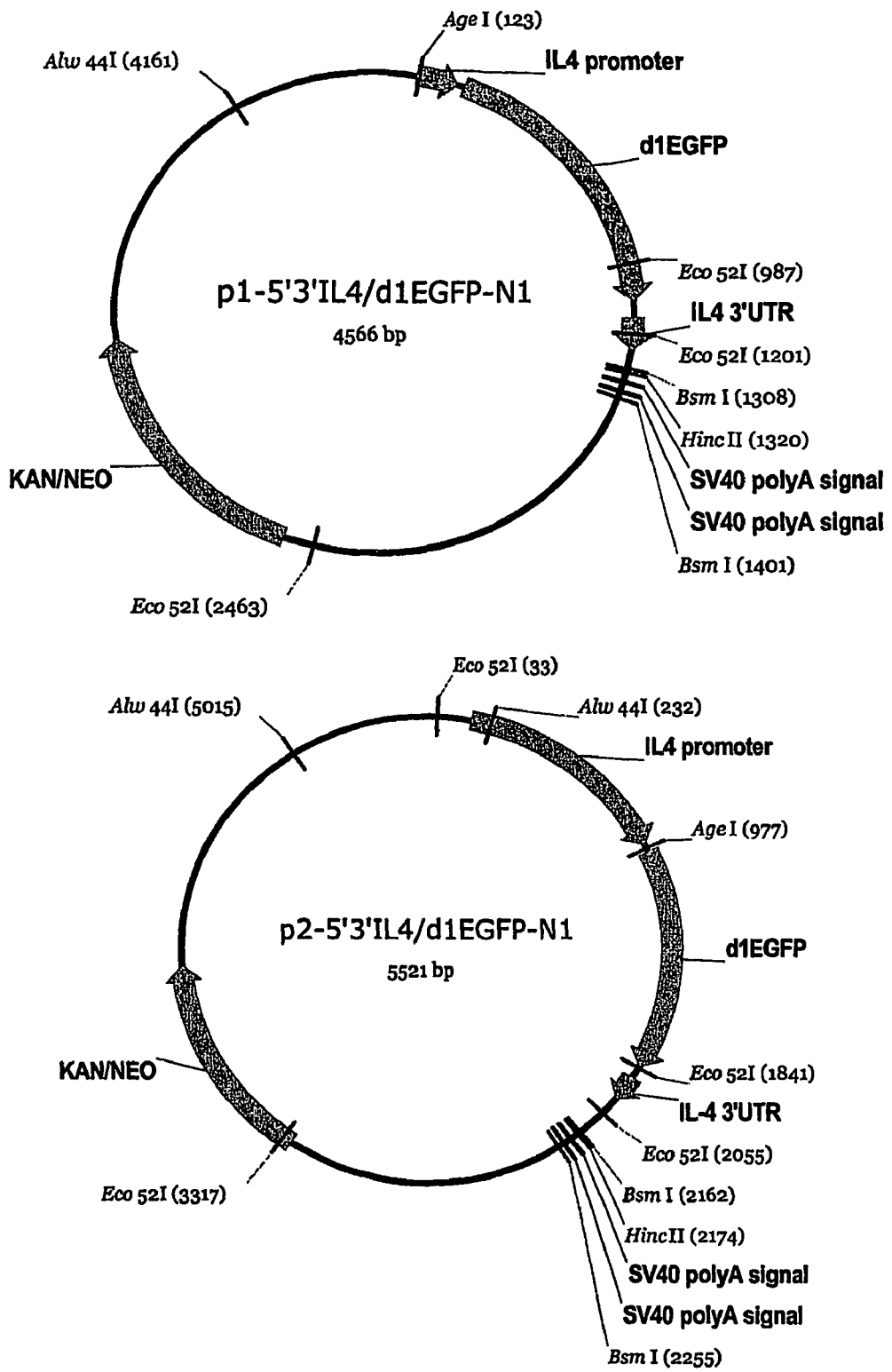
Figure 17:
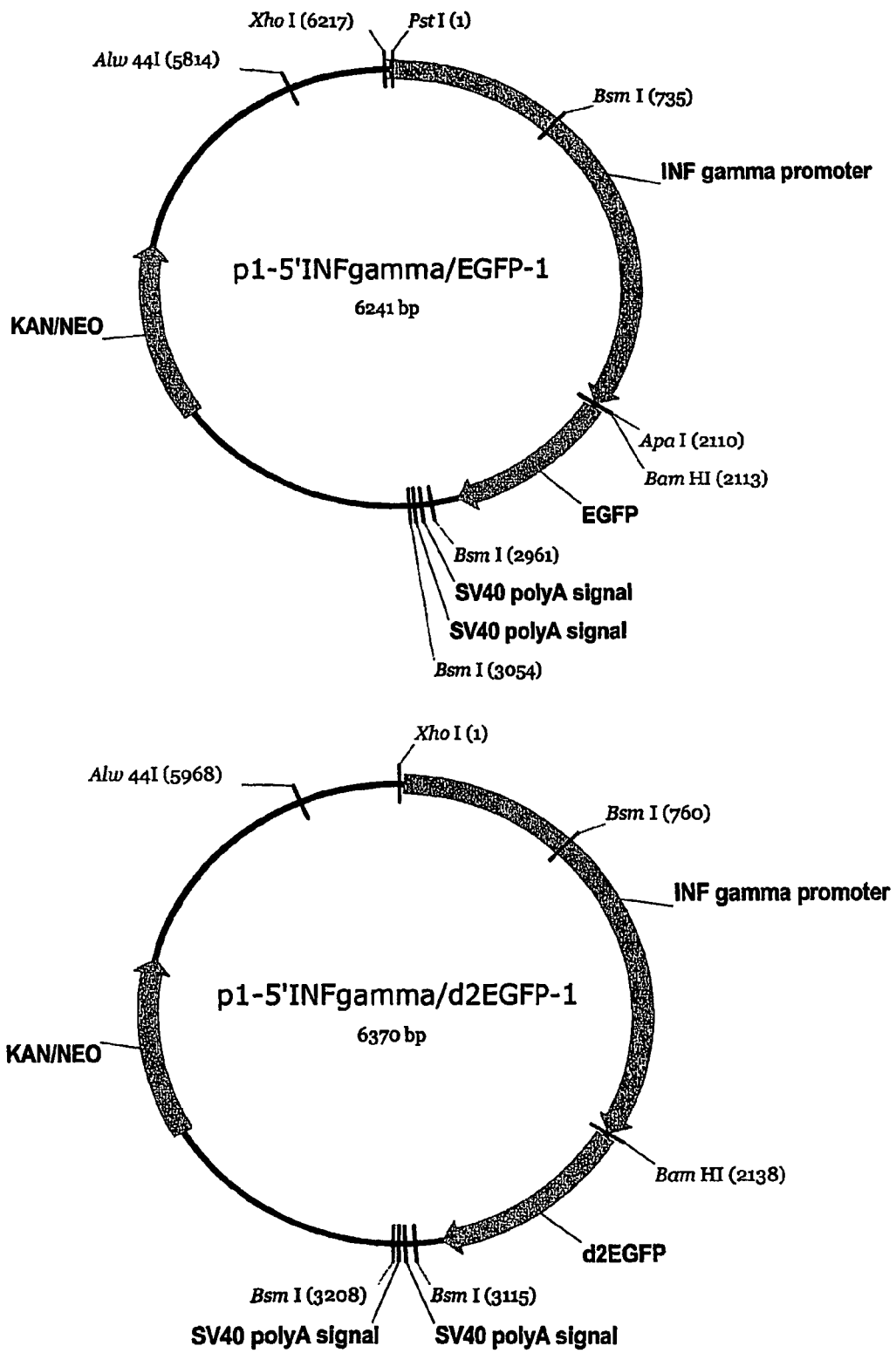
Figure 19:
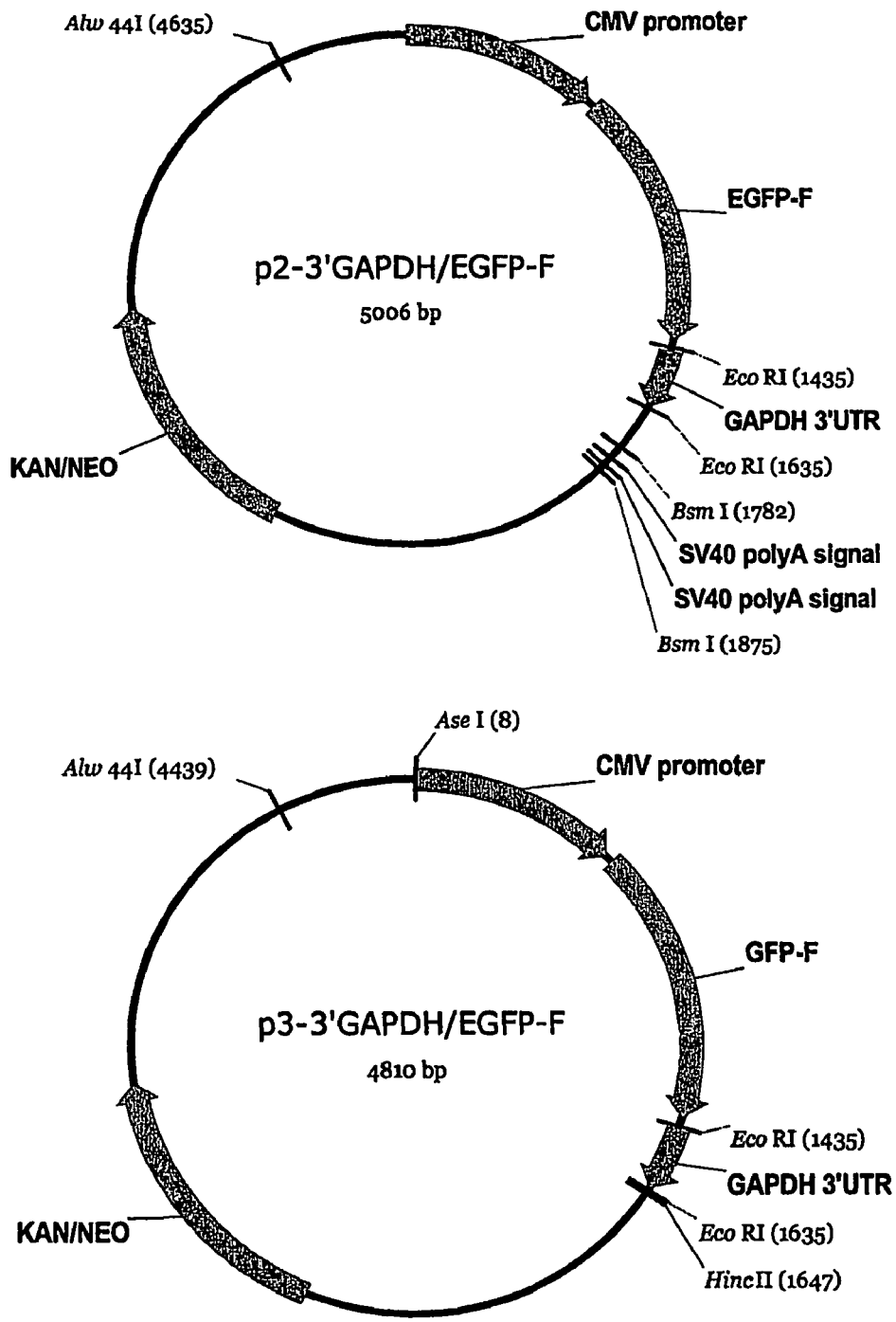

FIGS. 22-25 present the results of preliminary tests of reporter cell lines, which has been described in Example 7.

FIGS. 26-32 present results of testing the effect of certain substances using the prototype cell chip.

DETAILED DESCRIPTION OF THE INVENTION

In order to obtain reporter cell lines of the desirable phenotype, immortalized mammalian cell lines derived from different lineages of the immune system, as well as some non-immune cell types were tranfected with reporter genes encoding fluorescent protein. Reporter genes consist of sequences coding for fluorescent protein and regulatory sequences controlling cytokine expression. Different experimental approaches were used to generate reporter cell lines. Example 1 and Example 2 describe approaches employing a stable transfection system in which reporter genes are randomly incorporated into chromosome. Possible shortcomings detected in reporter cell lines obtained employing this experimental protocol will be corrected later by modifications of the original expression vectors and generation another series of transfectants in Example 3 and Example 4. In order to reproduce the complex regulatory mechanisms controlling cytokine gene expression in a given lineage of immune cells gene targeting technologies were employed next in Example 5 and Example 6. Reporter cell lines obtained with these genetic modifications were characterized for phenotype and were tested using selected xenobiotics in Example 7. Next, the set of selected cell lines, the fluorescent cell chip, was assembled and tested. This cell chip underwent the process of testing and prevalidation described in Example 8. Patterns of signals detecting the modulation of cytokine expression obtained with a selected xenobiotic in the fluorescent cell chip were then compared to results obtained with existing tests, and with available clinical data.

The main aspect of the invention involves a preparation of the system for in vitro immunotoxicity testing. This requires preparation of cell lines, in which signals regulating expression of several cytokines will generate increase in specific fluorescence. The following combinations of cytokine genes and cell lines presented in Table I were used as a starting point for the development of a "cell chip".

TABLE I

| Cytokine gene | Cell lines transfected with a reporter plasmid | Reporter gene |
|---|---|---|
| IL-2 | T cell leukemia (EL4) | EGFP/dEGFP |
|  | Thymoma (BW5147.3) | EGFP/dEGFP |
| IFN-γ | T cell leukemia (EL4) | EGFP/dEGFP |
|  | Thymoma (BW5147.3) | EGFP/dEGFP |
| IL-4 | T cell leukemia (EL4) | EGFP/dEGFP |
|  | Mast cells (C57.1) | EGFP/dEGFP |
| TNF-α | Macrophage-monocytes (J774A.1) | EGFP/dEGFP |
|  | Fibroblasts (3T3 L1) | EGFP/dEGFP |
|  | Mast cells (MC/9, C57.1) | dEGFP |
| IL-1β | Macrophage-monocytes (J774A.1) | dEGFP |
|  | Keratinocytes (HEL-30) | dEGFP |
|  | Fibroblasts (3T3 L1) | dEGFP |

TABLE I-continued

| Cytokine gene | Cell lines transfected with a reporter plasmid | Reporter gene |
|---|---|---|
| Control | Mast cells (C57.1) | dEGFP |
| (CMV promoter or | Fibroblasts (3T3 L1) | EGFP/dEGFP |
| B-actin promoter) | Keratinocytes (HEL-30) | dEGFP |
|  | T cell leukemia (EL4) | EGFP/dEGFP |
|  | Thymoma (BW5147.3) | EGFP |
|  | Macrophage-monocytes (J774A.1) | EGFP/dEGFP |

For testing and pre-validation of the prototype cell chip, compounds from the list of chemicals with already established immunotoxic potential, and in some cases with a partially understood mechanism of action, were employed. The list of compounds is presented in Table II.

TABLE II

| Substance | Type of activity | Possible action on cytokine gene expression |
|---|---|---|
| Cyclosporin | Suppression | Inhibition of cytokine production |
| Dioxin | Suppression | Alteration of cytokine production (inhibition and/or activation) |
| Pentamidine | Suppression | Inhibition of cytokine expression |
| Rapamycin | Suppression | Alterations in transcriptional mechanism regulating cytokine production |
| Thalidomide | Suppression | Alterations in transcriptional mechanism regulating cytokine production |
| TBTO, Bis-(tri-n-butyltin)-oxide | Suppression | Possible inhibition of cytokine production |
| House dust mite allergen | Antigen | Unknown |
| Benzocaine | Allergen | Unknown |
| Penicilline | Allergen | Unknown |
| TDI, Toluene-2,4-diisocyanate | Allergen | Induction of TH2 cytokine expression |
| MDI, Diphenylmethane-4,4'-diisocyanate | Allergen | Unknown |
| DNCB, Dinitrochloro-benzene | Contact allergen | Induction of cytokine expression |
| Dicyclohexyl methane-4,4'-diisocyanate | Contact Allergen | Unknown |
| HCB, Hexachlorobenzene | Immunostimulation Induction of autoimmunity Immunomodulation | Activation of cytokine expression |
| HgCl$_2$ | Induction of autoimmunity Immunomodulation | Induction of TH2 cytokine expression |
| Platinum salt (Tetrachloro-platinate) | Immunostimulation Respiratory allergen | Unknown |
| SDS | Irritant | Unknown |

According to the one of the embodiments of the present invention, unique cell lines were obtained and selected, which may serve to embody the method according to the present invention as well as being an example collection of cell lines according to the present invention. Said lines were deposited in the European Collection of Cell Cultures (ECACC), Health Protection Agency, Porton Down, Salisbury, SP4 0JG, United Kingdom. They are presented in Table III. Each of the cell lines listed in Table III was deposited in the ECACC on Sep. 12, 2003.

TABLE III

| Name | Provisional Accession No assigned by ECACC | Parental cell line | Transfected with |
|---|---|---|---|
| C/pCA-EGFP-F/2 | 3091201 | C57.1 | pCA-EGFP-F |
| C/p1-5'3'TNFα-dEGFP/2 | 3091202 | C57.1 | p1-5'3'TNFα/d1EGFP-N1 |
| EL/pCA-dEGFP/9 | 3091203 | EL4 | pCA-d1EGFP |
| EL/p1-5'IL2-dEGFP/6 | 3091204 | EL4 | p1-5'IL2/d2EGFP-1 |
| EL/p2-5'IL4-dEGFP/2 | 3091205 | EL4 | p2-5'IL4/d1EGFP-N1 |
| EL/p1-5'IFNγ-dEGFP/3 | 3091206 | EL4 | p1-5'IFNγ/d2EGFP-1 |
| EL/p2-5'IL10-dEGFP/5 | 3091207 | EL4 | p2-5'IL10/d2EGFP-5 |
| J/p4-5'IL1β-dEGFP/4 | 3091208 | J774A.1 | p4-5'IL1β/d1EGFP-N1 | each of these lines has been selected from among the collection of cell lines obtained on the basis of favourable characteristics summarised below. These were determined in accordance with the detailed description included in each example.

C/pCA-EGFP-F/2 is a control cell line. It was tested for EGFP fluorescence by FACS and fluorescence microscopy. It shows stable expression of EGFP.

EL/pCA-dEGFP/9 is a control cell line. It was tested for EGFP fluorescence by FACS and fluorescence microscopy. It shows stable expression of EGFP C/p1-5'3'TNFαdEGFP/2 is a cell line in which EGFP expression parallels the expression of TNF-. EGFP fluorescence is stimulated with PMA/ionomycine and antigen/IgE. This cell line demonstrated weak inhibition of EGFP fluorescence in the presence of immunossuppresive substances. Thus it detects the inhibitory action of chemical compounds, which could result in immunosuppression.

EL/p1-5'IL2-dEGFP/6 is a cell line in which EGFP expression parallels expression of IL-2. EGFP fluorescence is stimulated with PMA/ionomycine. This cell line demonstrated inhibition of EGFP fluorescence in the presence of immunossuppresive substances. Thus it detects the inhibitory action of chemical compounds, which could result in immunosuppression.

EL/p1-5'IFNγ-dEGFP/3 is a cell line in which EGFP expression parallel expression of IFNγ. EGFP fluorescence is stimulated with PMA/ionomycine. This cell line demonstrated inhibition of EGFP fluorescence in the presence of immunossuppresive substances. Thus it detects the inhibitory action of chemical compounds, which could result in immunosuppression. This cell line demonstrated increased EGFP fluorescence in the presence of a possible immunomodulator. Thus it detects the activatory action of chemical compounds, which could result in immunomodulation.

EL/p2-5'IL4-dEGFP/2 is a cell line in which EGFP expression parallels expression of IL-4. EGFP fluorescence is stimulated with PMA/ionomycine EL/p2-5'IL10-dEGFP/5 is a cell line in which EGFP expression parallels expression of IL-10. EGFP fluorescence is stimulated with PMA/ionomycine.

J/p4-5'IL1β-dEGFP/4 is a cell line in which EGFP expression parallels expression of IL-1. EGFP fluorescence is stimulated with LPS. This cell line demonstrated increase in EGFP fluorescence in the presence of immunostimulatory substance. Thus it detects the action of a chemical compound, which could result in immunomodulation.

In order to present the sense of invention, the description of invention is expanded by examples 1-8. However, it is not our intention to introduce claims limited to embodiments described in examples, because basing on presented sense of invention combined with knowledge generally available, experts will be able to prepare other variants comprised in defined claims.

EXAMPLE 1

Construction of Expression Vectors for Stable Transfection

To generate DNA constructs in which the expression of a reporter fluorescent protein depends on regulatory sequences derived from different cytokine genes. These expression vectors are necessary tools for the genetic modification of cell lines and will be used in Example 2.

Methodology and Study Materials

Several sequences containing regulatory elements of promoter regions from 5' upstream of cytokine genes, including IL-2, IFN-γ, IL-4, IL-1α, and TNF-α were collected. DNA was acquired from three sources; clones that are available in the public domain, PCR amplification of desired DNA fragments from genomic DNA followed by PCR product cloning, and chemical synthesis of oligonucleotides. Commercially available plasmids containing the GFP gene were used as the backbone of the construct. The promoter sequence of interest was cloned immediately upstream of the GFP transcription start site, using standard techniques of directional cloning with synthetic oligonucleotide adapters when necessary. Positive clones were selected and the DNA sequences of plasmids were verified with automated DNA sequencing.

Next, the regulatory sequences in 3'UTR fragments of the same selected cytokine genes were collected. The plasmids from the first series of GFP constructs were used to develop the second series of constructs. The 3'UTR sequences covering the polyA signal and mRNA stabilizing signals present in the original GFP plasmid were replaced with DNA coding for 3' UTR sequences of cytokine gene inserted immediately downstream of GFP stop codon. Synthetic oligonucleotide adapters were used when necessary. Positive clones were selected and the DNA sequences of plasmids were verified by automated DNA sequencing.

Consequently, construction of at least 5 expression vectors containing only promoter sequences and at least 5 expression vectors containing both promoter and downstream (3'UTR) sequences derived from cytokine genes were obtained.

Collection of 5' Upstream Regulatory Sequences

Sequences containing regulatory elements of the promoter region from 5' upstream of IL-4 cloned into plasmid pCAT were obtained as a gift from Dr. Melissa Brown (Atlanta University, Atlanta, USA). Promoter sequences for: IL-2, IFN-γ, IL-1β, and TNF-α were obtained by PCR based cloning using mouse genomic DNA isolated from Balb/c as a template.

For cloning of IL-2 and IFN-γderived sequences, genomic DNA was prepared from the tail tip of a Balb/c mouse. This DNA served as a template for the PCR amplification. PCR primers were designed based on the genomic sequences of murine IL-2 (X52618) and IFN-γ (M28381), available from GenBank. The primers were designed to encompass the upstream region of IL-2 from position −2686 to +25, and INF-γ from the position −2001 to +34, relative to the transcription start site denoted as +1. The rationale was to include a large upstream region in order to include many putative regulatory elements. The primers (TAG Copenhagen) were then used for PCR amplification using the "PCR core kit" (Roche Biochemicals). PCR products of the correct size were excised from an agarose gel, purified using a QiaQuick gel extraction kit (Qiagen), checked for integrity on an agarose gel and ligated into the PCR cloning vector pGEM-T Easy (Promega). The ligation was transformed into JM109 E. coli cells and colonies containing inserts were selected using ampicillin. Plasmid DNA was extracted from a number of clones using a QiaSpin miniprep kit (Qiagen). The plasmids were then screened for the presence and orientation of the PCR product using multiple restriction digests. Finally, the presence and orientation of the IL-2 and IFN-γ 5' upstream regulatory regions were confirmed by automated sequencing (ABI 377 DNA sequenator) from both ends using primers annealing to the vector.

It was decided to clone promoter of IL-1β instead of IL-1α. The reason to change the original plan was the fact that unlike the sequence of the IL-1α promoter, the entire DNA sequence of the murine IL-1β promoter was available in genetic databases. Although there might be differences in transcriptional regulation of IL-1 alpha and IL-1 beta genes IL-1α and IL-1β act through the same cell surface receptor, and have similar functions.

For cloning of TNF-α and IL-1β derivative sequences, genomic DNA was prepared from the liver of a Balb/c mouse. This DNA served as a template for PCR amplification. PCR primers were designed based on the genomic sequence of murine TNF-α (U066950) and IL-1β (X04964), available in databases. A 511 bp fragment of mouse IL-1β promoter (−500/+11) was amplified by PCR using Taq polymerase (MBI Fermentas). The PCR product was cloned into TA-cloning vector pTAdvance (Clontech). A 4104 bp of fragment of IL1-β promoter (−4093/+11) was amplified by PCR using the high-fidelity AccuTaq LA thermostable polymerase (Sigma). The PCR product was ligated into the pCR-Blunt II-TOPO blunt-end cloning vector (Invitrogen). The ligation mixture was transformed into JM109 E. coli cells and colonies containing inserts were selected using kanamycin. Bacterial clones were screened for the presence of IL1-β promoter using PCR. Plasmid DNA was extracted from a number of bacterial clones using Plasmid Miniprep Plus kit (A&A Biotechnology) and the presence and orientation of the IL1-β promoter containing insert was verified using multiple restriction digests. Finally, the sequence and orientation of the IL-1β5' upstream regulatory regions were confirmed by automated sequencing (ABI 377 DNA sequenator) using primers annealing to the vector. A 2276 bp fragment of the mouse TNF-α promoter (−2013/+263) was obtained using similar experimental protocol. Briefly, PCR was performed using AccuTaq LA polymerase and the PCR product was cloned into pCR-Blunt II-TOPO vector. Following bacterial transformation the bacterial clones were screened for the presence and orientation of the TNF-α promoter region using PCR and restriction analysis. Finally, the sequence and orientation of the TNF-α promoter was confirmed by automated sequencing.

Generation of the First Series of Reporter Constructs

The first series of reporter constructs consists of a number of plasmids where expression of the reporter gene is driven by promoter sequences of cytokines: IL-4, IL-2, IFN-γ, IL-1β, and TNF-α. All reporter constructs are based either on the plasmid pEGFP-1 (Clontech) containing enhanced green fluorescent protein (EGFP) as a reporter gene or on the plasmid pd1EGFP-N1 (Clontech) containing destabilized enhanced green fluorescent protein (d1EGFP) as a reporter gene.

To obtain the GFP reporter construct under the control of the IL-4 promoter a 120 bp DNA fragment containing the minimal IL-4 promoter sequence was excised from −87IL-4 pCAT plasmid using HindIII and XbaI restriction enzymes. This DNA was then ligated into pTAdvance plasmid (Clontech). In the next step, the IL-4 promoter was excised from pTAdvance plasmid using HindIII and ApaI, purified by agarose electrophoresis and ligated into the pEGFP-1 plasmid digested with the same enzymes. Plasmid DNA was isolated from kanamycin resistant bacterial clones and the integrity of the reporter construct was confirmed by ApaI/HindIII and HindIII/HindIII digestions, and by sequencing. Obtained plasmid was named p1-5'IL4/EGFP-1.

To obtain the GFP reporter constructs under the control of IL-2 and IFN-γ promoters the PCR cloned IL-2 and IFN-γ 5' regulatory regions were excised from pGEM-T Easy plasmids containing the inserts in negative orientation, using the restriction enzymes ApaI and PstI. The obtained DNA fragments were purified by agarose gel electrophoresis and a QiaQuick gel extraction kit (Qiagen), checked for the integrity on an agarose gel and ligated into the vector pEGFP-1 digested with ApaI and PstI in the multiple cloning site immediately upstream of the gene encoding EGFP. Following transformation, colonies were picked and isolated plasmids were screened for insertion of the IL-2 or IFN-γ promoters using multiple restriction digests. The integrity of the reporter constructs was confirmed by automated sequencing (ABI 377 DNA sequenator) from both ends using primers annealing to the vector. The obtained plasmids were named p1-5'IL2/EGFP-1 and p1-5'INFγ/EGFP-1.

To obtain the GFP reporter construct under the control of the IL-1β promoter, a 511 bp fragment of mouse IL-1β 5' regulatory region excised from pTAdvance plasmid using AseI and EcoRV (NEB) was used to replace the CMV promoter in the pd1EGFP-N1. The CMV promoter was removed using AseI and Eco47III restriction enzymes (NEB, MBI Fermentas). The presence of the IL-1β 5' regulatory region was confirmed by PCR and BamHI (NEB) digest. The integrity of the reporter construct, named p1-5'ILβ/d1EGFP-N1, was confirmed by automated sequencing using primers annealing to the vector. Next, a 4104 bp fragment of IL1β 5' regulatory region was excised from pCR-Blunt II-TOPO vector using EcoRV and KpnI (NEB). The pd1EGFP-N1 vector was modified by removal of the CMV promoter using AseI and NheI (NEB) restriction, treated with Mung Bean Nuclease (NEB) to generate blunt ends, and ligated. EcoRV/KpnI IL1-β promoter was then ligated with modified pd1EGFP-N1 plasmid restricted with SmaI and KpnI. The presence of IL-1β promoter was confirmed by PCR and restriction with Eco88I (MBI Fermentas). The integrity of the obtained plasmid, named p3-5'IL1β/d1EGFP-N1, was confirmed by sequencing. To obtain the GFP reporter construct under the control of the TNF-α promoter, a 2526 bp TNF-α 5' regulatory region was excised from pCR-Blunt II-TOPO with the use of AseI/EcoRV (NEB). CMV promoter in pd1EGFP-N1 plasmid was excised by Ec1136II/VspI (MBI Fermentas) digestion. Both the 2526 bp insert and the resulting 4251 bp promoterless vector were purified by agarose gel electrophoresis and ligated using T4 ligase (Gibco BRL). Following screening of the bacterial clones for a proper ligation product a 6777 bp plasmid, named p1-5'TNFα/d1EGFP-N1, was identified and purified. The sequence was verified using automated sequencing. This plasmid contains the entire TNF-α promoter region followed by 107 bp of TNF-α ORF and 80 bp of randomly generated linker at the beginning of d1EGFP ORF.

To obtain the EGFP reporter construct under the control of the actin promoter, a CAG promoter containing CMV enhancer and a chicken beta-actin promoter was excised with AseI and Eco47III restriction enzymes from commercially available plasmid pQE-TriSystem (Qiagen) and ligated into pEGFP-F plasmid (Clontech) in the place of CMV promoter (cut out with AseI and Eco47III restriction enzymes), upstream of EGFP coding sequence. The sequence of the resultant construct, pCA-EGFP-F, was confirmed by restriction enzyme maping.

Collection of 3' Downstream Regulatory Sequences

For cloning of 3'UTR regulatory sequences derived from IL-4, IL-2, IFN-γ, IL-1β, and TNF-α the respective sequences were amplified by PCR from genomic DNA obtained from the tail tips (IL-2 and IFN-γ) or from the livers (IL-4, IL-1β, and TNF-α) of Balb/c mice.

To clone IL-4 3'UTR, primers based on the IL-4 genomic sequence (X05253) were designed to encompass the entire IL-4 3'UTR, including the polyadenylation signal. Using these primers, a 154 bp long DNA fragment was amplified by PCR and cloned into pTAdvance vector (Clontech). The sequence of the cloned IL-4 3'UTR was verified by automated sequencing.

To obtain the regulatory elements present in the 3'UTR of IL-2 and IFN-γ, the PCR primers were designed to encompass the 3'UTRs, including the translational stop codon and the polyadenylation signal. Primers were designed based on the mRNA sequences of IL-2 (X01772) and IFN-γ (K00083), available in databases. The downstream primers were designed to include AflIII restriction sites. The 357 bp IL-2 3'UTR and the 645 bp IFN-γ 3'UTR amplified by PCR from genomic DNA were cloned non-directionally into the pGEM-T Easy vector (Promega). The identity and orientation of the inserts were then confirmed using multiple restriction digests.

To clone IL-1β 3'UTR, primers based on IL-1β genomic sequence (X04964) were designed to encompass the entire IL-1β 3'UTR, including the polyadenylation signal. Using these primers, a 455 bp long DNA fragment was amplified by PCR and cloned into the pTAdvance vector (Clontech). The sequence of the cloned IL-1β 3'UTR was verified by automated sequencing.

To obtain the regulatory elements present in the TNF-α 3'UTR PCR primers based on the TNF-α genomic sequence (U06950) were designed to encompass the entire TNF-α 3'UTR including the poly-adenylation signal. Using these primers, a 994 bp long DNA fragment amplified by PCR was cloned into the pTAdvance vector. The sequence of the cloned TNF-α 3'UTR was verified by automated sequencing.

To obtain the regulatory elements present in the GAPDH 3'UTR, PCR primers based on GAPDH genomic sequence (M32599) were designed to encompass the entire GAPDH 3'UTR including the polyadenylation signal. Using these primers, a 184 bp long DNA fragment amplified by PCR was cloned into the pTAdvance vector. The sequence of the cloned GAPDH 3'UTR was verified by automated sequencing.

Generation of the Second Series of Reporter Constructs

The second series of reporter constructs consists of a number of plasmids where the expression of the reporter gene is under the regulation of promoter sequences and 3'UTRs of cytokines: IL-4, IL-2, IFN-γ, IL-1β, and TNF-α. Reporter constructs are based on the plasmids pEGFP-1, pEGFP-F, and pd1EGFP-N1, pd2EGFP-1 (Clontech), containing enhanced green fluorescent protein (EGFP) and destabilized enhanced green fluorescent protein (dEGFP) as a reporter gene, respectively.

To obtain EGFP expression vector in which 3' downstream regulatory sequences of IL-4 gene control the mRNA stability of the EGFP transcript, the pTAdvance vector containing the entire 3'UTR for IL-4 was digested with EcoRI (NEB) and the obtained fragment was ligated downstream of EGFP stop codon into the pEGFP-F vector using the EcoRI site. The presence of the IL-4 3'UTR was confirmed by an EcoRI digest and by PCR. The right orientation of the IL-4 3'UTR was confirmed by ScaI and BsmI (NEB) digests. Finally, the sequence was confirmed by automated sequencing. The constructed vector, named p2-3'IL4/EGFP-F, contains SV40 derived 3'UTR sequences including polyadenylation sites. Northern blot experiments showed that these polyadenylation sites were utilized during transcription process. Thus, in the next step, the p2-3'IL4/EGFP-F vector was modified by removing the interfering SV40 polyadenylation signals. This plasmid was digested with BsmI (NEB) and Bal-31 nuclease (NEB), re-ligated and transformed into E. coli cells. Following plasmid isolation, the absence of the sequence containing SV40 polyadenylation signals in the modified plasmid, named p3-3'IL4/EGFP-F, was confirmed by a BsmI digest and sequencing. In the next step, IL-4 3UTR was excised from pTAdvance plasmid with EagI (NEB) and ligated into NotI (NEB) site downstream of EGFP stop codon in the pd1EGFP-N1 vector. Insert presence was confirmed by PCR and an EagI digest, and orientation was checked with a PstI (MBI Fermentas) digest. The sequence of the obtained plasmid, named p1-3'IL4/d1EGFP-N1, was confirmed by sequencing. To obtain the EGFP expression vector in which both 5' upstream and 3' downstream regulatory sequences of IL-4 gene control the expression of the reporter gene, vector p1-5'IL4/d1EGFP-N1, containing IL-4 promoter and d1EGFP ORF and vector p1-3'IL4/d1EGFP-N1 containing d1EGFP ORF and IL-4 3'UTR were both digested with AgeI (MBI Fermentas) and HincII (NEB) enzymes. DNA fragment containing d1EGFP ORF and IL-4 3'UTR obtained from p1-3'IL4/d1EGFP-N1 digest was next ligated with DNA fragment containing vector sequence and IL-4 promoter derived from p1-5'IL4/d1EGFP-N1. The restriction map of the new construct, named p1-5'3'IL4/EGFP-N1, was verified by digestion with Eco52I (MBI Fermentas), followed by sequencing.

To obtain EGFP expression vectors in which both 5' upstream and 3' downstream regulatory sequences of IL-2 and INF-γ genes control the expression of the reporter gene the following strategy was used. First, the respective 3'UTRs were cloned into the pd2EGFP-1 vector. To this end the SV40 derived polyadenylation signals present in the pd2EGFP-1 vector were removed using the restriction enzymes NotI and AflII. The 3'UTR's were then excised from the PCR cloning vector pGEM-T Easy using the restriction enzymes NotI and AflII, and the 3'UTRs containing fragments were ligated into NotI/AflII restricted pd2EGFP-1 vector. In the next step, the IL-2 and INF-γ promoter regions were cut out from the plasmids p1-5'IL2/EGFP-1 and p1-5'INFγ/EGFP-1, respectively, using the restriction enzymes XhoI and BamHI. These fragments were then gel-purified and ligated into the pd2EGFP-1 vectors containing 3'UTRs using XhoI and BamHI sites in the multiple cloning site upstream of d2 EGFP gene. Restriction maps of the new constructs, named p1-5'3'IL2/d2EGFP-1 and p1-5'3'INFγ/d2EGFP-1, were verified by multiple restriction digests and sequencing.

Two EGFP expression vectors in which both 5' upstream and 3' downstream regulatory sequences of IL-1β control the expression of the reporter gene were constructed. IL-1β 3'UTR was excised from pTAdvance vector with Eco52I (MBI Fermentas) and ligated into p1-5'IL1β/d1EGFP-N1 and p3-5'IL1β/d1EGFP-N1 vectors digested with NotI (NEB). The presence of the IL-1β 3'UTR in both plasmids was confirmed by PCR and its orientation was checked by HincII (NEB) digest. Sequences of new vectors, named p1-5'3'IL1β/d1EGFP-N1 and p3-5'3'IL1β/d1EGFP-N1, were confirmed by sequencing.

To obtain the EGFP expression vector in which 3' downstream regulatory sequences of TNF-α gene control the mRNA stability of the EGFP transcript, the pTAdvance vector containing the entire 3'UTR for TNF-α was digested with HindIII and EcoRV (NEB) and the obtained fragment was ligated downstream of EGFP stop codon into pEGFP-F vector using sites HindIII and SmaI. The presence of the TNF-α 3'UTR was confirmed by EcoRI and SspI (NEB) digest and by PCR. The sequence of TNF-α 3'UTR was confirmed by automated sequencing. Resultant vector, named p2-3'TNFα/EGFP-F, contains SV-40 derived 3'UTR sequences including polyadenylation sites. As Northern blot experiments conducted with p2-3'IL4/EGFP-F plasmid showed that SV-40 derived polyadenylation sites are utilized during transcription process the p2-3'TNFα/EGFP-F vector was modified by removing SV40 polyadenylation sequences. Plasmid p3-3'IL4/EGFP-F was digested with AseI and HincII to remove CMV-GFP-3'UTR IL-4 box and ligated with CMV-GFP-3'UTR THF-α box cut out from the plasmid p2-3'TNFα/EGFP-F using AseI and HincII. The presence of TNF-α 3'UTR in the resulting plasmid, named p3-3'TNFα/EGFP-F, was confirmed by PCR and the absence of SV40 polyadenylation sites by BsmI digest. In the next step, TNF-α 3'UTR was excised from pTAdvance plasmid with EagI (NEB) and ligated into the NotI (NEB) site downstream of EGFP stop codon into the pd1EGFP-N1 vector. Insert presence was confirmed by PCR and by Eco52I digest, and the right orientation of TNF-α 3'UTR was confirmed BglII and Bsu36I (MBI Fermentas) digest. The sequence of the constructed p1-3'TNFα/d1EGFP-N1 plasmid was confirmed by sequencing. To obtain EGFP expression vector in which both 5' upstream and 3' downstream regulatory sequences of TNF-α control the expression of the reporter gene the following strategy was used. First, SV40 3'UTR from p1-5'TNFα/d1EGFP-N1 plasmid was removed by sequential digestions with the following enzymes: Mva12691 (MBI fermentas), Mung Bean nuclease (NEB) and NotI (NEB). The 6684 bp vector fragment without SV40 3'UTR was next ligated with the 1039 bp fragment containing TNF-α 3'UTR excised from the p1-3'TNFα/d1EGFP-N1 using NotI and EcoRV endonucleases. The integrity of constructed vector named p1-5'3'TNFα/d1EGFP-N1 was confirmed by sequencing.

To obtain the EGFP expression vector in which 3' downstream regulatory sequences of GAPDH (the control housekeeping gene) control the mRNA stability of the EGFP transcript, the pTAdvance vector containing the entire 3'UTR for GAPDH was digested with EcoRI (NEB) and the obtained fragment was ligated downstream of EGFP stop codon into pEGFP-F vector (Clontech) using the EcoRI site. The presence of the GAPDH 3'UTR was confirmed by EcoRI digest and by PCR. The right orientation of the GAPDH 3'UTR was confirmed by StyI (NEB) digest. Finally, the sequence of the construct was confirmed by automated sequencing. The resulting vector, named p2-3'GAPDH/EGFP-F, contains SV40 derived 3'UTR sequences, including polyadenylation sites. As Northern blot experiments conducted with p2-3'IL4/EGFP-F plasmid showed that SV-40 derived polyadenylation sites are utilized during transcription process, the p2-3'GAPDH/EGFP-F vector was modified by removing SV40 polyadenylation sequences. Plasmid p3-3'IL4/EGFP-F was digested with AseI and HincII to remove CMV-GFP-3'UTR IL-4 cassette and ligated with CMV-GFP-3'UTR GAPDH cassette cut out from the plasmid p2-3'GAPDH/EGFP-F using AseI and HincII. The presence of GAPDH 3'UTR in the resulting plasmid named p3-3'GAPDH/EGFP-F was confirmed by PCR and the absence of SV40 polyadenylation sites by BsmI digest. In the next step, GAPDH 3'UTR was excised from the pTAdvance plasmid with EagI (NEB) and ligated into the NotI (NEB) site downstream of the EGFP stop codon into the pd1EGFP-N1 vector (Clontech). The presence of the insert was confirmed by PCR and by Eco52I digest, and the right orientation of GAPDH 3'UTR was confirmed PstI (MBI Fermentas) digest. The sequence of the resultant p1-3'GAPDH/d1EGFP-N1 plasmid was confirmed by sequencing.

Consequently, a set of expression vectors was obtained, in which the GFP coding sequence is under the control of 5' upstream regulatory sequences derived from cytokine gene, in a form of highly purified DNA available for transfection of mammalian cells. Moreover, a set of expression vectors was obtained, in which the GFP coding sequence is under the control of 5' upstream and 3' downstream regulatory sequences derived from cytokine genes, in a the form of highly purified DNA available for transfection of mammalian cells.

EXAMPLE 2

Cloning of the First Set of Reporter Cell Lines

To obtain several cell lines (The First Generation of Reporter Cell Lines) of desirable phenotype for testing immunotoxicity by introduction of the reporter gene into existing immortalized cells under the control of cytokine gene-derived regulatory DNA sequences.
Methodology and Study Materials Work started with the transfection of selected cell lines with the expression vectors obtained in Example 1. T cells and T cell hybridoma, mast cell lines, monocyte-macrophage, fibroblasts and keratinocyte cell lines were used. Plasmids were linearized by digestion and cells were transfected using electroporation.

Given cell lines were transfected with GFP constructs corresponding to cytokine genes known to be expressed at a relatively high level by this cell line upon activation. Transfectants were selected in culture by selective media (G-418) and cellular clones were developed by limiting dilution cloning. Clones were expanded and tested with RT-PCR for the presence of vector derived sequences. Positive clones underwent another round of cloning followed by screening with RT-PCR. Resultant clones were expanded in large-scale cultures and multiple aliquots were frozen. Cell lines obtained at this stage were used for further testing and development of stable cell lines. Several characteristics of developed cell lines were determined, such as the expression of cell surface markers and lineage specific functional responses (CD3 dependent proliferation, IgE-mediated degranulation, LPS induced phagocytosis). Next, immunological and pharmacological stimuli were used to activate cells and measure their GFP expression, and endogenous cytokine expression. This reveals whether there is a parallel activation of reporter gene and a cytokine gene of interest. Next the cytotoxicity test compatible with the fluorescence assays was developed. This is necessary to monitor tested compounds for frank cytotoxicity. For that purpose flourescent dyes based a cell viability assay, measurements of autoflorescence and the level of flourescence associated with expression of control GFP construct were tested. These experiments resulted in the development of the experimental protocol that would be used in Example 7 to measure kinetics of cell viability and cytokine expression inducing signal in parallel.

Consequently, some of the cell lines tested in Example 7, were used to assemble the panel of reporter cell line i.e. "a prototype of a cell-chip".

Development of an Assay for Cell Viability Compatible with GFP Detection

Three viability assays have been chosen for preliminary tests: NRU (Neutral Red Uptake), NRR (Neutral Red Release), and MTT (MTT Assay). In these assays 3T3-L1 fibroblasts and two immunotoxic compounds $HgCl_2$ and SDS (two of the chemicals from the list of model immunotoxins in the Table II of the Technical Annex) were used. As a result, the effective concentration of $HgCl_2$ and SDS that leads to death of 50% of cells in the population (EC50) were determined.

Organisation of the Cell Line Banking System

For storage of the cell clones generated during the project a distinct room in the NIOM facility was assigned. To assure the free space needed for cell samples additional liquid nitrogen cryogenic storage vessels were arranged. The standard protocol for collection and freezing of samples was elaborated. The control system of sample banking was prepared in detail.

Optimization of Protocols for Stable Transfection and EGFP Detection

Several protocols for stable transfection have been used to generate reporter cell lines. For adherent cell lines the transfection technique using lipofectamine was employed. In a standard experimental protocol, $2 \times 10^5$ cells seeded in a 24-well plate in complete DME medium (Sigma) were washed with serum free medium and incubated for about 2 h in 37° C., 5% $CO_2$. Next, DNA with lipofectamine (Gibco) was added and cells were incubated for another 5 h. Following this incubation medium containing 20% FCS was added and cells were cultured for 24 h. This medium was then replaced with a medium containing 10% FCS. 72 h after transfection, selecting medium containing G-418 (Gibco) at a concentration appropriate for a given cell line was added and cells were cultured for about 7 days. Limiting dilution was used next to clone the transgene positive cells. Expression of GFP was verified by FACS and using fluorescent microscope.

For cell lines which grow in suspension, the electroporation based transfection technique was employed. In a standard experimental protocol $1 \times 10^7$ cells grown in an appropriate medium were electroporated with 20 to 50 μg of DNA. Cells were allowed to recover in normal growth medium for 48 hours before the selecting antibiotic (G-418) was added. Next, the cells were either directly cloned by limiting dilution, or were first cultured in selecting medium for additional 1-2 weeks and then cloned. Resistant clones were expanded, frozen and characterized phenotypically.

To test the transfection protocol and techniques for GFP detection easily transfectable human T cell line Jurkat was used. Jurkat cells were transfected with the pEGFP-F plasmid where EGFP expression is driven by CMV promoter. As a result several cell clones with a high expression of EGFP were obtained. These cell lines were used by DBAPAS to test EGFP expression with a phosphorimager Multimager Typhoon 8600 (Molecular Dynamics).

Cloning of the First Set of Reporter Cell Lines

To obtain several cell lines of desirable phenotype for testing immunotoxicity with the reporter gene under the control of cytokine gene-derived regulatory DNA sequences several cell lines listed in the Table I of the Technical Annex were transfected with reporter GFP constructs. First, cells were transfected with plasmids, in which EGFP is under the control of a strong viral promoter (CMV). Thus, C57.1 mast cell line and HEL-30 keratinocytes were transfected with pEGFP-F plasmid, and 3T3-L1 fibroblasts were transfected with pEGFP-F and pEGFP-N1 plasmids. EL4 and BW5147.3 lymphocytes were transfected with pEGFP-C3 plasmid. As a result, several cell lines expressing different levels of EGFP have been generated, and are used to characterize the effects of stable transfection and EGFP expression on the cell line phenotype. In one of these transfection experiments, monitoring of GFP expression with Multimager was applied at early stages of cloning of 3T3-L1 fibroblast transfected with pEGFP-F. The resultant fibroblast cell line T/pEGFP-F/1 was used to develop alternative GFP detection technique (see WP.7). C57.1 mast cells expressing EGFP under control of the CMV promoter were employed in a series of experiments to assess the effect of stable EGFP transfection on their morphological and functional features. These cells expressed EGFP at a level easily detectable by FACS or under the fluorescent microscope. C57/CMV-EGFP cells shoed morphology identical to the maternal cell line. An increase in the number of giant cells as compared to the maternal cell line was observed. When tested in functional assays these cells exhibited the normal characteristics of mast cells. They were sensitized with monoclonal IgE in vitro and responded to an antigen by exocytosis and cytokine production. The level of mediator release and cytokine production in C57/CMV-EGFP cells were comparable to those observed with maternal C57.1 mast cells.

Next, DNA constructs developed in Example 1, in which GFP expression was under the control of 5' upstream or 3' UTRregulatory sequences of cytokine genes were used. Thus, C57.1 mast cells were transfected with the EGFP reporter plasmid for IL-4 gene, p1-5'IL4/EGFP-1. The plasmid was linearized and cells were transfected using electroporation. Several neomycin resistant clones were obtained and were expanded in large-scale cultures. Following second round of cloning one of these clones has been found to have a proper phenotypic characteristic of mast cells and detectable EGFP expression. This resultant cell line in which IL-4 minimal promoter controls EGFP expression was named C57/5'IL4/1 (renamed to C/p1-5'IL4-EGFP/002, in accordance with the labeling system in the reporter cell line database) and is the M1 milestone of the project. This cell line was employed in a series of experiments testing the level of EGFP expression in resting cells and cells challenged with ionophore. The conclusion of these tests was that there was a high EGFP expression in resting cells, which was due to the high stability of the EGFP protein. This feature in turn seems to obscure the increase in EGFP expression following cell stimulation. Based on this data the conclusion was drawn to also employ the destabilized EGFP variant, called dEGFP. in addition to EGFP (see Example 3).

Lymphocytic cell lines EL4 and BW5147.3 were transfected with reporter constructs for IL-2 and IFN-γ, p1-5'INFγ/EGFP-1 and p1-5'IL2/EGFP-1, respectively. Several resistant clones resulting from these transfections have already been frozen. EL4 cells transfected with the p1-5'IL2/EGFP-1 plasmid were used to test spontaneous and phorbol ester mediated expression of EGFP mRNA. For each type of reporter cell line a minimum of 3 clones have been obtained. The clones were initially analyzed on the basis of GFP basal expression and inducibility. Initial analysis was performed using fluorescence microscopy, demonstrating this to be a good method to detect GFP expression. Attempts to use Fluorescence microscope reader resulted in the need for further optimization of experimental protocols and technical details. Subsequent functional analyses have been performed using flow cytometry (FACS). Basal GFP expression relative to non-transfected cells, as well as inducibility of expression after the activation of cells with TPA+ionomycin was tested. Regarding the EL4 derived clones with GFP under control of regulatory elements from IL2 or IFNγ, several clones with low basal and high inducible GFP expression were identified. Regarding the BW5 147.3 derived clones, all tested clones show a detectable basal GFP expression but none of the clones showed an increased expression of GFP following activation with TPA and ionomycin.

Lymphocytic cell line EL4 was transfected with a reporter construct for IL-4 p1-5'IL-4/EGFP-1. Multiple resistant clones resulting from these transfections have been tested using FACS and fluorescence microscopy for basal and inducible EGFP expression. None of the clones showed an increased expression of GFP following activation with TPA and calcium ionophore.

Consequently, the set of reporter cell lines with a proper phenotypic characteristic containing reporter genes incorporated into chromosomal DNA was obtained. Moreover, the assay for cell viability compatible with the fluorescence assay for GFP expression was obtained.

EXAMPLE 3

Construction of Modified Expression Vectors for Stable Transfections

To modify the DNA constructs in which the expression of reporter fluorescent protein depends on regulatory sequences derived from cytokine genes by introduction of additional regulatory sequences and/or modification of fluorescence protein coding sequences. These modifications shall result in an increase in the ratio of maximal to baseline expression of reporter gene. This objective was reached by one or several of the following changes: Lowering the spontaneous baseline expression of fluorescent protein; (and/or) increasing the amount of reporter protein expressed upon stimulation; (and/or) changing the cellular localization of fluorescent protein; (and/or) changing the type of fluorescent protein. These modified expression vectors (Modified Expression Vectors for Stable Transfection) are tools for genetic modification of cell lines and will be used in Example 4.

Methodology and Study Materials

The GFP constructs obtained in Example 1 were modified using standard molecular biology techniques, by restriction enzyme digestion and directional cloning of desired sequences. The sequences of interest were either derived from commercially available expression vectors or were introduced as synthetic oligonucleotides. Positive clones were selected and the sequence of the obtaining plasmids verified. The detailed changes in the design of expression vectors depend of the results obtained. Lowering of the baseline level of GFP expression may require the introduction of additional regulatory elements such as silencers into the upstream of GFP coding sequence. Additional "heterologous" motif destabilizing mRNA can be also introduced into the 3' UTR-downstream of GFP open reading frame.

To increase the level of expression the repeated tandem regulatory sequences of cytokine promoter can be used and known "heterologous" motifs stabilizing mRNA can also be introduced into the 3' UTRdownstream of GFP open reading frame.

The ladder sequences in the GFP open reading frame can be modified resulting into different trafficking of GFP into cellular compartment. The fluorescent protein itself can be replaced with one of several modified fluorescent proteins, which may change the signal to noise ratio in fluorimetric readout of gene expression due to different level of overlap with autofluorescence. The bioluminescence based reporter gene can also be tested as a possible alternative for GFP system.

All this modification were obtained by changing the existing expression vectors using standard molecular biology techniques, such as restriction enzyme digestion, PCR and ligation.

Generation of the dEGFP Reporter Constructs Containing Cytokine 5' Regulatory Regions Two reporter constructs containing dEGFP under control of IL-4 5' upstream regulatory sequences were created. The first one was generated based on the p1-5'IL4/EGFP-1 plasmid (see WP1) digested with SmaI and XhoI enzymes (MBI Fermentas). The excised fragment containing minimal promoter for IL-4 (−87/+5), was cloned into the the pd1EGFP-N1* plasmid (pd1EGFP-N1 modified by removal of CMV promoter, see WP1) digested with the same pair of enzymes. Ligation products were screened with SmaI and Alw44I digestion. The sequence of constructed plasmid, named p1-5'IL4/d1EGFP-N1, was confirmed by automated sequencing. For the second reporter construct, a longer IL-4 promoter region (−797/+5) was obtained by PCR (Taq Polymerase; MBI Fermentas) using the −797pCAT plasmid as a template (a gift from Dr. Melisa Brown, Atlanta University, Atlanta, USA). PCR product was cloned into pTAdvance vector. Next, IL-4 promoter was excised from the pTAdvance vector with SmaI and VspI (MBI Fermentas) and cloned into pd1EGFP-N1* digested with the same pair of enzymes. The effect of the ligation was confirmed by HindII and by Eco52I digestions. The sequence of the constructed plasmid, named p2-5'IL4/d1EGFP-N1, was verified by sequencing.

Reporter constructs containing dEGFP under control of IL-2 and IFN-γ 5' upstream regulatory sequences are based on reporter constructs containing EGFP. The IL-2 and IFN-γ promoter regions were excised using XhoI and BamHI from plasmids p1-5'IL2/EGFP-1 and p1-5'IFγ/EGFP-1, respectively. The obtained DNA fragments were then gel-purified and ligated into the pd2EGFP-1 plasmid (Clontech), digested with the same pair of enzymes. Ligation products were analysed using multiple restriction digests. Sequences of the obtained constructs, named p1-5'IL2/d2EGFP-1 and p1-5'INFγ/d2EGFP-1, were confirmed by sequencing.

Two improved reporter constructs containing dEGFP under control of IL-1β 5' upstream regulatory sequences were created. The rationale was to obtain reporter constructs with intronic sequences of IL-1β, which are thought to possess regulatory capacity. The PCR primers were designed to encompass the sequence from −4093 bp or −500 bp upstream of transcription start to the beginning of exon 2 (+820 bp) of the IL-1β gene. −500/+820 and −4093/+820 fragments of IL-1β obtained by PCR using Balb/c mouse genomic DNA as a template and a high-fidelity AccuTaq polymerase (Sigma) were cloned into pCR-Blunt II-TOPO vector (Invitrogen). The IL-1β derived sequences were then released from this vector using EcoRV (NEB) and KpnI (NEB) and cloned into pd1EGFP-N1* digested with SmaI (MBI Fermentas) and KpnI (NEB). The presence of the −500/+820 IL-1β promoter in the first obtained plasmid, named p2-5'IL1β/d1EGFP-N1, was confirmed by PCR and HincII digest. The presence of the −4093/+820 IL-1β promoter in the second obtained plasmid, named p4-5'IL1β/d1EGFP-N1, was confirmed by PCR, and by digestion with Eco88I (MBI Fermentas).

Sequences of the p2-5'IL1β/d1EGFP-N1 and p4-5'IL1β/d1EGFP-N1 plasmids were confirmed by automated sequencing.

To obtain dEGFP reporter construct under control of actin promoter, CAG promoter, which consists of CMV enhancer and chicken β-actin proximal promoter was cut out with AseI and Eco47III restriction enzymes from commercially available pQE-TriSystem vector (Qiagen) and ligated into pd1EGFP-N1 vector (Clontech) in the place of CMV promoter (cut out with AseI and Eco47III restriction enzymes), upstream of EGFP coding sequence. The sequence of resultant construct pCA-d1EGFP was confirmed by restriction enzyme maping.

Generation of the dEGFP Reporter Constructs Containing Cytokine 5' and 3 Regulatory Regions To obtain dEGFP reporter construct containing both, the −87 promoter and 3' UTR of IL-4 gene, the plasmids p1-5'IL4/d1EGFP-N1 and p1-3'IL4/d1EGFP-N1 were digested with AgeI (MBIFermentas) and HincII (NEB) The fragment containing d1EGFP and 3' UTR excised from p1-3'IL4/d1EGFP-N1 plasmid was next cloned into p1-5'IL4/d1 EGFP-N1, immediately downstream of IL-4 promoter. A restriction map of a new construct, named p1-5'3'IL4/d1EGFP-N1, was analysed by Eco52I (MBI Fermentas) digestion and the sequence of this plasmid was verified by automated sequencing. To obtain dEGFP reporter construct containing both, the −797 promoter and 3' UTR of IL-4 gene, the plasmids p2-5'IL4/d1 EGFP-N1 and p1-3'IL4/d1EGFP-N1 were digested with AgeI (MBI Fermentas) and HincII (NEB). The fragment containing d1EGFP and 3' UTR excised from p1-3'IL4/d1EGFP-N1 plasmid was next cloned into p2-5'IL4/d1EGFP-N1, immediately downstream of IL-4 promoter. A restriction map of the new construct, named p2-5'3'IL4/d1EGFP-N1, was analysed by Eco52I and SspI (NEB) digestion and the sequence of this plasmid was verified by automated sequencing.

To obtain dEGFP reporter construct containing both, the −500/+820 5' regulatory region and 3' UTR of IL1β gene, the IL-1β 3' UTR was excised from pTAdvance with EagI (NEB), and ligated into p2-5'IL-1β/d1EGFP-N1 digested with NotI (NEB). The presence of the insert was confirmed by PCR and its orientation was analysed by Ecl136II (MBI Fermentas) digestion. The sequence of the obtained plasmid, named p2-5'3'IL1/d1EGFP-N1, was confirmed by automated sequencing. To obtain the dEGFP reporter construct containing both, the −4093/+820 5' regulatory region and 3' UTR of IL-1β gene, the IL-1β 3' UTR was excised from pTAdvance with EagI (NEB), and ligated into p4-5'IL1β/d1EGFP-N1 digested with NotI (NEB). The presence of the insert was confirmed by PCR and its orientation was determined by an Ecl136 (MBI Fermentas) digest. The sequence of the obtained plasmid, named p4-5'3'IL1β/d1EGFP-N1, was confirmed by automated sequencing.

Consequently, a set of modified expression vectors was obtained, in the form of highly purified plasmid DNA available for transfection of mammalian cells.

EXAMPLE 4

Cloning of the Improved Reporter Cell Lines

To obtain several cell lines (The Second Generation of Reporter Cell Lines) of phenotype characteristics improved as compared to the first generation of reporter cell lines for testing immunotoxicity.

Methodology and Study Materials

Work will start with transfection of selected cell lines using the GFP expression vectors modified as described in Example 3. Linearized plasmid DNA will be employed to transfect cells using electroporation. Transfectants that underwent random insertion of extrachromosomal DNA will be selected by culture in the presence of G-418 and cloned with limited dilution cell cloning. Clones will be expanded, verified for the presence of vector DNA with PCR, and expanded in large-scale cultures. Multiple aliquots will be frozen. Next, all the important phenotype characteristics of these cell lines will be investigated using a similar approach to that described in Example 2. The level of GFP expression and the signal to noise ratio will be determined. These data will be compared to the parameters observed in the cell lines obtained in Example 2. It will show whether the modifications of the GFP reporter gene constructs will improve the detection of inducible gene expression using fluorimetric or luminometric assays. It is desirable to clone and characterize 3 to 4 cell lines transfected with modified GFP expression vectors. This number of cell lines should be sufficient for the verification of our assumptions. Some of these cell lines will be used in Example 7 to build the panel of reporter cell lines "a prototype of a cell chip".

Results

To obtain several cell lines of phenotype characteristics improved as compared to the first generation of reporter cell lines for testing immunotoxicity the lymphocytic cell lines EL4 and BW5147.3 were transfected with dEGFP reporter constructs for IL-2 and IFN-γ, p1-5'IL2/d2EGFP-1 and p1-5'INFγ/d2EGFP-1, respectively (Example 3). Several neomycin resistant clones resulting from these transfections were expanded and characterized. Some of them have shown low basal dEGFP expression, which was upregulated upon activation with TPA/ionomycin to the level easily detected by FACS or fluorescence microscopy. In such a manner, the reporter cell line EL/p1-5'L2-dEGFP/7 was obtained. Although clones carrying destabilized variant of EGFP show lower basal expression when compared to EGFP transfected cells the maximum level of inducible dEGFP expression was also lower as compared to activated EL4 clones carrying dEGFP transgene. Lymphocytic cell line EL4 was also transfected with a reporter constructs for IL-4 p1-5'IL4/d1EGFP-N1 and p1-5'3'IL4/d1EGFP-N1. These transfections resulted in multiple neomycin resistant clones, which were tested for basal and inducible EGFP expression using FACS and fluorescence microscopy. None of the clones showed an increased expression of GFP following activation with TPA and calcium ionophore.

C57.1 mast cells were transfected with reporter constructs for IL-4 p1-5'IL4/d1EGFP-N1 and p1-5'3'IL4/d1EGFP-N1. Resultant clones were characterized for basal and inducible GFP expression and did not show induction of GFP expression. The transfection protocol using the same plasmids was repeated and generated multiple resistant clones. J774.1A monocytes-macrophages were transfected with the reporter constructs for TNF-α, p1-5'TNF-α/d1EGFP-N1. Multiple resistant clones were selected and cloned. Resultant clones were characterized for basal and inducible GFP expression using FACS. One of these clones was found to respond to activation with LPS by upregulation of GFP fluorescence.

C57.1 mast cells were transfected with two reporter constructs for TNF-α, p1-5' TNF-α/d1EGFP-N1 and p1-5'TNF-α/d1EGFP-N1. Multiple resistant clones were selected and cloned. Resultant clones were characterized for basal and inducible GFP expression using fluorescence microscopy and FACS. 10 of these clones have been found to respond to activation with TPA and A23 ionophore by upregulation of GFP fluorescence, easily detected under fluorescence microscopy and FACS.

EL4 cells and C57 cells were transfected control plasmid pCA-d1EGFP, in which dEGFP expression is under control of the actin promoter. Resultant cell clones were tested for GFP expression and showed a basal expression that is not inducible upon activation.

3T3-L1 fibroblasts, Hel-30 keratinocytes, and J774.1A monocytes-macrophages were transfected with the IL-1β reporter constructs p2-5'IL1β/d1EGFP-N1 and p4-5IL$^1$β/d1EGFP-N1. HEL-30 derived resistant cells were found to be difficult to clone and propagate due to very strong adhesion to plastic. An alternative technique for transfection of this cell line is currently being tested. Transfection of J774A.1 yielded multiple resistant clones that were characterized for selected phenotypic features and GFP expression. Analysis of cell size performed on a Coulter Multisizer II confirmed observations conducted on these cell lines under microscope, which suggested a greater cell size for the original J774A.1 line. The clones together with the original line were stimulated with LPS (1 µg/ml) and assessed for: NO production using the Griess reaction, IL-1β protein synthesis (using DuoSet ELISA Development kit (R&D), GFP and IL-1β mRNA expression (RT-PCR using RevertAid™ (Invitrogen), and GFP fluorescence with a fluorescence microscope equipped with CCD camera.

Data from the nitric oxide production assay suggested that LPS activated both the nontransfected J744 A.1 cells and all tested clones to similar extent. IL-1β protein synthesis measurements showed no detectable concentrations in the supernatants of stimulated cells but high quantities of IL-1β in cell lysates. All stimulated clones (in 25 cm$^2$ culture flasks, 70-80% confluency) expressed mRNA for GFP, which was associated by simultaneous IL-1β mRNA expression. GFP expression was observed after 6 and 12 h of LPS stimulation and then slowly declined on 24$^{th}$ hour. Interestingly however, only two among these five clones showed increase in GFP fluorescence following stimulation.

Transfection of 3T3-L1 yielded multiple resistant clones that were characterized for basal and inducible GFP expression. 40 resultant clones were tested for their response to stimulation with LPS using FACS. Two of these clones responded to LPS by upregulation of GFP fluorescence.

EXAMPLE 5

Construction of Expression Vectors for Gene Targeting

To prepare a series of DNA vectors designed for gene targeting. These targeting vectors are tools necessary for development of immune cells (Example 6) in which selected loci of cytokine genes will be replaced with a reporter gene.
Methodology and Study Materials Gene-targeting strategy utilizing a targeting vector with a long contiguous sequence homologous to the targeted loci will be used. First, several clones of genomic DNA will be collected, overlapping or mapped close to murine cytokine genes. The restriction map of the relevant part of murine chromosomal DNA covering loci for IL-4, IL-5, and IFN-γ are available, and these genes were successfully targeted in mice resulting in a "knockout phenotype". The gene targeting constructs will contain a 6 kB fragment of DNA overlapping the coding region of targeted cytokine gene. For each targeted locus it is desirable to prepare three vectors, each of them containing the same long homologous sequence but differ in the type of selectable markers. Construction of targeting vectors will start based on a backbone of a standard pBluescript vector. GFP coding region with 3' UTR cytokine sequences adjacent to its Stop codon will be derived from GFP vectors obtained in Example 1. In the first type of vectors, GFP coding sequences followed by 3' UTR of cytokine genes will be inserted into the 6 kB long fragment homologous sequence to replace the cytokine open reading frame. A Neo or Hyg box flanked with a pair of loxP sequences will be inserted downstream of the transcription termination signal for the cytokine gene followed by long contiguous fragment of targeting homologous sequence. Inserting a tk gene close to the end of the 3kB long downstream homologous sequence will develop the second type of targeting vector, which allows the use of the positive-negative cell selection technique (PNS). Vectors will be constructed using standard DNA manipulation techniques, including restriction enzyme digestion and ligation. The synthetic oligonucleotide adapters and PCR generated DNA fragments will be used if necessary to connect the desired DNA sequences and to introduce particular sequences into the construct. Following transformation the positive E. coli clones will be selected with a miniprep analysis. After verification of plasmid sequences with automated sequencing, large quantities of plasmid DNA will be amplified and purified.
Results Experimental work exploring the gene-targeting approach for development of reporter cell lines started by using the 9 kb IL-2/GFP targeting construct obtained from Dr. Hua Gu (Laboratory of Immunology, NIH Rockville, USA). This plasmid, containing the 2 kb sequence that encompasses IL-2 upstream region, GFO ORF from pGgreenLantern (Life Technologies), Neo box and 4 kb of IL-2 genomic DNA, had been successfully applied for generation of transgenic mice (Immunity 9: 209-216). The integrity of this vector has been verified, amplified and purified plasmid DNA and employed in a series of experiments. The original plasmid is modified by addition of TK box at the 3' end, which allows the use the positive-negative cell selection technique (PNS). To this end the pPNT plasmid containing the herpes simplex virus thymidine kinase gene under control of the mouse phosphoglycerate kinase-1 promoter (BCCM/LMBP plasmid and DNA collection, Ghent, Belgium) was used. An extensive restriction mapping was performed to identify sites in the pIL-2/GFP plasmid that could be used to clone in the TK-cassette. Only a few single cutters that did not disrupt the IL2/GFP targeting sequence were identified. These restriction sites does not correspond to any available in the pPNT plasmid. To overcome the lack of sites in the targeting construct the 2.8 kb TK cassette was sub-cloned into pBluescript. An alternative PCR based cloning strategy was also tested.

Censequently, it is desirable to obtain a set of gene targeting vectors, containing long fragments of DNA overlapping the coding region of a targeted cytokine, GFP coding sequence and selectable marker or markers, in the form of highly purified DNA available for transfection of mammalian cells.

EXAMPLE 6

Exploring the Gene Targeting Technology for Generation of Reporter Cell Lines

To engineer immortalized immune cells, in which signals regulating transient expression of cytokine gene would instead regulate the expression of reporter gene. Thus, the entire complexity of regulatory mechanisms controlling cytokine production with all cis and trans acting elements would influence the level of GFP expression.
Methodology and Study Materials Vectors obtained in Example 5 will be used to target DNA sequences into the selected cytokine gene loci. Vectors designed for positive selection with neomycin (G418) or hygromycin and vectors for positive-negative selection (PNS) will be used. Cutting at the unique restriction enzyme site will linearize the vectors, which will be then electroporated into cells. Cells will be placed in selecting media. Selection of cells will be based on G418 or hygromycin in case of positive selection process or on G418 followed with gancyclovir in a positive-negative selection process. Resistant cells will be cloned by limiting dilution procedure. Clones will be screened for desired genomic modification using PCR. The selected clones will be further tested for successful gene targeting using southern blot, and expanded in large-scale cultures. Cell lines obtained at this stage will undergo tests for phenotypic characteristics. In the next step it will be desirable to activate these cells and measure GFP expression. The successful incorporation of a transgenic insert into the specific loci will result in a single allele modified to express GFP instead of cytokine mRNA. In the next step it will be desirable to replace both alleles of the gene with GFP and compare the resulting phenotype with that of a single replacement. To do this, cell lines with single transgenic insertions and which target the other allele will be used. One possible strategy is to use the targeting vector with different selectable markers and to screen transfectants for double resistance. An alternative strategy is to remove the neomycin cassette from the transgenic insert and use the neomycin resistance marker for selection once again. Clones will be tested using PCR and clones negative for the neo box and sensitive to neomycin will be selected. From this point the second round of gene targeting is similar for both strategies described above and follows the experimental procedure described for the first gene targeting experiment. The difference will be used for screening in the PCR primers and Southern probe. They will be designed to verify the complete absence of cytokine coding sequences in the genomic DNA.

Results

The 9 kb IL-2/GFP targetting construct was linearized and used for electroporation-based transfection of EL4 cells. Transfected cells underwent G-418 based selection. Limited dilution cloning of neomycin resistant cells yielded 26 clones, which were characterized for the type of insertion. For that purpose the Southern blot of EcoRI digested genomic DNA isolated from these clones has been performed. Although one of these clones gave signal of distinct size other than expected from unmodified IL-2 loci, the final conclusion was that only random DNA incorporations took place. Thus, the original plasmid is now being modified by addition of TK cassette at the 3' end, which will allow us to use the positive-negative cell selection technique (PNS). Although none of the resistant clones demonstrated an incorporation of GFP transgene in locus sevral clones have shown proper phenotypic characteristics and were added to the reporter cell line collection. Consequently, it is still desirable to deliver cell line or cell lines genetically engineered to replace one or two alleli of cytokine gene with coding region of GFP reporter gene.

EXAMPLE 7

Development of the Experimental Protocol for Testing the Response of Reporter Cell Lines to Xenobiotics To verify if responses of reporter cell lines to the set of characterized immunotoxins are detectable and reproducible. To select cell lines for the assemble of the prototypic panel of reporter cell lines. To prepare standardized experimental protocol that could be used for testing substance of interest employing this prototypic panel of reporter cell lines.

Methodology and Study Materials

The cell culture and assay condition will be optimized to obtain comparable level of baseline fluorescence and the best signal to noise ratio. The preferable format for these experiments will be testing cells placed in multiwell plate. Selected immunomodulatory substances will be added at increasing concentrations and the expression of GFP in tested cells will be measured. For that purpose activated or resting cells will be incubated in the presence or absence of tested compounds and the kinetic assay of GFP specific fluorescence will be performed. This fluorescence signal will provide information on possible modulation of cellular response leading to enhancement or inhibition of cytokine expression. Based on obtained data a common experimental protocol will be designed which would allow the usage of several cell lines representing different cell lineage in a single assay. Results will facilitate the selection of cell lines for assembling and testing of the entire panel of reporter cell lines, the prototype of a cell chip. The cell line selected for the cell chip has to fulfill following criteria:

The phenotypic characteristics identical with the original cell line

The ability to generate detectable fluorescence signal in response to lineage specific immunological and pharmacological stimuli The low level of spontaneous GFP associated fluorescence The stability of all desired characteristics observed following several passages (several months of culture)

This is desirable to obtain the knowledge critical for optimization of the prototype cell chip. Specifically generation of experimental data on the level of sensitivity of fluorescence detection of changes in gene expression observed with selected xenobiotics.

The resultant data shall point to the possible problems and suggest future development. Based on the result obtained with commercially available fluoroimagers we may also specify the technical requirements of fluorescence detector that may further improve this assay.

Propagation of Reporter Cell Lines

Cell clones were propagated and transferred for banking. More than fifty reporter GFP transfected cell clones with the proper phenotypic characteristics are stored in multiple aliquots in a cell banking facility.

Phenotypic Characterisation of Reporter Cell Lines

Since TPA/ionomycin treatment only mimics T-cell activation to a limited extent, other modes of activation of EL4 derived reporter cell lines were tested. The feasibility of anti-CD3 antibody for activation of EL4 T-cells was tested. In series of experiments EL4 reporter clones were cultured on plates coated with anti-CD3 antibodies. FACS analysis of GFP expression showed that the anti-CD3 treatment did not induce GFP expression. To test the functionality of the anti-CD3 plate a proliferation assay was then performed. The results show that treatment with the anti-CD3 antibody inhibited proliferation of the EL4 cells, as has been demonstrated earlier. The usage of Concavalin A, another T cell activator is currently being tested.

In order to correlate the GFP expression data with effects on the expression of endogenous cytokine mRNA, RT-PCR analysis was performed. Non-transfected EL4 and BW5147.3 cells were activated with TPA/ionomycin or anti-CD3 and RNA was prepared. Following cDNA synthesis PCR was performed to detect expression of IL-2, IFNγ, and GAPDH (control). The results generally agree with the GFP expression data. In BW5147.3 cells neither IL-2, nor IFNγ mRNA, could be detected in non-induced cells or after activation. In EL4 cells, IL-2 and IFNγ expression could be induced by TPA/ionomycin, but not anti-CD3.

Detection of Green Fluorescent Protein

Two laboratories have compared different methods to measure GFP fluorescence in reporter cell lines. Preliminary testing using the cells with constitutive expression of GFP, have showed that detection of GFP with fluorescence ELISA readers is possible. At NIPH, FluoStar and FACS were compared, while at RIVM FluoStar, FluoImager and fluorescence microscopy were compared. Good quantitative correlations were seen between the results obtained using FluoStar and FACS, and between FluoStar and FluoImager, respectively, and a good qualitative correlation to fluorescence microscopy.

Cells—Viability Testing

The work to determine the toxic range of all the chemicals listed in Table II for all the cell lines developed in the project has progressed. The basic cytotoxicty assay employed was LDH release. Several cytotoxicity assays were performed independently in two laboratories. Data, which are presented in FIG. 20 and FIG. 21, respectively, were compared and analyzed and will allow us to decide on the range of concentrations to be used for testing of the Fluorescence Cell Chip. In addition, the cytotoxicity associated with the solvent was also tested to eliminate the possibility of interference in the test outcome.

Preliminary Tests of Reporter Cell Lines for Their Responses to Model Xenobiotics.

The effect of tetrachloroplatinate and nickel sulfate on reporter cell line J/p4-5'IL1β-dEGFP/4 was investigated. First, the NO levels in the supernatants of tested cells exposed to these substances were measured. Both, tetrachloroplatinate and nickel sulfate induced elevated levels of NO. Although reporter cells stimulated with these compounds didn't show noticeable fluorescence under microscope, upregulation of mRNA for GFP in the clone stimulated for 6 h with tetrachloroplatinate (100 μM) was observed (FIG. 22).

The effect of Cyclosporin A, Rapamycin and TCDD (dioxin) on selected lymphocytic reporter cell lines were determined independently in three laboratories. EL4 and reporter cells for IL-2, EL/p1-5'IL2-EGFP/3 and EL/p1-5'IL2-dEGFP/6, were treated with Cyclosporin A, Rapamycin and TCDD (dioxin) to test the effect on basal and induced GFP expression. For EL4 derived cells basal GFP expression was not affected following treatment with any of the above chemicals. Activation of EL4 cells with TPA/ionophore resulted in the upregulation of EGFP fluorescence as observed by FACS, fluorescence microscope and Fluorostar plate reader. Cyclosporin A was shown to completely inhibit the activation induced GFP expression down to basal levels (FIG. 23, FIG. 24). This inhibitory effect of Cyclosporine was observed independently in all three laboratories performing such experiments. Furthermore, this inhibition of EGFP expression was detected with all three techniques emplyed for EGFP measurements (i.e. FACS, fluorescence microscope, and Fluorostar). Rapamycin or TCDD did not have any effect on the activation induced GFP expression. Thus the important proof of the concept of Fluorescence Cell Chip testing has been obtained, namely the microplate based readout detected the presence of model immunosupresive xenobiotic (Cyclosporin A; FIG. 24). Additional RT-PCR based analysis showed that Cyclosporin A treatment inhibited the upregulation of expression of IL-2 and IFNγ in activated reporter cell lines, while Rapamycin or TCDD had no effect (FIG. 25).

These results show that Cyclosporin A inhibited in parallel the induction of endogenous cytokine genes and the GFP reporter transgene.

BW5147.3 derived GFP transfected cell clones have been also used to test the effects of immunomodulatory compounds. Cyclosporin A, Rapamycin and TCDD did not affect the basal GFP expression and since the GFP expression could not be induced, the effect on activated expression could not be analysed.

EXAMPLE 8

Pre-validation of the New Test Against Available Data on Animal and Human Immunotoxicity. Prototype of Cell-chip Methodology and Study Materials Work will start from providing all participants with the panel of reporter cell lines—the prototype of a cell chip assembled in previous examples. The standardized experimental protocol developed in Example 7 for performing such test will be implemented in all collaborating laboratories. All laboratories will next employ the same set of tested substances. In this example it will be used not only the set of xenobiotics with defined immunotoxic properties (see Table 2) but also a set of inert substances that are unlikely to have any immunotoxic effects in vivo. All the experiments will be performed with the entire set of reporter cell lines, the prototype cell chip. Collection of several patterns of response for these xenobiotic will allow to compare these patterns with available data. Comparison of patterns generated by model immunotoxins, substances that may be classified as irritants but do not posses immunomodulatory activity and control inert compounds will be performed. This analysis shall reveal if the new technology is capable to distinguish immunotoxins from other xenobiotics. Testing known and unknown (blind) samples of xenobiotic in parallel experiments will next be performed in all laboratories. A comparison of data obtained independently in participating laboratories will provide preliminary data on reproducibility of responses of reporter cell lines, and the sensitivity of this technology to minor differences in experimental protocols. It is desirable to obtain information in a format of "two dimensional" pattern that describes the action of several "model xenobiotics" (substances already known for their immunomodulatory activities in vivo) on different genes in various cell lineages.

Results

Preparation for the Experimental Work

Fluorstar Galaxy Multiwell (BMG Labtechnologies) fluorescence, luminescence, and an absorbance reader were used for fluorescence detection. Two laboratories received two cell lines 3T3-L1/CMV-EGFP and HEL-30/CMV-EGFP and employed them for testing both the cell culture and the fluorescence assay protocols.

Exposure to Xenobiotics/The Cell Chip Lay-out

Cells were plated in 24 well microtiter plates at a density of $0.5 \times 10^6$ cells/mL and with a final volume of 1.5 mL/well. Two controls were included for each cell line, in each experiment. One control consisted of cells in growth medium and the second control was cells in the presence of the induction mix (Ionomycin calcium salt, (cat. no#1-0634, Sigma) and 10 ng/mL PMA (Sigma). In some cases, induction mix contained only ionomycin or LPS at concentration 100 ng/ml rather than PMA and ionomycin. Cells were incubated with different chemicals at the concentration that led to 10% cytotoxicity and concentrations 10× and 100× more diluted in the absence and presence of the induction mix. Cells were incubated in a humidified atmosphere, 37° C. and 5% $CO_2$, and after 4 h 0.5 mL was removed from each test sample and analyzed by flow cytometry. The remaining sample was further incubated for 20 h (total 24 h) before flow cytometry.

Flow Cytometry

Samples were analyzed in an EPICS® XL-MCL Coulter flow cytometer with Expo v.2 Analysis Software/Expo32 Analysis Software (Applied Cytometry Systems, Sheffield, UK). or any other suitable flow cytometer. Viable and dead cells were gated separately and results were determined based on fluorescence associated with viable cells only. Regions were set in control cells and the same regions were used in induction controls and chemically challenged cells. Percent positive cells and fluorescence intensity were noted and used in further calculations.

Data Presentation

Index numbers were calculated from the median fluorescence intensity of viable cells. Cells incubated in the absence or presence of ionomycin/PMA were analysed separately. Each clone incubated with or without ionomycin/PMA, but without further chemicals/compounds was defined as index number=1, and the index numbers for the other exposures were calculated from this. Experiments with the same exposures were pooled to perform statistical analysis, using SigmaStat 2.03 statistical analysis software (SPSS Inc., Chicago, Ill. USA).

Statistical Analysis

One way ANOVAs (one way analysis of variance) were performed. In cases where normality failed, we used Kruskal-Wallis One Way Analysis of Variance on Ranks. If the differences between groups were statistically significant ($p<0.05$), we continued with tests for multiple comparisons. In normally distributed data we used Bonferroni t-test and multiple comparisons versus the control. The control was chosen to be the sample incubated in the presence or absence of ionomycin/PMA only. When normality failed we used Dunnett's Method for multiple comparisons versus the control.

Chemicals Used for Testing the Prototype Cell Chip

Cyclosporin A (for molecular biology, Tolypocladium inflatum, minimum purity 95%, Sigma) was diluted in ethanol to a stock concentration of 5 mg/mL and kept at −20° C. The stock solution was diluted in medium prior to experiments. Rapamycin (minimum purity 95%, Sigma) was dissolved in DMSO to a concentration of 2 mg/mL and kept at −20° C. The stock solution was diluted in medium prior to experiments. Pentamidine isethionate salt (Sigma) was dissolved in DMSO to a final concentration of 25 mg/mL and kept at −20° C. The stock solution was diluted in medium prior to experiments. (+/−)—Thalidomide (purity>98%, Sigma). A 0.2 M stock solution of Thalidomide in DMSO was prepared and kept at −20° C. Prior to experiments, the stock solution was diluted in medium, which led to a white precipitate. The solution was resuspended and used for further dilutions. Bis(tri-n-butyltin) oxide (TBTO) (purity 96%, Aldrich) was diluted in ethanol to a stock concentration of 10 mM, kept at −20° C. and diluted in medium before use. House dust mite D-pteronyssinus (Alutard SQ Depot allergen extract) (suspension for injection, 100 000 SQ-U/mL solution, ALK-Abelló, Hørsholm, Denmark) was kept at 4-8° C. as instructed by the manufacturer and diluted in medium directly before use. 1-Chloro-2,4-dinitrobenzene (DNCB) (purity minimum 98%, Sigma) was diluted in ethanol to a stock solution of 2 mM, kept at −20° C. and diluted in medium before use. Benzocaine (Ethyl-4-Aminobenzoate, Sigma) was diluted to a 0.5 M stock solution in ethanol, kept at −20° C. and diluted in medium before use. Tolylene 2,4-diisocyanate (TDI) (Sigma, purity 95%). On the day of the experiment, TDI was first dissolved in DMSO to a concentration of 0.1 M. This stock solution was further diluted in medium to 1 mM, before further dilution in medium. It is noteworthy that the TDI/DMSO solution is of higher density than medium and sinks to the bottom of the tube as well as becoming insoluble. The white precipitate was resuspended to an even suspension before dilution. Potassium tetrachloro-platinate (II) (purity 99.99%, Aldrich) was diluted in medium to a stock solution of 30 mM, kept at −20° C. and diluted in medium before use. Penicillin G (Benzylpenicillin) sodium salt (activity>1477 U/mg, Sigma) was diluted in medium to a stock solution of 200 mM, kept at −20° C. and further diluted in medium before use. SDS (purity>85%, Merck) was diluted in DMSO to a stock solution of 100 mM, kept at −20° C. and diluted in medium before use. Mercury (II) chloride (minimum purity 99.5%, Merck) was diluted in ethanol to a stock solution of 6 mM, kept at −20° C. and diluted in medium before use.

Prototype of Cell-chip

The following cell lines: EL/pCA-dEGFP/9, EL/p1-5'IL2-dEGFP/6, EL/p2-5' IL4-dEGFP/2, EL/p1-5'IFNγ-dEGFP/3, and EL/p2-5'IL10-dEGFP/5, obtained by transfection with the DNA constructs containing promoter region derived from β-actin, IL2, IL4, INF-γ, and IL10 were employed to design the prototype cell chip. The prototype cell chip was used to test the activity of different substances.

Results of Testing the Effect of Different Substances Using the Prototype Cell Chip Immunosuppressants Cyclosporin A (CsA) and Rapamycin are well-known immunosuppressive drugs used in organ transplantation. Pentamidine is used as an antiprotozoal drug, but has also been shown to reduce expression of several cytokines. Thalidomide is used as an anti-inflammatory drug. Bis(tri-n-butyltin) oxide (TBTO) has also been shown previously to be immunosuppressive, both in vivo and in vitro.

Cyclosporin A

Figure 26:
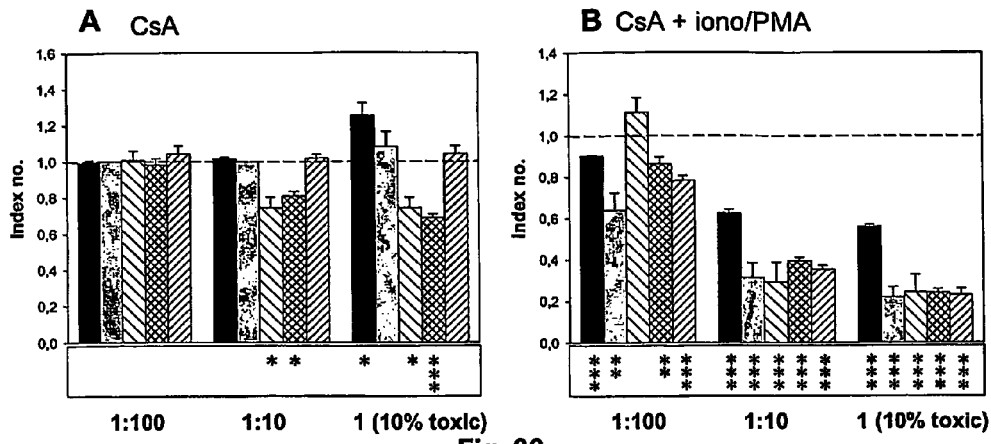

FIG. 26 presents results of testing the effect of Cyclosporin A using the prototype cell chip: cells transfected with the regulatory elements from actin (black bars), IL-2 (grey bars), IL-4 (wide striped bars), IL-10 (diamond bars) and IFN-γ (narrow striped bars) fused to EGFP were exposed to 1 μM CsA, which led to 10% cytotoxicity, and 1:10 or 1:100 dilution of this for 24 h in the absence (A) or presence (B) of ionomycin/PMA (1 μM/10 ng/mL). In non-induced cells (A) at the highest concentration, we found statistically significant differences compared to the control for actin, IL-4 and IL-10. At the 1:10 dilution, only IL-4 and IL-10 were statistically significantly different from their control. In stimulated cells (B) expression of all genes tested were statistically significantly different from their control, except for IL-4 at the 1:100 dilution. The graphs show the mean values with SEM (n=3). Statistically significant findings with $p<0.05$ are noted by *, $p<0.01$ are noted by  and $p<0.001$ are noted by *. The dashed line represents the control level.

In the absence of ionomycin/PMA, we found a statistically significant dose-dependent decrease in IL-4 and IL-10 at 1 and 0.1 μM. Surprisingly, we found a significantly higher expression of actin at the highest concentration (1 μM) (FIG. 26A). In the presence of ionomycin/PMA we found significantly lower induction in all clones, at all concentrations, except for IL-4 at the lowest concentration (FIG. 26B). The suppressive action of CsA in stimulated cells was confirmed for IL-2 and IFN-γ, by using clones transfected with the same regulatory elements, but fused to a stabile form of EGFP. In these clones in the presence of ionomycin/PMA, CsA exposure resulted in a dose-dependent reduction of IL-2 expression at 0.01 μM and 0.1 μM ($p<0.01$) and of IFN-γ expression at 0.01 µM (p<0.01) and 0.1 µM (p<0.001). In the absence of ionomycin/PMA these cells failed to show exposure effects (data not shown).

Rapamycin

Figure 27:
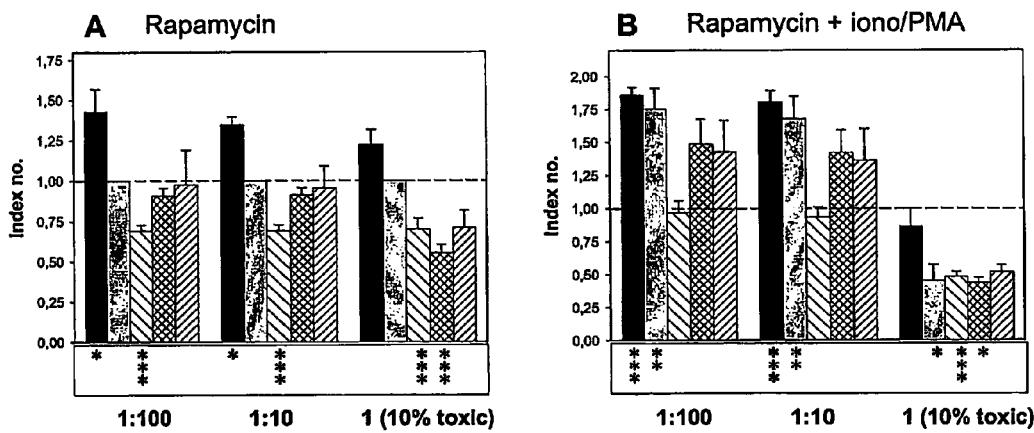

FIG. 27 presents results of testing the effect of rapamycin using the prototype cell chip: cells transfected with the regulatory elements from actin (black bars), IL-2 (grey bars), IL-4 (wide striped bars), IL-10 (diamond bars) and IFN-γ (narrow striped bars) fused to EGFP were exposed to 10 µg/mL rapamycin, which led to 10% cytotoxicity, and 1:10 or 1:100 dilution of this for 24 h in the absence (A) or presence (B) of ionomycin/PMA (1 µM/10 ng/mL). In non-induced cells (A) at the highest concentration, we found a statistically significant decrease in fluorescence compared to the control for IL-4 and IL-10. At the 1:10 dilution, IL-4 was still inhibited while actin was statistically significantly increased. In stimulated cells (B) at the highest concentration IL-2, IL-4 and IL-10 were statistically significantly different from their controls. At the 1:10 and 1:100 dilutions, actin and IL-2 showed a statistically significant increase compared to their controls. The graphs show the mean values with SEM (n=3 for IL-10 and IFN-γ, n=4 for actin and IL-4, n=5 for IL-2). Statistically significant findings with p<0.05 are noted by *, p<0.01 are noted by  and p<0.001 are noted by *. The dashed line represents the control level.

In the absence of ionomycin/PMA, we found a significant reduction of IL-4 at all tested concentrations of rapamycin (10, 1 and 0.1 µg/mL), while IL-10 showed expression only at the highest concentration. However, we also found a significant increase of actin at the two lowest concentrations (FIG. 27A). In the presence of ionomycin/PMA, at the highest concentration, rapamycin induced suppression of IL-2, IL-4 and IL-10. IFN-γ was also suppressed at the highest concentration, but statistical analysis did not confirrm the trend, due to low power of the test (FIG. 27B). At the two lowest concentrations (1 and 0.1 µg/ml) IL-2 and actin showed a significant increase. IL-10 and INF-γ showed a trend towards an increase, while IL-4 was not affected.

Pentamidine

Figure 28:
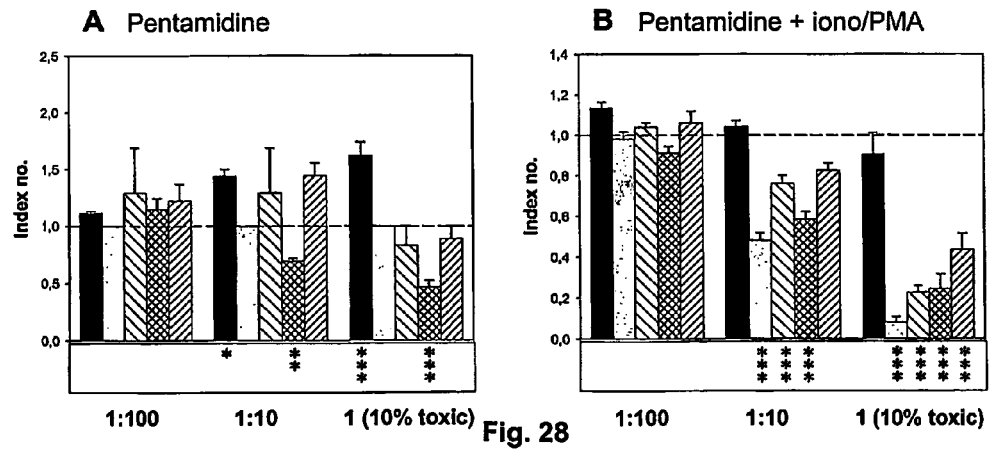

FIG. 28 presents results of testing the effect of rapamycin using the prototype cell chip: cells transfected with the regulatory elements from actin (black bars), IL-2 (grey bars), IL-4 (wide striped bars), IL-10 (diamond bars) and IFN-γ (narrow striped bars) fused to EGFP were exposed to 30 µg/mL pentamidine, which led to 10% cytotoxicity, and 1:10 or 1:100 dilutions of this for 24 h in the absence (A) or presence (B) of ionomycin/PMA (1 µM/10 ng/mL). In non-induced cells (A) at the highest concentration and 1:10 dilution, we found statistically significant differences compared to the control for actin and IL-10. In stimulated cells (B) at the highest concentration all tested cytokines were statistically significantly different from their controls. At the 1:10 dilution, IL-2, IL-4 and IL-10 were statistically significantly different from their controls. The graphs show the mean values with SEM (n=3 except n=4 for IL-2). Statistically significant findings with p<0.05 are noted by *, p<0.01 are noted by  and p<0.001 are noted by *. The dashed line represents the control level.

We found an increase in actin at the two highest concentrations of pentamidine (30 and 3 µg/mL), while IL-10 was clearly inhibited at these concentrations in the absence of ionomycin/PMA (FIG. 28A). In the presence of ionomycin/PMA, pentamidine exerted suppressive activity, since at the highest concentration all cytokines were suppressed, while at the 1:10 dilution all cytokines except INF-γ were suppressed (FIG. 28B). The expression of actin was not altered in the presence of pentamidine at any of the concentrations tested in ionomycin/PMA activated cells.

Thalidomide

We did not find thalidomide to be toxic in the LDH-assay and used 1 mM as the highest concentration. Cells exposed to thalidomide in the absence of ionomycin/PMA did not show any significant changes compared to their controls, except for actin at 1 mM (p<0.05) and even there the reduction was very small (5-10% inhibition; data not shown). The same result was apparent in the presence of ionomycin/PMA, with only actin inhibited (p<0.01). However, experiments using IL-2 and IFN-γ fused to a stabile form of EGFP in the absence of ionomycin/PMA showed a significant inhibition of 10% for IL-2 at 1 mM (p<0.05). In the presence of ionomycin/PMA both IL-2 and IFN-γ showed a dose-dependent inhibition at 1 mM (p<0.001). Thalidomide exposure did not show detectable effects at the two lowest concentrations.

Bis(tri-n-butyltin)oxide (TBTO)

Experiments using IL-2 and IFN-γ fused to a stabile form of EGFP, in the absence of ionomycin/PMA at any TBTO concentration tested (50, 5 and 0.5 µM), failed to show altered expression of both IL-2 and IFN-γ. In the presence of ionomycin/PMA, a statistically significant inhibition of IL-2 at the 1:10 dilution 10% (5 nM) was found (p<0.01).

Allergens and Autoimmunity Inducing Agents

We also wanted to examine the possible use of the "Cell Chip" panel to detect (and distinguish) different kinds of allergens. Substances representing three classes of allergens were included: (1) IgE-mediated respiratory allergy to protein allergens, exemplified by the mite allergen Der p I, (2) contact allergy to low molecular weight substances mediated by hapten-protein conjugate specific T lymphocytes, exemplified by 1-chloro-2,4-dinitrobenzene (strong allergen) and benzocaine (weak allergen), and (3) low-molecular weight chemical allergens, causing clinical symptoms similar to IgE-mediated allergy but with unknown mechanisms, exemplified by tolylene 2,4-diisocyanate where specific IgE is demonstrable only in a minority of cases and potassium tetrachloroplatinate where specific IgE is regularly demonstrable. Penicillin G was included because it is known to induce drug hypersensitivity in humans. Furthermore, an irritant (sodium dodecyl sulphate) was included, because the distinction between irritants and contact allergens is an important problem in contact allergy testing. Finally, mercuric chloride was included since it is known to induce Th1 and Th2 subsets leading to autoimmunity.

Der p-dust Mite Allergen

FIG. 29 presents results of testing the effect of Der p-mite allergen using the prototype cell chip: cells transfected with the regulatory elements from actin (black bars), IL-2 (grey bars), IL-4 (wide striped bars), IL-10 (diamond bars) and IFN-γ (narrow striped bars) fused to EGFP were exposed to 3000 SQU/mL Der p, as the highest concentration, and 1:10 or 1:100' dilution of this for 24 h in the absence (A) or presence (B) of ionomycin/PMA (1 µM/10 ng/mL). In non-induced cells (A) at the highest concentration, a statistically significant increase in fluorescence compared to the control was found for all clones except IL-10. In the presence of stimulation no alterations in fluorescence were found (B). The graphs show the mean values with SEM (n=3 for IL-10, n=4 for actin and IL-4, n=5 for IFN-γ and n=7 for IL-2). Statistically significant findings with p<0.05 are noted by *. The dashed line represents the control level.

We used a Der p solution produced for skin prick testing, and added it to cells at 3000, 300 and 30 Standard Quality U/mL. We found that Der p increased the fluorescence at the highest concentration in the absence of ionomycin/PMA for all clones except IL-10 (FIG. 29A). No significant changes were observed in the presence of ionomycin/PMA (FIG. 29B).

1-Chloro-2,4-dinitrobenzene (DNCB)

FIG. 30 presents results of testing the effect of DNCB using the prototype cell chip: cells transfected with the regulatory elements from actin (black bars), IL-2 (grey bars), IL-4 (wide striped bars), IL-10 (diamond bars) and INF-γ (narrow striped bars) fused to EGFP were exposed to 10 μM DNCB, which led to 10% cytotoxicity, and 1:10 or 1:100 dilutions of this for 24 h in the absence (A) or presence (B) of ionomycin/PMA (1 μM/10 ng/mL). In non-induced cells (A) at the highest concentration, we found a statistically significant increase in fluorescence compared to the control for actin, IL-2, IL-4 and IFN-γ. In the presence of stimulation, no statistically significant effects were found (B). The graphs show the mean values with SEM (n=3). Statistically significant findings with $p<0.05$ are noted by *, $p<0.01$ are noted by  and $p<0.001$ are noted by *. The dashed line represents the control level.

In the absence of ionomycin/PMA, at the highest concentration (10 μM) of DNCB, an increased expression was seen for all clones, except IL-10. The largest increase was observed in cells transfected with actin regulatory elements (FIG. 30A). In the presence of ionomycin/PMA, no statistically significant changes were found but the trend was towards a decrease in fluorescence at the highest concentration (FIG. 30B). For cells transfected with a stable form of EGFP, similar results were found. DNCB failed to alter expression of IL-2 or IFN-γ in the presence of ionomycin/PMA, while in the absence of these stimuli IFN-γ showed an apparently dose-dependent increase reaching statistical significance at the highest concentration ($p<0.001$).

Benzocaine

FIG. 31 presents results of testing the effect of benzocaine using the prototype cell chip: cells transfected with the regulatory elements from actin (black bars), IL-2 (grey bars), IL-4 (wide striped bars), IL-10 (diamond bars) and IFN-γ (narrow striped bars) fused to EGFP were exposed to 1 mM benzocaine as the highest concentration and 1:10 or 1:100 dilution of this for 24 h in the absence (A) or presence (B) of ionomycin/PMA (1 μM/10 ng/mL). In non-induced cells (A) at the highest concentration, a statistical increase in fluorescence compared to the control for actin is apparent. In the presence of stimulation, IL-2, IL-10 and IFN-γ are reduced at the highest concentration. IL-2 and IL-10 are also reduced at the 1:10 dilution (B). The graphs show the mean values with SEM (n=3). Statistically significant findings with $p<0.05$ are noted by *, $p<0.01$ are noted by ** and $p<0.001$ are noted by * The dashed line represents the control level.

We did not find benzocaine to be toxic in the LDH-assay and used 1 mM as the highest concentration. In the absence of ionomycin/PMA, only actin at the highest concentration was significantly increased (FIG. 31A). In the presence of ionomycin/PMA, a statistically significant inhibitory effect on IL-2 and IL-10 was seen at the two highest concentrations. IFN-γ was also inhibited, but only at the highest concentration (FIG. 31B).

3.2.4 Tolylene 2,4-diisocyanate (TDI)

FIG. 32 presents results of testing the effect of TDI using the prototype cell chip: cells transfected with the regulatory elements from actin (black bars), IL-2 (grey bars), IL-4 (wide striped bars), IL-10 (diamond bars) and IFN-γ (narrow striped bars) fused to EGFP were exposed to 500 μM TDI, which led to 10% cytotoxicity, and 1:10 or 1:100 dilutions of this for 24 h in the absence (A) or presence (B) of ionomycin/PMA (1 μM/10 ng/mL). In non-induced cells (A) at the highest concentration, we found a statistically significant increase in fluorescence compared to the control for IFN-γ. However, in stimulated cells (B) at the highest concentration IL-4 was the only one that was statistically significantly different from the control. The graphs show the mean values with SEM (n=3 for actin, IL-4 and IL-10, n=7 for IL-2 and IFN-γ). Statistically significant findings with $p<0.05$ are noted by *. The dashed line represents the control level.

Cells were exposed to TDI at 500, 50 or 5 μM. In the absence of ionomycin/PMA, only IFN-γ showed a significant induction and only at the highest concentration (FIG. 32A). However, in the presence of ionomycin/PMA a statistically significant increase was seen for IL-4 and again only at the highest concentration (FIG. 32B).

Potassium Tetrachloroplatinate—$K_2PtCl_4$

In experiments using IL-2 or IFN-γ fused to a stabile form of EGFP, cells were exposed to $K_2PtCl_4$ at 100, 10 or 1 μM. In the presence of ionomycin/PMA, exposure resulted in a dose-dependent reduction of IL-2 and IFN-γ expression. Statistically significant values were found at 100 μM, with $p<0.001$ for IL-2 and $p<0.05$ for IFN-γ. In the absence of ionomycin/PMA, exposure effects were not observed.

Penicillin G

We did not find penicillin G to be toxic. At the tested concentrations (10, 1 and 0.1 mM), penicillin G exposure failed to alter expression of either IL-2 or IFN-γ in cells transfected with IL-2 or IFN-γ fused to a stabile form of EGFP. This was found both in the presence and absence of ionomycin/PMA.

Sodium Dodecyl Sulphate (SDS)

Cells were exposed to SDS at 300, 30 or 3 μM. In cells transfected with IL-2 or IFN-γ fused to a stabile form of EGFP, in the presence of ionomycin/PMA, exposure resulted in an apparently dose-dependent reduction of IL-2 expression, with $p<0.05$ at the highest concentration. IFN-γ expression was, however, not affected. In the absence of ionomycin/PMA exposure effects were not observed.

Mercuric Chloride—$HgCl_2$

Cells transfected with IL-2 or IFN-γ fused to a stabile form of EGFP were exposed to mercuric chloride at 6, 0.6 and 0.06. μM. In the presence of ionomycin/PMA exposure resulted in an apparently dose-dependent reduction of IFN-γ expression reaching statistical significance at 6 μM ($p<0.05$). IL-2 expression was, however, not affected. In the absence of ionomycin/PMA exposure effects were not observed.

CONCLUSION

Described embodiment of in vitro immunotoxicity screening system has several important advantages. Other methods to measure cytokine expression, such as RT-PCR or ELISA are more time-consuming. Exemplified system is based on fluorescence technology, which enables concurrent viability assessment. Several methods for detection of fluorescence are available, such as Fluostar plate reader, fluorescence microscopy and flow cytometry. Although the project started off employing both flow cytometry and plate-based assays, we soon decided to use flow cytometry based on the advantages of concurrent assessment of viability, the possibility to measure fluorescence intensity per cell and possible effects on cell shape and size.

Several quality controls have been performed and are described elsewhere. Firstly, the transfected cell lines and the parent cell line have similar gene expression, both basal and in response to stimulation. Secondly, the fluorescence intensity is correlated to EGFP gene expression and parent gene expression (parent meaning e.g. the IL-4 gene in IL-4/EGFP transfected) and finally the cytokine levels correlate to the fluorescence intensities.

The tested panel consisted of only one type of cells (EL4; T-cells). An increased selection of cell types and cytokines will most probably enhance the precision and sensitivity of the "Cell Chip". One limitation with exemplified in vitro systems is the absence of antigen presenting cells. For a substance to give an effect in exemplified system, it must interact directly with the cells. A high level of protein in the medium might possibly reduce substance-cell interactions. Immunosuppressive compounds often exert their effects directly on T-cells, suggesting that the T-cell lymphoma used in the exemplified embodiment is a suitable target cell line to evaluate immunosuppressive potential. Sensitizers, however, often exert their effects on other cell types such as keratinocytes (KC) and dendritic cells (DC), suggesting that T-cells may not be a suitable target to assess sensitising potential.

This notion is supported by the fact that the exemplified embodiment that employs a T cell line was more successful in identifying immunosuppressive compounds than sensitising compounds. Cell lines of KC and DC origin should thus be included in the panel of cells used in the cell chip approach.

Most in vitro exposure models lack organ architecture, thereby diminishing the possibilities for cell-cell interaction, especially if one of the cell types is sessile. This lack of interaction often hampers cell maturation, precluding the evaluation of the sensitivity of cells to toxic compounds at different stages of development.

Both stable and destabilised EGFP have provided meaningful results. A choice between these types requires additional testing. In conclusion, exemplified embodiment of "cell chip" approach may be useful as a pre-screen to identify immunotoxicity. Cell lines derived from other origins and additional compounds, shall be tested and possibly used in other embodiments of the "cell chip" according to the invention.

The invention claimed is:

1. An expression vector comprising a plasmid comprising one of the nucleic acid sequences selected from the group consisting of: SEQ ID NO: 3 (p1-5'IL1β/d1EGFP-N1), SEQ ID NO:4 (p2-5'ILβ/d1EGFP-N1), SEQ ID NO:5 (p3-5'IL1β/d1EGFP-N1), SEQ ID NO:6 (p4-5'IL1β/d1EGFP-N1), SEQ ID NO:7 (p1-5'3'IL1β/d1EGFP-N1), SEQ ID NO:8 (p2-5'3'IL1β/d1EGFP-N1), SEQ ID NO:9 (p3-5'3'IL1β/d1EGFP-N1), SEQ ID NO: 10 (p4-5'3'IL1β/d1EGFP-N1), SEQ ID NO:11 (p1-5'IL2/EGFP-1), SEQ ID NO:12 (p1-5'IL2/d2EGFP-1), SEQ ID NO:13 (p1-5'3'IL2/d2EGFP-1), SEQ ID NO:14 (p1-3'TNFα/d1EGFP-N1), SEQ ID NO: 15 (p2-3'TNFα/EGFP-F), SEQ ID NO:16 (p3-3'TNFα/EGFP-F), SEQ ID NO:17 (p1-5'TNFα/d1EGFP-N1), SEQ ID NO:18 (p1-5'3'TNFα/d1EGFP-N1), SEQ ID NO:19 (p1-3'IL4/d1EGFP-N1), SEQ ID NO:20 (p2-3'IL4/EGFP-F), SEQ ID NO:21 (p3-3'IL4/EGFP-F), SEQ ID NO:22 (p4-3'IL4/CA-EGFP), SEQ ID NO:23 (p5-3'IL4/d1EGFP-N1), SEQ ID NO:24 (p1-5'IL4/EGFP-1), SEQ ID NO:26 (p1-5'IL4/d1EGFP-N1), SEQ ID NO:25 (p2-5'IL4/EGFP-1), SEQ ID NO:27 (p2-5'IL4/d1EGFP-N1), SEQ ID NO:30 (p1-5'3'IL4/EGFP-1), SEQ ID NO:28 (p1-5'3'IL4/d1EGFP-N1), SEQ ID NO:29 (p2-5'3'IL4/d1EGFP-N1), SEQ ID NO:31 (p1-5'INFγ/EGFP-1), SEQ ID NO:32 (p1-5'INFγ/d2EGFP-1), SEQ ID NO:33 (p1-5'3'INFγ/d2EGFP-1), SEQ ID NO:37 (p1-5'IL10/EGFP-1), SEQ ID NO:39 (p1-5'3'IL10/EGFP-1), SEQ ID NO:38 (p2-5'IL10/d2EGFP-1), and SEQ ID NO:40 (p2-5'3'IL10/d2EGFP-1).

2. The expression vector of claim 1, wherein the plasmid comprises one of the nucleic acid sequences selected from the group consisting of: SEQ ID NO:6 (p4-5'IL1β/d1EGFP-N1), SEQ ID NO:12 (p1-5'IL2/d2EGFP-1), SEQ ID NO: 18 (p1-5'3'TNFα/d1EGFP-N1), SEQ ID NO:27 (p2-5'IL4/d1EGFP-N1), SEQ ID NO:32 (p1-5'INFγ/d2EGFP-1), and SEQ ID NO: 38 (p2-5'IL10/d2EGFP-1).

3. A single-celled host comprising the expression vector according to claim 1.

4. The single-celled host according to claim 3, characterised in that it is selected from the group consisting of bacteria, yeast, mammalian cells, plant cells, insect cells, and eukaryotic cell lines.

5. The single-celled host according to claim 4, characterised in that it is an immortal mammalian cell line.

6. The single-celled host according to claim 4, characterised in that it is a cell line selected from the group consisting of T cell leukemia cells, thymoma, mast cells, macrophage-monocytes, fibroblasts and keratinocytes.

7. The single-celled host according to claim 4, characterised in that it is a cell line selected from the group consisting of EL4, BW5147.3, C57.1, J774A.1, 3T3 L1, MC/9 and HEL-30.

8. The single-celled host according to claim 4, characterised in that it is a cell line selected from the group consisting of: C/p1-5'3'TNFα-dEGFP/2 (deposited in ECACC, Accession No. 3091202), EL/p1-5'IL2-dEGFP/6 (deposited in ECACC, Accession No. 3091204), EL/p2-5'IL4-dEGFP/2 (deposited in ECACC, Accession No. 3091205), EL/p1-5'IFNγ-dEGFP/3 (deposited in ECACC, Accession No. 3091206), EL/p2-5'IL10-dEGFP/5 (deposited in ECACC, Accession No. 3091207), and J/p4-5'IL1β-dEGFP/4 (deposited in ECACC, Accession No. 3091208).

9. A method of obtaining characteristics of a tested substance, characterised in that
   a) the tested substance is put into contact with the single-celled host according to claim 3,
   b) a change in the level of expression of a green fluorescent protein caused by the tested substance is determined,
   c) the change in the level of expression described in (b) is accepted as a characteristic of the tested substance.

10. A collection of cell lines comprising the single celled host of claim 8 and a positive control cell line which constitutively expresses a green fluorescent protein.

11. The collection of cell lines of claim 10, wherein the positive control cell line is a cell line which has been transformed with a plasmid comprising one of the nucleic acid sequences selected from the group consisting of: SEQ ID NO:34 (p1-3'GAPDH/d1EGFP-N1), SEQ ID NO:35 (p2-

3'GAPDH/EGFP-F), SEQ ID NO:36 (p3-3'GAPDH/EGFP-F), SEQ ID NO:1 (pCA-EGFP-F), and SEQ ID NO:2 (pCA-d1EGFP).

12. The collection of cell lines of claim 10, wherein the positive control cell line is a cell line selected from the group consisting of C/pCA-EGFP-F/2 (deposited in ECACC, Accession No. 3091201) and EL/pCA-dEGFP/9 (deposited in ECACC, Accession No. 3091203).

13. The collection of cell lines according to claim 10, wherein the positive control cell line is a bacterial cell line, a yeast cell line, a mammalian cell line, a plant cell line, or an insect cell line.

14. A collection of cell lines according to claim 10, characterized in that the positive control cell line is an immortal mammalian cell line.

15. A collection of cell lines according to claim 10, characterized in that in the positive control cell line a gene sequence encoding the green fluorescent protein is operationally bound to a regulatory sequence selected from the group consisting of 3'UTR GAPDH, CMV promoter/enhancer, and actin promoter.

* * * * *

UNITED STATES PATENT AND TRADEMARK OFFICE
CERTIFICATE OF CORRECTION

PATENT NO.       : 8,361,711 B2                                    Page 1 of 1
APPLICATION NO.  : 10/577268
DATED            : January 29, 2013
INVENTOR(S)      : Ringerike et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1847 days.

Signed and Sealed this
First Day of September, 2015

Michelle K. Lee
*Director of the United States Patent and Trademark Office*

SEQUENCE LISTING

```
<160> NUMBER OF SEQ ID NOS: 40

<210> SEQ ID NO 1
<211> LENGTH: 4994
<212> TYPE: DNA
<213> ORGANISM: Artificial Sequence
<220> FEATURE:
<223> OTHER INFORMATION: pCA-EGFP-F

<400> SEQUENCE: 1
taatagtaat caattacggg gtcattagtt catagcccat atatggagtt ccgcgttaca      60
taacttacgg taaatggccc gcctggctga ccgcccaacg acccccgccc attgacgtca     120
ataatgacgt atgttcccat agtaacgcca tagggactt tccattgacg tcaatgggtg      180
gactatttac ggtaaactgc ccacttggca gtacatcaag tgtatcatat gccaagtacg     240
ccccctattg acgtcaatga cggtaaatgg cccgcctggc attatgccca gtacatgacc     300
ttatgggact ttcctacttg gcagtacatc tacgtattag tcatcgctat taccatgcat     360
ggtcgaggtg agccccacgt tctgcttcac tctccccatc tccccccct cccaccccc      420 aattttgtat ttatttattt tttaattatt ttgtgcagcg atggggggcgg ggggggggg     480 ggggcgcgcg ccaggcgggg cggggcgggg cgaggggcgg ggcggggcga ggcggagagg     540
tgcggcggca gccaatcaga gcggcgcgct ccgaaagttt cctttttatgg cgaggcggcg     600 gcggcggcgg ccctataaaa agcgaagcgc gcggcgggcg ggagtcgctg cgacgctgcc     660
ttcgccccgt gccccgctcc gccgccgcct cgcgccgccc gccccggctc tgactgaccg     720
cgttactccc acaggtgagc gggcgggacg gcccttctcc ttcgggctgt aattagcgct     780
accggtcgcc accatggtga gcaagggcga ggagctgttc accggggtgg tgcccatcct     840
ggtcgagctg gacggcgacg taaacggcca caagttcagc gtgtccggcg agggcgaggg     900
cgatgccacc tacggcaagc tgaccctgaa gttcatctgc accaccggca agctgcccgt     960
gccctggccc accctcgtga ccaccctgac ctacggcgtg cagtgcttca gccgctaccc    1020
cgaccacatg aagcagcacg acttcttcaa gtccgccatg cccgaaggct acgtccagga    1080
gcgcaccatc ttcttcaagg acgacggcaa ctacaagacc cgcgccgagg tgaagttcga    1140
gggcgacacc ctggtgaacc gcatcgagct gaagggcatc gacttcaagg aggacggcaa    1200
catcctgggg cacaagctgg agtacaacta caacagccac aacgtctata tcatggccga    1260
```

```
caagcagaag aacggcatca aggtgaactt caagatccgc cacaacatcg aggacggcag    1320
cgtgcagctc gccgaccact accagcagaa caccccatc ggcgacggcc ccgtgctgct     1380
gcccgacaac cactacctga gcacccagtc cgccctgagc aaagacccca acgagaagcg    1440
cgatcacatg gtcctgctgg agttcgtgac cgccgccggg atcactctcg gcatggacga   1500
gctgtacaag tccggactca gatctaagct gaaccctcct gatgagagtg ccccggctg    1560 catgagctgc aagtgtgtgc tctcctgagg atccagatct cgagctcaag cttcgaattc    1620
tgcagtcgac ggtaccgcgg gcccgggatc caccggatct agataactga tcataatcag    1680
ccataccaca tttgtagagg ttttacttgc tttaaaaaac ctcccacacc tccccctgaa    1740
cctgaaacat aaaatgaatg caattgttgt tgttaacttg tttattgcag cttataatgg    1800
ttacaaataa agcaatagca tcacaaattt cacaaataaa gcatttttt cactgcattc     1860 tagttgtggt ttgtccaaac tcatcaatgt atcttaacgc gtaaattgta agcgttaata    1920
ttttgttaaa attcgcgtta aattttgtt aaatcagctc attttttaac caataggccg     1980
aaatcggcaa aatcccttat aaatcaaaag aatagaccga gatagggttg agtgttgttc    2040
cagtttggaa caagagtcca ctattaaaga acgtggactc caacgtcaaa gggcgaaaaa    2100
ccgtctatca gggcgatggc ccactacgtg aaccatcacc ctaatcaagt tttttggggt    2160
cgaggtgccg taaagcacta atcggaacc ctaaagggag ccccgattt agagcttgac      2220 ggggaaagcc ggcgaacgtg gcgagaaagg aagggaagaa agcgaaagga gcgggcgcta    2280
gggcgctggc aagtgtagcg gtcacgctgc gcgtaaccac cacacccgcc gcgcttaatg    2340
cgccgctaca gggcgcgtca ggtggcactt ttcggggaaa tgtgcgcgga accctattt    2400 gtttatttt ctaaatacat tcaaatatgt atccgctcat gagacaataa ccctgataaa     2460
tgcttcaata atattgaaaa aggaagagtc ctgaggcgga agaaccagc tgtggaatgt     2520 gtgtcagtta gggtgtggaa agtccccagg ctccccagca ggcagaagta tgcaaagcat    2580
gcatctcaat tagtcagcaa ccaggtgtgg aaagtcccca ggctccccag caggcagaag    2640
tatgcaaagc atgcatctca attagtcagc aaccatagtc cgcccctaa ctccgcccat     2700 cccgccccta actccgccca gttccgccca ttctccgccc catggctgac taattttttt    2760
tatttatgca gaggccgagg ccgcctcggc ctctgagcta ttccagaagt agtgaggagg    2820
cttttttgga ggcctaggct tttgcaaaga tcgatcaaga acaggatga ggatcgtttc     2880 gcatgattga caagatgga ttgcacgcag gttctccggc cgcttgggtg gagaggctat     2940
tcggctatga ctgggcacaa cagacaatcg gctgctctga tgccgccgtg ttccggctgt    3000
cagcgcaggg gcgcccggtt ctttttgtca agaccgacct gtccggtgcc ctgaatgaac    3060
tgcaagacga ggcagcgcgg ctatcgtggc tggccacgac gggcgttcct tgcgcagctg    3120
tgctcgacgt tgtcactgaa gcgggaaggg actggctgct attgggcgaa gtgccggggc    3180
aggatctcct gtcatctcac cttgctcctg ccgagaaagt atccatcatg gctgatgcaa    3240
tgcggcggct gcatacgctt gatccggcta cctgcccatt cgaccaccaa gcgaaacatc    3300
gcatcgagcg agcacgtact cggatggaag ccggtcttgt cgatcaggat gatctggacg    3360
aagagcatca ggggctcgcg ccagccgaac tgttcgccag gctcaaggcg agcatgcccg    3420
acggcgagga tctcgtcgtg acccatggcg atgcctgctt gccgaatatc atggtggaaa    3480
atggccgctt ttctggattc atcgactgtg gccggctggg tgtggcggac cgctatcagg    3540
acatagcgtt ggctacccgt gatattgctg aagagcttgg cggcgaatgg gctgaccgct    3600
tcctcgtgct ttacggtatc gccgctcccg attcgcagcg catcgccttc tatcgccttc    3660
```

```
ttgacgagtt cttctgagcg ggactctggg gttcgaaatg accgaccaag cgacgcccaa    3720
cctgccatca cgagatttcg attccaccgc cgccttctat gaaaggttgg gcttcggaat    3780
cgttttccgg gacgccggct ggatgatcct ccagcgcggg gatctcatgc tggagttctt    3840
cgcccaccct aggggggaggc taactgaaac acggaaggag acaataccgg aaggaacccg    3900
cgctatgacg gcaataaaaa gacagaataa aacgcacggt gttgggtcgt tgttcataa     3960 acgcggggtt cggtcccagg gctggcactc tgtcgatacc ccaccgagac cccattgggg    4020
ccaatacgcc cgcgtttctt ccttttcccc accccacccc caagttcgg gtgaaggccc     4080 agggctcgca gccaacgtcg gggcggcagg ccctgccata gcctcaggtt actcatatat    4140
actttagatt gatttaaaac ttcatttta atttaaaagg atctaggtga agatccttt      4200 tgataatctc atgaccaaaa tcccttaacg tgagttttcg ttccactgag cgtcagaccc    4260
cgtagaaaag atcaaaggat cttcttgaga tcctttttt ctgcgcgtaa tctgctgctt     4320
gcaaacaaaa aaaccaccgc taccagcggt ggtttgtttg ccggatcaag agctaccaac    4380 tcttttttccg aaggtaactg gcttcagcag agcgcagata ccaaatactg tccttctagt    4440
gtagccgtag ttaggccacc acttcaagaa ctctgtagca ccgcctacat acctcgctct    4500
gctaatcctg ttaccagtgg ctgctgccag tggcgataag tcgtgtctta ccgggttgga    4560
ctcaagacga tagttaccgg ataaggcgca gcggtcgggc tgaacggggg gttcgtgcac    4620
acagcccagc ttggagcgaa cgacctacac cgaactgaga tacctacagc gtgagctatg    4680
agaaagcgcc acgcttcccg aagggagaaa ggcggacagg tatccggtaa gcggcagggt    4740
cggaacagga gagcgcacga gggagcttcc agggggaaac gcctggtatc tttatagtcc    4800
tgtcgggttt cgccacctct gacttgagcg tcgattttg tgatgctcgt cagggggcg     4860 gagcctatgg aaaaacgcca gcaacgcggc cttttacgg ttcctggcct tttgctggcc     4920
ttttgctcac atgttctttc ctgcgttatc ccctgattct gtggataacc gtattaccgc    4980
catgcattag ttat                                                      4994
```

<210> SEQ ID NO 2
<211> LENGTH: 5050
<212> TYPE: DNA
<213> ORGANISM: Artificial Sequence
<220> FEATURE:
<223> OTHER INFORMATION: pCA-d1EGFP

<400> SEQUENCE: 2

```
taatagtaat caattacggg gtcattagtt catagcccat atatggagtt ccgcgttaca     60
taacttacgg taaatggccc gcctggctga ccgcccaacg acccccgccc attgacgtca    120
ataatgacgt atgttcccat agtaacgcca atagggactt tccattgacg tcaatgggtg    180
gactatttac ggtaaactgc ccacttggca gtacatcaag tgtatcatat gccaagtacg    240
ccccctattg acgtcaatga cggtaaatgg cccgcctggc attatgccca gtacatgacc    300
ttatgggact ttcctacttg gcagtacatc tacgtattag tcatcgctat taccatgcat    360
ggtcgaggtg agccccacgt tctgcttcac tctccccatc tccccccccct ccccacccccc   420 aattttgtat ttatttattt tttaattatt ttgtgcagcg atggggggcgg ggggggggg   480 ggggcgcgcg ccaggcgggg cggggcgggg cgaggggcgg ggcggggcga ggcggagagg   540
tgcggcggca gccaatcaga gcggcgcgct ccgaaagttt ccttttatgg cgaggcggcg   600
gcggcggcgg ccctataaaa agcgaagcgc gcggcgggcg ggagtcgctg cgacgctgcc   660
ttcgccccgt gccccgctcc gccgccgcct cgcgccgccc gccccggctc tgactgaccg   720
```

```
cgttactccc acaggtgagc gggcgggacg gcccttctcc ttcgggctgt aattagcgct    780
accggactca gatctcgagc tcaagcttcg aattctgcag tcgacggtac cgcgggcccg    840
ggatccaccg gtcgccacca tggtgagcaa gggcgaggag ctgttcaccg gggtggtgcc    900
catcctggtc gagctggacg gcgacgtaaa cggccacaag ttcagcgtgt ccggcgaggg    960
cgagggcgat gccacctacg gcaagctgac cctgaagttc atctgcacca ccggcaagct   1020
gcccgtgccc tggcccaccc tcgtgaccac cctgacctac ggcgtgcagt gcttcagccg   1080
ctaccccgac cacatgaagc agcacgactt cttcaagtcc gccatgcccg aaggctacgt   1140
ccaggagcgc accatcttct tcaaggacga cggcaactac aagacccgcg ccgaggtgaa   1200
gttcgagggc gacaccctgg tgaaccgcat cgagctgaag ggcatcgact tcaaggagga   1260
cggcaacatc ctggggcaca agctggagta caactacaac agccacaacg tctatatcat   1320
ggccgacaag cagaagaacg gcatcaaggt gaacttcaag atccgccaca acatcgagga   1380
cggcagcgtg cagctcgccg accactacca gcagaacacc cccatcggcg acggccccgt   1440
gctgctgccc gacaaccact acctgagcac ccagtccgcc ctgagcaaag accccaacga   1500
gaagcgcgat cacatggtcc tgctggagtt cgtgaccgcc gccgggatca ctctcggcat   1560
ggacgagctg tacaagaagc ttagccatgg cttcccgccg gcggtggcgg cgcaggatga   1620
tggcacgctg cccatgtctt gtgcccagga gagcgggatg gaccgtcacc ctgcagcctg   1680
tgcttctgct aggatcaatg tgtagatgcg cggccgcgac tctagatcat aatcagccat   1740
accacatttg tagaggtttt acttgcttta aaaaacctcc cacacctccc cctgaacctg   1800
aaacataaaa tgaatgcaat tgttgttgtt aacttgttta ttgcagctta taatggttac   1860
aaataaagca atagcatcac aaatttcaca aataaagcat ttttttcact gcattctagt   1920
tgtggtttgt ccaaactcat caatgtatct taaggcgtaa attgtaagcg ttaatatttt   1980
gttaaaattc gcgttaaatt tttgttaaat cagctcattt tttaaccaat aggccgaaat   2040
cggcaaaatc ccttataaat caaaagaata gaccgagata gggttgagtg ttgttccagt   2100
ttggaacaag agtccactat taaagaacgt ggactccaac gtcaaagggc gaaaaaccgt   2160
ctatcagggc gatggcccac tacgtgaacc atcaccctaa tcaagttttt tggggtcgag   2220
gtgccgtaaa gcactaaatc ggaacctaa agggagcccc cgatttagag cttgacgggg   2280
aaagccggcg aacgtggcga aaaggaagg gaagaaagcg aaaggagcgg cgctagggc    2340
gctggcaagt gtagcggtca cgctgcgcgt aaccaccaca cccgccgcgc ttaatgcgcc   2400
gctacagggc gcgtcaggtg gcacttttcg gggaaatgtg cgcggaaccc ctatttgttt   2460
atttttctaa atacattcaa atatgtatcc gctcatgaga caataaccct gataaatgct   2520
tcaataatat tgaaaaagga agagtcctga ggcggaaaga accagctgtg aatgtgtgt    2580
cagttagggt gtggaaagtc cccaggctcc ccagcaggca gaagtatgca aagcatgcat   2640
ctcaattagt cagcaaccag gtgtggaaag tccccaggct ccccagcagg cagaagtatg   2700
caaagcatgc atctcaatta gtcagcaacc atagtcccgc ccctaactcc gcccatcccg   2760
cccctaactc cgcccagttc cgcccattct ccgccccatg ctgactaatt ttttttatt    2820
tatgcagagg ccgaggccgc ctcggcctct gagctattcc agaagtagtg aggaggcttt   2880
tttggaggcc taggcttttg caaagatcga tcaagagaca ggatgaggat cgtttcgcat   2940
gattgaacaa gatggattgc acgcaggttc tccggccgct tgggtggaga ggctattcgg   3000
ctatgactgg gcacaacaga caatcggctg ctctgatgcc gccgtgttcc ggctgtcagc   3060
gcaggggcgc ccggttcttt ttgtcaagac cgacctgtcc ggtgccctga atgaactgca   3120
```

-continued

```
agacgaggca gcgcggctat cgtggctggc cacgacgggc gttccttgcg cagctgtgct    3180
cgacgttgtc actgaagcgg aagggactg gctgctattg ggcgaagtgc cggggcagga     3240
tctcctgtca tctcaccttg ctcctgccga gaaagtatcc atcatggctg atgcaatgcg    3300
gcggctgcat acgcttgatc cggctacctg cccattcgac caccaagcga acatcgcat    3360 cgagcgagca cgtactcgga tggaagccgg tcttgtcgat caggatgatc tggacgaaga    3420
gcatcagggg ctcgcgccag ccgaactgtt cgccaggctc aaggcgagca tgcccgacgg    3480
cgaggatctc gtcgtgaccc atggcgatgc ctgcttgccg aatatcatgg tggaaaatgg    3540
ccgcttttct ggattcatcg actgtggccg gctgggtgtg gcggaccgct atcaggacat    3600
agcgttggct acccgtgata ttgctgaaga gcttggcggc gaatgggctg accgcttcct    3660
cgtgctttac ggtatcgccg ctcccgattc gcagcgcatc gccttctatc gccttcttga    3720
cgagttcttc tgagcgggac tctggggttc gaaatgaccg accaagcgac gcccaacctg    3780
ccatcacgag atttcgattc caccgccgcc ttctatgaaa ggttgggctt cggaatcgtt    3840
ttccgggacg ccggctggat gatcctccag cgcggggatc tcatgctgga gttcttcgcc    3900 cacccctaggg ggaggctaac tgaaacacgg aaggagacaa taccggaagg aacccgcgct   3960
atgacggcaa taaaagaca gaataaaacg cacggtgttg ggtcgtttgt tcataaacgc     4020
ggggttcggt cccagggctg gcactctgtc gatacccac cgagaccca ttggggccaa      4080 tacgcccgcg tttcttcctt ttccccaccc caccccccaa gttcgggtga aggcccaggg    4140
ctcgcagcca acgtcgggc ggcaggccct gccatagcct caggttactc atatatactt     4200
tagattgatt taaaacttca ttttaatt aaaaggatct aggtgaagat ccttttgat       4260 aatctcatga ccaaaatccc ttaacgtgag ttttcgttcc actgagcgtc agaccccgta    4320
gaaaagatca aggatcttc ttgagatcct ttttttctgc gcgtaatctg ctgcttgcaa     4380
acaaaaaaac caccgctacc agcggtggtt tgtttgccgg atcaagagct accaactctt    4440
tttccgaagg taactggctt cagcagagcg cagataccaa atactgtcct tctagtgtag    4500
ccgtagttag gccaccactt caagaactct gtagcaccgc ctacatacct cgctctgcta    4560
atcctgttac cagtggctgc tgccagtggc gataagtcgt gtcttaccgg gttggactca    4620
agacgatagt taccggataa ggcgcagcgg tcgggctgaa cggggggttc gtgcacacag    4680
cccagcttgg agcgaacgac ctacaccgaa ctgagatacc tacagcgtga gctatgagaa    4740
agcgccacgc ttcccgaagg gagaaaggcg gacaggtatc cggtaagcgg cagggtcgga    4800
acaggagagc gcacgaggga gcttccaggg ggaaacgcct ggtatcttta gtgcctgtc     4860 gggtttcgcc acctctgact tgagcgtcga ttttttgtgat gctcgtcagg ggggcggagc   4920
ctatggaaaa acgccagcaa cgcggccttt ttacggttcc tggccttttg ctggcctttt    4980
gctcacatgt tctttcctgc gttatcccct gattctgtgg ataaccgtat taccgccatg    5040
cattagttat                                                           5050
```

<210> SEQ ID NO 3
<211> LENGTH: 4989
<212> TYPE: DNA
<213> ORGANISM: Artificial Sequence
<220> FEATURE:
<223> OTHER INFORMATION: p1-5'IL1beta/d1EGFP-N1

<400> SEQUENCE: 3

```
taatgtgagt tagctcactc attaggcacc ccaggcttta cactttatgc ttccggctcg      60
tatgttgtgt ggaattgtga gcggataaca atttcacaca ggaaacagct atgaccatga    120
```

```
ttacgccaag cttggtaccg agctcggatc cactagtaac ggccgccagt gtgctggaat    180
tcggcttaag tgcgtgtctc tccagaagcc cctgctaaca cagttgatgg agagcacaga    240
agcaccatcc agttaccaaa ctccaactgc aaagctccct cagcttaagc acaaggaggc    300
gagagaggtg acacacttct gggtgtgcat ctacgtgcct acctttgttc cgcacatcct    360
gacttaaaat gtacagctaa cccaggaaaa cccaatattt ttaatattga caccatctgc    420
acaattgtcc aggggaaat aatgccatt tccaccacga tgacacactt gcgaatgtgt     480
cactatctgc caccccttga cttccaggga ttagaaatta tttcagggta gcaatagcct    540
cttcccctaa gaattcccat caagcttctc cccctcccc caccctttcag ttttgttgtg    600 aaatcagtta acccaaggga aaatttcaca gctcttcact tctgctttt aggactataa     660 aacaagggag gaaaacaag ttggacaaca accctgcaa gccgaattct gcagatgcta     720
ccggactcag atctcgagct caagcttcga attctgcagt cgacggtacc gcgggcccgg    780
gatccaccgg tcgccaccat ggtgagcaag ggcgaggagc tgttcaccgg ggtggtgccc    840
atcctggtcg agctggacgg cgacgtaaac ggccacaagt tcagcgtgtc cggcgagggc    900
gagggcgatg ccacctacgg caagctgacc ctgaagttca tctgcaccac cggcaagctg    960
cccgtgccct ggcccaccct cgtgaccacc ctgacctacg gcgtgcagtg cttcagccgc   1020
taccccgacc acatgaagca gcacgacttc ttcaagtccg ccatgcccga aggctacgtc   1080
caggagcgca ccatcttctt caaggacgac ggcaactaca gacccgcgc cgaggtgaag   1140 ttcgagggcg acaccctggt gaaccgcatc gagctgaagg gcatcgactt caaggaggac   1200
ggcaacatcc tggggcacaa gctggagtac aactacaaca gccacaacgt ctatatcatg   1260
gccgacaagc agaagaacgg catcaaggtg aacttcaaga tccgccacaa catcgaggac   1320
ggcagcgtgc agctcgccga ccactaccag cagaacaccc ccatcggcga cggccccgtg   1380
ctgctgcccg acaaccacta cctgagcacc cagtccgccc tgagcaaaga ccccaacgag   1440
aagcgcgatc acatggtcct gctggagttc gtgaccgccg ccgggatcac tctcggcatg   1500
gacgagctgt acaagaagct tagccatggc ttccccgccgg cggtggcggc gcaggatgat   1560
ggcacgctgc ccatgtcttg tgcccaggag agcgggatgg accgtcaccc tgcagcctgt   1620
gcttctgcta ggatcaatgt gtagatgcgc ggccgcgact ctagatcata atcagccata   1680
ccacatttgt agaggtttta cttgctttaa aaaacctccc acacctcccc ctgaacctga   1740
aacataaaat gaatgcaatt gttgttgtta acttgtttat tgcagcttat aatggttaca   1800
aataaagcaa tagcatcaca aatttcacaa ataaagcatt ttttcactg cattctagtt   1860 gtggtttgtc caaactcatc aatgtatctt aaggcgtaaa ttgtaagcgt taatattttg   1920
ttaaaattcg cgttaaattt ttgttaaatc agctcatttt ttaaccaata ggccgaaatc   1980
ggcaaaatcc cttataaatc aaaagaatag accgagatag ggttgagtgt tgttccagtt   2040
tggaacaaga gtccactatt aaagaacgtg gactccaacg tcaaagggcg aaaaaccgtc   2100
tatcagggcg atggcccact acgtgaacca tcaccctaat caagtttttt ggggtcgagg   2160
tgccgtaaag cactaaatcg gaaccctaaa gggagccccc gatttagagc ttgacgggga   2220
aagccggcga acgtggcgag aaaggaaggg aagaaagcga aggagcgggg cgctagggcg   2280
ctggcaagtg tagcggtcac gctgcgcgta accaccacac ccgccgcgct taatgcgccg   2340
ctacagggcg cgtcaggtgg cacttttcgg ggaaatgtgc gcggaacccc tatttgttta   2400
tttttctaaa tacattcaaa tatgtatccg ctcatgagac aataaccctg ataaatgctt   2460
caataatatt gaaaaaggaa gagtcctgag gcggaaagaa ccagctgtgg aatgtgtgtc   2520
```

```
agttagggtg tggaaagtcc ccaggctccc cagcaggcag aagtatgcaa agcatgcatc   2580
tcaattagtc agcaaccagg tgtggaaagt ccccaggctc cccagcaggc agaagtatgc   2640
aaagcatgca tctcaattag tcagcaacca tagtcccgcc cctaactccg cccatcccgc   2700
ccctaactcc gcccagttcc gcccattctc cgccccatgg ctgactaatt ttttttattt   2760
atgcagaggc cgaggccgcc tcggcctctg agctattcca gaagtagtga ggaggctttt   2820
ttggaggcct aggcttttgc aaagatcgat caagagacag gatgaggatc gtttcgcatg   2880
attgaacaag atggattgca cgcaggttct ccggccgctt gggtggagag gctattcggc   2940
tatgactggg cacaacagac aatcggctgc tctgatgccg ccgtgttccg gctgtcagcg   3000
caggggcgcc cggttctttt tgtcaagacc gacctgtccg gtgccctgaa tgaactgcaa   3060
gacgaggcag cgcggctatc gtggctggcc acgacgggcg ttccttgcgc agctgtgctc   3120
gacgttgtca ctgaagcggg aagggactgg ctgctattgg gcgaagtgcc ggggcaggat   3180
ctcctgtcat ctcaccttgc tcctgccgag aaagtatcca tcatggctga tgcaatgcgg   3240
cggctgcata cgcttgatcc ggctacctgc ccattcgacc accaagcgaa acatcgcatc   3300
gagcgagcac gtactcggat ggaagccggt cttgtcgatc aggatgatct ggacgaagag   3360
catcaggggc tcgcgccagc cgaactgttc gccaggctca aggcgagcat gcccgacggc   3420
gaggatctcg tcgtgaccca tggcgatgcc tgcttgccga atatcatggt ggaaaatggc   3480
cgcttttctg gattcatcga ctgtggccgg ctgggtgtgg cggaccgcta tcaggacata   3540
gcgttggcta cccgtgatat tgctgaagag cttggcggcg aatgggctga ccgcttcctc   3600
gtgctttacg gtatcgccgc tcccgattcg cagcgcatcg ccttctatcg ccttcttgac   3660
gagttcttct gagcgggact ctggggttcg aaatgaccga ccaagcgacg cccaacctgc   3720
catcacgaga tttcgattcc accgccgcct tctatgaaag gttgggcttc ggaatcgttt   3780
tccgggacgc cggctggatg atcctccagc gcggggatct catgctggag ttcttcgccc   3840
accctagggg gaggctaact gaaacacgga aggagacaat accggaagga acccgcgcta   3900
tgacggcaat aaaagacag aataaaacgc acgtgttgg gtcgtttgtt cataaacgcg   3960
gggttcggtc ccagggctgg cactctgtcg atacccccacc gagaccccat tggggccaat   4020
acgcccgcgt ttcttccttt tccccacccc accccccaag ttcgggtgaa ggcccagggc   4080
tcgcagccaa cgtcggggcg gcaggccctg ccatagcctc aggttactca tatatacttt   4140
agattgattt aaaacttcat ttttaattta aaaggatcta ggtgaagatc cttttgata   4200
atctcatgac caaaatccct taacgtgagt tttcgttcca ctgagcgtca gaccccgtag   4260
aaaagatcaa aggatcttct tgagatcctt ttttctgcg cgtaatctgc tgcttgcaaa   4320
caaaaaaacc accgctacca gcggtggttt gtttgccgga tcaagagcta ccaactcttt   4380
ttccgaaggt aactggcttc agcagagcgc agataccaaa tactgtcctt ctagtgtagc   4440
cgtagttagg ccaccacttc aagaactctg tagcaccgcc tacatacctc gctctgctaa   4500
tcctgttacc agtggctgct gccagtggcg ataagtcgtg tcttaccggg ttggactcaa   4560
gacgatagtt accggataag cgcagcggt cgggctgaac gggggggttcg tgcacacagc   4620
ccagcttgga gcgaacgacc tacaccgaac tgagatacct acagcgtgag ctatgagaaa   4680
gcgccacgct tcccgaaggg agaaaggcgg acaggtatcc ggtaagcggc agggtcggaa   4740
caggagagcg cacgagggag cttccagggg gaaacgcctg gtatctttat agtcctgtcg   4800
ggtttcgcca cctctgactt gagcgtcgat ttttgtgatg ctcgtcaggg gggcggagcc   4860
tatggaaaaa cgccagcaac gcggcctttt tacggttcct ggccttttgc tggccttttg   4920
```

```
ctcacatgtt ctttcctgcg ttatcccctg attctgtgga taaccgtatt accgccatgc    4980
attagttat                                                            4989

<210> SEQ ID NO 4
<211> LENGTH: 5654
<212> TYPE: DNA
<213> ORGANISM: Artificial Sequence
<220> FEATURE:
<223> OTHER INFORMATION: p2-5'IL1beta/d1EGFP-N1

<400> SEQUENCE: 4
cgagctcgga tccactagta acggccgcca gtgtgctgga attcgccctt aagtgcgtgt      60
ctctccagaa gcccctgcta acacagttga tggagagcac agaagcacca tccagttacc     120
aaactccaac tgcaaagctc cctcagctta agcacaagga ggcgagagag gtgacacact     180
tctgggtgtg catctacgtg cctacctttg ttccgcacat cctgacttaa aatgtacagc     240
taacccagga aaacccaata ttttttaatat tgacaccatc tgcacaattg tccaggggga     300
aataatgccc atttccacca cgatgacaca cttgcgaatg tgtcactatc tgccacccct     360
tgacttccag ggattagaaa ttatttcagg gtagcaatag cctcttcccc taagaattcc     420
catcaagctt ctccccccctc ccccacccctt cagttttgtt gtgaaatcag ttaacccaag     480
ggaaaatttc acagctcttc acttctgctt tttaggacta taaaacaagg gagggaaaac     540
aagttggaca acaaaccctg cagtggttcg aggcctaata ggctcatctg ggatcctctc     600
cagccaagct tccttgtgca agtaagtctc tctctctctc tgtctctctc tctctctgtc     660
tctctctatc tctctctctc tctctgtctc tgtctgtctc tctctctgtc     720
tctgtctgtc tatctctctc tctctctgtc tgtctctgtc tctctctgtc tgtctctctc     780
tgtctctctg tctctctctc tgtctctctc tgtctctctc tctctctctc tttccccccc     840
ccccactgat ggactttggg cttttttattt ataaaaagta gctgtacctc catggttttgt     900 gaagtactct ggaaatgagt actgtctgta tagccgctga catctaaaag gcagctcctg     960
tcttgtagga agcttctttt attagggttt ggctctgctg ttgcttcctt ccagagcatc    1020
ttcctaatgc tgttccccat gttgtagtga cccccacac accctaaaat tattttcatt    1080
gctacttcat aactataatt ttgctactgt tatgaagtgt aaatatctgt gttatccaat    1140
ggtcttaggt gaccccctgtg aaagggccac ttgactccaa aagggccact ggtctagacc    1200
tatacaacgg ctcctccgtt ccttcattcc tcagagacca gtttagcatg cctgccctga    1260
actagagcta agagaaacac atatgaagga cgccctcgg ggagctaacg ctggatgccc    1320
acccactttc tttcttcaca caggtgtctg aagcagctat ggcaactgtt aagggcgaat    1380
tctgcagatg ggatccaccg gtcgccacca tggtgagcaa gggcgaggag ctgttcaccg    1440
ggtggtgccc catcctggtc gagctggacg gcgacgtaaa cggccacaag ttcagcgtgt    1500
ccggcgaggg cgagggcgat gccacctacg gcaagctgac cctgaagttc atctgcacca    1560
ccggcaagct gcccgtgccc tggcccaccc tcgtgaccac cctgacctac ggcgtgcagt    1620
gcttcagccg ctaccccgac cacatgaagc agcacgactt cttcaagtcc gccatgcccg    1680
aaggctacgt ccaggagcgc accatcttct tcaaggacga cggcaactac aagacccgcg    1740
ccgaggtgaa gttcgagggc gacacccctgg tgaaccgcat cgagctgaag ggcatcgact    1800
tcaaggagga cggcaacatc ctggggcaca agctggagta caactacaac agccacaacg    1860
tctatatcat ggccgacaag cagaagaacg gcatcaaggt gaacttcaag atccgccaca    1920
acatcgagga cggcagcgtg cagctcgccg ccactaccac gcagaacacc cccatcggcg    1980
```

```
acggccccgt gctgctgccc gacaaccact acctgagcac ccagtccgcc ctgagcaaag    2040 acccaacga gaagcgcgat cacatggtcc tgctggagtt cgtgaccgcc gccgggatca     2100
ctctcggcat ggacgagctg tacaagaagc ttagccatgg cttcccgccg gcggtggcgg    2160
cgcaggatga tggcacgctg cccatgtctt gtgcccagga gagcgggatg gaccgtcacc    2220
ctgcagcctg tgcttctgct aggatcaatg tgtagatgcg cggccgcgac tctagatcat    2280
aatcagccat accacatttg tagaggtttt acttgcttta aaaaacctcc cacacctccc    2340
cctgaacctg aaacataaaa tgaatgcaat tgttgttgtt aacttgttta ttgcagctta    2400
taatggttac aaataaagca atagcatcac aaatttcaca aataaagcat tttttttcact   2460 gcattctagt tgtggtttgt ccaaactcat caatgtatct taaggcgtaa attgtaagcg    2520
ttaatatttt gttaaaattc gcgttaaatt tttgttaaat cagctcattt tttaaccaat    2580
aggccgaaat cggcaaaatc ccttataaat caaaagaata gaccgagata gggttgagtg    2640
ttgttccagt ttggaacaag agtccactat taaagaacgt ggactccaac gtcaaagggc    2700
gaaaaaccgt ctatcagggc gatggcccac tacgtgaacc atcaccctaa tcaagttttt    2760
tggggtcgag gtgccgtaaa gcactaaatc ggaaccctaa agggagcccc cgatttagag    2820
cttgacgggg aaagccggcg aacgtggcga gaaaggaagg gaagaaagcg aaaggagcgg    2880
gcgctagggc gctggcaagt gtagcggtca cgctgcgcgt aaccaccaca cccgccgcgc    2940
ttaatgcgcc gctacagggc gcgtcaggtg gcacttttcg gggaaatgtg cgcggaaccc    3000
ctatttgttt attttttctaa atacattcaa atatgtatcc gctcatgaga caataaccct    3060
gataaatgct tcaataatat tgaaaaagga agagtcctga ggcggaaaga accagctgtg    3120
gaatgtgtgt cagttagggt gtggaaagtc cccaggctcc ccagcaggca gaagtatgca    3180
aagcatgcat ctcaattagt cagcaaccag gtgtggaaag tccccaggct ccccagcagg    3240
cagaagtatg caaagcatgc atctcaatta gtcagcaacc atagtcccgc ccctaactcc    3300
gcccatcccg cccctaactc cgcccagttc cgcccattct ccgccccatg ctgactaat     3360 ttttttttatt tatgcagagg ccgaggccgc ctcggcctct gagctattcc agaagtagtg    3420
aggaggcttt tttggaggcc taggcttttg caaagatcga tcaagagaca ggatgaggat    3480
cgtttcgcat gattgaacaa gatggattgc acgcaggttc tccggccgct tgggtggaga    3540
ggctattcgg ctatgactgg gcacaacaga caatcggctg ctctgatgcc gccgtgttcc    3600
ggctgtcagc gcaggggcgc ccggttcttt ttgtcaagac cgacctgtcc ggtgccctga    3660
atgaactgca agacgaggca gcgcggctat cgtggctggc cacgacgggc gttccttgcg    3720
cagctgtgct cgacgttgtc actgaagcgg gaagggactg gctgctattg ggcgaagtgc    3780
cggggcagga tctcctgtca tctcaccttg ctcctgccga gaaagtatcc atcatggctg    3840
atgcaatgcg gcggctgcat acgcttgatc cggctacctg cccattcgac caccaagcga    3900
aacatcgcat cgagcgagca cgtactcgga tggaagccgg tcttgtcgat caggatgatc    3960
tggacgaaga gcatcagggg ctcgcgccag ccgaactgtt cgccaggctc aaggcgagca    4020
tgcccgacgc cgaggatctc gtcgtgaccc atggcgatgc ctgcttgccg aatatcatgg    4080
tggaaaatgg ccgcttttct ggattcatcg actgtggccg gctgggtgtg gcggaccgct    4140
atcaggacat agcgttggct acccgtgata ttgctgaaga gcttggcggc gaatgggctg    4200
accgcttcct cgtgctttac ggtatcgccg ctcccgattc gcagcgcatc gccttctatc    4260
gccttcttga cgagttcttc tgagcgggac tctggggttc gaaatgaccg accaagcgac    4320
gcccaacctg ccatcacgag atttcgattc caccgccgcc ttctatgaaa ggttgggctt    4380
```

-continued

| | |
|---|---|
| cggaatcgtt ttccgggacg ccggctggat gatcctccag cgcggggatc tcatgctgga | 4440 |
| gttcttcgcc caccctaggg ggaggctaac tgaaacacgg aaggagacaa taccggaagg | 4500 |
| aacccgcgct atgacggcaa taaaaagaca gaataaaacg cacggtgttg ggtcgtttgt | 4560 |
| tcataaacgc ggggttcggt cccagggctg cactctgtc gatacccac cgagacccca | 4620 |
| ttggggccaa tacgcccgcg tttcttcctt ttccccaccc cacccccaa gttcgggtga | 4680 |
| aggcccaggg ctcgcagcca acgtcggggc ggcaggccct gccatagcct caggttactc | 4740 |
| atatatactt tagattgatt taaaacttca ttttttaattt aaaaggatct aggtgaagat | 4800 |
| ccttttttgat aatctcatga ccaaaatccc ttaacgtgag ttttcgttcc actgagcgtc | 4860 |
| agacccgta gaaaagatca aggatcttc ttgagatcct ttttttctgc gcgtaatctg | 4920 |
| ctgcttgcaa acaaaaaaac caccgctacc agcggtggtt tgtttgccgg atcaagagct | 4980 |
| accaactctt tttccgaagg taactggctt cagcagagcg cagataccaa atactgtcct | 5040 |
| tctagtgtag ccgtagttag gccaccactt caagaactct gtagcaccgc ctacatacct | 5100 |
| cgctctgcta atcctgttac cagtggctgc tgccagtggc gataagtcgt gtcttaccgg | 5160 |
| gttggactca agacgatagt taccggataa ggcgcagcgg tcgggctgaa cggggggttc | 5220 |
| gtgcacacag cccagcttgg agcgaacgac ctacaccgaa ctgagatacc tacagcgtga | 5280 |
| gctatgagaa agcgccacgc ttcccgaagg gagaaaggcg gacaggtatc cggtaagcgg | 5340 |
| cagggtcgga acaggagagc gcacgaggga gcttccaggg ggaaacgcct ggtatcttta | 5400 |
| tagtcctgtc gggtttcgcc acctctgact tgagcgtcga ttttgtgat gctcgtcagg | 5460 |
| ggggcggagc ctatggaaaa acgccagcaa cgcggccttt ttacggttcc tggccttttg | 5520 |
| ctggcctttt gctcacatgt tctttcctgc gttatcccct gattctgtgg ataaccgtat | 5580 |
| taccgccatg cattagttat cgctaccgga ctcagatctc gagctcaagc ttcgaattct | 5640 |
| gcagtcgacg gtac | 5654 |

<210> SEQ ID NO 5
<211> LENGTH: 8438
<212> TYPE: DNA
<213> ORGANISM: Artificial Sequence
<220> FEATURE:
<223> OTHER INFORMATION: p3-5'IL1beta/d1EGFP-N1

<400> SEQUENCE: 5

| | |
|---|---|
| cgctaccgga ctcagatctc gagctcaagc ttcgaattct gcagtcgacg gtaccgagct | 60 |
| cggatccact agtaacggcc gccagtgtgc tggaattcgc ccttggatcc tctaagggc | 120 |
| ttgagttact tctgcagctc agcccttttgt agcacaaaca gcttgtcttt taggatttgg | 180 |
| ctggctccac tccactgctg ctgctgttct tgatggtcat cccatggtac ttgcatctcc | 240 |
| aaaatgctgg ggtcttctgc tgcaactggg ctggacttat accagtactc tcctgggctc | 300 |
| tcttcatggt gacaagcctc aacttctctg tatgacccttt tcaatcctgg ccttcagct | 360 |
| gccactgagg ctgtattgtc agtgccaaga ctcagctgct cttccatgaa ccagtgtcac | 420 |
| ctgggtggct cttccacagg accaaatttg gctgccagtg gagaaataca actttggcca | 480 |
| tctctggaaa acagcttctg tgtgctctca gaaaacactt cccagaagat tcacctcaa | 540 |
| taatgctgga cttttcttag tcactgctaa tttctcagct ccagctcacc agcactgagt | 600 |
| atctaagcaa agcaaaggtt tcattttttag tggttctgga atcttgttta tcgatgccta | 660 |
| ttcttcagcc ccagctaatg agatattatg ttatcacgga atcttaattc aatataacaa | 720 |
| atggccctga agaagtcttt aagcttccctt ctgaagcttc acaagtcagg cctccatctt | 780 |

```
tgtgttgccc tcaacgtccc tatcttccaa gttcctagga acagctcacc aagaattgac    840
cactctatgg gttttcttgt acaaagtcct tccaaaacaa tatgctcagg tctgtcacag    900
tcatgtcaca gtaaatcttg gtgccaattc attttcattt aggttactat tactataatg    960
aaactccatg atcaaagcaa cttggggagg aaaggatgta ttctgcttac atttccacat   1020
cacagtttat catcaaagga agtcaggaca ggaactcaag caaggcagga acctggaacc   1080
aggagctgat gcagcgatca tggagggatg ctgctcactg gcttgctcct catggcttgt   1140
caacctactt tcttatagaa ccctggacca ccagcccagg gatggcacca cccacaacag   1200
gctgatttct ccccaagtaa ataccaatta ataaaatttc ctacaggctt gcctacagac   1260
agatcttttg gatgtatttt gtcagttaag gctcccttct ctctgatgat tctagcttgt   1320
gtctagttga cataaaacta accaggacag aaaagatgag agggaaagaa cagacccccta  1380 aggcctgtgc taagtcgtca acttaaggaa taagacaagg tctggagaaa gtaatgagga   1440
cagtcattgc ttagctctgt tctgagcaag aggataagta aagaagatgt agaacacata   1500
catcaactgg gcctgggagc tcgtgcctgt aatctcagtc cttgggagac aaatgcagga   1560
gaattgtcat gtacttgaag ccagtctggg ctgcacagta gtcatggtta tcacagcaat   1620
agaaagtaag taaaacaggt agcaaggcac tttcagcttt gaagaaatgc ctgcctccat   1680
cttggaggaa tgagatgtca gaacagaggg aaccttacag cttaaaagtg ctgagtgagt   1740
caagagctga aaagttcccc aaaagctaga gtgcccgtca ccatcctggc tttgccgact   1800
tcctcttttg ctttgttcat ttcctttgcc aacatcatca tcagtatcgt catcactatg   1860
ccacaccccc agcataacaa tttctatagt gagttatttc ttctactcat tggggaccaa   1920
aaaggaagtg tggtctgaga gacagggttt gatatacatg ttgtgcaact tgcctgctct   1980
ataacgacaa ggggaggaaa tttggagccc aagtcacagg gccaggatga ggtttgatag   2040
aacaatagag taccgaggc attgcccagt agttccaaaa tctccctcta gaagcaaaag    2100
aatcatcaac cagatcattg cctcctccca gacaaacctc ctcccatctc ttcatctctt   2160
actcacgatt aaatggccat tcgtcttcat gcatgtgcct tcctccaaat cctcccagac   2220
aaccactcct ctcaggcatc agctcaaggg tttaggagtg ttataactag cagatggtga   2280
agaagattct gtaactagac tgagctcaag gctcctgaaa aatcatccag ggagaaggga   2340
cttggagctg acactcaggc ccctagttac ccttctctgt cccctggttt tcaccatccc   2400
tggttcaact cacatcagca gaccaaagga gtctccaata atctctgtca ggacagccca   2460
taaaatcatc agaccttcca gccctgcaca caggctctga ggaaggtgtt agtccctcca   2520
ggcatagttt gaaatgtgga ccctgtgaag gcagaacaga aaaatgaacc agatggccca   2580
gacaggacct ctggattgtc tgcagaacta gataatacat cttataagac cttagtgctg   2640
agaactgacc attgctcacc aaactcaaaa gcaactgaga ccctgaacca tcttcagatt   2700
tcaaatcaaa catatagctg gtcaaaggca ggattcttct gtttgccttc ctgaaatcga   2760
gatgctgtga accaaattag gcaaagaag gctgcctagt aagtaaacct tgtttcatag   2820
tagagccttg tctattcctc cttccaattc tgtctgtcta tttcccttca gtgctgcaga   2880
ataagctcag taaccaaaac atactaggta caaactcatc tgaatgaaca cattgccaaa   2940
ttcctactca cccgggctag ctcctactgc ctgcatccat ctgccaggca ctgtggagac   3000
ctggctctaa tggagtccac agactctctg agggctcagc aaaggagtta ggtttccact   3060
gaggattcta ctatactgta gatgtgccca agagactgta tgcagcattc atatggcctg   3120
gttgctcatt ccatccaagc aagaagagct cccctgggta ggctccctgg gctctctgag   3180
```

```
ttagcagtct agtgatgctt gatatggcca agagacttgg tctccccaga tcttatagaa   3240
acaagaattt tccaaaacaa ttttttaggc aaagactatc tcttcacttt ttaagatgga   3300
ctgtgctcat gaacaggcag atgcctcgtt caccacctttt gcactgtgca acttaattca  3360
ggctcattct gctgatcacc tagcactgat atggtttcaa catgagactg ctatggtat    3420
tataagtacc ctggcagggc aggaaagcag gagtgggtgg gtgagtgggg agcatcctc    3480
atagaggcag gggaggggga gaggataggg ggtttccgga ggggagacct ggaaaaggga   3540
taacatttga aatgtaaata aagaaaatat ccaataaaag aaaaaaataa gcaccctggc   3600
attatcagac tgcataggct tgcttccaga gttccctgac cctatgataa gtctacactg   3660
atacctgcat actgtgtgtg ccctgaccca cacaaggaag tgcgtgtctc tccagaagcc   3720
cctgctaaca cagttgatgg agagcacaga agcaccatcc agttaccaaa ctccaactgc   3780
aaagctccct cagcttaagc acaaggaggc gagagaggtg acacacttct gggtgtgcat   3840
ctacgtgcct acctttgttc cgcacatcct gacttaaaat gtacagctaa cccaggaaaa   3900
cccaatattt ttaatattga caccatctgc acaattgtcc aggggaaat aatgcccatt    3960
tccaccacga tgcacacttt gcgaatgtgt cactatctgc cacccttga cttccaggga   4020
ttagaaatta tttcagggta gcaatagcct cttcccctaa gaattcccat caagcttctc   4080
cccccctcccc caccctttcag ttttgttgtg aaatcagtta acccaaggga aaatttcaca  4140
gctcttcact tctgcttttt aggactataa acaagggag ggaaaacaag ttggacaaca    4200
aaccctgcaa gggcgaattc tgcagatggg atccaccggt cgccaccatg gtgagcaagg   4260
gcgaggagct gttcaccggg gtggtgccca tcctggtcga gctggacggc gacgtaaacg   4320
gccacaagtt cagcgtgtcc ggcgagggcg agggcgatgc cacctacggc aagctgaccc   4380
tgaagttcat ctgcaccacc ggcaagctgc ccgtgccctg gcccaccctc gtgaccaccc   4440
tgacctacgg cgtgcagtgc ttcagccgct accccgacca catgaagcag cacgacttct   4500
tcaagtccgc catgcccgaa ggctacgtcc aggagcgcac catcttcttc aaggacgacg   4560
gcaactacaa gacccgcgcc gaggtgaagt tcgagggcga cacccttggtg aaccgcatcg  4620
agctgaaggg catcgacttc aaggaggacg gcaacatcct ggggcacaag ctggagtaca   4680
actacaacag ccacaacgtc tatatcatgg ccgacaagca gaagaacggc atcaaggtga   4740
acttcaagat ccgccacaac atcgaggacg gcagcgtgca gctcgccgac cactaccagc   4800
agaacacccc catcggcgac ggccccgtgc tgctgcccga caaccactac ctgagcaccc   4860
agtccgccct gagcaaagac cccaacgaga gcgcgatca catggtcctg ctggagttcg   4920
tgaccgccgc cgggatcact ctcggcatgg acgagctgta caagaagctt agccatggct   4980
tcccgccggc ggtggcggcg caggatgatg cacgctgcc catgtcttgt gcccaggaga   5040
gcgggatgga ccgtcaccct gcagcctgtg cttctgctag gatcaatgtg tagatgcgcg   5100
gccgcgactc tagatcataa tcagccatac cacatttgta gaggttttac ttgctttaaa   5160
aaacctccca cacctccccc tgaacctgaa acataaaatg aatgcaattg ttgttgttaa   5220
cttgtttatt gcagcttata atggttacaa ataaagcaat agcatcacaa atttcacaaa   5280
taaagcatt ttttcactgc attctagttg tggtttgtcc aaactcatca atgtatctta    5340
aggcgtaaat tgtaagcgtt aatattttgt taaaattcgc gttaaatttt tgttaaatca   5400
gctcattttt taaccaatag gccgaaatcg gcaaaatccc ttataaatca aagaatagaa   5460
ccgagatagg gttgagtgtt gttccagttt ggaacaagag tccactatta agaacgtgg    5520
actccaacgt caaagggcga aaaccgtct atcagggcga tggcccacta cgtgaaccat   5580
```

```
caccctaatc aagttttttg gggtcgaggt gccgtaaagc actaaatcgg aaccctaaag   5640
ggagcccccg atttagagct tgacgggaa  agccggcgaa cgtggcgaga aaggaaggga   5700
agaaagcgaa aggagcgggc gctagggcgc tggcaagtgt agcggtcacg ctgcgcgtaa   5760
ccaccacacc cgccgcgctt aatgcgccgc tacagggcgc gtcaggtggc acttttcggg   5820
gaaatgtgcg cggaacccct atttgtttat ttttctaaat acattcaaat atgtatccgc   5880
tcatgagaca ataaccctga taaatgcttc aataatattg aaaaggaag  agtcctgagg   5940
cggaaagaac cagctgtgga atgtgtgtca gttagggtgt ggaaagtccc caggctcccc   6000
agcaggcaga agtatgcaaa gcatgcatct caattagtca gcaaccaggt gtggaaagtc   6060
cccaggctcc ccagcaggca gaagtatgca aagcatgcat ctcaattagt cagcaaccat   6120
agtcccgccc ctaactccgc ccatcccgcc cctaactccg cccagttccg cccattctcc   6180
gccccatggc tgactaattt ttttattta  tgcagaggcc gaggccgcct cggcctctga   6240
gctattccag aagtagtgag gaggcttttt tggaggccta ggcttttgca agatcgatc    6300
aagagacagg atgaggatcg tttcgcatga ttgaacaaga tggattgcac gcaggttctc   6360
cggccgcttg ggtggagagg ctattcggct atgactgggc acaacagaca atcggctgct   6420
ctgatgccgc cgtgttccgg ctgtcagcgc agggcgcc   ggttcttttt gtcaagaccg   6480
acctgtccgg tgccctgaat gaactgcaag acgaggcagc gcggctatcg tggctggcca   6540
cgacgggcgt tccttgcgca gctgtgctcg acgttgtcac tgaagcggga agggactggc   6600
tgctattggg cgaagtgccg gggcaggatc tcctgtcatc tcaccttgct cctgccgaga   6660
aagtatccat catggctgat gcaatgcggc ggctgcatac gcttgatccg gctacctgcc   6720
cattcgacca ccaagcgaaa catcgcatcg agcgagcacg tactcggatg aagccggtc    6780
ttgtcgatca ggatgatctg gacgaagagc atcaggggct cgcgccagcc gaactgttcg   6840
ccaggctcaa ggcgagcatg cccgacgcg  aggatctcgt cgtgacccat ggcgatgcct   6900
gcttgccgaa tatcatggtg gaaaatggcc gcttttctgg attcatcgac tgtggccggc   6960
tgggtgtggc ggaccgctat caggacatag cgttggctac ccgtgatatt gctgaagagc   7020
ttggcggcga atgggctgac cgcttcctcg tgctttacgg tatcgccgct cccgattcgc   7080
agcgcatcgc cttctatcgc cttcttgacg agttcttctg agcgggactc tggggttcga   7140
aatgaccgac caagcgacgc ccaacctgcc atcacgagat ttcgattcca ccgccgcctt   7200
ctatgaaagg ttgggcttcg gaatcgtttt ccgggacgcc ggctggatga tcctccagcg   7260
cggggatctc atgctggagt tcttcgccca ccctaggggg aggctaactg aaacacggaa   7320
ggagacaata ccggaaggaa cccgcgctat gacggcaata aaaagacaga ataaaacgca   7380
cggtgttggg tcgtttgttc ataaacgcgg ggttcggtcc cagggctggc actctgtcga   7440
taccccaccg agacccccatt ggggccaata cgcccgcgtt tcttcctttt ccccacccca   7500
cccccaagt tcgggtgaag gcccaggct cgcagccaac gtcggggcgg caggccctgc    7560
catagcctca ggttactcat atatacttta gattgattta aaacttcatt tttaatttaa    7620
aaggatctag gtgaagatcc ttttttgataa tctcatgacc aaaatccctt aacgtgagtt   7680
ttcgttccac tgagcgtcag accccgtaga aaagatcaaa ggatcttctt gagatccttt   7740
ttttctgcgc gtaatctgct gcttgcaaac aaaaaaacca ccgctaccag cggtggtttg   7800
tttgccggat caagagctac caactctttt tccgaaggta actggcttca gcagagcgca   7860
gataccaaat actgtccttc tagtgtagcc gtagttaggc caccacttca agaactctgt   7920
agcaccgcct acatacctcg ctctgctaat cctgttacca gtggctgctg ccagtggcga   7980
```

-continued

| | |
|---|---|
| taagtcgtgt cttaccgggt tggactcaag acgatagtta ccggataagg cgcagcggtc | 8040 |
| gggctgaacg gggggttcgt gcacacagcc cagcttggag cgaacgacct acaccgaact | 8100 |
| gagataccta cagcgtgagc tatgagaaag cgccacgctt cccgaaggga gaaaggcgga | 8160 |
| caggtatccg gtaagcggca gggtcggaac aggagagcgc acgagggagc ttccaggggg | 8220 |
| aaacgcctgg tatctttata gtcctgtcgg gtttcgccac ctctgacttg agcgtcgatt | 8280 |
| tttgtgatgc tcgtcagggg gcggagcct atggaaaaac gccagcaacg cggcctttt | 8340 |
| acggttcctg gccttttgct ggccttttgc tcacatgttc tttcctgcgt tatcccctga | 8400 |
| ttctgtggat aaccgtatta ccgccatgca ttagttat | 8438 |

<210> SEQ ID NO 6
<211> LENGTH: 9247
<212> TYPE: DNA
<213> ORGANISM: Artificial Sequence
<220> FEATURE:
<223> OTHER INFORMATION: p4-5'IL1beta/d1EGFP-N1

<400> SEQUENCE: 6

| | |
|---|---|
| cgctaccgga ctcagatctc gagctcaagc ttcgaattct gcagtcgacg gtaccgagct | 60 |
| cggatccact agtaacggcc gccagtgtgc tggaattcgc ccttggatcc tctaaggggc | 120 |
| ttgagttact tctgcagctc agccctttgt agcacaaaca gcttgtcttt taggatttgg | 180 |
| ctggctccac tccactgctg ctgctgttct tgatggtcat cccatggtac ttgcatctcc | 240 |
| aaaatgctgg ggtcttctgc tgcaactggg ctggacttat accagtactc tcctgggctc | 300 |
| tcttcatggt gacaagcctc aacttctctg tatgacccctt tcaatcctgg gccttcagct | 360 |
| gccactgagg ctgtattgtc agtgccaaga ctcagctgct cttccatgaa ccagtgtcac | 420 |
| ctgggtggct cttccacagg accaaatttg gctgccagtg agaaatacaa ctttggcca | 480 |
| tctctggaaa acagcttctg tgtgctctca gaaaacactt cccagaagat ttcacctcaa | 540 |
| taatgctgga cttttcttag tcactgctaa tttctcagct ccagctcacc agcactgagt | 600 |
| atctaagcaa agcaaaggtt tcatttttag tggttctgga atcttgttta tcgatgccta | 660 |
| ttcttcagcc ccagctaatg agatattatg ttatcacgga atcttaattc aatataacaa | 720 |
| atggccctga agaagtcttt aagcttcctt ctgaagcttc acaagtcagg cctccatctt | 780 |
| tgtgttgccc tcaacgtccc tatcttccaa gttcctagga acagctcacc aagaattgac | 840 |
| cactctatgg gttttcttgt acaaagtcct tccaaaacaa tatgctcagg tctgtcacag | 900 |
| tcatgtcaca gtaaatcttg gtgccaattc attttcattt aggttactat tactataatg | 960 |
| aaactccatg atcaaagcaa cttggggagg aaaggatgta ttctgcttac atttccacat | 1020 |
| cacagtttat catcaaagga agtcaggaca ggaactcaag caaggcagga acctggaacc | 1080 |
| aggagctgat gcagcgatca tggagggatg ctgctcactg gcttgctcct catggcttgt | 1140 |
| caacctactt tcttatagaa ccctggacca ccagcccagg gatggcacca cccacaacag | 1200 |
| gctgatttct ccccaagtaa ataccaatta ataaaatttc ctacaggctt gcctacagac | 1260 |
| agatcttttg gatgtatttt gtcagttaag gctcccttct ctctgatgat tctagcttgt | 1320 |
| gtctagttga cataaaacta accaggacag aaaagatgag agggaaagaa cagaccccta | 1380 |
| aggcctgtgc taagtcgtca acttaaggaa taagacaagg tctggagaaa gtaatgagga | 1440 |
| cagtcattgc ttagctctgt tctgagcaag aggataagta aagaagatgt agaacacata | 1500 |
| catcaactgg gcctgggagc tcgtgcctgt aatctcagtc cttgggagac aaatgcagga | 1560 |
| gaattgtcat gtacttgaag ccagtctggg ctgcacagta gtcatggtta tcacagcaat | 1620 |

```
agaaagtaag taaaacaggt agcaaggcac tttcagcttt gaagaaatgc ctgcctccat    1680
cttggaggaa tgagatgtca gaacagaggg aaccttacag cttaaaagtg ctgagtgagt    1740
caagagctga aaagttcccc aaaagctaga gtgcccgtca ccatcctggc tttgccgact    1800
tcctcttttg ctttgttcat ttcctttgcc aacatcatca tcagtatcgt catcactatg    1860
ccacaccccc agcataacaa tttctatagt gagttatttc ttctactcat tggggaccaa    1920
aaaggaagtg tggtctgaga cagggtttt gatatacatg ttgtgcaact tgcctgctct    1980
ataacgacaa ggggaggaaa tttggagccc aagtcacagg gccaggatga ggtttgatag    2040
aacaatagag taccgaggc attgcccagt agttccaaaa tctccctcta gaagcaaaag    2100
aatcatcaac cagatcattg cctcctccca gacaaacctc ctcccatctc ttcatctctt    2160
actcacgatt aaatggccat tcgtcttcat gcatgtgcct tcctccaaat cctcccagac    2220
aaccactcct ctcaggcatc agctcaaggg tttaggagtg ttataactag cagatggtga    2280
agaagattct gtaactagac tgagctcaag gctcctgaaa aatcatccag ggagaaggga    2340
cttggagctg acactcaggc cctagttac ccttctctgt ccctggttt tcaccatccc    2400 tggttcaact cacatcagca gaccaaagga gtctccaata atctctgtca ggacagccca    2460
taaaatcatc agaccttcca gccctgcaca caggctctga ggaaggtgtt agtccctcca    2520
ggcatagttt gaaatgtgga ccctgtgaag gcagaacaga aaaatgaacc agatggccca    2580
gacaggacct ctggattgtc tgcagaacta gataatacat cttataagac cttagtgctg    2640
agaactgacc attgctcacc aaactcaaaa gcaactgaga ccctgaacca tcttcagatt    2700
tcaaatcaaa catatagctg gtcaaaggca ggattcttct gtttgccttc ctgaaatcga    2760
gatgctgtga accaaattag gcaaaagaag gctgcctagt aagtaaacct tgtttcatag    2820
tagagccttg tctattcctc cttccaattc tgtctgtcta tttcccttca gtgctgcaga    2880
ataagctcag taaccaaaac atactaggta caaactcatc tgaatgaaca cattgccaaa    2940
ttcctactca cccgggctag ctcctactgc ctgcatccat ctgccaggca ctgtggagac    3000
ctggctctaa tggagtccac agactctctg agggctcagc aaaggagtta ggtttccact    3060
gaggattcta ctatactgta gatgtgccca agagactgta tgcagcattc atatggcctg    3120
gttgctcatt ccatccaagc aagaagagct cccctgggta ggctccctgg gctctctgag    3180
ttagcagtct agtgatgctt gatatggcca agagacttgg tctccccaga tcttatagaa    3240
acaagaattt tccaaaacaa ttttttaggc aaagactatc tcttcacttt ttaagatgga    3300
ctgtgctcat gaacaggcag atgcctcgtt caccacctt gcactgtgca acttaattca    3360
ggctcattct gctgatcacc tagcactgat atggtttcaa catgagactg gctatggtat    3420
tataagtacc ctggcagggc aggaaagcag gagtgggtgg gtgagtgggg gagcatcctc    3480
atagaggcag gggaggggga gaggataggg ggtttccgga ggggagacct ggaaaaggga    3540
taacatttga aatgtaaata aagaaaatat ccaataaaag aaaaaaataa gcaccctggc    3600
attatcagac tgcataggct tgcttccaga gttccctgac cctatgataa gtctacactg    3660
atacctgcat actgtgtgtg ccctgaccca cacaaggaag tgcgtgtctc tccagaagcc    3720
cctgctaaca cagttgatgg agagcacaga agcaccatcc agttaccaaa ctccaactgc    3780
aaagctccct cagcttaagc acaaggaggc gagagaggtg acacacttct gggtgtgcat    3840
ctacgtgcct acctttgttc cgcacatcct gacttaaaat gtacagctaa cccaggaaaa    3900
cccaatattt ttaatattga caccatctgc acaattgtcc aggggaaat aatgcccatt    3960 tccaccacga tgacacactt gcgaatgtgt cactatctgc caccccttga cttccaggga    4020
```

```
ttagaaatta tttcagggta gcaatagcct cttcccctaa gaattcccat caagcttctc    4080
cccccctccc caccccttcag ttttgttgtg aaatcagtta acccaaggga aaatttcaca    4140
gctcttcact tctgcttttt aggactataa acaagggag ggaaaacaag ttggacaaca      4200
aaccctgcag tggttcgagg cctaataggc tcatctggga tcctctccag ccaagcttcc    4260
ttgtgcaagt aagtctctct ctctctctgt ctctctctct ctctgtctct ctctatctct    4320
ctctctctgt ctctctctct ctgtctctgt ctgtctctct ctctgtctct gtctgtctat    4380
ctctctctct ctctgtctgt ctctgtctct ctctgtctgt ctctctctgt ctctctgtct    4440
ctctctctgt ctctctctgt ctctctctct ctctctcttt cccccccccc cactgatgga    4500
ctttgggctt tttatttata aaagtagct gtacctccat ggtttgtgaa gtactctgga      4560
aatgagtact gtctgtatag ccgctgacat ctaaaaggca gctcctgtct tgtaggaaag    4620
cttctttatt agggtttggc tctgctgttg cttccttcca gagcatcttc ctaatgctgt    4680
tccccatgtt gtagtgaccc cccacacacc ctaaaattat tttcattgct acttcataac    4740
tataattttg ctactgttat gaagtgtaaa tatctgtgtt atccaatggt cttaggtgac    4800
ccctgtgaaa gggccacttg actccaaaag ggccactggt ctagacctat acaacggctc    4860
ctccgttcct tcattcctca gagaccagtt tagcatgcct gccctgaact agagctaaga    4920
gaaacacata tgaaggacgc ccctcgggga gctaacgctg gatgcccacc cactttcttt    4980
cttcacacag gtgtctgaag cagctatggc aactgttaag ggcgaattct gcagatggga    5040
tccaccggtc gccaccatgg tgagcaaggg cgaggagctg ttcaccgggg tggtgcccat    5100
cctggtcgag ctggacggcg acgtaaacgg ccacaagttc agcgtgtccg gcgagggcga    5160
gggcgatgcc acctacggca agctgaccct gaagttcatc tgcaccaccg gcaagctgcc    5220
cgtgccctgg cccaccctcg tgaccaccct gacctacggc gtgcagtgct tcagccgcta    5280
ccccgaccac atgaagcagc acgacttctt caagtccgcc atgcccgaag gctacgtcca    5340
ggagcgcacc atcttcttca aggacgacgg caactacaag acccgcgccg aggtgaagtt    5400
cgagggcgac accctggtga accgcatcga gctgaagggc atcgacttca aggaggacgg    5460
caacatcctg gggcacaagc tggagtacaa ctacaacagc cacaacgtct atatcatggc    5520
cgacaagcag aagaacggca tcaaggtgaa cttcaagatc cgccacaaca tcgaggacgg    5580
cagcgtgcag ctcgccgacc actaccagca gaacaccccc atcggcgacg gccccgtgct    5640
gctgcccgac aaccactacc tgagcaccca gtccgccctg agcaaagacc ccaacgagaa    5700
gcgcgatcac atggtcctgc tggagttcgt gaccgccgcc gggatcactc tcggcatgga    5760
cgagctgtac aagaagctta gccatggctt cccgccggcg gtggcggcgc aggatgatgg    5820
cacgctgccc atgtcttgtg cccaggagag cgggatggac cgtcaccctg cagcctgtgc    5880
ttctgctagg atcaatgtgt agatgcgcgg ccgcgactct agatcataat cagccatacc    5940
acatttgtag aggttttact tgctttaaaa aacctcccac acctcccct gaacctgaaa      6000
cataaaatga atgcaattgt tgttgttaac ttgtttattg cagcttataa tggttacaaa    6060
taaagcaata gcatcacaaa tttcacaaat aaagcatttt tttcactgca ttctagttgt    6120
ggtttgtcca aactcatcaa tgtatcttaa ggcgtaaatt gtaagcgtta atattttgtt    6180
aaaattcgcg ttaaattttt gttaaatcag ctcatttttt aaccaatagg ccgaaatcgg    6240
caaaatccct tataaatcaa agaatagac cgagataggg ttgagtgttg ttccagtttg      6300
gaacaagagt ccactattaa agaacgtgga ctccaacgtc aaagggcgaa aaaccgtcta    6360
tcagggcgat ggcccactac gtgaaccatc accctaatca agttttttgg ggtcgaggtg    6420
```

```
ccgtaaagca ctaaatcgga accctaaagg gagcccccga tttagagctt gacggggaaa    6480
gccggcgaac gtggcgagaa aggaagggaa gaaagcgaaa ggagcgggcg ctagggcgct    6540
ggcaagtgta gcggtcacgc tgcgcgtaac caccacaccc gccgcgctta atgcgccgct    6600
acagggcgcg tcaggtggca cttttcgggg aaatgtgcgc ggaaccccta tttgtttatt    6660
tttctaaata cattcaaata tgtatccgct catgagacaa taaccctgat aaatgcttca    6720
ataatattga aaaggaaga gtcctgaggc ggaaagaacc agctgtggaa tgtgtgtcag    6780
ttagggtgtg aaagtcccc aggctcccca gcaggcagaa gtatgcaaag catgcatctc    6840
aattagtcag caaccaggtg tggaaagtcc ccaggctccc cagcaggcag aagtatgcaa    6900
agcatgcatc tcaattagtc agcaaccata gtcccgcccc taactccgcc catcccgccc    6960
ctaactccgc ccagttccgc ccattctccg ccccatggct gactaatttt ttttatttat    7020
gcagaggccg aggccgcctc ggcctctgag ctattccaga agtagtgagg aggcttttt    7080 ggaggcctag gcttttgcaa agatcgatca agagacagga tgaggatcgt ttcgcatgat    7140
tgaacaagat ggattgcacg caggttctcc ggccgcttgg gtggagaggc tattcggcta    7200
tgactgggca caacagacaa tcggctgctc tgatgccgcc gtgttccggc tgtcagcgca    7260
ggggcgcccg gttcttttg tcaagaccga cctgtccggt gccctgaatg aactgcaaga    7320
cgaggcagcg cggctatcgt ggctggccac gacgggcgtt ccttgcgcag ctgtgctcga    7380
cgttgtcact gaagcgggaa gggactggct gctattgggc gaagtgccgg ggcaggatct    7440
cctgtcatct caccttgctc ctgccgagaa agtatccatc atggctgatg caatgcggcg    7500
gctgcatacg cttgatccgg ctacctgccc attcgaccac caagcgaaac atcgcatcga    7560
gcgagcacgt actcggatgg aagccggtct tgtcgatcag gatgatctgg acgaagagca    7620
tcaggggctc gcgccagccg aactgttcgc caggctcaag gcgagcatgc ccgacggcga    7680
ggatctcgtc gtgacccatg gcgatgcctg cttgccgaat atcatggtgg aaaatggccg    7740
cttttctgga ttcatcgact gtggccggct gggtgtggcg accgctatc aggacatagc    7800 gttggctacc cgtgatattg ctgaagagct tggcggcgaa tgggctgacc gcttcctcgt    7860
gctttacggt atcgccgctc ccgattcgca gcgcatcgcc ttctatcgcc ttcttgacga    7920
gttcttctga gcgggactct ggggttcgaa atgaccgacc aagcgacgcc aacctgcca    7980 tcacgagatt tcgattccac cgccgccttc tatgaaaggt tgggcttcgg aatcgttttc    8040
cgggacgccg gctggatgat cctccagcgc ggggatctca tgctggagtt cttcgcccac    8100 cctagggga ggctaactga aacacggaag gagacaatac cggaaggaac ccgcgctatg    8160
acggcaataa aaagacagaa taaaacgcac ggtgttgggt cgtttgttca taaacgcggg    8220
gttcggtccc agggctggca ctctgtcgat accccaccga gaccccattg ggccaatac    8280 gcccgcgttt cttcctttc cccaccccac ccccaagtt cgggtgaagg cccagggctc    8340
gcagccaacg tcgggcggc aggccctgcc atagcctcag gttactcata tactttag    8400 attgatttaa aacttcattt ttaatttaaa aggatctagg tgaagatcct ttttgataat    8460
ctcatgacca aaatccctta acgtgagttt cgttccact gagcgtcaga ccccgtagaa    8520
aagatcaaag gatcttcttg agatcctttt tttctgcgcg taatctgctg cttgcaaaca    8580
aaaaaaccac cgctaccagc ggtggtttgt ttgccggatc aagagctacc aactctttt    8640 ccgaaggtaa ctggcttcag cagagcgcag ataccaaata ctgtccttct agtgtagccg    8700
tagttaggcc accacttcaa gaactctgta gcaccgccta catacctcgc tctgctaatc    8760
ctgttaccag tggctgctgc cagtggcgat aagtcgtgtc ttaccgggtt ggactcaaga    8820
```

```
cgatagttac cggataaggc gcagcggtcg ggctgaacgg ggggttcgtg cacacagccc    8880
agcttggagc gaacgaccta caccgaactg agatacctac agcgtgagct atgagaaagc    8940
gccacgcttc ccgaagggag aaaggcggac aggtatccgg taagcggcag ggtcggaaca    9000
ggagagcgca cgagggagct tccaggggga aacgcctggt atctttatag tcctgtcggg    9060
tttcgccacc tctgacttga gcgtcgattt ttgtgatgct cgtcaggggg cggagccta    9120 tggaaaaacg ccagcaacgc ggcctttta cggttcctgg ccttttgctg gccttttgct    9180
cacatgttct ttcctgcgtt atcccctgat tctgtggata accgtattac cgccatgcat    9240
tagttat                                                               9247

<210> SEQ ID NO 7
<211> LENGTH: 5504
<212> TYPE: DNA
<213> ORGANISM: Artificial Sequence
<220> FEATURE:
<223> OTHER INFORMATION: p1-5'3'IL1beta/d1EGFP-N1

<400> SEQUENCE: 7
ggccgccagt gtgctggaat tcggctttgt ttgtttgttt aatgaaattt atttcatact      60
catcaaagca atgtgctaat gcttcattca taaaaattct catccatatt ataggaacct     120
atttattctc agcttcaatg aaagacctca agtgcaaggc tatgaccaat tcatccccca     180
cacgttgaca gctaggttct gttctagaga gtgctgccta atgtcccctt gaatcaactt     240
aaatagatca accaatcaat aaatacataa ataaataggt aagtggttgc ccatcagagg     300
caaggaggaa acacaggctc tctttgaaca gaatgtgcca tggtttcttg tgaccctgag     360
cgacctgtct tggccgagga ctaaggagtg tcctagagat tgagctgtct gctcattcat     420
gacaagggag ctccttcaca tgccctgggg aaggcattag aaacagtcca gcccatactt     480
taaagccgaa ttctgcagat atccatcaca ctggcggccg cgactctaga tcataatcag     540
ccataccaca tttgtagagg ttttacttgc tttaaaaaac ctcccacacc tccccctgaa     600
cctgaaacat aaaatgaatg caattgttgt tgttaacttg tttattgcag cttataatgg     660
ttacaaataa agcaatagca tcacaaattt cacaaataaa gcatttttt cactgcattc     720 tagttgtggt ttgtccaaac tcatcaatgt atcttaaggc gtaaattgta agcgttaata     780
ttttgttaaa attcgcgtta aattttgtt aaatcagctc attttttaac caataggccg     840
aaatcggcaa aatcccttat aaatcaaaag aatagaccga gatagggttg agtgttgttc     900
cagtttggaa caagagtcca ctattaaaga acgtggactc caacgtcaaa gggcgaaaaa     960
ccgtctatca gggcgatggc ccactacgtg aaccatcacc ctaatcaagt ttttgggt     1020 cgaggtgccg taaagcacta atcggaaccc taaagggag cccccgattt agagcttgac    1080
ggggaaagcc ggcgaacgtg gcgagaaagg aagggaagaa agcgaaagga gcgggcgcta    1140
gggcgctggc aagtgtagcg gtcacgctgc gcgtaaccac cacacccgcc gcgcttaatg    1200
cgccgctaca gggcgcgtca ggtggcactt ttcggggaaa tgtgcgcgga accctatttt    1260
gtttattttt ctaaatacat tcaaatatgt atccgctcat gagacaataa ccctgataaa    1320
tgcttcaata atattgaaaa aggaagagtc ctgaggcgga agaaccagc tgtggaatgt    1380 gtgtcagtta gggtgtggaa agtccccagg ctccccagca ggcagaagta tgcaaagcat    1440
gcatctcaat tagtcagcaa ccaggtgtgg aaagtcccca ggctcccag caggcagaag    1500 tatgcaaagc atgcatctca attagtcagc aaccatagtc cgcccctaa ctccgcccat    1560 cccgccccta actccgccca gttccgccca ttctccgccc catggctgac taattttttt    1620
```

```
tatttatgca gaggccgagg ccgcctcggc ctctgagcta ttccagaagt agtgaggagg      1680
cttttttgga ggcctaggct tttgcaaaga tcgatcaaga gacaggatga ggatcgtttc      1740
gcatgattga acaagatgga ttgcacgcag gttctccggc cgcttgggtg gagaggctat      1800
tcggctatga ctgggcacaa cagacaatcg gctgctctga tgccgccgtg ttccggctgt      1860
cagcgcaggg gcgcccggtt cttttgtca agaccgacct gtccggtgcc ctgaatgaac       1920
tgcaagacga ggcagcgcgg ctatcgtggc tggccacgac gggcgttcct tgcgcagctg      1980
tgctcgacgt tgtcactgaa gcgggaaggg actggctgct attgggcgaa gtgccggggc      2040
aggatctcct gtcatctcac cttgctcctg ccgagaaagt atccatcatg gctgatgcaa      2100
tgcggcggct gcatacgctt gatccggcta cctgcccatt cgaccaccaa gcgaaacatc      2160
gcatcgagcg agcacgtact cggatggaag ccggtcttgt cgatcaggat gatctggacg      2220
aagagcatca ggggctcgcg ccagccgaac tgttcgccag gctcaaggcg agcatgcccg      2280
acggcgagga tctcgtcgtg acccatggcg atgcctgctt gccgaatatc atggtggaaa      2340
atggccgctt ttctggattc atcgactgtg gccggctggg tgtggcggac cgctatcagg      2400
acatagcgtt ggctacccgt gatattgctg aagagcttgg cggcgaatgg gctgaccgct      2460
tcctcgtgct ttacggtatc gccgctcccg attcgcagcg catcgccttc tatcgccttc      2520
ttgacgagtt cttctgagcg ggactctggg gttcgaaatg accgaccaag cgacgcccaa      2580
cctgccatca cgagatttcg attccaccgc cgccttctat gaaaggttgg gcttcggaat      2640
cgttttccgg gacgccggct ggatgatcct ccagcgcggg gatctcatgc tggagttctt      2700
cgcccaccct agggggaggc taactgaaac acggaaggag acaataccgg aaggaacccg      2760
cgctatgacg gcaataaaaa gacagaataa aacgcacggt gttgggtcgt ttgttcataa      2820
acgcggggtt cggtcccagg gctggcactc tgtcgatacc ccaccgagac cccattgggg      2880
ccaatacgcc cgcgtttctt ccttttcccc accccacccc caagttcgg gtgaaggccc       2940 agggctcgca gccaacgtcg gggcggcagg ccctgccata gcctcaggtt actcatatat      3000
actttagatt gatttaaaac ttcatttta atttaaaagg atctaggtga agatccttt        3060 tgataatctc atgaccaaaa tcccttaacg tgagttttcg ttccactgag cgtcagaccc      3120
cgtagaaaag atcaaaggat cttcttgaga tccttttttt ctgcgcgtaa tctgctgctt      3180
gcaaacaaaa aaaccaccgc taccagcggt ggtttgtttg ccggatcaag agctaccaac      3240 tcttttttccg aaggtaactg gcttcagcag agcgcagata ccaaatactg tccttctagt     3300
gtagccgtag ttaggccacc acttcaagaa ctctgtagca ccgcctacat acctcgctct      3360
gctaatcctg ttaccagtgg ctgctgccag tggcgataag tcgtgtctta ccgggttgga     3420
ctcaagacga tagttaccgg ataaggcgca gcggtcgggc tgaacggggg gttcgtgcac     3480
acagcccagc ttggagcgaa cgacctacac cgaactgaga tacctacagc gtgagctatg     3540
agaaagcgcc acgcttcccg aagggagaaa ggcggacagg tatccggtaa gcggcagggt    3600
cggaacagga gagcgcacga gggagcttcc agggggaaac gcctggtatc tttatagtcc    3660
tgtcgggttt cgccacctct gacttgagcg tcgatttttg tgatgctcgt caggggggcg    3720
gagcctatgg aaaaacgcca gcaacgcggc ctttttacgg ttcctggcct tttgctggcc    3780
ttttgctcac atgttctttc ctgcgttatc ccctgattct gtggataacc gtattaccgc    3840
catgcattag ttattaatgt gagttagctc actcattagg caccccaggc tttacacttt    3900
atgcttccgg ctcgtatgtt gtgtggaatt gtgagcggat aacaatttca cacaggaaac    3960
agctatgacc atgattacgc caagcttggt accgagctcg gatccactag taacggccgc    4020
```

| | |
|---|---|
| cagtgtgctg gaattcggct taagtgcgtg tctctccaga agcccctgct aacacagttg | 4080 |
| atggagagca cagaagcacc atccagttac caaactccaa ctgcaaagct ccctcagctt | 4140 |
| aagcacaagg aggcgagaga ggtgacacac ttctgggtgt gcatctacgt gcctaccttt | 4200 |
| gttccgcaca tcctgactta aaatgtacag ctaacccagg aaaacccaat attttaata | 4260 |
| ttgacaccat ctgcacaatt gtccaggggg aaataatgcc catttccacc acgatgacac | 4320 |
| acttgcgaat gtgtcactat ctgccacccc ttgacttcca gggattagaa attatttcag | 4380 |
| ggtagcaata gcctcttccc ctaagaattc ccatcaagct tctccccct ccccaccct | 4440 |
| tcagttttgt tgtgaaatca gttaacccaa gggaaaattt cacagctctt cacttctgct | 4500 |
| ttttaggact ataaaacaag ggagggaaaa caagttggac aacaaaccct gcaagccgaa | 4560 |
| ttctgcagat gctaccggac tcagatctcg agctcaagct tcgaattctg cagtcgacgg | 4620 |
| taccgcgggc ccgggatcca ccggtcgcca ccatggtgag caagggcgag gagctgttca | 4680 |
| ccggggtggt gcccatcctg gtcgagctgg acggcgacgt aaacggccac aagttcagcg | 4740 |
| tgtccggcga gggcgagggc gatgccacct acggcaagct gaccctgaag ttcatctgca | 4800 |
| ccaccggcaa gctgcccgtg ccctggccca cctcgtgac cacctgacc tacggcgtgc | 4860 |
| agtgcttcag ccgctacccc gaccacatga agcagcacga cttcttcaag tccgccatgc | 4920 |
| ccgaaggcta cgtccaggag cgcaccatct tcttcaagga cgacggcaac tacaagaccc | 4980 |
| gcgccgaggt gaagttcgag ggcgacaccc tggtgaaccg catcgagctg aagggcatcg | 5040 |
| acttcaagga ggacggcaac atcctggggc acaagctgga gtacaactac aacagccaca | 5100 |
| acgtctatat catggccgac aagcagaaga acggcatcaa ggtgaacttc aagatccgcc | 5160 |
| acaacatcga ggacggcagc gtgcagctcg ccgaccacta ccagcagaac ccccccatcg | 5220 |
| gcgacggccc cgtgctgctg cccgacaacc actacctgag cacccagtcc gccctgagca | 5280 |
| aagaccccaa cgagaagcgc gatcacatgg tcctgctgga gttcgtgacc gccgccggga | 5340 |
| tcactctcgg catggacgag ctgtacaaga agcttagcca tggcttcccg ccggcggtgg | 5400 |
| cggcgcagga tgatggcacg ctgcccatgt cttgtgccca ggagagcggg atggaccgtc | 5460 |
| accctgcagc ctgtgcttct gctaggatca atgtgtagat gcgc | 5504 |

<210> SEQ ID NO 8
<211> LENGTH: 6169
<212> TYPE: DNA
<213> ORGANISM: Artificial Sequence
<220> FEATURE:
<223> OTHER INFORMATION: p2-5'3'IL1beta/d1EGFP-N1

<400> SEQUENCE: 8

| | |
|---|---|
| ggccgccagt gtgctggaat tcggctttgt ttgtttgttt aatgaaattt atttcatact | 60 |
| catcaaagca atgtgctaat gcttcattca taaaaattct catccatatt ataggaacct | 120 |
| atttattctc agcttcaatg aaagacctca agtgcaaggc tatgaccaat tcatccccca | 180 |
| cacgttgaca gctaggttct gttctagaga gtgctgccta atgtcccctt gaatcaactt | 240 |
| aaatagatca accaatcaat aaatacataa ataataggg aagtggttgc ccatcagagg | 300 |
| caaggaggaa acacaggctc tctttgaaca gaatgtgcca tggtttcttg tgaccctgag | 360 |
| cgacctgtct tggccgagga ctaaggagtg tcctagagat tgagctgtct gctcattcat | 420 |
| gacaagggag ctccttcaca tgccctgggg aaggcattag aaacagtcca gcccatactt | 480 |
| taaagccgaa ttctgcagat atccatcaca ctggcggccg cgactctaga tcataatcag | 540 |
| ccataccaca tttgtagagg ttttacttgc tttaaaaaac ctcccacacc tccccctgaa | 600 |

```
cctgaaacat aaaatgaatg caattgttgt tgttaacttg tttattgcag cttataatgg    660
ttacaaataa agcaatagca tcacaaattt cacaaataaa gcattttttt cactgcattc    720
tagttgtggt ttgtccaaac tcatcaatgt atcttaaggc gtaaattgta agcgttaata    780
ttttgttaaa attcgcgtta aattttgtt aaatcagctc attttttaac caataggccg     840
aaatcggcaa aatcccttat aaatcaaaag aatagaccga gatagggttg agtgttgttc    900
cagtttggaa caagagtcca ctattaaaga acgtggactc caacgtcaaa gggcgaaaaa    960
ccgtctatca gggcgatggc ccactacgtg aaccatcacc ctaatcaagt ttttgggggt   1020
cgaggtgccg taaagcacta aatcggaacc ctaaagggag ccccgatttt agagcttgac   1080
ggggaaagcc ggcgaacgtg gcgagaaagg aagggaagaa agcgaaagga gcgggcgcta   1140
gggcgctggc aagtgtagcg gtcacgctgc gcgtaaccac cacacccgcc gcgcttaatg   1200
cgccgctaca gggcgcgtca ggtggcactt tcggggaaa tgtgcgcgga acccctatt    1260 gtttatttt ctaaatacat tcaaatatgt atccgctcat gagacaataa ccctgataaa    1320
tgcttcaata atattgaaaa aggaagagtc ctgaggcgga aagaaccagc tgtggaatgt   1380
gtgtcagtta gggtgtggaa agtccccagg ctccccagca ggcagaagta tgcaaagcat   1440
gcatctcaat tagtcagcaa ccaggtgtgg aaagtcccca ggctccccag caggcagaag   1500
tatgcaaagc atgcatctca attagtcagc aaccatagtc ccgcccctaa ctccgcccat   1560
cccgccccta actccgccca gttccgccca ttctccgccc catggctgac taatttttt    1620 tatttatgca gaggccgagg ccgcctcggc ctctgagcta ttccagaagt agtgaggagg   1680
cttttttgga ggcctaggct tttgcaaaga tcgatcaaga gacaggatga ggatcgtttc   1740
gcatgattga acaagatgga ttgcacgcag gttctccggc cgcttgggtg gagaggctat   1800
tcggctatga ctgggcacaa cagacaatcg gctgctctga tgccgccgtg ttccggctgt   1860
cagcgcaggg gcgcccggtt cttttgtca agaccgacct gtccggtgcc ctgaatgaac    1920
tgcaagacga ggcagcgcgg ctatcgtggc tggccacgac gggcgttcct tgcgcagctg   1980
tgctcgacgt tgtcactgaa gcgggaaggg actggctgct attgggcgaa gtgccggggc   2040
aggatctcct gtcatctcac cttgctcctg ccgagaaagt atccatcatg gctgatgcaa   2100
tgcggcggct gcatacgctt gatccggcta cctgcccatt cgaccaccaa gcgaaacatc   2160
gcatcgagcg agcacgtact cggatggaag ccggtcttgt cgatcaggat gatctggacg   2220
aagagcatca ggggctcgcg ccagccgaac tgttcgccag gctcaaggcg agcatgcccg   2280
acggcgagga tctcgtcgtg acccatggcg atgcctgctt gccgaatatc atggtggaaa   2340
atggccgctt ttctggattc atcgactgtg gccggctggg tgtggcggac cgctatcagg   2400
acatagcgtt ggctacccgt gatattgctg aagagcttgg cggcgaatgg gctgaccgct   2460
tcctcgtgct ttacggtatc gccgctcccg attcgcagcg catcgccttc tatcgccttc   2520
ttgacgagtt cttctgagcg ggactctggg gttcgaaatg accgaccaag cgacgcccaa   2580
cctgccatca cgagatttcg attccaccgc cgccttctat gaaaggttgg gcttcggaat   2640
cgttttccgg gacgccggct ggatgatcct ccagcgcggg gatctcatgc tggagttctt   2700
cgcccaccct aggggggaggc taactgaaac acggaaggag acaataccgg aaggaacccg   2760
cgctatgacg gcaataaaaa gacagaataa acgcacggt gttgggtcgt tgttcataa    2820 acgcggggtt cggtcccagg gctggcactc tgtcgatacc ccaccgagac cccattgggg   2880
ccaatacgcc cgcgtttctt cctttccccc accccacccc caagttcgg gtgaaggccc    2940 agggctcgca gccaacgtcg gggcggcagg ccctgccata gcctcaggtt actcatatat   3000
```

```
actttagatt gatttaaaac ttcatttta atttaaaagg atctaggtga agatccttt      3060
tgataatctc atgaccaaaa tcccttaacg tgagttttcg ttccactgag cgtcagaccc     3120
cgtagaaaag atcaaaggat cttcttgaga tccttttttt ctgcgcgtaa tctgctgctt     3180
gcaaacaaaa aaaccaccgc taccagcggt ggtttgtttg ccggatcaag agctaccaac     3240
tcttttccg aaggtaactg gcttcagcag agcgcagata ccaaatactg tccttctagt      3300
gtagccgtag ttaggccacc acttcaagaa ctctgtagca ccgcctacat acctcgctct     3360
gctaatcctg ttaccagtgg ctgctgccag tggcgataag tcgtgtctta ccgggttgga     3420
ctcaagacga tagttaccgg ataaggcgca gcggtcgggc tgaacggggg gttcgtgcac     3480
acagcccagc ttggagcgaa cgacctacac cgaactgaga tacctacagc gtgagctatg     3540
agaaagcgcc acgcttcccg aagggagaaa ggcggacagg tatccggtaa gcggcagggt     3600
cggaacagga gagcgcacga gggagcttcc agggggaaac gcctggtatc tttatagtcc     3660
tgtcgggttt cgccacctct gacttgagcg tcgatttttg tgatgctcgt cagggggcg      3720
gagcctatgg aaaaacgcca gcaacgcggc cttttttacgg ttcctggcct tttgctggcc    3780
ttttgctcac atgttctttc ctgcgttatc ccctgattct gtggataacc gtattaccgc     3840
catgcattag ttatcgctac cggactcaga tctcgagctc aagcttcgaa ttctgcagtc     3900
gacggtaccg agctcggatc cactagtaac ggccgccagt gtgctggaat tcgcccttaa     3960
gtgcgtgtct ctccagaagc ccctgctaac acagttgatg gagagcacag aagcaccatc     4020
cagttaccaa actccaactg caaagctccc tcagcttaag cacaaggagg cgagagaggt     4080
gacacacttc tgggtgtgca tctacgtgcc taccttttgtt ccgcacatcc tgacttaaaa    4140
tgtacagcta acccaggaaa acccaatatt tttaatattg acaccatctg cacaattgtc     4200
caggggaaa taatgcccat ttccaccacg atgacacact tgcgaatgtg tcactatctg      4260
ccaccccttg acttccaggg attagaaatt atttcagggt agcaatagcc tcttccccta    4320
agaattccca tcaagcttct ccccctccc ccacccttca gttttgttgt gaaatcagtt      4380
aacccaaggg aaaatttcac agctcttcac ttctgctttt taggactata aacaaggga     4440
gggaaaacaa gttggacaac aaaccctgca gtggttcgag gcctaatagg ctcatctggg     4500
atcctctcca gccaagcttc cttgtgcaag taagtctctc tctctctctg tctctctctc     4560
tctctgtctc tctctatctc tctctctctg tctctctctc tctgtctctg tctgtctctc     4620
tctctgtctc tgtctgtcta tctctctctc tctctgtctg tctctgtctc tctctgtctg    4680
tctctctctg tctctctgtc tctctctctg tctctctctg tctctctctc tctctctctt     4740
tccccccccc ccactgatgg actttgggct ttttatttat aaaaagtagc tgtacctcca    4800
tggtttgtga agtactctgg aaatgagtac tgtctgtata gccgctgaca tctaaaaggc     4860
agctcctgtc ttgtaggaaa gcttctttat tagggtttgg ctctgctgtt gcttccttcc    4920
agagcatctt cctaatgctg ttccccatgt tgtagtgacc cccacacac cctaaaatta     4980
ttttcattgc tacttcataa ctataatttt gctactgtta tgaagtgtaa atatctgtgt     5040
tatccaatgg tcttaggtga cccctgtgaa agggccactt gactccaaaa gggccactgg     5100
tctagaccta tacaacggct cctccgttcc ttcattcctc agagaccagt ttagcatgcc    5160
tgccctgaac tagagctaag agaaacacat atgaaggacg cccctcgggg agctaacgct     5220
ggatgcccac ccactttctt tcttcacaca ggtgtctgaa gcagctatgg caactgttaa    5280
gggcgaattc tgcagatggg atccaccggt cgccaccatg gtgagcaagg gcgaggagct     5340
gttcaccggg gtggtgccca tcctggtcga gctggacggc gacgtaaacg ccacaagtt     5400
```

| | |
|---|---|
| cagcgtgtcc ggcgagggcg agggcgatgc cacctacggc aagctgaccc tgaagttcat | 5460 |
| ctgcaccacc ggcaagctgc ccgtgccctg gcccaccctc gtgaccaccc tgacctacgg | 5520 |
| cgtgcagtgc ttcagccgct accccgacca catgaagcag cacgacttct tcaagtccgc | 5580 |
| catgcccgaa ggctacgtcc aggagcgcac catcttcttc aaggacgacg gcaactacaa | 5640 |
| gacccgcgcc gaggtgaagt tcgagggcga caccctggtg aaccgcatcg agctgaaggg | 5700 |
| catcgacttc aaggaggacg gcaacatcct ggggcacaag ctggagtaca actacaacag | 5760 |
| ccacaacgtc tatatcatgg ccgacaagca agaacggc atcaaggtga acttcaagat | 5820 |
| ccgccacaac atcgaggacg gcagcgtgca gctcgccgac cactaccagc agaacacccc | 5880 |
| catcggcgac ggccccgtgc tgctgcccga caaccactac ctgagcaccc agtccgccct | 5940 |
| gagcaaagac cccaacgaga gcgcgatca catggtcctg ctggagttcg tgaccgccgc | 6000 |
| cgggatcact ctcggcatgg acgagctgta caagaagctt agccatggct cccgccggc | 6060 |
| ggtggcggcg caggatgatg gcacgctgcc catgtcttgt gcccaggaga gcgggatgga | 6120 |
| ccgtcaccct gcagcctgtg cttctgctag gatcaatgtg tagatgcgc | 6169 |

<210> SEQ ID NO 9
<211> LENGTH: 8953
<212> TYPE: DNA
<213> ORGANISM: Artificial Sequence
<220> FEATURE:
<223> OTHER INFORMATION: p3-5'3'IL1beta/d1EGFP-N1

<400> SEQUENCE: 9

| | |
|---|---|
| ggccgccagt gtgctggaat tcggctttgt ttgtttgttt aatgaaattt atttcatact | 60 |
| catcaaagca atgtgctaat gcttcattca taaaaattct catccatatt ataggaacct | 120 |
| atttattctc agcttcaatg aaagaccctca agtgcaaggc tatgaccaat tcatccccca | 180 |
| cacgttgaca gctaggttct gttctagaga gtgctgccta atgtcccctt gaatcaactt | 240 |
| aaatagatca accaatcaat aaatacataa ataataggg agtggttgc ccatcagagg | 300 |
| caaggaggaa acacaggctc tctttgaaca gaatgtgcca tggtttcttg tgaccctgag | 360 |
| cgacctgtct tggccgagga ctaaggagtg tcctagagat tgagctgtct gctcattcat | 420 |
| gacaagggag ctccttcaca tgccctgggg aaggcattag aaacagtcca gcccatactt | 480 |
| taaagccgaa ttctgcagat atccatcaca ctggcggccg cgactctaga tcataatcag | 540 |
| ccataccaca tttgtagagg ttttacttgc tttaaaaaac ctcccacacc tccccctgaa | 600 |
| cctgaaacat aaaatgaatg caattgttgt tgttaacttg tttattgcag cttataatgg | 660 |
| ttacaaataa agcaatagca tcacaaattt cacaaataaa gcatttttt cactgcattc | 720 |
| tagttgtggt ttgtccaaac tcatcaatgt atcttaaggc gtaaattgta agcgttaata | 780 |
| ttttgttaaa attcgcgtta aattttgtt aaatcagctc atttttaac caataggccg | 840 |
| aaatcggcaa aatccctat aaatcaaaag aatagaccga gatagggttg agtgttgttc | 900 |
| cagtttggaa caagagtcca ctattaaaga acgtggactc caacgtcaaa gggcgaaaaa | 960 |
| ccgtctatca gggcgatggc ccactacgtg aaccatcacc ctaatcaagt ttttttgggt | 1020 |
| cgaggtgccg taaagcacta atcggaacc ctaagggag ccccgattt agagcttgac | 1080 |
| ggggaaagcc ggcgaacgtg gcgagaaagg aaggaagaa agcgaaagga gcgggcgcta | 1140 |
| gggcgctggc aagtgtagcg gtcacgctgc gcgtaaccac cacacccgcc gcgcttaatg | 1200 |
| cgccgctaca gggcgcgtca ggtggcactt ttcggggaaa tgtgcgcgga acccctattt | 1260 |
| gtttattttt ctaaatacat tcaaatatgt atccgctcat gagacaataa ccctgataaa | 1320 |

```
tgcttcaata atattgaaaa aggaagagtc ctgaggcgga agaaccagc tgtggaatgt    1380 gtgtcagtta gggtgtggaa agtccccagg ctccccagca ggcagaagta tgcaaagcat    1440
gcatctcaat tagtcagcaa ccaggtgtgg aaagtcccca ggctcccag caggcagaag     1500 tatgcaaagc atgcatctca attagtcagc aaccatagtc cgcccctaa ctccgcccat     1560 ccgcccccta actccgccca gttccgccca ttctccgccc catggctgac taattttttt    1620
tatttatgca gaggccgagg ccgcctcggc ctctgagcta ttccagaagt agtgaggagg    1680
cttttttgga ggcctaggct tttgcaaaga tcgatcaaga gacaggatga ggatcgtttc    1740
gcatgattga acaagatgga ttgcacgcag gttctccggc cgcttgggtg gagaggctat    1800
tcggctatga ctgggcacaa cagacaatcg gctgctctga tgccgccgtg ttccggctgt    1860
cagcgcaggg gcgcccggtt cttttgtca agaccgacct gtccggtgcc ctgaatgaac     1920
tgcaagacga ggcagcgcgg ctatcgtggc tggccacgac gggcgttcct tgcgcagctg    1980
tgctcgacgt tgtcactgaa gcgggaaggg actggctgct attgggcgaa gtgccggggc    2040
aggatctcct gtcatctcac cttgctcctg ccgagaaagt atccatcatg gctgatgcaa    2100
tgcggcggct gcatacgctt gatccggcta cctgcccatt cgaccaccaa gcgaaacatc    2160
gcatcgagcg agcacgtact cggatggaag ccggtcttgt cgatcaggat gatctggacg    2220
aagagcatca ggggctcgcg ccagccgaac tgttcgccag gctcaaggcg agcatgcccg    2280
acggcgagga tctcgtcgtg acccatggcg atgcctgctt gccgaatatc atggtggaaa    2340
atggccgctt ttctggattc atcgactgtg gccggctggg tgtggcggac cgctatcagg    2400
acatagcgtt ggctacccgt gatattgctg aagagcttgg cggcgaatgg gctgaccgct    2460
tcctcgtgct ttacggtatc gccgctcccg attcgcagcg catcgccttc tatcgccttc    2520
ttgacgagtt cttctgagcg ggactctggg gttcgaaatg accgaccaag cgacgcccaa    2580
cctgccatca cgagatttcg attccaccgc cgccttctat gaaaggttgg gcttcggaat    2640
cgttttccgg gacgccggct ggatgatcct ccagcgcggg gatctcatgc tggagttctt    2700
cgcccaccct aggggggaggc taactgaaac acggaaggag acaataccgg aaggaacccg    2760
cgctatgacg gcaataaaaa gacagaataa acgcacggt gttgggtcgt ttgttcataa     2820
acgcggggtt cggtcccagg ctggcactc tgtcgatacc ccaccgagac cccattgggg     2880
ccaatacgcc cgcgtttctt cctttccccc accccacccc caagttcgg gtgaaggccc     2940 agggctcgca gccaacgtcg gggcggcagg ccctgccata gcctcaggtt actcatatat    3000
actttagatt gatttaaaac ttcattttta atttaaaagg atctaggtga agatcctttt    3060
tgataatctc atgaccaaaa tcccttaacg tgagttttcg ttccactgag cgtcagaccc    3120
cgtagaaaag atcaaaggat cttcttgaga tcctttttt ctgcgcgtaa tctgctgctt     3180
gcaaacaaaa aaaccaccgc taccagcggt ggtttgtttg ccggatcaag agctaccaac    3240 tcttttccg aaggtaactg gcttcagcag agcgcagata ccaaatactg tccttctagt     3300
gtagccgtag ttaggccacc acttcaagaa ctctgtagca ccgcctacat acctcgctct    3360
gctaatcctg ttaccagtgg ctgctgccag tggcgataag tcgtgtctta ccgggttgga    3420
ctcaagacga tagttaccgg ataaggcgca gcggtcgggc tgaacggggg gttcgtgcac    3480
acagcccagc ttggagcgaa cgacctacac cgaactgaga tacctacagc gtgagctatg    3540
agaaagcgcc acgcttcccg aagggagaaa ggcggacagg tatccggtaa gcggcagggt    3600
cggaacagga gagcgcacga gggagcttcc agggggaaac gcctggtatc tttatagtcc    3660
tgtcgggttt cgccacctct gacttgagcg tcgatttttg tgatgctcgt cagggggggcg    3720
```

-continued

```
gagcctatgg aaaaacgcca gcaacgcggc cttttttacgg ttcctggcct tttgctggcc    3780
ttttgctcac atgttctttc ctgcgttatc ccctgattct gtggataacc gtattaccgc    3840
catgcattag ttatcgctac cggactcaga tctcgagctc aagcttcgaa ttctgcagtc    3900
gacggtaccg agctcggatc cactagtaac ggccgccagt gtgctggaat tcgcccttgg    3960
atcctctaag gggcttgagt tacttctgca gctcagccct ttgtagcaca aacagcttgt    4020
cttttaggat ttggctggct ccactccact gctgctgctg ttcttgatgg tcatcccatg    4080
gtacttgcat ctccaaaatg ctggggtctt ctgctgcaac tgggctggac ttataccagt    4140
actctcctgg gctctcttca tggtgacaag cctcaacttc tctgtatgac cctttcaatc    4200
ctgggccttc agctgccact gaggctgtat tgtcagtgcc aagactcagc tgctcttcca    4260
tgaaccagtg tcacctgggt ggctcttcca caggaccaaa tttggctgcc agtggagaaa    4320
tacaactttg gccatctctg gaaaacagct tctgtgtgct ctcagaaaac acttcccaga    4380
agatttcacc tcaataatgc tggacttttc ttagtcactg ctaatttctc agctccagct    4440
caccagcact gagtatctaa gcaaagcaaa ggtttcattt ttagtggttc tggaatcttg    4500
tttatcgatg cctattcttc agccccagct aatgagatat tatgttatca cggaatctta    4560
attcaatata acaaatggcc ctgaagaagt ctttaagctt ccttctgaag cttcacaagt    4620
caggcctcca tctttgtgtt gccctcaacg tccctatctt ccaagttcct aggaacagct    4680
caccaagaat tgaccactct atgggttttc ttgtacaaag tccttccaaa acaatatgct    4740
caggtctgtc acagtcatgt cacagtaaat cttggtgcca attcatttc atttaggtta    4800
ctattactat aatgaaactc catgatcaaa gcaacttggg gaggaaagga tgtattctgc    4860
ttacatttcc acatcacagt ttatcatcaa aggaagtcag acaggaact caagcaaggc    4920
aggaacctgg aaccaggagc tgatgcagcg atcatggagg gatgctgctc actggcttgc    4980
tcctcatggc ttgtcaacct actttcttat agaaccctgg accaccagcc cagggatggc    5040
accacccaca acaggctgat ttctccccaa gtaaatacca attaataaaa tttcctacag    5100
gcttgcctac agacagatct tttggatgta ttttgtcagt taaggctccc ttctctctga    5160
tgattctagc ttgtgtctag ttgacataaa actaaccagg acagaaaaga tgagagggaa    5220
agaacagacc cctaaggcct gtgctaagtc gtcaacttaa ggaataagac aaggtctgga    5280
gaaagtaatg aggacagtca ttgcttagct ctgttctgag caagaggata agtaaagaag    5340
atgtagaaca catacatcaa ctgggcctgg gagctcgtgc ctgtaatctc agtccttggg    5400
agacaaatgc aggagaattg tcatgtactt gaagccagtc tgggctgcac agtagtcatg    5460
gttatcacag caatagaaag taagtaaaac aggtagcaag gcactttcag ctttgaagaa    5520
atgcctgcct ccatcttgga ggaatgagat gtcagaacag agggaacctt acagcttaaa    5580
agtgctgagt gagtcaagag ctgaaaagtt ccccaaaagc tagagtgccc gtcaccatcc    5640
tggctttgcc gacttcctct tttgctttgt tcatttcctt tgccaacatc atcatcagta    5700
tcgtcatcac tatgccacac ccccagcata acaatttcta tagtgagtta tttcttctac    5760
tcattgggga ccaaaaagga agtgtggtct gagagacagg gtttgatata catgttgtgc    5820
aacttgcctg ctctataacg acaaggggag gaaatttgga gcccaagtca cagggccagg    5880
atgaggtttg ataggaacaat agagtaccag aggcattgcc cagtagttcc aaaatctccc    5940
tctagaagca aaagaatcat caaccagatc attgcctcct cccagacaaa cctcctccca    6000
tctcttcatc tcttactcac gattaaatgg ccattcgtct tcatgcatgt gccttcctcc    6060
aaatcctccc agacaaccac tcctctcagg catcagctca agggtttagg agtgttataa    6120
```

```
ctagcagatg gtgaagaaga ttctgtaact agactgagct caaggctcct gaaaaatcat    6180
ccagggagaa gggacttgga gctgacactc aggcccctag ttacccttct ctgtcccctg    6240
gttttcacca tccctggttc aactcacatc agcagaccaa aggagtctcc aataatctct    6300
gtcaggacag cccataaaat catcagacct tccagccctg cacacaggct ctgaggaagg    6360
tgttagtccc tccaggcata gtttgaaatg tggaccctgt gaaggcagaa cagaaaaatg    6420
aaccagatgg cccagacagg acctctggat tgtctgcaga actagataat acatcttata    6480
agaccttagt gctgagaact gaccattgct caccaaactc aaaagcaact gagaccctga    6540
accatcttca gatttcaaat caaacatata gctggtcaaa ggcaggattc ttctgtttgc    6600
cttcctgaaa tcgagatgct gtgaaccaaa ttaggcaaaa gaaggctgcc tagtaagtaa    6660
accttgtttc atagtagagc cttgtctatt cctccttcca attctgtctg tctatttccc    6720
ttcagtgctg cagaataagc tcagtaacca aaacatacta ggtacaaact catctgaatg    6780
aacacattgc caaattccta ctcacccggg ctagctccta ctgcctgcat ccatctgcca    6840
ggcactgtgg agacctggct ctaatggagt ccacagactc tctgagggct cagcaaagga    6900
gttaggtttc cactgaggat tctactatac tgtagatgtg cccaagagac tgtatgcagc    6960
attcatatgg cctggttgct cattccatcc aagcaagaag agctcccctg ggtaggctcc    7020
ctgggctctc tgagttagca gtctagtgat gcttgatatg gccaagagac ttggtctccc    7080
cagatcttat agaaacaaga atttttccaaa acaattttt aggcaaagac tatctcttca    7140
ctttttaaga tggactgtgc tcatgaacag gcagatgcct cgttccacac ctttgcactg    7200
tgcaacttaa ttcaggctca ttctgctgat cacctagcac tgatatggtt tcaacatgag    7260
actggctatg gtattataag taccctggca gggcaggaaa gcaggagtgg gtgggtgagt    7320
gggggagcat cctcatagag gcaggggagg gggagaggat aggggttttc cggaggggag    7380
acctggaaaa gggataacat ttgaaatgta aataaagaaa atatccaata aaagaaaaaa    7440
ataagcaccc tggcattatc agactgcata ggcttgcttc cagagttccc tgaccctatg    7500
ataagtctac actgatacct gcatactgtg tgtgccctga cccacacaag gaagtgcgtg    7560
tctctccaga agcccctgct aacacagttg atggagagca cagaagcacc atccagttac    7620
caaactccaa ctgcaaagct ccctcagctt aagcacaagg aggcgagaga ggtgacacac    7680
ttctgggtgt gcatctacgt gcctaccttt gttccgcaca tcctgactta aaatgtacag    7740
ctaacccagg aaaacccaat attttaata ttgacaccat ctgcacaatt gtccagggg     7800 aaataatgcc catttccacc acgatgacac acttgcgaat gtgtcactat ctgccacccc    7860
ttgacttcca gggattagaa attatttcag ggtagcaata gcctcttccc ctaagaattc    7920
ccatcaagct tctccccct ccccacccct tcagttttgt tgtgaaatca gttaacccaa     7980
gggaaaattt cacagctctt cacttctgct ttttaggact ataaacaag ggagggaaaa     8040 caagttggac aacaaaccct gcaagggcga attctgcaga tgggatccac cggtcgccac    8100
catggtgagc aagggcgagg agctgttcac cggggtggtg cccatcctgg tcgagctgga    8160
cggcgacgta aacggccaca gttcagcgt gtccggcgag ggcgagggcg atgccaccta     8220
cggcaagctg accctgaagt tcatctgcac caccggcaag ctgcccgtgc cctggcccac    8280
cctcgtgacc accctgacct acggcgtgca gtgcttcagc cgctacccc accacatgaa     8340 gcagcacgac ttcttcaagt ccgccatgcc cgaaggctac gtccaggagc gcaccatctt    8400
cttcaaggac gacggcaact acaagacccg cgccgaggtg aagttcgagg gcgacaccct    8460
ggtgaaccgc atcgagctga agggcatcga cttcaaggag gacggcaaca tcctggggca    8520
```

| | |
|---|---|
| caagctggag tacaactaca acagccacaa cgtctatatc atggccgaca agcagaagaa | 8580 |
| cggcatcaag gtgaacttca agatccgcca caacatcgag gacggcagcg tgcagctcgc | 8640 |
| cgaccactac cagcagaaca ccccatcgg cgacggccc gtgctgctgc ccgacaacca | 8700 |
| ctacctgagc acccagtccg ccctgagcaa agacccaac gagaagcgcg atcacatggt | 8760 |
| cctgctggag ttcgtgaccg ccgccgggat cactctcggc atggacgagc tgtacaagaa | 8820 |
| gcttagccat ggcttcccgc cggcggtggc ggcgcaggat gatggcacgc tgcccatgtc | 8880 |
| ttgtgcccag gagagcggga tggaccgtca ccctgcagcc tgtgcttctg ctaggatcaa | 8940 |
| tgtgtagatg cgc | 8953 |

<210> SEQ ID NO 10
<211> LENGTH: 9762
<212> TYPE: DNA
<213> ORGANISM: Artificial Sequence
<220> FEATURE:
<223> OTHER INFORMATION: p4-5'3'IL1beta/d1EGFP-N1

<400> SEQUENCE: 10

| | |
|---|---|
| ggccgccagt gtgctggaat tcggctttgt ttgtttgttt aatgaaattt atttcatact | 60 |
| catcaaagca atgtgctaat gcttcattca taaaaattct catccatatt ataggaacct | 120 |
| atttattctc agcttcaatg aaagacctca agtgcaaggc tatgaccaat tcatccccca | 180 |
| cacgttgaca gctaggttct gttctagaga gtgctgccta atgtcccctt gaatcaactt | 240 |
| aaatagatca accaatcaat aaatacataa ataaataggt aagtggttgc ccatcagagg | 300 |
| caaggaggaa acacaggctc tctttgaaca gaatgtgcca tggtttcttg tgaccctgag | 360 |
| cgacctgtct tggccgagga ctaaggagtg tcctagagat tgagctgtct gctcattcat | 420 |
| gacaagggag ctccttcaca tgccctgggg aaggcattag aaacagtcca gcccatactt | 480 |
| taaagccgaa ttctgcagat atccatcaca ctggcggccg cgactctaga tcataatcag | 540 |
| ccataccaca tttgtagagg ttttacttgc tttaaaaaac ctcccacacc tccccctgaa | 600 |
| cctgaaacat aaaatgaatg caattgttgt tgttaacttg tttattgcag cttataatgg | 660 |
| ttacaaataa agcaatagca tcacaaattt cacaaataaa gcattttttt cactgcattc | 720 |
| tagttgtggt ttgtccaaac tcatcaatgt atcttaaggc gtaaattgta agcgttaata | 780 |
| ttttgttaaa attcgcgtta aattttgtt aaatcagctc attttttaac caataggccg | 840 |
| aaatcggcaa aatcccttat aaatcaaaag aatagaccga gatagggttg agtgttgttc | 900 |
| cagtttggaa caagagtcca ctattaaaga acgtggactc caacgtcaaa gggcgaaaaa | 960 |
| ccgtctatca gggcgatggc ccactacgtg aaccatcacc ctaatcaagt ttttttgggt | 1020 |
| cgaggtgccg taaagcacta aatcggaacc ctaaagggag cccccgattt agagcttgac | 1080 |
| ggggaaagcc ggcgaacgtg gcgagaaagg aagggaagaa agcgaaagga gcgggcgcta | 1140 |
| gggcgctggc aagtgtagcg gtcacgctgc gcgtaaccac cacacccgcc gcgcttaatg | 1200 |
| cgccgctaca gggcgcgtca ggtggcactt ttcggggaaa tgtgcgcgga acccctattt | 1260 |
| gtttattttt ctaaatacat tcaaatatgt atccgctcat gagacaataa ccctgataaa | 1320 |
| tgcttcaata atattgaaaa aggaagagtc ctgaggcgga agaaccagc tgtggaatgt | 1380 |
| gtgtcagtta gggtgtggaa agtccccagg ctccccagca ggcagaagta tgcaaagcat | 1440 |
| gcatctcaat tagtcagcaa ccaggtgtgg aaagtcccca ggctcccag caggcagaag | 1500 |
| tatgcaaagc atgcatctca attagtcagc aaccatagtc cgcccctaa ctccgcccat | 1560 |
| cccgccccta actccgccca gttccgccca ttctccgccc catggctgac taatttttt | 1620 |

```
tatttatgca gaggccgagg ccgcctcggc ctctgagcta ttccagaagt agtgaggagg   1680
cttttttgga ggcctaggct tttgcaaaga tcgatcaaga gacaggatga ggatcgtttc   1740
gcatgattga acaagatgga ttgcacgcag gttctccggc cgcttgggtg gagaggctat   1800
tcggctatga ctgggcacaa cagacaatcg gctgctctga tgccgccgtg ttccggctgt   1860
cagcgcaggg gcgcccggtt cttttgtca agaccgacct gtccggtgcc ctgaatgaac   1920
tgcaagacga ggcagcgcgg ctatcgtggc tggccacgac gggcgttcct tgcgcagctg   1980
tgctcgacgt tgtcactgaa gcgggaaggg actggctgct attgggcgaa gtgccggggc   2040
aggatctcct gtcatctcac cttgctcctg ccgagaaagt atccatcatg gctgatgcaa   2100
tgcggcggct gcatacgctt gatccggcta cctgcccatt cgaccaccaa gcgaaacatc   2160
gcatcgagcg agcacgtact cggatggaag ccggtcttgt cgatcaggat gatctggacg   2220
aagagcatca ggggctcgcg ccagccgaac tgttcgccag gctcaaggcg agcatgcccg   2280
acggcgagga tctcgtcgtg acccatggcg atgcctgctt gccgaatatc atggtggaaa   2340
atggccgctt ttctggattc atcgactgtg gccggctggg tgtggcggac cgctatcagg   2400
acatagcgtt ggctacccgt gatattgctg aagagcttgg cggcgaatgg gctgaccgct   2460
tcctcgtgct ttacggtatc gccgctcccg attcgcagcg catcgccttc tatcgccttc   2520
ttgacgagtt cttctgagcg ggactctggg gttcgaaatg accgaccaag cgacgcccaa   2580
cctgccatca cgagatttcg attccaccgc cgccttctat gaaaggttgg gcttcggaat   2640
cgttttccgg gacgccggct ggatgatcct ccagcgcggg gatctcatgc tggagttctt   2700
cgcccaccct aggggaggc taactgaaac acggaaggag acaataccgg aaggaacccg   2760
cgctatgacg gcaataaaaa gacagaataa aacgcacggt gttgggtcgt ttgttcataa   2820
acgcggggtt cggtcccagg gctggcactc tgtcgatacc ccaccgagac cccattgggg   2880
ccaatacgcc cgcgtttctt ccttttcccc accccacccc caagttcgg gtgaaggccc   2940
agggctcgca gccaacgtcg gggcggcagg ccctgccata gcctcaggtt actcatatat   3000
actttagatt gatttaaaac ttcatttta atttaaaagg atctaggtga agatccttt   3060
tgataatctc atgaccaaaa tcccttaacg tgagttttcg ttccactgag cgtcagaccc   3120
cgtagaaaag atcaaaggat cttcttgaga tcctttttt ctgcgcgtaa tctgctgctt   3180
gcaaacaaaa aaaccaccgc taccagcggt ggtttgtttg ccggatcaag agctaccaac   3240
tcttttccg aagtaactg gcttcagcag agcgcagata ccaaatactg tccttctagt   3300
gtagccgtag ttaggccacc acttcaagaa ctctgtagca ccgcctacat acctcgctct   3360
gctaatcctg ttaccagtgg ctgctgccag tggcgataag tcgtgtctta ccgggttgga   3420
ctcaagacga tagttaccgg ataaggcgca gcggtcgggc tgaacggggg gttcgtgcac   3480
acagcccagc ttggagcgaa cgacctacac cgaactgaga tacctacagc gtgagctatg   3540
agaaagcgcc acgcttcccg aagggagaaa ggcggacagg tatccggtaa gcggcagggt   3600
cggaacagga gagcgcacga gggagcttcc agggggaaac gcctggtatc tttatagtcc   3660
tgtcgggttt cgccacctct gacttgagcg tcgatttttg tgatgctcgt cagggggcg   3720
gagcctatgg aaaaacgcca gcaacgcggc cttttacgg ttcctggcct tttgctggcc   3780
ttttgctcac atgttctttc ctgcgttatc ccctgattct gtggataacc gtattaccgc   3840
catgcattag ttatcgctac cggactcaga tctcgagctc aagcttcgaa ttctgcagtc   3900
gacggtaccg agctcggatc cactagtaac ggccgccagt gtgctggaat tcgcccttgg   3960
atcctctaag gggcttgagt tacttctgca gctcagccct ttgtagcaca aacagcttgt   4020
```

```
cttttaggat tggctggct ccactccact gctgctgctg ttcttgatgg tcatcccatg    4080
gtacttgcat ctccaaaatg ctggggtctt ctgctgcaac tgggctggac ttataccagt    4140
actctcctgg gctctcttca tggtgacaag cctcaacttc tctgtatgac cctttcaatc    4200
ctgggccttc agctgccact gaggctgtat tgtcagtgcc aagactcagc tgctcttcca    4260
tgaaccagtg tcacctgggt ggctcttcca caggaccaaa tttggctgcc agtggagaaa    4320
tacaactttg gccatctctg gaaaacagct tctgtgtgct ctcagaaaac acttcccaga    4380
agatttcacc tcaataatgc tggacttttc ttagtcactg ctaatttctc agctccagct    4440
caccagcact gagtatctaa gcaaagcaaa ggtttcattt ttagtggttc tggaatcttg    4500
tttatcgatg cctattcttc agccccagct aatgagatat tatgttatca cggaatctta    4560
attcaatata acaaatggcc ctgaagaagt ctttaagctt ccttctgaag cttcacaagt    4620
caggcctcca tctttgtgtt gccctcaacg tccctatctt ccaagttcct aggaacagct    4680
caccaagaat tgaccactct atgggttttc ttgtacaaag tccttccaaa acaatatgct    4740
caggtctgtc acagtcatgt cacagtaaat cttggtgcca attcattttc atttaggtta    4800
ctattactat aatgaaactc catgatcaaa gcaacttggg gaggaaagga tgtattctgc    4860
ttacatttcc acatcacagt ttatcatcaa aggaagtcag gacaggaact caagcaaggc    4920
aggaacctgg aaccaggagc tgatgcagcg atcatggagg gatgctgctc actggcttgc    4980
tcctcatggc ttgtcaacct actttcttat agaaccctgg accaccagcc cagggatggc    5040
accacccaca acaggctgat ttctccccaa gtaaatacca attaataaaa tttcctacag    5100
gcttgcctac agacagatct tttggatgta ttttgtcagt taaggctccc ttctctctga    5160
tgattctagc ttgtgtctag ttgacataaa actaaccagg acagaaaaga tgagagggaa    5220
agaacagacc cctaaggcct gtgctaagtc gtcaacttaa ggaataagac aaggtctgga    5280
gaaagtaatg aggacagtca ttgcttagct ctgttctgag caagaggata agtaaagaag    5340
atgtagaaca catacatcaa ctgggcctgg gagctcgtgc ctgtaatctc agtccttggg    5400
agacaaatgc aggagaattg tcatgtactt gaagccagtc tgggctgcac agtagtcatg    5460
gttatcacag caatagaaag taagtaaaac aggtagcaag gcactttcag ctttgaagaa    5520
atgcctgcct ccatcttgga ggaatgagat gtcagaacag agggaacctt acagcttaaa    5580
agtgctgagt gagtcaagag ctgaaaagtt ccccaaaagc tagagtgccc gtcaccatcc    5640
tggctttgcc gacttcctct tttgctttgt tcatttcctt tgccaacatc atcatcagta    5700
tcgtcatcac tatgccacac ccccagcata acaatttcta tagtgagtta tttcttctac    5760
tcattgggga ccaaaaagga agtgtggtct gagagacagg gtttgatata catgttgtgc    5820
aacttgcctg ctctataacg acaagggggag gaaatttgga gcccaagtca cagggccagg    5880
atgaggtttg atagaacaat agagtaccag aggcattgcc cagtagttcc aaaatctccc    5940
tctagaagca aaagaatcat caaccagatc attgcctcct cccagacaaa cctcctccca    6000
tctcttcatc tcttactcac gattaaatgg ccattcgtct tcatgcatgt gccttcctcc    6060
aaatcctccc agacaaccac tcctctcagg catcagctca agggtttagg agtgttataa    6120
ctagcagatg gtgaagaaga ttctgtaact agactgagct caaggctcct gaaaaatcat    6180
ccagggagaa gggacttgga gctgacactc aggcccctag ttacccttct ctgtcccctg    6240
gttttcacca tccctggttc aactcacatc agcagaccaa aggagtctcc aataatctct    6300
gtcaggacag cccataaaat catcagacct tccagccctg cacacaggct ctgaggaagg    6360
tgttagtccc tccaggcata gtttgaaatg tggaccctgt gaaggcagaa cagaaaaatg    6420
```

-continued

```
aaccagatgg cccagacagg acctctggat tgtctgcaga actagataat acatcttata  6480
agaccttagt gctgagaact gaccattgct caccaaactc aaaagcaact gagaccctga  6540
accatcttca gatttcaaat caaacatata gctggtcaaa ggcaggattc ttctgtttgc  6600
cttcctgaaa tcgagatgct gtgaaccaaa ttaggcaaaa gaaggctgcc tagtaagtaa  6660
accttgtttc atagtagagc cttgtctatt cctccttcca attctgtctg tctatttccc  6720
ttcagtgctg cagaataagc tcagtaacca aaacatacta ggtacaaact catctgaatg  6780
aacacattgc caaattccta ctcacccggg ctagctccta ctgcctgcat ccatctgcca  6840
ggcactgtgg agacctggct ctaatggagt ccacagactc tctgagggct cagcaaagga  6900
gttaggtttc cactgaggat tctactatac tgtagatgtg cccaagagac tgtatgcagc  6960
attcatatgg cctggttgct cattccatcc aagcaagaag agctcccctg ggtaggctcc  7020
ctgggctctc tgagttagca gtctagtgat gcttgatatg ccaagagac ttggtctccc  7080 cagatcttat agaaacaaga attttccaaa acaattttt aggcaaagac tatctcttca  7140
ctttttaaga tggactgtgc tcatgaacag gcagatgcct cgttccaccac ctttgcactg  7200 tgcaacttaa ttcaggctca ttctgctgat cacctagcac tgatatggtt tcaacatgag  7260
actggctatg gtattataag taccctggca gggcaggaaa gcaggagtgg gtgggtgagt  7320
gggggagcat cctcatagag gcaggggagg gggagaggat agggggtttc cggaggggag  7380
acctggaaaa gggataacat ttgaaatgta aataaagaaa atatccaata aagaaaaaa  7440 ataagcaccc tggcattatc agactgcata ggcttgcttc cagagttccc tgacccctatg 7500 ataagtctac actgatacct gcatactgtg tgtgccctga cccacacaag gaagtgcgtg  7560
tctctccaga agcccctgct aacacagttg atggagagca cagaagcacc atccagttac  7620
caaactccaa ctgcaaagct ccctcagctt aagcacaagg aggcgagaga ggtgacacac  7680
ttctgggtgt gcatctacgt gcctaccttt gttccgcaca tcctgactta aaatgtacag  7740
ctaacccagg aaaacccaat attttaata ttgacaccat ctgcacaatt gtccaggggg  7800
aaataatgcc catttccacc acgatgacac acttgcgaat gtgtcactat ctgccacccc  7860
ttgacttcca gggattagaa attatttcag ggtagcaata gcctcttccc ctaagaattc  7920
ccatcaagct tctcccccct cccccaccct tcagttttgt tgtgaaatca gttacccaa  7980 gggaaaattt cacagctctt cacttctgct ttttaggact ataaacaag ggagggaaaa  8040 caagttggac aacaaaccct gcagtggttc gaggcctaat aggctcatct gggatcctct  8100
ccagccaagc ttccttgtgc aagtaagtct ctctctctct ctgtctctct ctctctctgt  8160
ctctctctat ctctctctct ctgtctctct ctctctgtct ctgtctgtct ctctctctgt  8220
ctctgtctgt ctatctctct ctctctctgt ctgtctctgt ctctctctgt ctgtctctct  8280
ctgtctctct gtctctctct ctgtctctct ctgtctctct ctctctctct ctttccccc  8340 ccccactga tggactttgg cttttatt tataaaagt agctgtacct ccatggtttg  8400
tgaagtactc tggaaatgag tactgtctgt atagccgctg acatctaaaa ggcagctcct  8460
gtcttgtagg aaagcttctt tattagggtt tggctctgct gttgcttcct tccagagcat  8520
cttcctaatg ctgttcccca tgttgtagtg accccccaca caccctaaaa ttatttcat  8580 tgctacttca taactataat tttgctactg ttatgaagtg taaatatctg tgttatccaa  8640
tggtcttagg tgaccctgt gaaagggcca cttgactcca aaagggccac tggtctagac  8700
ctatacaacg gctcctccgt tccttcattc ctcagagacc agtttagcat gcctgccctg  8760
aactagagct aagagaaaca catatgaagg acgcccctcg gggagctaac gctggatgcc  8820
```

```
cacccactttc ctttcttcac acaggtgtct gaagcagcta tggcaactgt taagggcgaa    8880
ttctgcagat gggatccacc ggtcgccacc atggtgagca agggcgagga gctgttcacc    8940
ggggtggtgc ccatcctggt cgagctggac ggcgacgtaa acggccacaa gttcagcgtg    9000
tccggcgagg gcgagggcga tgccacctac ggcaagctga ccctgaagtt catctgcacc    9060
accggcaagc tgcccgtgcc ctggcccacc ctcgtgacca ccctgaccta cggcgtgcag    9120
tgcttcagcc gctaccccga ccacatgaag cagcacgact tcttcaagtc cgccatgccc    9180
gaaggctacg tccaggagcg caccatcttc ttcaaggacg acggcaacta caagacccgc    9240
gccgaggtga agttcgaggg cgacaccctg gtgaaccgca tcgagctgaa gggcatcgac    9300
ttcaaggagg acggcaacat cctggggcac aagctggagt acaactacaa cagccacaac    9360
gtctatatca tggccgacaa gcagaagaac ggcatcaagg tgaacttcaa gatccgccac    9420
aacatcgagg acggcagcgt gcagctcgcc gaccactacc agcagaacac ccccatcggc    9480
gacggccccg tgctgctgcc cgacaaccac tacctgagca cccagtccgc cctgagcaaa    9540
gaccccaacg agaagcgcga tcacatggtc ctgctggagt tcgtgaccgc cgccgggatc    9600
actctcggca tggacgagct gtacaagaag cttagccatg gcttcccgcc ggcggtggcg    9660
gcgcaggatg atggcacgct gcccatgtct tgtgcccagg agagcgggat ggaccgtcac    9720
cctgcagcct gtgcttctgc taggatcaat gtgtagatgc gc                       9762
```

<210> SEQ ID NO 11
<211> LENGTH: 6917
<212> TYPE: DNA
<213> ORGANISM: Artificial Sequence
<220> FEATURE:
<223> OTHER INFORMATION: p1-5'IL2/EGFP-1

<400> SEQUENCE: 11

```
ggcggccgcg aattcactag tgatgtaagc aacaggtgac aggttccccg ggcagcatct      60
ctagggtctg ggcctgcctt cacttctagg agcagctgga acagctaata ctgagcagta     120
gagctctgtg gcttatgaca catgtggtag tcaggcagcg actgattaca tcacctctcc     180
agccagaaac cccagctgct gtgtcaagga tgttaaaaat ggaaagtgca ccacagctgt     240
tggtagcttt ctccccaagc atcttaagaa actgggaggc caacctttgt aatgctgcca     300
attatgcaat gctctgtagg ggtgaacctt ggccccagga actcattcta caggctttta     360
gaaacgcggc catgtaaatt tctctaatgg aaacagctgg agaaatagag atgttgagcc     420
catgaggaca tcaaaggccc cactgtgtgg aaaagccccc acacaggaaa atgtgtgggc     480
ctgactcctt ccattctgga aggggaggcc tgagttgctt gggctgggat gagatgctga     540
agatctgaga agagagacaa gagcattgag gctgagagtt attaggtaga tgcccctcac     600
gatggcatgc ttaatctgaa ggcacagaag gtgatgatga ctaggagatt tgtccccatc     660
ctgctttcct tcagacatgc caacagggcc actatgatac cagaagttgt caagcttact     720
gcaagataca tgcagagttt tttgttgttt tctagaatac tgtccaatga ttggagaact     780
atcccagaac cattctctgt tctttgtgag agactttagg ccaacattcc ttacattgct     840
tagtcttcct gctttcacta ttccccagca tcaaaattac acttaaagta actatctcaa     900
aactctttac attgcccaac atccaacatt tctaggatgt tatctgtctc catccaagga     960
tcaggtcaat aggaagacag atggtgtgag agtagattct ggagtcagaa cattctagtt    1020
tcgaatcttc accctacccct ttactggcaa taaggctgag taacctcaat gatttatcta    1080
atctacccac agtgtgcatg tagcagtcaa agacaacttg tggagtcagt gagaactgac    1140
```

```
ttccaccttt atgtaagttc agggatcaga gagcaaggtt tgtatagcaa gccccttagt    1200
catctcatca ccctacatcc tcagttttca aatctacaaa atggggtagg tgtgtggtga    1260
ggcttatgtt aatctgtgta tttgcacata ttttctccct ttctatgtac cccaggatgt    1320
tttagatggt agataaatgt ctgcataaag actagaccag tacaagttat tagaaatggg    1380
gacaccacag gcaagctccc taagaaagac cccgtctcta ccagttgatt tggaactatg    1440
ttcctactcc atcacgcagc cagtgtacta cacggaggat aaggaatcca atgtatccta    1500
ttcaggtgac ccactgagaa cacgtgggat agtccctagc tattactctc agagtgccca    1560
ggtactttta ggataaaccc aaatctactg aattaggggg aagaaggttg gcaagatgcc    1620
tcagtggtaa aggctaggta gaggctagta gcagaggtag gcacacagac tggatgactt    1680
ttgtgtttag atttctgagt cacacaaggt gacaggagag aagttactag caagagttgg    1740
tctctgacct ccacaggtgt actgtggcac acacacacac acacactcat aatacatgtg    1800
cacaaatgca tgtacacata catacacaca tgcatacatg cacacacaca cactcatata    1860
cacacgcaca taaacatgct cacacacaca tacatgtgca cgcacatgca catactcata    1920
cacacatgaa cacatgtgtg tgtacacacg tgaaaatatt ttttaaaaat gaaagtgcaa    1980
ctagagacat ataaaataac accaacatcc ttagatgcaa cccttcctga gaatttgttg    2040
gacatcatac tctttttaaa aagcataata aacatcaaga cacttacaca aaatatgtta    2100
aattaaattt aaaacaacaa cgacaaaata gtacctcaag ctcaacaagc attttaggtg    2160
tccttagctt actatttctc tggctaactg tatgaagcca tctatcaccc tgtgtgcaat    2220
tagctcattg tgtagataag aaggtaaaac catcttgaaa caggaaacca atatccttcc    2280
tgtctaatca acaaatctaa aagatttatt cttttcatct atctcctctt gcgtttgtcc    2340
accacaacag gctgcttaca ggttcaggat ggttttgaca aagagaacat tttcatgagt    2400 tactttgtg tctccacccc aaagaggaaa atttgtttca tacagaaggc gttcattgta    2460
tgaattaaaa ctgccaccta agtgtgggct aacccgacca agaggatttt cacctaaatc    2520
cattcagtca gtgtatgggg gtttaaagaa attccagaga gtcatcagaa gaggaaaaac    2580
aaaggtaatg ctttctgcca cacaggtaga ctctttgaaa atatgtgtaa tatgtaaaac    2640
atcgtgacac ccccatatta tttttccagc attaacagta taaattgcct cccatgctga    2700
agagctgcct atcacccttg ctaatcactc ctcacatcga attcccgcgg ccgccatggc    2760
ggccgggagc atgcgacgtc gggcccggga tccaccggtc gccaccatgg tgagcaaggg    2820
cgaggagctg ttcaccgggg tggtgcccat cctggtcgag ctggacgcg acgtaaacgg    2880 ccacaagttc agcgtgtccg gcgagggcga gggcgatgcc acctacggca agctgaccct    2940
gaagttcatc tgcaccaccg gcaagctgcc cgtgccctgg cccaccctcg tgaccaccct    3000
gacctacggc gtgcagtgct tcagccgcta ccccgaccac atgaagcagc acgacttctt    3060
caagtccgcc atgcccgaag gctacgtcca ggagcgcacc atcttcttca aggacgacgg    3120
caactacaag acccgcgccg aggtgaagtt cgagggcgac accctggtga accgcatcga    3180
gctgaagggc atcgacttca aggaggacgg caacatcctg gggcacaagc tggagtacaa    3240
ctacaacagc cacaacgtct atatcatggc cgacaagcag aagaacggca tcaaggtgaa    3300
cttcaagatc cgccacaaca tcgaggacgg cagcgtgcag ctcgccgacc actaccagca    3360
gaacaccccc atcggcgacg gccccgtgct gctgcccgac aaccactacc tgagcaccca    3420
gtccgccctg agcaaagacc ccaacgaaaa gcgcgatcac atggtcctgc tggagttcgt    3480
gaccgccgcc gggatcactc tcggcatgga cgagctgtac aagtaaagcg gccgcgactc    3540
```

```
tagatcataa tcagccatac cacatttgta gaggttttac ttgctttaaa aaacctccca    3600
cacctccccc tgaacctgaa acataaaatg aatgcaattg ttgttgttaa cttgtttatt    3660
gcagcttata atggttacaa ataaagcaat agcatcacaa atttcacaaa taaagcattt    3720
ttttcactgc attctagttg tggttttgtcc aaactcatca atgtatctta aggcgtaaat   3780
tgtaagcgtt aatattttgt taaaattcgc gttaaatttt tgttaaatca gctcattttt    3840
taaccaatag gccgaaatcg gcaaaatccc ttataaatca aaagaataga ccagatagg     3900 gttgagtgtt gttccagttt ggaacaagag tccactatta agaacgtgg actccaacgt     3960 caaagggcga aaaaccgtct atcagggcga tgggccacta cgtgaaccat caccctaatc    4020
aagttttttg gggtcgaggt gccgtaaagc actaaatcgg aaccctaaag ggagcccccg    4080
atttagagct tgacggggaa agccggcgaa cgtggcgaga aggaaggga agaaagcgaa     4140 aggagcgggc gctagggcgc tggcaagtgt agcggtcacg ctgcgcgtaa ccaccacacc    4200
cgccgcgctt aatgcgccgc tacagggcgc gtcaggtggc acttttcggg gaaatgtgcg    4260
cggaacccct atttgtttat ttttctaaat acattcaaat atgtatccgc tcatgagaca    4320
ataaccctga taaatgcttc aataatattg aaaaaggaag agtcctgagg cggaaagaac    4380
cagctgtgga atgtgtgtca gttagggtgt ggaaagtccc caggctcccc agcaggcaga    4440
agtatgcaaa gcatgcatct caattagtca gcaaccaggt gtggaaagtc cccaggctcc    4500
ccagcaggca gaagtatgca aagcatgcat ctcaattagt cagcaaccat agtcccgccc    4560
ctaactccgc ccatcccgcc cctaactccg cccagttccg cccattctcc gccccatggc    4620
tgactaattt ttttttattta tgcagaggcc gaggccgcct cggcctctga gctattccag    4680
aagtagtgag gaggcttttt tggaggccta ggcttttgca aagatcgatc aagagacagg    4740
atgaggatcg tttcgcatga ttgaacaaga tggattgcac gcaggttctc cggccgcttg    4800
ggtggagagg ctattcggct atgactgggc acaacagaca atcggctgct ctgatgccgc    4860
cgtgttccgg ctgtcagcgc aggggcgccc ggttcttttt gtcaagaccg acctgtccgg    4920
tgccctgaat gaactgcaag acgaggcagc gcggctatcg tggctggcca cgacgggcgt    4980
tccttgcgca gctgtgctcg acgttgtcac tgaagcggga agggactggc tgctattggg    5040
cgaagtgccg gggcaggatc tcctgtcatc tcaccttgct cctgccgaga agtatccat    5100 catggctgat gcaatgcggc ggctgcatac gcttgatccg gctacctgcc cattcgacca    5160
ccaagcgaaa catcgcatcg agcgagcacg tactcggatg aagccggtc ttgtcgatca     5220 ggatgatctg gacgaagagc atcagggct cgcgccagcc gaactgttcg ccaggctcaa    5280
ggcgagcatg cccgacggcg aggatctcgt cgtgacccat ggcgatgcct gcttgccgaa    5340
tatcatggtg gaaaatggcc gcttttctgg attcatcgac tgtggccggc tgggtgtggc    5400
ggaccgctat caggacatag cgttggctac ccgtgatatt gctgaagagc ttggcggcga    5460
atgggctgac cgcttcctcg tgctttacgg tatcgccgct cccgattcgc agcgcatcgc    5520
cttctatcgc cttcttgacg agttcttctg agcgggactc tggggttcga aatgaccgac    5580
caagcgacgc ccaacctgcc atcacgagat ttcgattcca ccgccgcctt ctatgaaagg    5640
ttgggcttcg gaatcgtttt ccgggacgcc ggctggatga tcctccagcg cggggatctc    5700
atgctggagt tcttcgccca ccctagggggg aggctaactg aaaacacgaa ggagacaata    5760
ccggaaggaa cccgcgctat gacggcaata aaaagacaga ataaaacgca cggtgttggg    5820
tcgtttgttc ataaacgcgg ggttcggtcc cagggctggc actctgtcga taccccaccg    5880
agaccccatt ggggccaata cgcccgcgtt tcttcctttt ccccaccca cccccccaagt    5940
```

```
tcgggtgaag gcccagggct cgcagccaac gtcggggcgg caggccctgc catagcctca    6000
ggttactcat atatacttta gattgattta aaacttcatt tttaatttaa aaggatctag    6060
gtgaagatcc tttttgataa tctcatgacc aaaatccctt aacgtgagtt ttcgttccac    6120
tgagcgtcag accccgtaga aaagatcaaa ggatcttctt gagatccttt ttttctgcgc    6180
gtaatctgct gcttgcaaac aaaaaaacca ccgctaccag cggtggtttg tttgccggat    6240
caagagctac caactctttt tccgaaggta actggcttca gcagagcgca gataccaaat    6300
actgtccttc tagtgtagcc gtagttaggc caccacttca agaactctgt agcaccgcct    6360
acatacctcg ctctgctaat cctgttacca gtggctgctg ccagtggcga taagtcgtgt    6420
cttaccgggt tggactcaag acgatagtta ccggataagg cgcagcggtc gggctgaacg    6480
gggggttcgt gcacacagcc cagcttggag cgaacgacct acaccgaact gagatacccta   6540
cagcgtgagc tatgagaaag cgccacgctt cccgaaggga gaaaggcgga caggtatccg    6600
gtaagcggca gggtcggaac aggagagcgc acgagggagc ttccaggggg aaacgcctgg    6660
tatctttata gtcctgtcgg gtttcgccac ctctgacttg agcgtcgatt tttgtgatgc    6720
tcgtcagggg gcggagcct  atggaaaaac gccagcaacg cggcctttt  acggttcctg    6780
gccttttgct ggccttttgc tcacatgttc tttcctgcgt tatcccctga ttctgtggat    6840
aaccgtatta ccgccatgca ttagttatta ctagcgctac cggactcaga tctcgagctc    6900
aagcttcgaa ttctgca                                                   6917

<210> SEQ ID NO 12
<211> LENGTH: 7046
<212> TYPE: DNA
<213> ORGANISM: Artificial Sequence
<220> FEATURE:
<223> OTHER INFORMATION: p1-5'IL2/d2EGFP-1

<400> SEQUENCE: 12
tcgagctcaa gcttcgaatt ctgcaggcgg ccgcgaattc actagtgatg taagcaacag      60
gtgacaggtt ccccgggcag catctctagg gtctgggcct gccttcactt ctaggagcag    120
ctggaacagc taatactgag cagtagagct ctgtggctta tgacacatgt ggtagtcagg    180
cagcgactga ttcatcacc  tctccagcca gaaaccccag ctgctgtgtc aaggatgtta    240
aaaatggaaa gtgcaccaca gctgttggta gctttctccc caagcatctt aagaaactgg    300
gaggccaacc tttgtaatgc tgccaattat gcaatgctct gtaggggtga accttggccc    360
caggaactca ttctacaggc ttttagaaac gcggccatgt aaatttctct aatgaaaaca    420
gctggagaaa tagagatgtt gagcccatga ggacatcaaa ggccccactg tgtggaaaag    480
cccccacaca ggaaaatgtg tgggcctgac tccttccatt ctggaagggg aggcctgagt    540
tgcttgggct gggatgagat gctgaagatc tgagaagaga acaagagca ttgaggctga     600
gagttattag gtagatgccc ctcacgatgg catgcttaat ctgaaggcac agaaggtgat    660
gatgactagg agatttgtcc ccatcctgct ttccttcaga catgccaaca gggccactat    720
gataccagaa gttgtcaagc ttactgcaag atacatgcag agtttttgt  tgttttctag    780
aatactgtcc aatgattgga gaactatccc agaaccattc tctgttcttt gtgagagact    840
ttaggccaac attccttaca ttgcttagtc ttcctgcttt cactattccc cagcatcaaa    900
attacactta agtaactat  ctcaaaactc tttacattgc ccaacatcca acatttctag    960
gatgttatct gtctccatcc aaggatcagg tcaataggaa gacagatggt gtgagagtag   1020
attctggagt cagaacattc tagtttcgaa tcttcacccct accctttact ggcaataagg   1080
```

```
ctgagtaacc tcaatgattt atctaatcta cccacagtgt gcatgtagca gtcaaagaca    1140
acttgtggag tcagtgagaa ctgacttcca cctttatgta agttcaggga tcagagagca    1200
aggtttgtat agcaagcccc ttagtcatct catcacccta catcctcagt tttcaaatct    1260
acaaaatggg gtaggtgtgt ggtgaggctt atgttaatct gtgtatttgc acatattttc    1320 tcccttteta tgtaccccag gatgttttag atggtagata aatgtctgca taaagactag    1380
accagtacaa gttattagaa atggggacac cacaggcaag ctccctaaga aagaccccgt    1440
ctctaccagt tgatttggaa ctatgttcct actccatcac gcagccagtg tactacacgg    1500
aggataagga atccaatgta tcctattcag gtgacccact gagaacacgt gggatagtcc    1560
ctagctatta ctctcagagt gcccaggtac ttttaggata aacccaaatc tactgaatta    1620
gggggaagaa ggttggcaag atgcctcagt ggtaaaggct aggtagaggc tagtagcaga    1680
ggtaggcaca cagactggat gacttttgtg tttagatttc tgagtcacac aaggtgacag    1740
gagagaagtt actagcaaga gttggtctct gacctccaca ggtgtactgt ggcacacaca    1800
cacacacaca ctcataatac atgtgcacaa atgcatgtac acatacatac acacatgcat    1860
acatgcacac acacacactc atatacacac gcacataaac atgctcacac acacatacat    1920
gtgcacgcac atgcacatac tcatacacac atgaacacat gtgtgtgtac acacgtgaaa    1980 atattttta aaaatgaaag tgcaactaga gacatataaa ataacaccaa catccttaga    2040
tgcaaccctt cctgagaatt tgttggacat catactcttt ttaaaaagca taataaacat    2100
caagacactt acacaaaata tgttaaatta aatttaaaac aacaacgaca aaatagtacc    2160
tcaagctcaa caagcatttt aggtgtcctt agcttactat ttctctggct aactgtatga    2220
agccatctat caccctgtgt gcaattagct cattgtgtag ataagaaggt aaaaccatct    2280
tgaaacagga aaccaatatc cttcctgtct aatcaacaaa tctaaaagat ttattctttt    2340
catctatctc ctcttgcgtt tgtccaccac aacaggctgc ttacaggttc aggatggttt    2400
tgacaaagag aacattttca tgagttactt ttgtgtctcc accccaaaga ggaaaatttg    2460
tttcatacag aaggcgttca ttgtatgaat taaaactgcc acctaagtgt gggctaaccc    2520
gaccaagagg gatttcacct aaatccattc agtcagtgta tgggggttta aagaaattcc    2580
agagagtcat cagaagagga aaacaaagg taatgctttc tgccacacag gtagactctt    2640
tgaaaatatg tgtaatatgt aaaacatcgt gacaccccca tattattttt ccagcattaa    2700
cagtataaat tgcctcccat gctgaagagc tgcctatcac ccttgctaat cactcctcac    2760
atcgaattcc cgcggccgcc atggcggccg ggagcatgcg acgtcgggcc cgggatccac    2820
cggtcgccac catggtgagc aagggcgagg agctgttcac cggggtggtg cccatcctgg    2880
tcgagctgga cggcgacgta aacggccaca agttcagcgt gtccggcgag ggcgagggcg    2940
atgccaccta cggcaagctg accctgaagt tcatctgcac caccggcaag ctgcccgtgc    3000
cctggcccac cctcgtgacc accctgacct acggcgtgca gtgcttcagc cgctaccccg    3060
accacatgaa gcagcacgac ttcttcaagt ccgccatgcc cgaaggctac gtccaggagc    3120
gcaccatctt cttcaaggac gacggcaact acaagacccg cgccgaggtg aagttcgagg    3180
gcgacaccct ggtgaaccgc atcgagctga agggcatcga cttcaaggag gacggcaaca    3240
tcctggggca caagctggag tacaactaca acagccacaa cgtctatatc atggccgaca    3300
agcagaagaa cggcatcaag gtgaacttca agatccgcca caacatcgag gacggcagcg    3360
tgcagctcgc cgaccactac cagcagaaca cccccatcgg cgacggcccc gtgctgctgc    3420
ccgacaacca ctacctgagc acccagtccg ccctgagcaa agaccccaac gagaagcgcg    3480
```

```
atcacatggt cctgctggag ttcgtgaccg ccgccgggat cactctcggc atggacgagc   3540
tgtacaagaa gcttagccat ggcttcccgc cggaggtgga ggagcaggat gatggcacgc   3600
tgcccatgtc ttgtgcccag gagagcggga tggaccgtca ccctgcagcc tgtgcttctg   3660
ctaggatcaa tgtgtagatg cgcggccgcg actctagatc ataatcagcc ataccacatt   3720
tgtagaggtt ttacttgctt taaaaaacct cccacacctc cccctgaacc tgaaacataa   3780
aatgaatgca attgttgttg ttaacttgtt tattgcagct tataatggtt acaaataaag   3840
caatagcatc acaaatttca caaataaagc attttttca ctgcattcta gttgtggttt   3900
gtccaaactc atcaatgtat cttaaggcgt aaattgtaag cgttaatatt ttgttaaaat   3960
tcgcgttaaa ttttgttaa atcagctcat tttttaacca ataggccgaa atcggcaaaa   4020
tcccttataa atcaaaagaa tagaccgaga tagggttgag tgttgttcca gtttggaaca   4080
agagtccact attaaagaac gtggactcca acgtcaaagg gcgaaaaacc gtctatcagg   4140
gcgatggccc actacgtgaa ccatcaccct aatcaagttt tttggggtcg aggtgccgta   4200
aagcactaaa tcggaaccct aaagggagcc cccgatttag agcttgacgg ggaaagccgg   4260
cgaacgtggc gagaaaggaa gggaagaaag cgaaaggagc gggcgctagg gcgctggcaa   4320
gtgtagcggt cacgctgcgc gtaaccacca cacccgccgc gcttaatgcg ccgctacagg   4380
gcgcgtcagg tggcactttt cggggaaatg tgcgcggaac ccctatttgt ttatttttct   4440
aaatacattc aaatatgtat ccgctcatga caataaacc ctgataaatg cttcaataat   4500
attgaaaaag gaagagtcct gaggcggaaa gaaccagctg tggaatgtgt gtcagttagg   4560
gtgtggaaag tccccaggct ccccagcagg cagaagtatg caaagcatgc atctcaatta   4620
gtcagcaacc aggtgtggaa agtccccagg ctccccagca ggcagaagta tgcaaagcat   4680
gcatctcaat tagtcagcaa ccatagtccc gcccctaact ccgcccatcc cgcccctaac   4740
tccgcccagt tccgcccatt ctccgcccca tggctgacta atttttttta tttatgcaga   4800
ggccgaggcc gcctcggcct ctgagctatt ccagaagtag tgaggaggct ttttggagg   4860
cctaggcttt tgcaaagatc gatcaagaga caggatgagg atcgtttcgc atgattgaac   4920
aagatggatt gcacgcaggt tctccggccg cttgggtgga gaggctattc ggctatgact   4980
gggcacaaca gacaatcggc tgctctgatg ccgccgtgtt ccggctgtca gcgcaggggc   5040
gcccggttct ttttgtcaag accgacctgt ccggtgccct gaatgaactg caagacgagg   5100
cagcgcggct atcgtggctg gccacgacgg gcgttccttg cgcagctgtg ctcgacgttg   5160
tcactgaagc gggaagggac tggctgctat tgggcgaagt gccggggcag gatctcctgt   5220
catctcacct tgctcctgcc gagaaagtat ccatcatggc tgatgcaatg cggcggctgc   5280
atacgcttga tccggctacc tgcccattcg accaccaagc gaaacatcgc atcgagcgag   5340
cacgtactcg gatggaagcc ggtcttgtcg atcaggatga tctggacgaa gagcatcagg   5400
ggctcgcgcc agccgaactg ttcgccaggc tcaaggcgag catgcccgac ggcgaggatc   5460
tcgtcgtgac ccatggcgat gcctgcttgc cgaatatcat ggtggaaaat ggccgctttt   5520
ctggattcat cgactgtggc cggctgggtg tggcggaccg ctatcaggac atagcgttgg   5580
ctacccgtga tattgctgaa gagcttggcg gcgaatgggc tgaccgcttc ctcgtgcttt   5640
acggtatcgc cgctcccgat tcgcagcgca tcgccttcta tcgccttctt gacgagttct   5700
tctgagcggg actctggggt tcgaaatgac cgaccaagcg acgcccaacc tgccatcacg   5760
agatttcgat tccaccgccg ccttctatga aaggttgggc ttcggaatcg ttttccggga   5820
cgccggctgg atgatcctcc agcgcgggga tctcatgctg gagttcttcg cccacccta   5880
```

-continued

| | |
|---|---|
| gggggaggcta actgaaacac ggaaggagac aataccggaa ggaacccgcg ctatgacggc | 5940 |
| aataaaaaga cagaataaaa cgcacggtgt tgggtcgttt gttcataaac gcggggttcg | 6000 |
| gtcccagggc tggcactctg tcgatacccc accgagaccc cattgggggcc aatacgcccg | 6060 |
| cgtttcttcc ttttccccac cccacccccc aagttcgggt gaaggcccag ggctcgcagc | 6120 |
| caacgtcggg gcggcaggcc ctgccatagc ctcaggttac tcatatatac tttagattga | 6180 |
| tttaaaactt cattttttaat ttaaaaggat ctaggtgaag atccttttttg ataatctcat | 6240 |
| gaccaaaatc ccttaacgtg agttttcgtt ccactgagcg tcagacccccg tagaaaagat | 6300 |
| caaaggatct tcttgagatc cttttttttct gcgcgtaatc tgctgcttgc aaacaaaaaa | 6360 |
| accaccgcta ccagcggtgg tttgtttgcc ggatcaagag ctaccaactc ttttttccgaa | 6420 |
| ggtaactggc ttcagcagag cgcagatacc aaatactgtc cttctagtgt agccgtagtt | 6480 |
| aggccaccac ttcaagaact ctgtagcacc gcctacatac ctcgctctgc taatcctgtt | 6540 |
| accagtggct gctgccagtg gcgataagtc gtgtcttacc gggttggact caagacgata | 6600 |
| gttaccggat aaggcgcagc ggtcgggctg aacggggggt tcgtgcacac agcccagctt | 6660 |
| ggagcgaacg acctacaccg aactgagata cctacagcgt gagctatgag aaagcgccac | 6720 |
| gcttcccgaa gggagaaagg cggacaggta tccggtaagc ggcagggtcg gaacaggaga | 6780 |
| gcgcacgagg gagcttccag ggggaaacgc ctggtatctt tatagtcctg tcgggtttcg | 6840 |
| ccacctctga cttgagcgtc gatttttgtg atgctcgtca ggggggcgga gcctatggaa | 6900 |
| aaacgccagc aacgcggcct ttttacggtt cctggccttt tgctggcctt ttgctcacat | 6960 |
| gttctttcct gcgttatccc ctgattctgt ggataaccgt attaccgcca tgcattagtt | 7020 |
| attactagcg ctaccggact cagatc | 7046 |

<210> SEQ ID NO 13
<211> LENGTH: 7183
<212> TYPE: DNA
<213> ORGANISM: Artificial Sequence
<220> FEATURE:
<223> OTHER INFORMATION: p1-5'3'IL2/d2EGFP-1

<400> SEQUENCE: 13

| | |
|---|---|
| tcgagctcaa gcttcgaatt ctgcaggcgg ccgcgaattc actagtgatg taagcaacag | 60 |
| gtgacaggtt ccccgggcag catctctagg gtctgggcct gccttcactt ctaggagcag | 120 |
| ctggaacagc taatactgag cagtagagct ctgtggctta tgacacatgt ggtagtcagg | 180 |
| cagcgactga ttcatcacc tctccagcca gaaaccccag ctgctgtgtc aaggatgtta | 240 |
| aaaatggaaa gtgcaccaca gctgttggta gctttctccc caagcatctt aagaaactgg | 300 |
| gaggccaacc tttgtaatgc tgccaattat gcaatgctct gtaggggtga accttggccc | 360 |
| caggaactca ttctacaggc ttttagaaac gcggccatgt aaatttctct aatggaaaca | 420 |
| gctggagaaa tagagatgtt gagcccatga ggacatcaaa ggccccactg tgtgaaaag | 480 |
| cccccacaca ggaaaatgtg tgggcctgac tccttccatt ctggaagggg aggcctgagt | 540 |
| tgcttgggct gggatgagat gctgaagatc tgagaagaga caagagca ttgaggctga | 600 |
| gagttattag gtagatgccc ctcacgatgg catgcttaat ctgaaggcac agaaggtgat | 660 |
| gatgactagg agatttgtcc ccatcctgct ttccttcaga catgccaaca gggccactat | 720 |
| gataccagaa gttgtcaagc ttactgcaag atacatgcag agttttttgt tgttttctag | 780 |
| aatactgtcc aatgattgga gaactatccc agaaccattc tcgttctttt gtgagagact | 840 |
| ttaggccaac attccttaca ttgcttagtc ttcctgcttt cactattccc cagcatcaaa | 900 |

```
attacactta aagtaactat ctcaaaactc tttacattgc ccaacatcca acatttctag    960
gatgttatct gtctccatcc aaggatcagg tcaataggaa gacagatggt gtgagagtag   1020
attctggagt cagaacattc tagtttcgaa tcttcaccct acccttttact ggcaataagg  1080 ctgagtaacc tcaatgattt atctaatcta cccacagtgt gcatgtagca gtcaaagaca   1140
acttgtggag tcagtgagaa ctgacttcca cctttatgta agttcaggga tcagagagca   1200
aggtttgtat agcaagcccc ttagtcatct catcaccta catcctcagt tttcaaatct    1260
acaaaatggg gtaggtgtgt ggtgaggctt atgttaatct gtgtatttgc acatattttc   1320 tcccttttcta tgtaccccag gatgttttag atggtagata aatgtctgca taaagactag  1380
accagtacaa gttattagaa atggggacac cacaggcaag ctccctaaga aagaccccgt   1440
ctctaccagt tgatttggaa ctatgttcct actccatcac gcagccagtg tactacacgg   1500
aggataagga atccaatgta tcctattcag gtgacccact gagaacacgt gggatagtcc   1560
ctagctatta ctctcagagt gcccaggtac ttttaggata aacccaaatc tactgaatta   1620 ggggaagaa ggttggcaag atgcctcagt ggtaaaggct aggtagaggc tagtagcaga   1680
ggtaggcaca cagactggat gacttttgtg tttagatttc tgagtcacac aaggtgacag   1740
gagagaagtt actagcaaga gttggtctct gacctccaca ggtgtactgt ggcacacaca   1800
cacacacaca ctcataatac atgtgcacaa atgcatgtac acatacatac acacatgcat   1860
acatgcacac acacacactc atatacacac gcacataaac atgctcacac acacatacat   1920
gtgcacgcac atgcacatac tcatacacac atgaacacat gtgtgtgtac acacgtgaaa   1980
atatttttta aaaatgaaag tgcaactaga gacatataaa ataacaccaa catccttaga   2040
tgcaaccctt cctgagaatt tgttggacat catactcttt ttaaaaagca taataaacat    2100
caagacactt acacaaaata tgttaaatta aatttaaaac aacaacgaca aaatagtacc   2160
tcaagctcaa caagcatttt aggtgtcctt agcttactat ttctctggct aactgtatga   2220
agccatctat caccctgtgt gcaattagct cattgtgtag ataagaaggt aaaaccatct   2280
tgaaacagga aaccaatatc cttcctgtct aatcaacaaa tctaaaagat ttattctttt    2340
catctatctc ctcttgcgtt tgtccaccac aacaggctgc ttacaggttc aggatggttt   2400
tgacaaagag aacatttttca tgagttactt ttgtgtctcc accccaaaga ggaaaatttg   2460
tttcatacag aaggcgttca ttgtatgaat taaaactgcc acctaagtgt gggctaaccc   2520
gaccaagagg gatttcacct aaatccattc agtcagtgta tgggggttta agaaattcc    2580 agagagtcat cagaagagga aaaacaaagg taatgctttc tgccacacag gtagactctt   2640
tgaaaatatg tgtaatatgt aaaacatcgt gacacccca tattattttt ccagcattaa   2700
cagtataaat tgcctcccat gctgaagagc tgcctatcac ccttgctaat cactcctcac   2760
atcgaattcc cgcggccgcc atggcggccg ggagcatgcg acgtcgggcc cgggatccac   2820
cggtcgccac catggtgagc aagggcgagg agctgttcac cggggtggtg cccatcctgg   2880
tcgagctgga cggcgacgta aacggccaca gttcagcgt gtccggcgag ggcgagggcg    2940
atgccaccta cggcaagctg accctgaagt tcatctgcac caccggcaag ctgcccgtgc   3000
cctggcccac cctcgtgacc accctgacct acggcgtgca gtgcttcagc cgctaccccg   3060
accacatgaa gcagcacgac ttcttcaagt ccgccatgcc cgaaggctac gtccaggagc   3120
gcaccatctt cttcaaggac gacggcaact acaagacccg cgccgaggtg aagttcgagg   3180
gcgacaccct ggtgaaccgc atcgagctga agggcatcga cttcaaggag gacggcaaca   3240
tcctggggca caagctggag tacaactaca acagccacaa cgtctatatc atggccgaca   3300
```

```
agcagaagaa cggcatcaag gtgaacttca agatccgcca caacatcgag gacggcagcg    3360
tgcagctcgc cgaccactac cagcagaaca cccccatcgg cgacggcccc gtgctgctgc    3420
ccgacaacca ctacctgagc acccagtccg ccctgagcaa agaccccaac gagaagcgcg    3480
atcacatggt cctgctggag ttcgtgaccg ccgccgggat cactctcggc atggacgagc    3540
tgtacaagaa gcttagccat ggcttcccgc cggaggtgga ggagcaggat gatggcacgc    3600
tgcccatgtc ttgtgcccag gagagcggga tggaccgtca ccctgcagcc tgtgcttctg    3660
ctaggatcaa tgtgtagatg cgcggccgcg ggaattcgat gccctcaata actatgtacc    3720
tcctgcttac aacacataag gctctctatt tatttaaata tttaacttta atttattttt    3780
ggatgtattg tttactatct tttgtaacta ctagtcttca gatgataaat atggatcttt    3840
aaagattctt tttgtaagcc ccaagggctc aaaaatgttt taaactattt atctgaaatt    3900
atttattata ttgaattgtt aaatatcatg tgtaggtaga ctcattaata aaagtattta    3960
gatgattcaa atataaataa gctcagatgt ctgtcatttt taggacagca caaagtaagc    4020
gctaaaataa cttctcagtt attcctgtga actctatctt aaggcgtaaa ttgtaagcgt    4080
taatattttg ttaaaattcg cgttaaattt ttgttaaatc agctcatttt ttaaccaata    4140
ggccgaaatc ggcaaaatcc cttataaatc aaaagaatag accgagatag ggttgagtgt    4200
tgttccagtt tggaacaaga gtccactatt aagaacgtg gactccaacg tcaaagggcg    4260
aaaaaccgtc tatcagggcg atggcccact acgtgaacca tcaccctaat caagtttttt    4320
ggggtcgagg tgccgtaaag cactaaatcg gaaccctaaa gggagccccc gatttagagc    4380
ttgacgggga agccggcga acgtggcgag aaaggaaggg aagaaagcga aaggagcggg    4440
cgctagggcg ctggcaagtg tagcggtcac gctgcgcgta accaccacac ccgccgcgct    4500
taatgcgccg ctacagggcg cgtcaggtgg cacttttcgg ggaaatgtgc gcggaacccc    4560
tatttgttta ttttctaaa tacattcaaa tatgtatccg ctcatgagac aataaccctg    4620
ataaatgctt caataatatt gaaaaaggaa gagtcctgag gcggaaagaa ccagctgtgg    4680
aatgtgtgtc agttagggtg tggaaagtcc ccaggctccc cagcaggcag aagtatgcaa    4740
agcatgcatc tcaattagtc agcaaccagg tgtggaaagt ccccaggctc cccagcaggc    4800
agaagtatgc aaagcatgca tctcaattag tcagcaacca tagtcccgcc cctaactccg    4860
cccatcccgc ccctaactcc gcccagttcc gcccattctc cgccccatgg ctgactaatt    4920
ttttttattt atgcagaggc cgaggccgcc tcggcctctg agctattcca gaagtagtga    4980
ggaggctttt ttggaggcct aggcttttgc aaagatcgat caagagacag gatgaggatc    5040
gtttcgcatg attgaacaag atggattgca cgcaggttct ccggccgctt gggtggagag    5100
gctattcggc tatgactggg cacaacagac aatcggctgc tctgatgccg ccgtgttccg    5160
gctgtcagcg caggggcgcc cggttctttt tgtcaagacc gacctgtccg gtgccctgaa    5220
tgaactgcaa gacgaggcag cgcggctatc gtggctggcc acgacgggcg ttccttgcgc    5280
agctgtgctc gacgttgtca ctgaagcggg aagggactgg ctgctattgg gcgaagtgcc    5340
ggggcaggat ctcctgtcat ctcaccttgc tcctgccgag aaagtatcca tcatggctga    5400
tgcaatgcgg cggctgcata cgcttgatcc ggctacctgc ccattcgacc accaagcgaa    5460
acatcgcatc gagcgagcac gtactcggat ggaagccggt cttgtcgatc aggatgatct    5520
ggacgaagag catcaggggc tcgcgccagc cgaactgttc gccaggctca aggcgagcat    5580
gcccgacggc gaggatctcg tcgtgaccca tggcgatgcc tgcttgccga atatcatggt    5640
ggaaaatggc cgcttttctg gattcatcga ctgtggccgg ctgggtgtgg cggaccgcta    5700
```

| | | | | |
|---|---|---|---|---|
| tcaggacata | gcgttggcta | cccgtgatat | tgctgaagag | cttggcggcg | aatgggctga | 5760 |
| ccgcttcctc | gtgctttacg | gtatcgccgc | tcccgattcg | cagcgcatcg | ccttctatcg | 5820 |
| ccttcttgac | gagttcttct | gagcgggact | ctggggttcg | aaatgaccga | ccaagcgacg | 5880 |
| cccaacctgc | catcacgaga | tttcgattcc | accgccgcct | tctatgaaag | gttgggcttc | 5940 |
| ggaatcgttt | tccgggacgc | cggctggatg | atcctccagc | gcgggatct | catgctggag | 6000 |
| ttcttcgccc | accctagggg | gaggctaact | gaaacacgga | aggagacaat | accggaagga | 6060 |
| acccgcgcta | tgacggcaat | aaaaagacag | aataaaacgc | acggtgttgg | gtcgtttgtt | 6120 |
| cataaacgcg | gggttcggtc | ccagggctgg | cactctgtcg | ataccccacc | gagacccat | 6180 |
| tggggccaat | acgcccgcgt | tcttcctttt | tccccacccc | acccccaag | ttcgggtgaa | 6240 |
| ggcccagggc | tcgcagccaa | cgtcggggcg | gcaggccctg | ccatagcctc | aggttactca | 6300 |
| tatatacttt | agattgattt | aaaacttcat | ttttaattta | aaaggatcta | ggtgaagatc | 6360 |
| cttttgata | atctcatgac | caaaatccct | taacgtgagt | tttcgttcca | ctgagcgtca | 6420 |
| gaccccgtag | aaaagatcaa | aggatcttct | tgagatcctt | ttttctgcg | cgtaatctgc | 6480 |
| tgcttgcaaa | caaaaaaacc | accgctacca | gcggtggttt | gtttgccgga | tcaagagcta | 6540 |
| ccaactcttt | ttccgaaggt | aactggcttc | agcagagcgc | agataccaaa | tactgtcctt | 6600 |
| ctagtgtagc | cgtagttagg | ccaccacttc | aagaactctg | tagcaccgcc | tacatacctc | 6660 |
| gctctgctaa | tcctgttacc | agtggctgct | gccagtggcg | ataagtcgtg | tcttaccggg | 6720 |
| ttggactcaa | gacgatagtt | accggataag | gcgcagcggt | cgggctgaac | ggggggttcg | 6780 |
| tgcacacagc | ccagcttgga | gcgaacgacc | tacaccgaac | tgagatacct | acagcgtgag | 6840 |
| ctatgagaaa | gcgccacgct | tcccgaaggg | agaaaggcgg | acaggtatcc | ggtaagcggc | 6900 |
| agggtcggaa | caggagagcg | cacgagggag | cttccagggg | gaaacgcctg | gtatctttat | 6960 |
| agtcctgtcg | ggtttcgcca | cctctgactt | gagcgtcgat | ttttgtgatg | ctcgtcaggg | 7020 |
| gggcggagcc | tatggaaaaa | cgccagcaac | gcggcctttt | tacggttcct | ggccttttgc | 7080 |
| tggccttttg | ctcacatgtt | ctttcctgcg | ttatcccctg | attctgtgga | taaccgtatt | 7140 |
| accgccatgc | attagttatt | actagcgcta | ccggactcag | atc | | 7183 |

```
<210> SEQ ID NO 14
<211> LENGTH: 5916
<212> TYPE: DNA
<213> ORGANISM: Artificial Sequence
<220> FEATURE:
<223> OTHER INFORMATION: p1-3'TNFalfa/d1EGFP-N1

<400> SEQUENCE: 14
```

| | | | | |
|---|---|---|---|---|
| taatagtaat | caattacggg | gtcattagtt | catagcccat | atatggagtt | ccgcgttaca | 60 |
| taacttacgg | taaatggccc | gcctggctga | ccgcccaacg | acccccgccc | attgacgtca | 120 |
| ataatgacgt | atgttcccat | agtaacgcca | atagggactt | tccattgacg | tcaatgggtg | 180 |
| gagtatttac | ggtaaactgc | ccacttggca | gtacatcaag | tgtatcatat | gccaagtacg | 240 |
| ccccctattg | acgtcaatga | cggtaaatgg | cccgcctggc | attatgccca | gtacatgacc | 300 |
| ttatgggact | ttcctacttg | gcagtacatc | tacgtattag | tcatcgctat | taccatggtg | 360 |
| atgcggtttt | ggcagtacat | caatgggcgt | ggatagcggt | ttgactcacg | ggatttccaa | 420 |
| gtctccaccc | cattgacgtc | aatgggagt | ttgttttggc | accaaaatca | acgggacttt | 480 |
| ccaaaatgtc | gtaacaactc | cgccccattg | acgcaaatgg | gcggtaggcg | tgtacggtgg | 540 |
| gaggtctata | taagcagagc | tggtttagtg | aaccgtcaga | tccgctagcg | ctaccggact | 600 |

-continued

```
cagatctcga gctcaagctt cgaattctgc agtcgacggt accgcgggcc cgggatccac     660
cggtcgccac catggtgagc aagggcgagg agctgttcac cggggtggtg cccatcctgg     720
tcgagctgga cggcgacgta acggccaca  agttcagcgt gtccggcgag ggcgagggcg     780
atgccaccta cggcaagctg acctgaagt  tcatctgcac caccggcaag ctgcccgtgc     840
cctggcccac cctcgtgacc accctgacct acggcgtgca gtgcttcagc cgctaccccg     900
accacatgaa gcagcacgac ttcttcaagt ccgccatgcc cgaaggctac gtccaggagc     960
gcaccatctt cttcaaggac gacggcaact acaagacccg cgccgaggtg aagttcgagg    1020
gcgacaccct ggtgaaccgc atcgagctga agggcatcga cttcaaggag gacggcaaca    1080
tcctggggca caagctggag tacaactaca acagccacaa cgtctatatc atggccgaca    1140
agcagaagaa cggcatcaag gtgaacttca gatccgcca  caacatcgag gacggcagcg    1200
tgcagctcgc cgaccactac cagcagaaca cccccatcgg cgacggcccc gtgctgctgc    1260
ccgacaacca ctacctgagc acccagtccg ccctgagcaa agaccccaac gagaagcgcg    1320
atcacatggt cctgctggag ttcgtgaccg ccgccgggat cactctcggc atggacgagc    1380
tgtacaagaa gcttagccat ggcttcccgc cggcggtggc ggcgcaggat gatggcacgc    1440
tgcccatgtc ttgtgcccag gagagcggga tggaccgtca ccctgcagcc tgtgcttctg    1500
ctaggatcaa tgtgtagatg cgcggccgcc agtgtgctgg aattcggctg aagggaatgg    1560
gtgttcatcc attctctacc cagcccccac tctgacccct ttactctgac ccctttattg    1620
tctactcctc agagccccca gtctgtgtcc ttctaactta gaaggggat  tatggctcag    1680 agtccaactc tgtgctcaga gctttcaaca actactcaga aacacaagat gctgggacag    1740
tgacctggac tgtgggcctc tcatgcacca ccatcaagga ctcaaatggg cttt ccgaat   1800 tcactggagc ctcgaatgtc cattcctgag ttctgcaaag ggagagtggt caggttgcct    1860
ctgtctcaga atgaggctgg ataagatctc aggccttcct accttcagac ctttccagac    1920
tcttccctga ggtgcaatgc acagccttcc tcacagagcc agccccctc  tatttatatt    1980 tgcacttatt atttattatt tatttattat ttatttattt gcttatgaat gtatttattt    2040
ggaaggccgg ggtgtcctgg aggacccagt gtgggaagct gtcttcagac agacatgttt    2100
tctgtgaaaa cggagctgag ctgtccccac ctggcctctc taccttgttg cctcctcttt    2160
tgcttatgtt taaaacaaaa tatttatcta acccaattgt cttaataacg ctgatttggt    2220
gaccaggctg tcgctacatc actgaacctc tgctccccac gggagccgtg actgtaattg    2280
ccctacagtc aattgagaga aataaagatc gcttggaaaa gaaatgtgat ttctgtcttg    2340
ggatgaagtc tgcatccatc tctttgcgga ggcctaaagt ctctgggtcc agatctcagt    2400
ctttataccc ctgggccatt aagaccccca agaccccgt  ggaacaaaag gcagccaaca    2460
tccctacctc tcccccggaa acaggagcct aaccctaatt acctttgccc tggggcatgg    2520
gaatttccca ctctgggaat tcttaagccg aattctgcag atatccatca cactggcggc    2580
cgcgactcta gatcataatc agccatacca catttgtaga ggttttactt gctttaaaaa    2640
acctcccaca cctcccctg  aacctgaaac ataaaatgaa tgcaattgtt gttgttaact    2700
tgtttattgc agcttataat ggttacaaat aaagcaatag catcacaaat ttcacaaata    2760
aagcattttt ttcactgcat tctagttgtg gtttgtccaa actcatcaat gtatcttaag    2820
gcgtaaattg taagcgttaa tattttgtta aaattcgcgt taaattttg  ttaaatcagc    2880 tcatttttta accataggc  cgaaatcggc aaaatccctt ataaatcaaa agaatagacc    2940
gagatagggt tgagtgttgt tccagtttgg aacaagagtc cactattaaa gaacgtggac    3000
```

```
tccaacgtca aagggcgaaa aaccgtctat cagggcgatg ccccactacg tgaaccatca   3060
ccctaatcaa gttttttggg gtcgaggtgc cgtaaagcac taaatcggaa ccctaaaggg   3120
agcccccgat ttagagcttg acggggaaag ccggcgaacg tggcgagaaa ggaagggaag   3180
aaagcgaaag gagcgggcgc tagggcgctg gcaagtgtag cggtcacgct gcgcgtaacc   3240
accacacccg ccgcgcttaa tgcgccgcta cagggcgcgt caggtggcac ttttcgggga   3300
aatgtgcgcg gaacccctat tgtttatttt tctaaatac attcaaatat gtatccgctc    3360
atgagacaat aaccctgata aatgcttcaa taatattgaa aaggaagag tcctgaggcg    3420
gaaagaacca gctgtggaat gtgtgtcagt tagggtgtgg aaagtcccca ggctccccag   3480
caggcagaag tatgcaaagc atgcatctca attagtcagc aaccaggtgt ggaaagtccc   3540
caggctcccc agcaggcaga agtatgcaaa gcatgcatct caattagtca gcaaccatag   3600
tcccgcccct aactccgccc atcccgcccc taactccgcc cagttccgcc cattctccgc   3660
cccatggctg actaattttt ttatttatg cagaggccga ggcgcctcg gcctctgagc    3720
tattccagaa gtagtgagga ggcttttttg gaggcctagg cttttgcaaa gatcgatcaa   3780
gagacaggat gaggatcgtt tcgcatgatt gaacaagatg gattgcacgc aggttctccg   3840
gccgcttggg tggagaggct attcggctat gactgggcac aacagacaat cggctgctct   3900
gatgccgccg tgttccggct gtcagcgcag gggcgcccgg ttcttttgt caagaccgac    3960
ctgtccggtg ccctgaatga actgcaagac gaggcagcgc ggctatcgtg gctggccacg   4020
acgggcgttc cttgcgcagc tgtgctcgac gttgtcactg aagcgggaag gactggctg    4080
ctattgggcg aagtgccggg gcaggatctc ctgtcatctc accttgctcc tgccgagaaa   4140
gtatccatca tggctgatgc aatgcggcgg ctgcatacgc ttgatccggc tacctgccca   4200
ttcgaccacc aagcgaaaca tcgcatcgag cgagcacgta ctcggatgga agccggtctt   4260
gtcgatcagg atgatctgga cgaagagcat caggggctcg cgccagccga actgttcgcc   4320
aggctcaagg cgagcatgcc cgacggcgag gatctcgtcg tgacccatgg cgatgcctgc   4380
ttgccgaata tcatggtgga aaatggccgc ttttctggat tcatcgactg tggccggctg   4440
ggtgtggcgg accgctatca ggacatagcg ttggctaccc gtgatattgc tgaagagctt   4500
ggcggcgaat gggctgaccg cttcctcgtg ctttacggta tcgccgctcc cgattcgcag   4560
cgcatcgcct tctatcgcct tcttgacgag ttcttctgag cgggactctg ggttcgaaa    4620
tgaccgacca agcgacgccc aacctgccat cacgagattt cgattccacc gccgccttct   4680
atgaaaggtt gggcttcgga atcgttttcc gggacgccgg ctggatgatc ctccagcgcg   4740
gggatctcat gctggagttc ttcgcccacc ctagggggag gctaactgaa acacggaagg   4800
agacaatacc ggaaggaacc cgcgctatga cggcaataaa aagacagaat aaaacgcacg   4860
gtgttgggtc gtttgttcat aaacgcgggg ttcggtccca gggctggcac tctgtcgata   4920
ccccaccgag accccattgg ggccaatacg cccgcgtttc ttccttttcc caccccacc    4980
ccccaagttc gggtgaaggc ccagggctcg cagccaacgt cggggcggca ggccctgcca   5040
tagcctcagg ttactcatat atactttaga ttgatttaaa acttcatttt taatttaaaa   5100
ggatctaggt gaagatcctt tttgataatc tcatgaccaa aatcccttaa cgtgagtttt   5160
cgttccactg agcgtcagac cccgtagaaa agatcaaagg atcttcttga tccttttttt   5220
ttctgcgcgt aatctgctgc ttgcaaacaa aaaaaccacc gctaccagcg tggtttgtt    5280
tgccggatca agagctacca actctttttc cgaaggtaac tggcttcagc agagcgcaga   5340
taccaaatac tgtccttcta gtgtagccgt agttaggcca ccacttcaag aactctgtag   5400
```

```
caccgcctac atacctcgct ctgctaatcc tgttaccagt ggctgctgcc agtggcgata    5460
agtcgtgtct taccggggttg gactcaagac gatagttacc ggataaggcg cagcggtcgg    5520
gctgaacggg gggttcgtgc acacagccca gcttggagcg aacgacctac accgaactga    5580
gatacctaca gcgtgagcta tgagaaagcg ccacgcttcc cgaagggaga aaggcggaca    5640
ggtatccggt aagcggcagg gtcggaacag gagagcgcac gagggagctt ccagggggaa    5700
acgcctggta tctttatagt cctgtcgggt ttcgccacct ctgacttgag cgtcgatttt    5760
tgtgatgctc gtcagggggg cggagcctat ggaaaaacgc cagcaacgcg cctttttac    5820 ggttcctggc cttttgctgg cctttgctc acatgttctt tcctgcgtta tccctgatt    5880 ctgtggataa ccgtattacc gccatgcatt agttat                             5916

<210> SEQ ID NO 15
<211> LENGTH: 5841
<212> TYPE: DNA
<213> ORGANISM: Artificial Sequence
<220> FEATURE:
<223> OTHER INFORMATION: p2-3'TNFalfa/EGFP-F

<400> SEQUENCE: 15
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
atttccaagt ctccacccca ttgacgtcaa tgggagtttg ttttggcacc aaaatcaacg     480
ggactttcca aaatgtcgta acaactccgc cccattgacg caaatgggcg gtaggcgtgt     540
acggtgggag gtctatataa gcagagctgg tttagtgaac cgtcagatcc gctagcgcta     600
ccggtcgcca ccatggtgag caagggcgag gagctgttca ccggggtggt gcccatcctg     660
gtcgagctgg acggcgacgt aaacggccac aagttcagcg tgtccggcga gggcgagggc     720
gatgccacct acggcaagct gaccctgaag ttcatctgca ccaccggcaa gctgcccgtg     780
ccctggccca ccctcgtgac caccctgacc tacggcgtgc agtgcttcag ccgctacccc     840
gaccacatga agcagcacga cttcttcaag tccgccatgc ccgaaggcta cgtccaggag     900
cgcaccatct tcttcaagga cgacggcaac tacaagaccc gcgccgaggt gaagttcgag     960
ggcgacaccc tggtgaaccg catcgagctg aagggcatcg acttcaagga ggacggcaac    1020
atcctggggc acaagctgga gtacaactac aacagccaca acgtctatat catggccgac    1080
aagcagaaga acggcatcaa ggtgaacttc aagatccgcc acaacatcga ggacggcagc    1140
gtgcagctcg ccgaccacta ccagcagaac acccccatcg gcgacggccc cgtgctgctg    1200
cccgacaacc actacctgag cacccagtcc gccctgagca agacccccaa cgagaagcgc    1260
gatcacatgg tcctgctgga gttcgtgacc gccgccggga tcactctcgg catggacgag    1320
ctgtacaagt ccggactcag atctaagctg aaccctcctg atgagagtgg ccccggctgc    1380
atgagctgca gtgtgtgct ctcctgagga tccagatctc gagctcaagc ttggtaccga    1440
gctcggatcc actagtaacg gccgccagtg tgctggaatt cggctgaagg gaatgggtgt    1500
tcatccattc tctacccagc ccccactctg accccttac tctgacccct ttattgtcta    1560
```

```
ctcctcagag ccccccagtct gtgtccttct aacttagaaa ggggattatg gctcagagtc      1620
caactctgtg ctcagagctt tcaacaacta ctcagaaaca caagatgctg ggacagtgac      1680
ctggactgtg ggcctctcat gcaccaccat caaggactca aatgggcttt ccgaattcac      1740
tggagcctcg aatgtccatt cctgagttct gcaaagggag agtggtcagg ttgcctctgt      1800
ctcagaatga ggctggataa gatctcaggc cttcctacct tcagaccttt ccagactctt      1860
ccctgaggtc caatgcacag ccttcctcac agagccagcc cccctctatt tatatttgca      1920
cttattattt attatttatt tattatttat ttatttgctt atgaatgtat ttatttggaa      1980
ggccggggtc tcctggagga cccagtgtgg gaagctgtct tcagacagac atgttttctg      2040
tgaaaacgga gctgagctgt ccccacctgg cctctctacc ttgttgcctc ctcttttgct      2100
tatgtttaaa acaaaatatt tatctaaccc aattgtctta ataacgctga tttggtgacc      2160
aggctgtcgc tacatcactg aacctctgct ccccacggga gccgtgactg taattgccct      2220
acagtcaatt gagagaaata aagatcgctt ggaaaagaaa tgtgatttct gtcttgggat      2280
gaagtctgca tccatctctt tgcggaggcc taaagtctct gggtccagat ctcagtcttt      2340 ataccccctgg gccattaaga cccccaagac ccccgtggaa caaaaggcag ccaacatccc      2400
tacctctccc ccggaaacag gagcctaacc ctaattacct ttgccctggg gcatgggaat      2460
ttcccactct gggaattctt aagccgaatt ctgcagatgg gatccaccgg atctagataa      2520
ctgatcataa tcagccatac cacatttgta gaggttttac ttgctttaaa aaacctccca      2580
cacctccccc tgaacctgaa acataaaatg aatgcaattg ttgttgttaa cttgtttatt      2640
gcagcttata atggttacaa ataaagcaat agcatcacaa atttcacaaa taagcatttt      2700
ttttcactgc attctagttg tggttttgtcc aaactcatca atgtatctta acgcgtaaat      2760
tgtaagcgtt aatattttgt taaaattcgc gttaaatttt tgttaaatca gctcattttt      2820
taaccaatag gccgaaatcg gcaaaatccc ttataaatca aaagaataga ccgagatagg      2880
gttgagtgtt gttccagttt ggaacaagag tccactatta aagaacgtgg actccaacgt      2940
caaagggcga aaaccgtctg atcagggcga tgcccactac gtgaaccatc accctaatc      3000 aagttttttg gggtcgaggt gccgtaaagc actaaatcgg aacctaaaag ggagccccccg      3060 atttagagct tgacggggaa agccggcgaa cgtggcgaga aggaaggga agaaagcgaa      3120 aggagcgggc gctagggcgc tggcaagtgt agcggtcacg ctgcgcgtaa ccaccacacc      3180
cgccgcgctt aatgcgccgc tacagggcgc gtcaggtggc acttttcggg gaaatgtgcg      3240
cggaacccct atttgtttat ttttctaaat acattcaaat atgtatccgc tcatgagaca      3300
ataaccctga taaatgcttc aataatattg aaaaaggaag agtcctgagg cggaaagaac      3360
cagctgtgga atgtgtgtca gttagggtgt ggaaagtccc caggctcccc agcaggcaga      3420
agtatgcaaa gcatgcatct caattagtca gcaaccaggt gtggaaagtc cccaggctcc      3480
ccagcaggca gaagtatgca aagcatgcat ctcaattagt cagcaaccat agtcccgccc      3540
ctaactccgc ccatcccgcc cctaactccg cccagttccg cccattctcc gccccatggc      3600
tgactaattt tttttattta tgcagaggcc gaggccgcct cggcctctga gctattccag      3660
aagtagtgag gaggcttttt tggaggccta ggcttttgca aagatcgatc aagagacagg      3720
atgaggatcg tttcgcatga ttgaacaaga tggattgcac gcaggttctc cggccgcttg      3780
ggtggagagg ctattcggct atgactgggc acaacagaca atcggctgct ctgatgccgc      3840
cgtgttccgg ctgtcagcgc aggggcgccc ggttcttttt gtcaagaccg acctgtccgg      3900
tgccctgaat gaactgcaag acgaggcagc gcggctatcg tggctggcca cgacgggcgt      3960
```

```
tccttgcgca gctgtgctcg acgttgtcac tgaagcggga agggactggc tgctattggg   4020
cgaagtgccg gggcaggatc tcctgtcatc tcaccttgct cctgccgaga aagtatccat   4080
catggctgat gcaatgcggc ggctgcatac gcttgatccg gctacctgcc cattcgacca   4140
ccaagcgaaa catcgcatcg agcgagcacg tactcgatg  gaagccggtc ttgtcgatca   4200
ggatgatctg gacgaagagc atcaggggct cgcgccagcc gaactgttcg ccaggctcaa   4260
ggcgagcatg cccgacggcg aggatctcgt cgtgacccat ggcgatgcct gcttgccgaa   4320
tatcatggtg gaaaatggcc gcttttctgg attcatcgac tgtggccggc tgggtgtggc   4380
ggaccgctat caggacatag cgttggctac ccgtgatatt gctgaagagc ttggcggcga   4440
atgggctgac cgcttcctcg tgctttacgg tatcgccgct cccgattcgc agcgcatcgc   4500
cttctatcgc cttcttgacg agttcttctg agcgggactc tggggttcga atgaccgac   4560
caagcgacgc ccaacctgcc atcacgagat ttcgattcca ccgccgcctt ctatgaaagg   4620
ttgggcttcg gaatcgtttt ccgggacgcc ggctggatga tcctccagcg cggggatctc   4680
atgctggagt tcttcgccca ccctaggggg aggctaactg aaacacggaa ggagacaata   4740
ccggaaggaa cccgcgctat gacggcaata aaaagacaga ataaaacgca cggtgttggg   4800
tcgtttgttc ataaacgcgg ggttcggtcc cagggctggc actctgtcga taccccaccg   4860
agacccatt  ggggccaata cgcccgcgtt tcttccttt  ccccacccca ccccccaagt   4920
tcgggtgaag gcccagggct cgcagccaac gtcggggcgg caggccctgc catagcctca   4980
ggttactcat atatacttta gattgattta aaacttcatt tttaatttaa aaggatctag   5040
gtgaagatcc ttttttgataa tctcatgacc aaaatccctt aacgtgagtt ttcgttccac   5100
tgagcgtcag accccgtaga aaagatcaaa ggatcttctt gagatccttt ttttctgcgc   5160
gtaatctgct gcttgcaaac aaaaaaacca ccgctaccag cggtggtttg tttgccggat   5220
caagagctac caactctttt tccgaaggta actggcttca gcagagcgca gataccaaat   5280
actgtccttc tagtgtagcc gtagttaggc caccacttca agaactctgt agcaccgcct   5340
acatacctcg ctctgctaat cctgttacca gtggctgctg ccagtggcga taagtcgtgt   5400
cttaccgggt tggactcaag acgatagtta ccggataagg cgcagcggtc gggctgaacg   5460
gggggttcgt gcacacagcc cagcttggag cgaacgacct acaccgaact gagataccta   5520
cagcgtgagc tatgagaaag cgccacgctt cccgaaggga gaaaggcgga caggtatccg   5580
gtaagcggca gggtcggaac aggagagcgc acgagggagc ttccaggggg aaacgcctgg   5640
tatctttata gtcctgtcgg gtttcgccac ctctgacttg agcgtcgatt tttgtgatgc   5700
tcgtcagggg gcggagccta tggaaaaac  gccagcaacg cggcctttt  acggttcctg   5760
gccttttgct ggccttttgc tcacatgttc tttcctgcgt tatcccctga ttctgtggat   5820
aaccgtatta ccgccatgca t                                               5841
```

<210> SEQ ID NO 16  
<211> LENGTH: 5792  
<212> TYPE: DNA  
<213> ORGANISM: Artificial Sequence  
<220> FEATURE:  
<223> OTHER INFORMATION: p3-3'TNFalfa/EGFP-F

<400> SEQUENCE: 16

```
tagttattaa tagtaatcaa ttacggggtc attagttcat agcccatata tggagttccg    60
cgttacataa cttacggtaa atggcccgcc tggctgaccg cccaacgacc cccgcccatt   120
gacgtcaata atgacgtatg ttcccatagt aacgccaata gggactttcc attgacgtca   180
```

-continued

| | |
|---|---|
| atgggtggag tatttacggt aaactgccca cttggcagta catcaagtgt atcatatgcc | 240 |
| aagtacgccc cctattgacg tcaatgacgg taaatggccc gcctggcatt atgcccagta | 300 |
| catgacctta tgggactttc ctacttggca gtacatctac gtattagtca tcgctattac | 360 |
| catggtgatg cggttttggc agtacatcaa tgggcgtgga tagcggtttg actcacgggg | 420 |
| atttccaagt ctccacccca ttgacgtcaa tgggagtttg ttttggcacc aaaatcaacg | 480 |
| ggactttcca aaatgtcgta acaactccgc cccattgacg caaatgggcg gtaggcgtgt | 540 |
| acggtgggag gtctatataa gcagagctgg tttagtgaac cgtcagatcc gctagcgcta | 600 |
| ccggtcgcca ccatggtgag caagggcgag gagctgttca ccggggtggt gcccatcctg | 660 |
| gtcgagctgg acggcgacgt aaacggccac aagttcagcg tgtccggcga gggcgagggc | 720 |
| gatgccacct acggcaagct gaccctgaag ttcatctgca ccaccggcaa gctgcccgtg | 780 |
| ccctggccca ccctcgtgac caccctgacc tacggcgtgc agtgcttcag ccgctacccc | 840 |
| gaccacatga agcagcacga cttcttcaag tccgccatgc ccgaaggcta cgtccaggag | 900 |
| cgcaccatct tcttcaagga cgacggcaac tacaagaccc gcgccgaggt gaagttcgag | 960 |
| ggcgacaccc tggtgaaccg catcgagctg aagggcatcg acttcaagga ggacggcaac | 1020 |
| atcctggggc acaagctgga gtacaactac aacagccaca acgtctatat catggccgac | 1080 |
| aagcagaaga acggcatcaa ggtgaacttc aagatccgcc acaacatcga ggacggcagc | 1140 |
| gtgcagctcg ccgaccacta ccagcagaac acccccatcg gcgacggccc cgtgctgctg | 1200 |
| cccgacaacc actacctgag cacccagtcc gccctgagca agacccccaa cgagaagcgc | 1260 |
| gatcacatgg tcctgctgga gttcgtgacc gccgccggga tcactctcgg catggacgag | 1320 |
| ctgtacaagt ccggactcag atctaagctg aaccctcctg atgagagtgg ccccggctgc | 1380 |
| atgagctgca agtgtgtgct ctcctgagga tccagatctc gagctcaagc ttggtaccga | 1440 |
| gctcggatcc actagtaacg gccgccagtg tgctggaatt cggctgaagg gaatgggtgt | 1500 |
| tcatccattc tctacccagc ccccactctg acccctttac tctgacccct ttattgtcta | 1560 |
| ctcctcagag cccccagtct gtgtccttct aacttagaaa ggggattatg gctcagagtc | 1620 |
| caactctgtg ctcagagctt tcaacaacta ctcagaaaca caagatgctg ggacagtgac | 1680 |
| ctggactgtg ggcctctcat gcaccaccat caaggactca aatgggcttt ccgaattcac | 1740 |
| tggagcctcg aatgtccatt cctgagttct gcaaagggag agtggtcagg ttgcctctgt | 1800 |
| ctcagaatga ggctggataa gatctcaggc cttcctacct tcagaccttt ccagactctt | 1860 |
| ccctgaggtc aatgcacag ccttcctcac agagccagcc cccctctatt tatatttgca | 1920 |
| cttattattt attatttatt tattatttat ttatttgctt atgaatgtat ttatttggaa | 1980 |
| ggccggggtg tcctggagga cccagtgtgg gaagctgtct tcagacagac atgttttctg | 2040 |
| tgaaaacgga gctgagctgt ccccacctgg cctctctacc ttgttgcctc ctcttttgct | 2100 |
| tatgtttaaa acaaaatatt tatctaaccc aattgtctta ataacgctga tttggtgacc | 2160 |
| aggctgtcgc tacatcactg aacctctgct ccccacggga gccgtgactg taattgccct | 2220 |
| acagtcaatt gagagaaata aagatcgctt ggaaaagaaa tgtgatttct gtcttgggat | 2280 |
| gaagtctgca tccatctctt tgcggaggcc taaagtctct gggtccagat ctcagtcttt | 2340 |
| atacccctgg gccattaaga cccccaagac ccccgtggaa caaaggcag ccaacatccc | 2400 |
| tacctctccc ccggaaacag gagcctaacc ctaattacct ttgccctggg gcatgggaat | 2460 |
| ttcccactct gggaattctt aagccgaatt ctgcagatgg gatccaccgg atctagataa | 2520 |
| ctgatcataa tcagccatac cacatttgta gaggttttac ttgctttaaa aaacctccca | 2580 |

```
cacctccccc tgaacctgaa acataaaatg aatgcaattg ttgttgttga cggtaccgcg    2640
ggcccgggat ccaccggatc tagataactg atcataatca gccataccac atttgtagag    2700
gttttacttg ctttaagcgt taatattttg ttaaaattcg cgttaaattt ttgttaaatc    2760
agctcatttt ttaaccaata ggccgaaatc ggcaaaatcc cttataaatc aaaagaatag    2820
accgagatag ggttgagtgt tgttccagtt tggaacaaga gtccactatt aaagaacgtg    2880
gactccaacg tcaagggcg aaaaaccgtc tatcagggcg atggcccact acgtgaacca    2940
tcaccctaat caagtttttt ggggtcgagg tgccgtaaag cactaaatcg gaaccctaaa    3000
gggagccccc gatttagagc ttgacgggga aagccggcga acgtggcgag aaaggaaggg    3060
aagaaagcga aaggagcggg cgctagggcg ctggcaagtg tagcggtcac gctgcgcgta    3120
accaccacac ccgccgcgct taatgcgccg ctacagggcg cgtcaggtgg cacttttcgg    3180
ggaaatgtgc gcggaacccc tatttgttta ttttttctaaa tacattcaaa tatgtatccg    3240
ctcatgagac aataaccctg ataaatgctt caataatatt gaaaaaggaa gagtcctgag    3300
gcggaaagaa ccagctgtgg aatgtgtgtc agttagggtg tggaaagtcc ccaggctccc    3360
cagcaggcag aagtatgcaa agcatgcatc tcaattagtc agcaaccagg tgtggaaagt    3420
ccccaggctc cccagcaggc agaagtatgc aaagcatgca tctcaattag tcagcaacca    3480
tagtcccgcc cctaactccg cccatcccgc cctaactccg cccagttccg cccattctc    3540 cgccccatgg ctgactaatt ttttttattt atgcagaggc cgaggccgcc tcggcctctg    3600
agctattcca gaagtagtga ggaggctttt ttggaggcct aggcttttgc aaagatcgat    3660
caagagacag gatgaggatc gtttcgcatg attgaacaag atggattgca cgcaggttct    3720
ccggccgctt gggtggagag gctattcggc tatgactggg cacaacagac aatcggctgc    3780
tctgatgccg ccgtgttccg gctgtcagcg caggggcgcc cggttcttt tgtcaagacc    3840 gacctgtccg gtgccctgaa tgaactgcaa gacgaggcag cgcggctatc gtggctggcc    3900
acgacgggcg ttccttgcgc agctgtgctc gacgttgtca ctgaagcggg aagggactgg    3960
ctgctattgg gcgaagtgcc ggggcaggat ctcctgtcat ctcaccttgc tcctgccgag    4020
aaagtatcca tcatggctga tgcaatgcgg cggctgcata cgcttgatcc ggctacctgc    4080
ccattcgacc accaagcgaa acatcgcatc gagcgagcac gtactcggat ggaagccggt    4140
cttgtcgatc aggatgatct ggacgaagag catcaggggc tcgcgccagc cgaactgttc    4200
gccaggctca aggcgagcat gcccgacggc gaggatctcg tcgtgaccca tggcgatgcc    4260
tgcttgccga atatcatggt ggaaaatggc cgcttttctg gattcatcga ctgtggccgg    4320
ctgggtgtgg cggaccgcta tcaggacata gcgttggcta cccgtgatat tgctgaagag    4380
cttggcggcg aatgggctga ccgcttcctc gtgctttacg gtatcgccgc tcccgattcg    4440
cagcgcatcg ccttctatcg ccttcttgac gagttcttct gagcgggact ctggggttcg    4500
aaatgaccga ccaagcgacg cccaacctgc catcacgaga tttcgattcc accgccgcct    4560
tctatgaaag gttgggcttc ggaatcgttt tccgggacgc cggctggatg atcctccagc    4620
gcggggatct catgctggag ttcttcgccc accctagggg gaggctaact gaaacacgga    4680
aggagacaat accggaagga acccgcgcta tgacggcaat aaaaagacag aataaaacgc    4740
acggtgttgg gtcgtttgtt cataaacgcg gggttcggtc ccaggctggc actctgtcg    4800 atacccccacc gagacccat tggggccaat acgcccgcgt ttcttccttt tccccacccc    4860
accccccaag ttcgggtgaa ggcccagggc tcgcagccaa cgtcgggcg gcaggccctg    4920 ccatagcctc aggttactca tatatacttt agattgattt aaaacttcat ttttaattta    4980
```

```
aaaggatcta ggtgaagatc cttttttgata atctcatgac caaaatccct taacgtgagt    5040
tttcgttcca ctgagcgtca gacccccgtag aaaagatcaa aggatcttct tgagatcctt    5100
tttttctgcg cgtaatctgc tgcttgcaaa caaaaaaacc accgctacca gcggtggttt    5160
gtttgccgga tcaagagcta ccaactcttt ttccgaaggt aactggcttc agcagagcgc    5220
agataccaaa tactgtcctt ctagtgtagc cgtagttagg ccaccacttc aagaactctg    5280
tagcaccgcc tacatacctc gctctgctaa tcctgttacc agtggctgct gccagtggcg    5340
ataagtcgtg tcttaccggg ttggactcaa gacgatagtt accggataag cgcagcggt    5400 cgggctgaac ggggggttcg tgcacacagc ccagcttgga gcgaacgacc tacaccgaac    5460
tgagatacct acagcgtgag ctatgagaaa gcgccacgct tcccgaaggg agaaaggcgg    5520
acaggtatcc ggtaagcggc agggtcggaa caggagagcg cacgagggag cttccagggg    5580
gaaacgcctg gtatctttat agtcctgtcg ggtttcgcca cctctgactt gagcgtcgat    5640
ttttgtgatg ctcgtcaggg gggcggagcc tatggaaaaa cgccagcaac gcggcctttt    5700
tacggttcct ggccttttgc tggccttttg ctcacatgtt ctttcctgcg ttatcccctg    5760
attctgtgga taaccgtatt accgccatgc at                                  5792

<210> SEQ ID NO 17
<211> LENGTH: 6777
<212> TYPE: DNA
<213> ORGANISM: Artificial Sequence
<220> FEATURE:
<223> OTHER INFORMATION: p1-5'TNFalfa/d1EGFP-N1

<400> SEQUENCE: 17
tagttattaa tgtgagttag ctcactcatt aggcacccca ggctttacac tttatgcttc      60
cggctcgtat gttgtgtgga attgtgagcg gataacaatt tcacacagga aacagctatg     120
accatgatta cgccaagcta tttaggtgac actatagaat actcaagcta tgcatcaagc     180
ttggtaccga gctcggatcc actagtaacg gccgccagtg tgctggaatt cgcccttttc     240
tctggagaaa gctgctcccc cagggccatt cccactccca tctacctggc acacgaggtc     300 cagctcttt cctcccaata cccccttcat gtgcctctcc tcagtgcgca gaagtctgtg     360
tatccgggac ttcaaggacc gtgggtgcgc tcaatgtacc aggggggctgt gttcctgctc     420 agtaagggag accagctgtc cacccacacc gacggcatct cccatctaca cttcagcccc     480
agcagtgtat tctttggagc ctttgcactg tagattctaa agaaacccaa gaattggatt     540
ccaggcctcc atcctgaccg ttgtttcaag ggtcacatcc ccacagtctc cagccttccc     600
cactaaaata acctggagct ctcacgggag tctgagacac ttcaggggac tacatcttcc     660
ccagggccac tccagatgct cagggacga ctcaagccta cctagaagtt cctgcacaga     720
gcagggtttt tgtgggtcta ggtcggacag agacctggac atgaaggagg gacagacatg     780
ggagaggtgg ctgggaacag gggaaggttg actatttatg gagagaaaag ttaagttatt     840
tatttataga gaatagaaag aggggaaaaa tagaaagccg tcagatgaca actaggtccc     900
agacacaaag gtgtctcacc tcagacagga cccatctaag agagagatgg cgagagaatt     960
agatgtgggt gaccaagggg ttctagaaga aagcacgaag ctctaaaagc cagccactgc    1020
ttggctagac atccacaggg accccctgca ccatctgtga aacccaataa acctctttcc    1080
tctgagattc tgtctgcttg tgtctgtctt gcgttggggg agaaacttcc tggtctcttt    1140
aaggagtgga gcaggggaca gaggcctcag ttggtccatg ggatccgggc agagcaaaga    1200
gacatgagga gcaggcagct cccagagaca tggtggattc acgggagtga ggcagcttaa    1260
```

```
ctgccgagag acccaaagga tgagctaggg agatccatcc aagggtggag agagatgagg    1320
gttctgggga gaagtgactc cactggaggg tgggagagtg tttaggagtg ggagggtggg    1380 ggagggggaat ccttggaaga ccggggagtc atacggattg ggagaaatcc tggaagcagg    1440
gctgtgggac ctaaatgtct gagttgatgt accgcagtca agatatggca gaggctccgt    1500
ggaaaactca cttgggagca gggacccaaa gcagcagcct gagctcatga tcagagtgaa    1560
aggagaaggc ttgtgaggtc cgtgaattcc cagggctgag ttcattccct ctggggctgc    1620
cccatactca tcccattacc cccccacca gccctcccaa agcccatgca cacttcccaa    1680
ctctcaagct gctctgcctt cagccacttc ctccaagaac tcaaacaggg ggctttccct    1740
cctcaatatc atgtctcccc ccttatgcac ccagctttca gaagcacccc cccatgctaa    1800
gttctccccc atggatgtcc catttagaaa tcaaaaggaa atagaacacag gcatggtctt    1860 tctacaaaga aacagacaat gattagctct ggaggacaga gaagaaatgg gtttcagttc    1920
tcagggtcct atacaacaca cacacacaca cacacacaca cacacaccct    1980
cctgattggc cccagattgc cacagaatcc tggtggggac gacggggag agattccttg    2040 atgcctgggt gtccccaact ttccaaaccc tctgccccccg cgatggagaa gaaaccgaga    2100
cagaggtgta gggccactac cgcttcctcc acatgagatc atggttttct ccaccaagga    2160
agttttccga gggttgaatg agagcttttc cccgccctct tccccaaggg ctataaaggc    2220
ggccgtctgc acagccagcc agcagaagct ccctcagcga ggacagcaag ggactagcca    2280
ggagggagaa cagaaactcc agaacatctt ggaaatagct cccagaaaag caagcagcca    2340
accaggcagg ttctgtccct ttcactcact ggcccaaggc gccacatctc cctccagaaa    2400
agacaccatg agcacagaaa gcatgatccg cgacgtggaa ctggcagaag aggcactccc    2460
ccaaaagatg gggggcttcc agaactccag gcggtgccta tgtctcagcc tcttaagggc    2520
gaattctgca gatctcaagc ttcgaattct gcagtcgacg gtaccgcggg cccgggatcc    2580
accggtcgcc accatggtga gcaagggcga ggagctgttc accggggtgg tgcccatcct    2640
ggtcgagctg gacggcgacg taaacggcca caagttcagc gtgtccggcg agggcgaggg    2700
cgatgccacc tacggcaagc tgaccctgaa gttcatctgc accaccggca agctgcccgt    2760
gccctggccc accctcgtga ccaccctgac ctacggcgtg cagtgcttca gccgctaccc    2820
cgaccacatg aagcagcacg acttcttcaa gtccgccatg cccgaaggct acgtccagga    2880
gcgcaccatc ttcttcaagg acgacggcaa ctacaagacc cgcgccgagg tgaagttcga    2940
gggcgacacc ctggtgaacc gcatcgagct gaagggcatc gacttcaagg aggacggcaa    3000
catcctgggg cacaagctgg agtacaacta caacagccac aacgtctata tcatggccga    3060
caagcagaag aacggcatca aggtgaactt caagatccgc cacaacatcg aggacggcag    3120
cgtgcagctc gccgaccact accagcagaa cacccccatc ggcgacggcc ccgtgctgct    3180
gcccgacaac cactacctga gcacccagtc cgccctgagc aaagaccccca acgagaagcg    3240 cgatcacatg gtcctgctgg agttcgtgac cgccgccggg atcactctcg gcatggacga    3300
gctgtacaag aagcttagcc atggcttccc gccggcggtg gcggcgcagg atgatggcac    3360 gctgccccatg tcttgtgccc aggagagcgg gatggaccgt caccctgcag cctgtgcttc    3420
tgctaggatc aatgtgtaga tgcgcggccg cgactctaga tcataatcag ccataccaca    3480
tttgtagagg ttttacttgc tttaaaaaac ctcccacacc tccccctgaa cctgaaacat    3540
aaaatgaatg caattgttgt tgttaacttg tttattgcag cttataatgg ttacaaataa    3600
agcaatagca tcacaaattt cacaaataaa gcatttttt cactgcattc tagttgtggt    3660
```

```
ttgtccaaac tcatcaatgt atcttaaggc gtaaattgta agcgttaata ttttgttaaa   3720
attcgcgtta aattttttgtt aaatcagctc attttttaac caataggccg aaatcggcaa   3780
aatcccttat aaatcaaaag aatagaccga gatagggttg agtgttgttc cagtttggaa   3840
caagagtcca ctattaaaga acgtggactc caacgtcaaa gggcgaaaaa ccgtctatca   3900
gggcgatggc ccactacgtg aaccatcacc ctaatcaagt ttttgggg t cgaggtgccg   3960
taaagcacta atcggaacc ctaaagggag cccccgattt agagcttgac ggggaaagcc   4020
ggcgaacgtg gcgagaaagg aagggaagaa agcgaaagga gcgggcgcta gggcgctggc   4080
aagtgtagcg gtcacgctgc gcgtaaccac cacacccgcc gcgcttaatg cgccgctaca   4140
gggcgcgtca ggtggcactt tcggggaaa tgtgcgcgga acccctattt gtttattttt   4200
ctaaatacat tcaaatatgt atccgctcat gagacaataa ccctgataaa tgcttcaata   4260
atattgaaaa aggaagagtc ctgaggcgga agaaccagc tgtggaatgt gtgtcagtta   4320
gggtgtggaa agtccccagg ctccccagca ggcagaagta tgcaaagcat gcatctcaat   4380
tagtcagcaa ccaggtgtgg aaagtcccca ggctccccag caggcagaag tatgcaaagc   4440
atgcatctca attagtcagc aaccatagtc ccgcccctaa ctccgcccat cccgcccta    4500
actccgccca gttccgccca ttctccgccc catggctgac taattttttt tatttatgca   4560
gaggccgagg ccgcctcggc ctctgagcta ttccagaagt agtgaggagg cttttttgga   4620
ggcctaggct tttgcaaaga tcgatcaaga gacaggatga ggatcgtttc gcatgattga   4680
acaagatgga ttgcacgcag gttctccggc cgcttgggtg gagaggctat tcggctatga   4740
ctgggcacaa cagacaatcg gctgctctga tgccgccgtg ttccggctgt cagcgcaggg   4800
gcgcccggtt ctttttgtca agaccgacct gtccggtgcc ctgaatgaac tgcaagacga   4860
ggcagcgcgg ctatcgtggc tggccacgac gggcgttcct tgcgcagctg tgctcgacgt   4920
tgtcactgaa gcgggaaggg actggctgct attgggcgaa gtgccggggc aggatctcct   4980
gtcatctcac cttgctcctg ccgagaaagt atccatcatg gctgatgcaa tgcggcggct   5040
gcatacgctt gatccggcta cctgcccatt cgaccaccaa gcgaaacatc gcatcgagcg   5100
agcacgtact cggatggaag ccggtcttgt cgatcaggat gatctggacg aagagcatca   5160
ggggctcgcg ccagccgaac tgttcgccag gctcaaggcg agcatgcccg acggcgagga   5220
tctcgtcgtg acccatggcg atgcctgctt gccgaatatc atggtggaaa atggccgctt   5280
ttctggattc atcgactgtg gccggctggg tgtggcggac cgctatcagg acatagcgtt   5340
ggctacccgt gatattgctg aagagcttgg cggcgaatgg gctgaccgct tcctcgtgct   5400
ttacggtatc gccgctcccg attcgcagcg catcgccttc tatcgccttc ttgacgagtt   5460
cttctgagcg ggactctggg gttcgaaatg accgaccaag cgacgcccaa cctgccatca   5520
cgagatttcg attccaccgc cgccttctat gaaaggttgg gcttcggaat cgttttccgg   5580
gacgccggct ggatgatcct ccagcgcggg gatctcatgc tggagttctt cgcccaccct   5640
agggggaggc taactgaaac acggaaggag acaataccgg aaggaacccg cgctatgacg   5700
gcaataaaaa gacagaataa aacgcacggt gttgggtcgt tgttcataa acgcggggtt   5760
cggtcccagg gctggcactc tgtcgatacc ccaccgagac cccattgggg ccaatacgcc   5820
cgcgtttctt ccttttcccc accccacccc caagttcgg gtgaaggccc agggctcgca   5880
gccaacgtcg gggcggcagg ccctgccata gcctcaggtt actcatatat actttagatt   5940
gatttaaaac ttcatttta atttaaaagg atctaggtga agatcctttt tgataatctc   6000
atgaccaaaa tcccttaacg tgagttttcg ttccactgag cgtcagaccc cgtagaaaag   6060
```

| | |
|---|---|
| atcaaaggat cttcttgaga tccttttttt ctgcgcgtaa tctgctgctt gcaaacaaaa | 6120 |
| aaaccaccgc taccagcggt ggtttgtttg ccggatcaag agctaccaac tcttttccg | 6180 |
| aaggtaactg gcttcagcag agcgcagata ccaaatactg tccttctagt gtagccgtag | 6240 |
| ttaggccacc acttcaagaa ctctgtagca ccgcctacat acctcgctct gctaatcctg | 6300 |
| ttaccagtgg ctgctgccag tggcgataag tcgtgtctta ccgggttgga ctcaagacga | 6360 |
| tagttaccgg ataaggcgca gcggtcgggc tgaacggggg gttcgtgcac acagcccagc | 6420 |
| ttggagcgaa cgacctacac cgaactgaga tacctacagc gtgagctatg agaaagcgcc | 6480 |
| acgcttcccg aagggagaaa ggcggacagg tatccggtaa gcggcagggt cggaacagga | 6540 |
| gagcgcacga gggagcttcc agggggaaac gcctggtatc tttatagtcc tgtcgggttt | 6600 |
| cgccacctct gacttgagcg tcgatttttg tgatgctcgt caggggggcg agcctatgg | 6660 |
| aaaaacgcca gcaacgcggc cttttacgg ttcctggcct tttgctggcc ttttgctcac | 6720 |
| atgttctttc ctgcgttatc ccctgattct gtggataacc gtattaccgc catgcat | 6777 |

<210> SEQ ID NO 18
<211> LENGTH: 7616
<212> TYPE: DNA
<213> ORGANISM: Artificial Sequence
<220> FEATURE:
<223> OTHER INFORMATION: p1-5'3'TNFalfa/d1EGFP-N1

<400> SEQUENCE: 18

| | |
|---|---|
| tagttattaa tgtgagttag ctcactcatt aggcacccca ggctttacac tttatgcttc | 60 |
| cggctcgtat gttgtgtgga attgtgagcg gataacaatt tcacacagga acagctatg | 120 |
| accatgatta cgccaagcta tttaggtgac actatagaat actcaagcta tgcatcaagc | 180 |
| ttggtaccga gctcggatcc actagtaacg gccgccagtg tgctggaatt cgccttttc | 240 |
| tctggagaaa gctgctcccc cagggccatt cccactccca tctacctggc acacgaggtc | 300 |
| cagctctttt cctcccaata ccccttccat gtgcctctcc tcagtgcgca gaagtctgtg | 360 |
| tatccgggac ttcaaggacc gtgggtgcgc tcaatgtacc aggggctgt gttcctgctc | 420 |
| agtaagggag accagctgtc cacccacacc gacggcatct cccatctaca cttcagcccc | 480 |
| agcagtgtat tctttggagc ctttgcactg tagattctaa agaaacccaa gaattggatt | 540 |
| ccaggcctcc atcctgaccg ttgtttcaag ggtcacatcc ccacagtctc agccttccc | 600 |
| cactaaaata acctggagct ctcacgggag tctgagacac ttcaggggac tacatcttcc | 660 |
| ccagggccac tccagatgct caggggacga ctcaagccta cctagaagtt cctgcacaga | 720 |
| gcagggtttt tgtgggtcta ggtcggacag agacctggac atgaaggagg gacagacatg | 780 |
| ggagaggtgg ctgggaacag gggaaggttg actatttatg gagagaaaag ttaagttatt | 840 |
| tatttataga gaatagaaag aggggaaaaa tagaaagccg tcagatgaca actaggtccc | 900 |
| agacacaaag gtgtctcacc tcagacagga cccatctaag agagagatgg cgagagaatt | 960 |
| agatgtgggt gaccaagggg ttctagaaga aagcacgaag ctctaaaagc cagccactgc | 1020 |
| ttggctagac atccacaggg accccctgca ccatctgtga acccaataa acctctttc | 1080 |
| tctgagattc tgtctgcttg tgtctgtctt gcgttggggg agaaacttcc tggtctcttt | 1140 |
| aaggagtgga gcaggggaca gaggcctcag ttggtccatg ggatccgggc agagcaagga | 1200 |
| gacatgagga gcaggcagct cccagagaca tggtggattc acgggagtga ggcagcttaa | 1260 |
| ctgccgagag acccaaagga tgagctaggg agatccatcc aagggtggag agagatgagg | 1320 |
| gttctgggga gaagtgactc cactggaggg tgggagagtg tttaggagtg ggagggtggg | 1380 |

```
ggagggggaat ccttggaaga ccggggagtc atacggattg ggagaaatcc tggaagcagg    1440
gctgtgggac ctaaatgtct gagttgatgt accgcagtca agatatggca gaggctccgt    1500
ggaaaactca cttgggagca gggacccaaa gcagcagcct gagctcatga tcagagtgaa    1560
aggagaaggc ttgtgaggtc cgtgaattcc cagggctgag ttcattccct ctggggctgc    1620
cccatactca tcccattacc ccccccacca gccctcccaa agcccatgca cacttcccaa    1680
ctctcaagct gctctgcctt cagccacttc ctccaagaac tcaaacaggg gctttccct     1740 cctcaatatc atgtctcccc ccttatgcac ccagctttca gaagcacccc cccatgctaa    1800
gttctccccc atggatgtcc catttagaaa tcaaaaggaa atagacacag gcatggtctt    1860
tctacaaaga aacagacaat gattagctct ggaggacaga gaagaaatgg gtttcagttc    1920
tcagggtcct atacaacaca cacacacaca cacacacaca cacacaccct                1980
cctgattggc cccagattgc cacagaatcc tggtggggac gacggggag  agattccttg    2040 atgcctgggt gtccccaact ttccaaaccc tctgccccg  cgatggagaa gaaaccgaga    2100
cagaggtgta gggccactac cgcttcctcc acatgagatc atggttttct ccaccaagga    2160
agttttccga gggttgaatg agagcttttc ccgccctct  tccccaaggg ctataaaggc    2220
ggccgtctgc acagccagcc agcagaagct ccctcagcga ggacagcaag ggactagcca    2280
ggagggagaa cagaaactcc agaacatctt ggaaatagct cccagaaaag caagcagcca    2340
accaggcagg ttctgtccct ttcactcact ggcccaaggc gccacatctc cctccagaaa    2400
agacaccatg agcacagaaa gcatgatccg cgacgtggaa ctggcagaag aggcactccc    2460
ccaaaagatg gggggcttcc agaactccag gcggtgccta tgtctcagcc tcttaagggc    2520
gaattctgca gatctcaagc ttcgaattct gcagtcgacg gtaccgcggg cccgggatcc    2580
accggtcgcc accatggtga gcaagggcga ggagctgttc accggggtgg tgcccatcct    2640
ggtcgagctg gacggcgacg taaacggcca caagttcagc gtgtccggcg agggcgaggg    2700
cgatgccacc tacggcaagc tgaccctgaa gttcatctgc accaccggca agctgcccgt    2760
gccctggccc accctcgtga ccaccctgac ctacggcgtg cagtgcttca gccgctaccc    2820
cgaccacatg aagcagcacg acttcttcaa gtccgccatg cccgaaggct acgtccagga    2880
gcgcaccatc ttcttcaagg acgacggcaa ctacaagacc cgcgccgagg tgaagttcga    2940
gggcgacacc ctggtgaacc gcatcgagct gaagggcatc gacttcaagg aggacggcaa    3000
catcctgggg cacaagctgg agtacaacta caacagccac aacgtctata tcatggccga    3060
caagcagaag aacggcatca aggtgaactt caagatccgc cacaacatcg aggacggcag    3120
cgtgcagctc gccgaccact accagcagaa cacccccatc ggcgacggcc ccgtgctgct    3180
gcccgacaac cactacctga gcacccagtc cgccctgagc aaagaccccca acgagaagcg    3240 cgatcacatg gtcctgctgg agttcgtgac cgccgccggg atcactctcg gcatggacga    3300
gctgtacaag aagcttagcc atggcttccc gccggcggtg gcggcgcagg atgatggcac    3360 gctgccatg  tcttgtgccc aggagagcgg gatggaccgt caccctgcag cctgtgcttc    3420
tgctaggatc aatgtgtaga tgcgcggccg ccagtgtgct ggaattcggc tgaagggaat    3480
gggtgttcat ccattctcta cccagccccc actctgaccc ctttactctg acccctttat    3540
tgtctactcc tcagagcccc cagtctgtgt ccttctaact tagaaagggg attatggctc    3600
agagtccaac tctgtgctca gagctttcaa caactactca gaaacacaag atgctgggac    3660
agtgacctgg actgtgggcc tctcatgcac caccatcaag gactcaaatg gctttccga     3720 attcactgga gcctcgaatg tccattcctg agttctgcaa agggagagtg gtcaggttgc    3780
```

```
ctctgtctca gaatgaggct ggataagatc tcaggccttc ctaccttcag acctttccag    3840
actcttccct gaggtgcaat gcacagcctt cctcacagag ccagccccc tctatttata     3900 tttgcactta ttatttatta tttatttatt atttatttat ttgcttatga atgtatttat    3960
ttggaaggcc ggggtgtcct ggaggaccca gtgtgggaag ctgtcttcag acagacatgt    4020
tttctgtgaa aacggagctg agctgtcccc acctggcctc tctaccttgt tgcctcctct    4080
tttgcttatg tttaaaacaa aatatttatc taacccaatt gtcttaataa cgctgatttg    4140
gtgaccaggc tgtcgctaca tcactgaacc tctgctcccc acgggagccg tgactgtaat    4200
tgccctacag tcaattgaga gaaataaaga tcgcttggaa aagaaatgtg atttctgtct    4260
tgggatgaag tctgcatcca tctctttgcg gaggcctaaa gtctctgggt ccagatctca    4320
gtctttatac ccctgggcca ttaagacccc caagaccccc gtggaacaaa aggcagccaa    4380
catccctacc tctcccccgg aaacaggagc ctaaccctaa ttacctttgc cctggggcat    4440
gggaatttcc cactctggga attcttaagc cgaattctgc agatcattct agttgtggtt    4500
tgtccaaact catcaatgta tcttaaggcg taaattgtaa gcgttaatat tttgttaaaa    4560
ttcgcgttaa attttgtta aatcagctca ttttttaacc aataggccga aatcggcaaa     4620
atcccttata aatcaaaaga atagaccgag ataggggttga gtgttgttcc agtttggaac    4680
aagagtccac tattaaagaa cgtggactcc aacgtcaaag ggcgaaaaac cgtctatcag    4740
ggcgatggcc cactacgtga accatcaccc taatcaagtt ttttggggtc gaggtgccgt    4800
aaagcactaa atcggaaccc taagggagc ccccgattta gagcttgacg gggaaagccg      4860
gcgaacgtgg cgagaaagga agggaagaaa gcgaaaggag cgggcgctag ggcgctggca    4920
agtgtagcgg tcacgctgcg cgtaaccacc acacccgccg cgcttaatgc gccgctacag    4980
ggcgcgtcag gtggcacttt tcggggaaat gtgcgcggaa cccctatttg tttattttc     5040 taaatacatt caaatatgta tccgctcatg agacaataac cctgataaat gcttcaataa    5100
tattgaaaaa ggaagagtcc tgaggcggaa agaaccagct gtggaatgtg tgtcagttag    5160
ggtgtggaaa gtccccaggc tccccagcag gcagaagtat gcaaagcatg catctcaatt    5220
agtcagcaac caggtgtgga aagtccccag gctccccagc aggcagaagt atgcaaagca    5280
tgcatctcaa ttagtcagca accatagtcc cgcccctaac tccgcccatc ccgcccctaa    5340
ctccgcccag ttccgcccat tctccgcccc atggctgact aatttttttt atttatgcag    5400
aggccgaggc cgcctcggcc tctgagctat tccagaagta gtgaggaggc ttttttggag    5460
gcctaggctt ttgcaaagat cgatcaagag acaggatgag gatcgtttcg catgattgaa    5520
caagatggat tgcacgcagg ttctccggcc gcttgggtgg agaggctatt cggctatgac    5580
tgggcacaac agacaatcgg ctgctctgat gccgccgtgt tccggctgtc agcgcagggg    5640
cgcccggttc ttttttgtcaa gaccgacctg tccggtgccc tgaatgaact gcaagacgag    5700
gcagcgcggc tatcgtggct ggccacgacg ggcgttcctt gcgcagctgt gctcgacgtt    5760
gtcactgaag cgggaaggga ctggctgcta ttgggcgaag tgccggggca ggatctcctg    5820
tcatctcacc ttgctcctgc cgagaaagta tccatcatgg ctgatgcaat gcggcggctg    5880
catacgcttg atccggctac ctgcccattc gaccaccaag cgaaacatcg catcgagcga    5940
gcacgtactc ggatggaagc cggtcttgtc gatcaggatg atctggacga agagcatcag    6000
gggctcgcgc cagccgaact gttcgccagg ctcaaggcga gcatgcccga cggcgaggat    6060
ctcgtcgtga cccatggcga tgcctgcttg ccgaatatca tggtggaaaa tggccgcttt    6120
tctggattca tcgactgtgg ccggctgggt gtggcggacc gctatcagga catagcgttg    6180
```

```
gctacccgtg atattgctga agagcttggc ggcgaatggg ctgaccgctt cctcgtgctt    6240
tacggtatcg ccgctcccga ttcgcagcgc atcgccttct atcgccttct tgacgagttc    6300
ttctgagcgg gactctgggg ttcgaaatga ccgaccaagc gacgcccaac ctgccatcac    6360
gagatttcga ttccaccgcc gccttctatg aaaggttggg cttcggaatc gttttccggg    6420
acgccggctg gatgatcctc cagcgcgggg atctcatgct ggagttcttc gcccacccta    6480
gggggaggct aactgaaaca cggaaggaga caataccgga aggaacccgc gctatgacgg    6540
caataaaaag acagaataaa acgcacggtg ttgggtcgtt tgttcataaa cgcggggttc    6600
ggtcccaggg ctggcactct gtcgataccc caccgagacc ccattgggGC caatacgccc    6660
gcgtttcttc cttttcccca ccccacccCC caagttcggg tgaaggccca gggctcgcag    6720
ccaacgtcgg ggcggcaggc cctgccatag cctcaggtta ctcatatata ctttagattg    6780
atttaaaact tcattttttaa tttaaaagga tctaggtgaa gatcctttt gataatctca    6840 tgaccaaaat cccttaacgt gagttttcgt tccactgagc gtcagacccc gtagaaaaga    6900
tcaaaggatc ttcttgagat cctttttttc tgcgcgtaat ctgctgcttg caaacaaaaa    6960
aaccaccgct accagcggtg gtttgtttgc cggatcaaga gctaccaact cttttttccga    7020 aggtaactgg cttcagcaga gcgcagatac caaatactgt ccttctagtg tagccgtagt    7080
taggccacca cttcaagaac tctgtagcac cgcctacata cctcgctctg ctaatcctgt    7140
taccagtggc tgctgccagt ggcgataagt cgtgtcttac cgggttggac tcaagacgat    7200
agttaccgga taaggcgcag cggtcgggct gaacgggggg ttcgtgcaca cagcccagct    7260
tggagcgaac gacctacacc gaactgagat acctacagcg tgagctatga aaagcgcca    7320 cgcttcccga agggagaaag gcggacaggt atccggtaag cggcagggtc ggaacaggag    7380
agcgcacgag ggagcttcca gggggaaacg cctggtatct ttatagtcct gtcgggtttc    7440
gccacctctg acttgagcgt cgatttttgt gatgctcgtc aggggggcgg agcctatgga    7500
aaaacgccag caacgcggcc ttttacggtt cctggccttt tgctggcctt tttgctcaca    7560
tgttctttcc tgcgttatcc cctgattctg tggataaccg tattaccgcc atgcat    7616
```

<210> SEQ ID NO 19
<211> LENGTH: 5076
<212> TYPE: DNA
<213> ORGANISM: Artificial Sequence
<220> FEATURE:
<223> OTHER INFORMATION: p1-3'IL4/d1EGFP-N1

<400> SEQUENCE: 19

```
taatagtaat caattacggg gtcattagtt catagcccat atatggagtt ccgcgttaca      60
taacttacgg taaatggccc gcctggctga ccgcccaacg acccccgccc attgacgtca     120
ataatgacgt atgttcccat agtaacgcca atagggactt tccattgacg tcaatgggtg     180
gagtatttac ggtaaactgc ccacttggca gtacatcaag tgtatcatat gccaagtacg     240 cccectattg acgtcaatga cggtaaatgg cccgcctggc attatgccca gtacatgacc     300
ttatgggact ttcctacttg gcagtacatc tacgtattag tcatcgctat taccatggtg     360
atgcggtttt ggcagtacat caatgggcgt ggatagcggt ttgactcacg ggatttcca     420 agtctccacc ccattgacgt caatgggagt ttgttttggc accaaaatca acgggacttt     480
ccaaaatgtc gtaacaactc cgccccattg acgcaaatgg gcggtaggcg tgtacggtgg     540
gaggtctata taagcagagc tggtttagtg aaccgtcaga tccgctagcg ctaccggact     600
cagatctcga gctcaagctt cgaattctgc agtcgacggt accgcgggcc cgggatccac     660
```

```
cggtcgccac catggtgagc aagggcgagg agctgttcac cggggtggtg cccatcctgg    720
tcgagctgga cggcgacgta acgccacac agttcagcgt gtccggcgag ggcgagggcg      780
atgccaccta cggcaagctg accctgaagt tcatctgcac caccggcaag ctgcccgtgc    840
cctggcccac cctcgtgacc accctgacct acggcgtgca gtgcttcagc cgctaccccg    900
accacatgaa gcagcacgac ttcttcaagt ccgccatgcc cgaaggctac gtccaggagc    960
gcaccatctt cttcaaggac gacggcaact acaagacccg cgccgaggtg aagttcgagg   1020
gcgacaccct ggtgaaccgc atcgagctga agggcatcga cttcaaggag gacggcaaca   1080
tcctggggca caagctggag tacaactaca acagccacaa cgtctatatc atggccgaca   1140
agcagaagaa cggcatcaag gtgaacttca gatccgcca caacatcgag gacggcagcg    1200
tgcagctcgc cgaccactac cagcagaaca ccccccatcgg cgacgcccc gtgctgctgc    1260 ccgacaacca ctacctgagc acccagtccg ccctgagcaa agaccccaac gagaagcgcg   1320
atcacatggt cctgctggag ttcgtgaccg ccgccgggat cactctcggc atggacgagc   1380
tgtacaagaa gcttagccat ggcttcccgc cggcggtggc ggcgcaggat gatggcacgc   1440
tgcccatgtc ttgtgcccag gagagcggga tggaccgtca ccctgcagcc tgtgcttctg   1500
ctaggatcaa tgtgtagatg cgcggccgcc agtgtgatgg atatctgcag aattcggctt   1560
actcgtagta ctgagccacc atgctttaac ttatgaattt ttaatggttt tattttaat    1620 atttatatat ttataattca taaaataaaa tatttgtata atgtaacaga aatgataact   1680
aatgacactt catttgccat aaggtttcta ctgtaagccg aattccagca cactggcggc   1740
cgcgactcta gatcataatc agccatacca catttgtaga ggttttactt gctttaaaaa   1800
acctcccaca cctcccctg aacctgaaac ataaaatgaa tgcaattgtt gttgttaact    1860
tgtttattgc agcttataat ggttacaaat aaagcaatag catcacaaat ttcacaaata   1920
aagcattttt ttcactgcat tctagttgtg gtttgtccaa actcatcaat gtatcttaag   1980
gcgtaaattg taagcgttaa tattttgtta aaattcgcgt taaattttg ttaaatcagc    2040 tcatttttta accaataggc cgaaatcggc aaaatccctt ataaatcaaa agaatagacc    2100
gagatagggt tgagtgttgt tccagtttgg aacaagagtc cactattaaa gaacgtggac   2160
tccaacgtca aagggcgaaa aaccgtctat cagggcgatg gcccactacg tgaaccatca   2220
ccctaatcaa gttttttggg gtcgaggtgc cgtaaagcac taaatcggaa ccctaaaggg   2280
agcccccgat ttagagcttg acggggaaag ccggcgaacg tggcgagaaa ggaagggaag   2340
aaagcgaaag gagcgggcgc tagggcgctg gcaagtgtag cggtcacgct gcgcgtaacc   2400
accacacccg ccgcgcttaa tgcgccgcta cagggcgcgt caggtggcac ttttcgggga   2460
aatgtgcgcg gaacccctat ttgtttattt ttctaaatac attcaaatat gtatccgctc   2520
atgagacaat aaccctgata aatgcttcaa taatattgaa aaaggaagag tcctgaggcg    2580
gaaagaacca gctgtggaat gtgtgtcagt tagggtgtgg aaagtcccca ggctccccag    2640
caggcagaag tatgcaaagc atgcatctca attagtcagc aaccaggtgt ggaaagtccc   2700
caggctcccc agcaggcaga gtatgcaaag catgcatct caattagtca gcaaccatag    2760
tcccgcccct aactccgccc atcccgcccc taactccgcc cagttccgcc cattctccgc    2820 cccatgctg actaatttt ttatttatg cagaggccga ggccgcctcg gcctctgagc      2880
tattccagaa gtagtgagga ggctttttg gaggcctagg cttttgcaaa gatcgatcaa    2940
gagacaggat gaggatcgtt tcgcatgatt gaacaagatg gattgcacgc aggttctccg   3000
gccgcttggg tggagaggct attcggctat gactgggcac aacagacaat cggctgctct   3060
```

```
gatgccgccg tgttccggct gtcagcgcag gggcgcccgg ttcttttttgt caagaccgac    3120 ctgtccggtg ccctgaatga actgcaagac gaggcagcgc ggctatcgtg gctggccacg    3180
acgggcgttc cttgcgcagc tgtgctcgac gttgtcactg aagcgggaag ggactggctg    3240
ctattgggcg aagtgccggg gcaggatctc ctgtcatctc accttgctcc tgccgagaaa    3300
gtatccatca tggctgatgc aatgcggcgg ctgcatacgc ttgatccggc tacctgccca    3360
ttcgaccacc aagcgaaaca tcgcatcgag cgagcacgta ctcggatgga agccggtctt    3420
gtcgatcagg atgatctgga cgaagagcat caggggctcg cgccagccga actgttcgcc    3480
aggctcaagg cgagcatgcc cgacggcgag gatctcgtcg tgacccatgg cgatgcctgc    3540
ttgccgaata tcatggtgga aaatggccgc ttttctggat tcatcgactg tggccggctg    3600
ggtgtggcgg accgctatca ggacatagcg ttggctaccc gtgatattgc tgaagagctt    3660
ggcggcgaat gggctgaccg cttcctcgtg ctttacggta tcgccgctcc cgattcgcag    3720
cgcatcgcct tctatcgcct tcttgacgag ttcttctgag cgggactctg gggttcgaaa    3780
tgaccgacca agcgacgccc aacctgccat cacgagattt cgattccacc gccgccttct    3840
atgaaaggtt gggcttcgga atcgttttcc gggacgccgg ctggatgatc ctccagcgcg    3900
gggatctcat gctggagttc ttcgcccacc ctaggggggag gctaactgaa acacggaagg    3960
agacaatacc ggaaggaacc cgcgctatga cggcaataaa aagacagaat aaaacgcacg    4020
gtgttgggtc gtttgttcat aaacgcgggg ttcggtccca gggctggcac tctgtcgata    4080
ccccaccgag accccattgg ggccaatacg cccgcgtttc ttccttttcc caccccacc     4140 ccccaagttc gggtgaaggc ccagggctcg cagccaacgt cggggcggca ggccctgcca    4200
tagcctcagg ttactcatat atactttaga ttgatttaaa acttcatttt taatttaaaa    4260
ggatctaggt gaagatcctt tttgataatc tcatgaccaa aatcccttaa cgtgagtttt    4320
cgttccactg agcgtcagac cccgtagaaa agatcaaagg atcttcttga tccttttt     4380 ttctgcgcgt aatctgctgc ttgcaaacaa aaaaaccacc gctaccagcg gtggtttgtt    4440
tgccggatca agagctacca actctttttc cgaaggtaac tggcttcagc agagcgcaga    4500
taccaaatac tgtccttcta gtgtagccgt agttaggcca ccacttcaag aactctgtag    4560
caccgcctac atacctcgct ctgctaatcc tgttaccagt ggctgctgcc agtggcgata    4620
agtcgtgtct taccgggttg gactcaagac gatagttacc ggataaggcg cagcggtcgg    4680
gctgaacggg gggttcgtgc acacagccca gcttggagcg aacgacctac accgaactga    4740 gataccta
ca gcgtgagcta tgagaaagcg ccacgcttcc cgaagggaga aaggcggaca    4800
ggtatccggt aagcggcagg gtcggaacag gagagcgcac gagggagctt ccaggggggaa    4860 acgcctggta tctttatagt cctgtcgggt ttcgccacct ctgacttgag cgtcgatttt    4920
tgtgatgctc gtcagggggg cggagcctat ggaaaaacgc cagcaacgcg gccttttac     4980 ggttcctggc cttttgctgg ccttttgctc acatgttctt tcctgcgtta tcccctgatt    5040
ctgtggataa ccgtattacc gccatgcatt agttat                               5076

<210> SEQ ID NO 20
<211> LENGTH: 4976
<212> TYPE: DNA
<213> ORGANISM: Artificial Sequence
<220> FEATURE:
<223> OTHER INFORMATION: p2-3'IL4/EGFP-F

<400> SEQUENCE: 20
taatagtaat caattacggg gtcattagtt catagcccat atatggagtt ccgcgttaca     60
```

```
taacttacgg taaatggccc gcctggctga ccgcccaacg accccccgccc attgacgtca    120
ataatgacgt atgttcccat agtaacgcca atagggactt tccattgacg tcaatgggtg    180
gagtatttac ggtaaactgc ccacttggca gtacatcaag tgtatcatat gccaagtacg    240
ccccctattg acgtcaatga cggtaaatgg cccgcctggc attatgccca gtacatgacc    300
ttatgggact ttcctacttg gcagtacatc tacgtattag tcatcgctat taccatggtg    360
atgcggtttt ggcagtacat caatgggcgt ggatagcggt ttgactcacg ggatttccaa    420
agtctccacc ccattgacgt caatgggagt ttgttttggc accaaaatca acgggacttt    480
ccaaaatgtc gtaacaactc cgccccattg acgcaaatgg gcggtaggcg tgtacggtgg    540
gaggtctata taagcagagc tggtttagtg aaccgtcaga tccgctagcg ctaccggtcg    600
ccaccatggt gagcaagggc gaggagctgt tcaccggggt ggtgcccatc ctggtcgagc    660
tggacggcga cgtaaacggc cacaagttca gcgtgtccgg cgagggcgag ggcgatgcca    720
cctacggcaa gctgaccctg aagttcatct gcaccaccgg caagctgccc gtgccctggc    780
ccaccctcgt gaccaccctg acctacggcg tgcagtgctt cagccgctac cccgaccaca    840
tgaagcagca cgacttcttc aagtccgcca tgcccgaagg ctacgtccag gagcgcacca    900
tcttcttcaa ggacgacggc aactacaaga cccgcgccga ggtgaagttc gagggcgaca    960
cccctggtgaa ccgcatcgag ctgaagggca tcgacttcaa ggaggacggc aacatcctgg   1020
ggcacaagct ggagtacaac tacaacagcc acaacgtcta tatcatggcc gacaagcaga   1080
agaacggcat caaggtgaac ttcaagatcc gccacaacat cgaggacggc agcgtgcagc   1140
tcgccgacca ctaccagcag aacacccccca tcggcgacgg ccccgtgctg ctgcccgaca   1200
accactacct gagcacccag tccgccctga gcaaagaccc caacgagaag cgcgatcaca   1260
tggtcctgct ggagttcgtg accgccgccg ggatcactct cggcatggac gagctgtaca   1320
agtccggact cagatctaag ctgaaccctc ctgatgagag tggccccggc tgcatgagct   1380
gcaagtgtgt gctctcctga ggatccagat ctcgagctca agcttcgaat tcggcttact   1440
cgtagtactg agccaccatg ctttaactta tgaattttta atggttttat ttttaatatt   1500
tatatattta taattcataa aataaaatat ttgtataatg taacagaaat gataactaat   1560
gacacttcat ttgccataag gtttctactg taagccgaat tctgcagtcg acggtaccgc   1620
gggcccggga tccaccggat ctagataact gatcataatc agccatacca catttgtaga   1680
ggttttactt gctttaaaaa acctcccaca cctcccccctg aacctgaaac ataaaatgaa   1740
tgcaattgtt gttgttaact tgtttattgc agcttataat ggttacaaat aaagcaatag   1800
catcacaaat ttcacaaata aagcattttt tcactgcat tctagttgtg gtttgtccaa   1860
actcatcaat gtatcttaac gcgtaaattg taagcgttaa tattttgtta aaattcgcgt   1920
taaattttg ttaaatcagc tcatttttta accaataggc cgaaatcggc aaaatccctt   1980
ataaatcaaa agaatagacc gagataggt tgagtgttgt tccagtttgg aacaagagtc   2040
cactattaaa gaacgtggac tccaacgtca aagggcgaaa aaccgtctat cagggcgatg   2100
gcccactacg tgaaccatca ccctaatcaa gttttttggg gtcgaggtgc cgtaaagcac   2160
taaatcggaa ccctaaaggg agcccccgat ttagagcttg acggggaaag ccggcgaacg   2220
tggcgagaaa ggaagggaag aaagcgaaag gagcgggcgc tagggcgctg gcaagtgtag   2280
cggtcacgct gcgcgtaacc accacacccg ccgcgcttaa tgcgccgcta cagggcgcgt   2340
caggtggcac ttttcgggga aatgtgcgcg gaacccctat ttgtttattt ttctaaatac   2400
attcaaatat gtatccgctc atgagacaat aaccctgata aatgcttcaa taatattgaa   2460
```

```
aaaggaagag tcctgaggcg gaaagaacca gctgtggaat gtgtgtcagt tagggtgtgg   2520
aaagtcccca ggctccccag caggcagaag tatgcaaagc atgcatctca attagtcagc   2580
aaccaggtgt ggaaagtccc caggctcccc agcaggcaga agtatgcaaa gcatgcatct   2640
caattagtca gcaaccatag tcccgcccct aactccgccc atcccgcccc taactccgcc   2700
cagttccgcc cattctccgc cccatggctg actaattttt tttatttatg cagaggccga   2760
ggccgcctcg gcctctgagc tattccagaa gtagtgagga ggcttttttg gaggcctagg   2820
cttttgcaaa gatcgatcaa gagacaggat gaggatcgtt tcgcatgatt gaacaagatg   2880
gattgcacgc aggttctccg gccgcttggg tggagaggct attcggctat gactgggcac   2940
aacagacaat cggctgctct gatgccgccg tgttccggct gtcagcgcag ggcgcccgg    3000 ttcttttgt caagaccgac ctgtccggtg ccctgaatga actgcaagac gaggcagcgc    3060
ggctatcgtg gctggccacg acgggcgttc cttgcgcagc tgtgctcgac gttgtcactg    3120
aagcgggaag gactggctg ctattgggcg aagtgccggg gcaggatctc ctgtcatctc     3180
accttgctcc tgccgagaaa gtatccatca tggctgatgc aatgcggcgg ctgcatacgc    3240
ttgatccggc tacctgccca ttcgaccacc aagcgaaaca tcgcatcgag cgagcacgta    3300
ctcggatgga agccggtctt gtcgatcagg atgatctgga cgaagagcat caggggctcg    3360
cgccagccga actgttcgcc aggctcaagg cgagcatgcc cgacggcgag gatctcgtcg    3420
tgacccatgg cgatgcctgc ttgccgaata tcatggtgga aaatggccgc ttttctggat    3480
tcatcgactg tggccggctg ggtgtggcgg accgctatca ggacatagcg ttggctaccc    3540
gtgatattgc tgaagagctt ggcggcgaat gggctgaccg cttcctcgtg ctttacggta    3600
tcgccgctcc cgattcgcag cgcatcgcct tctatcgcct tcttgacgag ttcttctgag    3660
cgggactctg gggttcgaaa tgaccgacca agcgacgccc aacctgccat cacgagattt    3720
cgattccacc gccgccttct atgaaaggtt gggcttcgga atcgttttcc gggacgccgg    3780
ctggatgatc ctccagcgcg ggatctcat gctggagttc ttcgcccacc ctaggggag     3840 gctaactgaa acacggaagg agacaatacc ggaaggaacc cgcgctatga cggcaataaa    3900
aagacagaat aaaacgcacg gtgttgggtc gtttgttcat aaacgcgggg ttcggtccca    3960
gggctggcac tctgtcgata ccccaccgag accccattgg ggccaatacg cccgcgtttc    4020 ttcctttcc ccaccccacc ccccaagttc gggtgaaggc ccaggctcg cagccaacgt       4080 cggggcggca ggccctgcca tagcctcagg ttactcatat atactttaga ttgatttaaa    4140
acttcatttt taatttaaaa ggatctaggt gaagatcctt tttgataatc tcatgaccaa    4200
aatcccttaa cgtgagtttt cgttccactg agcgtcagac cccgtagaaa agatcaaagg    4260
atcttcttga tcctttttt ttctgcgcgt aatctgctgc ttgcaaacaa aaaaaccacc     4320
gctaccagcg gtggtttgtt tgccggatca agagctacca actcttttc cgaaggtaac     4380 tggcttcagc agagcgcaga taccaaatac tgtccttcta gtgtagccgt agttaggcca    4440
ccacttcaag aactctgtag caccgcctac atacctcgct ctgctaatcc tgttaccagt    4500
ggctgctgcc agtggcgata agtcgtgtct taccgggttg gactcaagac gatagttacc    4560
ggataaggcg cagcggtcgg gctgaacggg gggttcgtgc acacagccca gcttggagcg    4620
aacgacctac accgaactga gatacctaca gcgtgagcta tgagaaagcg ccacgcttcc    4680
cgaagggaga aaggcggaca ggtatccggt aagcggcagg gtcggaacag gagagcgcac    4740
gagggagctt ccaggggaa acgcctggta tctttatagt cctgtcgggt ttcgccacct    4800
ctgacttgag cgtcgatttt tgtgatgctc gtcagggggg cggagcctat ggaaaaacgc    4860
```

| cagcaacgcg gccttttac ggttcctggc cttttgctgg cctttgctc acatgttctt | 4920 |
| tcctgcgtta tccctgatt ctgtggataa ccgtattacc gccatgcatt agttat | 4976 |

<210> SEQ ID NO 21
<211> LENGTH: 4780
<212> TYPE: DNA
<213> ORGANISM: Artificial Sequence
<220> FEATURE:
<223> OTHER INFORMATION: p3-3'IL4/EGFP-F

<400> SEQUENCE: 21

| taatagtaat caattacggg gtcattagtt catagcccat atatggagtt ccgcgttaca | 60 |
| taacttacgg taaatggccc gcctggctga ccgcccaacg accccgccc attgacgtca | 120 |
| ataatgacgt atgttcccat agtaacgcca tagggactt tccattgacg tcaatgggtg | 180 |
| gagtatttac ggtaaactgc ccacttggca gtacatcaag tgtatcatat gccaagtacg | 240 |
| cccctattg acgtcaatga cggtaaatgg cccgcctggc attatgccca gtacatgacc | 300 |
| ttatgggact ttcctacttg gcagtacatc tacgtattag tcatcgctat taccatggtg | 360 |
| atgcggtttt ggcagtacat caatgggcgt ggatagcggt ttgactcacg ggatttcca | 420 |
| agtctccacc ccattgacgt caatgggagt ttgttttggc accaaaatca acgggacttt | 480 |
| ccaaaatgtc gtaacaactc cgccccattg acgcaaatgg gcggtaggcg tgtacggtgg | 540 |
| gaggtctata taagcagagc tggtttagtg aaccgtcaga tccgctagcg ctaccggtcg | 600 |
| ccaccatggt gagcaagggc gaggagctgt tcaccgggt ggtgcccatc ctggtcgagc | 660 |
| tggacggcga cgtaaacggc cacaagttca gcgtgtccgg cgagggcgag ggcgatgcca | 720 |
| cctacggcaa gctgaccctg aagttcatct gcaccaccgg caagctgccc gtgccctggc | 780 |
| ccaccctcgt gaccaccctg acctacggcg tgcagtgctt cagccgctac cccgaccaca | 840 |
| tgaagcagca cgacttcttc aagtccgcca tgcccgaagg ctacgtccag gagcgcacca | 900 |
| tcttcttcaa ggacgacggc aactacaaga cccgcgccga ggtgaagttc gagggcgaca | 960 |
| ccctggtgaa ccgcatcgag ctgaagggca tcgacttcaa ggaggacggc aacatcctgg | 1020 |
| ggcacaagct ggagtacaac tacaacagcc acaacgtcta tatcatggcc gacaagcaga | 1080 |
| agaacggcat caaggtgaac ttcaagatcc gccacaacat cgaggacggc agcgtgcagc | 1140 |
| tcgccgacca ctaccagcag aacacccca tcggcgacgg ccccgtgctg ctgcccgaca | 1200 |
| accactacct gagcacccag tccgccctga gcaaagaccc caacgagaag cgcgatcaca | 1260 |
| tggtcctgct ggagttcgtg accgccgcg ggatcactct cggcatggac gagctgtaca | 1320 |
| agtccggact cagatctaag ctgaaccctc ctgatgagag tggccccggc tgcatgagct | 1380 |
| gcaagtgtgt gctctcctga ggatccagat ctcgagctca agcttcgaat tcggctttac | 1440 |
| tcgtagtact gagccaccat gctttaactt atgaattttt aatggtttta ttttaatat | 1500 |
| ttatatattt ataattcata aaataaaata tttgtataat gtaacagaaa tgataactaa | 1560 |
| tgacacttca tttgccataa ggtttctact gaagccgaat tctgcagtcg acggtaccgc | 1620 |
| gggcccggga tccaccggat ctagataact gatcataatc agccatacca catttgtaga | 1680 |
| ggttttactt gctttaagcg ttaatatttt gttaaaattc gcgttaaatt tttgttaaat | 1740 |
| cagctcattt tttaaccaat aggccgaaat cggcaaaatc ccttataaat caaaagaata | 1800 |
| gaccgagata gggttgagtg ttgttccagt ttggaacaag agtccactat taaagaacgt | 1860 |
| ggactccaac gtcaaagggc gaaaaaccgt ctatcagggc gatggcccac tacgtgaacc | 1920 |
| atcaccctaa tcaagttttt tggggtcgag gtgccgtaaa gcactaaatc ggaaccctaa | 1980 |

```
agggagcccc cgatttagag cttgacgggg aaagccggcg aacgtggcga gaaaggaagg    2040
gaagaaagcg aaaggagcgg gcgctagggc gctggcaagt gtagcggtca cgctgcgcgt    2100
aaccaccaca cccgccgcgc ttaatgcgcc gctacagggc gcgtcaggtg cacttttcg     2160 gggaaatgtg cgcggaaccc ctatttgttt attttcctaa atacattcaa atatgtatcc    2220
gctcatgaga caataaccct gataaatgct tcaataatat tgaaaaagga agagtcctga    2280
ggcggaaaga accagctgtg gaatgtgtgt cagttagggt gtggaaagtc cccaggctcc    2340
ccagcaggca gaagtatgca aagcatgcat ctcaattagt cagcaaccag gtgtggaaag    2400
tccccaggct ccccagcagg cagaagtatg caaagcatgc atctcaatta gtcagcaacc    2460
atagtcccgc ccctaactcc gcccatcccg cccctaactc cgcccagttc cgcccattct    2520 ccgcccatg gctgactaat ttttttatt tatgcagagg ccgaggccgc ctcggcctct      2580
gagctattcc agaagtagtg aggaggcttt tttggaggcc taggcttttg caaagatcga    2640
tcaagacaca ggatgaggat cgtttcgcat gattgaacaa gatggattgc acgcaggttc    2700
tccggccgct tgggtggaga ggctattcgg ctatgactgg gcacaacaga caatcggctg    2760
ctctgatgcc gccgtgttcc ggctgtcagc gcagggcgc ccggttcttt ttgtcaagac     2820
cgacctgtcc ggtgccctga atgaactgca agacgaggca gcgcggctat cgtggctggc    2880
cacgacgggg gttccttgcg cagctgtgct cgacgttgtc actgaagcgg gaagggactg    2940
gctgctattg ggcgaagtgc cggggcagga tctcctgtca tctcaccttg ctcctgccga    3000
gaaagtatcc atcatggctg atgcaatgcg cggctgcat acgcttgatc cggctacctg     3060
cccattcgac caccaagcga aacatcgcat cgagcgagca cgtactcgga tggaagccgg    3120
tcttgtcgat caggatgatc tggacgaaga gcatcagggg ctcgcgccag ccgaactgtt    3180
cgccaggctc aaggcgagca tgcccgacgg cgaggatctc gtcgtgaccc atggcgatgc    3240
ctgcttgccg aatatcatgg tggaaaatgg ccgcttttct ggattcatcg actgtggccg    3300
gctgggtgtg gcggaccgct atcaggacat agcgttggct acccgtgata ttgctgaaga    3360
gcttggcggc gaatgggctg accgcttcct cgtgctttac ggtatcgccg ctcccgattc    3420
gcagcgcatc gccttctatc gccttcttga cgagttcttc tgagcgggac tctgggttc     3480 gaaatgaccg accaagcgac gcccaacctg ccatcacgag atttcgattc caccgccgcc    3540
ttctatgaaa ggttgggctt cggaatcgtt ttccgggacg ccggctggat gatcctccag    3600
cgcggggatc tcatgctgga gttcttcgcc cacc ctaggg ggaggctaac tgaaacacgg    3660
aaggagacaa taccggaagg aacccgcgct atgacggcaa taaaaagaca gaataaaacg    3720
cacggtgttg ggtcgtttgt tcataaacgc ggggttcggt cccagggctg gcactctgtc    3780 gatacccac cgagacccca ttggggccaa tacgcccgcg tttcttcctt ttccccaccc     3840 cacccccaa gttcgggtga aggcccaggg ctcgcagcca acgtcggggc ggcaggccct    3900
gccatagcct caggttactc atatatactt tagattgatt taaaacttca ttttaattt     3960 aaaaggatct aggtgaagat cctttttgat aatctcatga ccaaaatccc ttaacgtgag    4020
ttttcgttcc actgagcgtc agaccccgta gaaaagatca aaggatcttc ttgagatcct    4080
ttttttctgc gcgtaatctg ctgcttgcaa acaaaaaaac caccgctacc agcggtggtt    4140
tgtttgccgg atcaagagct accaactctt tttccgaagg taactggctt cagcagagcg    4200
cagataccaa atactgtcct tctagtgtag ccgtagttag gccaccactt caagaactct    4260
gtagcaccgc ctacatacct cgctctgcta atcctgttac cagtggctgc tgccagtggc    4320
gataagtcgt gtcttaccgg gttggactca agacgatagt taccggataa ggcgcagcgg    4380
```

-continued

```
tcgggctgaa cggggggttc gtgcacacag cccagcttgg agcgaacgac ctacaccgaa    4440
ctgagatacc tacagcgtga gctatgagaa agcgccacgc ttcccgaagg gagaaaggcg    4500
gacaggtatc cggtaagcgg cagggtcgga acaggagagc gcacgaggga gcttccaggg    4560
ggaaacgcct ggtatcttta tagtcctgtc gggtttcgcc acctctgact tgagcgtcga    4620 ttttgtgat gctcgtcagg ggggcggagc ctatggaaaa acgccagcaa cgcggccttt    4680
ttacggttcc tggccttttg ctggcctttt gctcacatgt tctttcctgc gttatcccct    4740
gattctgtgg ataaccgtat taccgccatg cattagttat                          4780
```

<210> SEQ ID NO 22
<211> LENGTH: 4968
<212> TYPE: DNA
<213> ORGANISM: Artificial Sequence
<220> FEATURE:
<223> OTHER INFORMATION: p4-3'IL4/CA-EGFP

<400> SEQUENCE: 22

```
taatagtaat caattacggg gtcattagtt catagcccat atatggagtt ccgcgttaca      60
taacttacgg taaatggccc gcctggctga ccgcccaacg accccgccc attgacgtca     120 ataatgacgt atgttcccat agtaacgcca atagggactt ccattgacg tcaatgggtg     180 gactatttac ggtaaactgc ccacttggca gtacatcaag tgtatcatat gccaagtacg     240 cccctattg acgtcaatga cggtaaatgg cccgcctggc attatgccca gtacatgacc     300
ttatgggact ttcctacttg gcagtacatc tacgtattag tcatcgctat taccatgcat     360
ggtcgaggtg agccccacgt tctgcttcac tctccccatc tccccccct cccaccccc      420 aattttgtat ttatttattt tttaattatt ttgtgcagcg atggggcgg gggggggg       480 gggcgcgcg ccaggcgggg cggggcgggg cgaggggcgg ggcggggcga ggcggagagg     540
tgcggcggca gccaatcaga gcggcgcgct ccgaaagttt ccttttatgg cgaggcggcg    600
gcggcggcgg ccctataaaa agcgaagcgc gcggcgggcg ggagtcgctg cgacgctgcc    660
ttcgccccgt gccccgctcc gccgccgcct cgcgccgccc gccccggctc tgactgaccg    720
cgttactccc acaggtgagc gggcgggacg gcccttctcc ttcgggctgt aattagcgct    780
accggtcgcc accatggtga gcaagggcga ggagctgttc accggggtgg tgcccatcct    840
ggtcgagctg gacggcgacg taaacggcca caagttcagc gtgtccggcg agggcgaggg    900
cgatgccacc tacggcaagc tgaccctgaa gttcatctgc accaccggca agctgcccgt    960
gccctggccc accctcgtga ccaccctgac ctacggcgtg cagtgcttca gccgctaccc   1020
cgaccacatg aagcagcacg acttcttcaa gtccgccatg cccgaaggct acgtccagga   1080
gcgcaccatc ttcttcaagg acgacggcaa ctacaagacc cgcgccgagg tgaagttcga   1140
gggcgacacc ctggtgaacc gcatcgagct gaagggcatc gacttcaagg aggacggcaa   1200
catcctgggg cacaagctgg agtacaacta caacagccac aacgtctata tcatggccga   1260
caagcagaag aacggcatca aggtgaactt caagatccgc cacaacatcg aggacggcag   1320
cgtgcagctc gccgaccact accagcagaa caccccate ggcgacggcc ccgtgctgct   1380
gcccgacaac cactacctga gcacccagtc cgccctgagc aaagacccca acgagaagcg   1440
cgatcacatg gtcctgctgg agttcgtgac cgccgccggg atcactctcg gcatggacga   1500
gctgtacaag tccggactca gatctaagct gaaccctcct gatgagagtg ccccggctg   1560 catgagctgc aagtgtgtgc tctcctgagg atccagatct cgagctcaag cttcgaattc    1620
ggctttactc gtagtactga gccaccatgc tttaacttat gaattttaa tggttttatt    1680
```

```
tttaatatttt atatatttat aattcataaa ataaaatatt tgtataatgt aacagaaatg    1740
ataactaatg acacttcatt tgccataagg tttctactga agccgaattc tgcagtcgac    1800
ggtaccgcgg gcccgggatc caccggatct agataactga tcataatcag ccataccaca    1860
tttgtagagg ttttacttgc tttaagcgtt aatattttgt taaaattcgc gttaaatttt    1920
tgttaaatca gctcattttt taaccaatag gccgaaatcg gcaaaatccc ttataaatca    1980
aaagaataga ccgagatagg gttgagtgtt gttccagttt ggaacaagag tccactatta    2040
aagaacgtgg actccaacgt caaagggcga aaaaccgtct atcagggcga tggcccacta    2100
cgtgaaccat caccctaatc aagttttttg gggtcgaggt gccgtaaagc actaaatcgg    2160
aaccctaaag ggagccccg atttagagct tgacgggga agccggcgaa cgtggcgaga    2220
aaggaaggga agaaagcgaa aggagcgggc gctaggcgc tggcaagtgt agcggtcacg    2280
ctgcgcgtaa ccaccacacc cgccgcgctt aatgcgccgc tacagggcgc gtcaggtggc    2340
acttttcggg gaaatgtgcg cggaaccccct atttgtttat ttttctaaat acattcaaat    2400
atgtatccgc tcatgagaca ataaccctga taaatgcttc aataatattg aaaaaggaag    2460
agtcctgagg cggaaagaac cagctgtgga atgtgtgtca gttagggtgt ggaaagtccc    2520
caggctcccc agcaggcaga agtatgcaaa gcatgcatct caattagtca gcaaccaggt    2580
gtggaaagtc cccaggctcc ccagcaggca gaagtatgca aagcatgcat ctcaattagt    2640
cagcaaccat agtcccgccc ctaactccgc ccatcccgcc cctaactccg cccagttccg    2700
cccattctcc gccccatggc tgactaattt ttttattta gcagaggcc gaggccgcct    2760 cggcctctga gctattccag aagtagtgag gaggcttttt tggaggccta ggcttttgca    2820
aagatcgatc aagagacagg atgaggatcg tttcgcatga ttgaacaaga tggattgcac    2880
gcaggttctc cggccgcttg ggtggagagg ctattcggct atgactgggc acaacagaca    2940
atcggctgct ctgatgccgc cgtgttccgg ctgtcagcgc aggggcgccc ggttctttt    3000 gtcaagaccg acctgtccgg tgccctgaat gaactgcaag acgaggcagc gcggctatcg    3060
tggctggcca cgacgggcgt tccttgcgca gctgtgctcg acgttgtcac tgaagcggga    3120
agggactggc tgctattggg cgaagtgccg gggcaggatc tcctgtcatc tcaccttgct    3180
cctgccgaga aagtatccat catggctgat gcaatgcggc ggctgcatac gcttgatccg    3240
gctacctgcc cattcgacca ccaagcgaaa catcgcatcg agcgagcacg tactcggatg    3300
gaagccggtc ttgtcgatca ggatgatctg gacgaagagc atcagggct cgcgccagcc    3360 gaactgttcg ccaggctcaa ggcgagcatg cccgacggcg aggatctcgt cgtgacccat    3420
ggcgatgcct gcttgccgaa tatcatggtg gaaaatggcc gcttttctgg attcatcgac    3480
tgtggccggc tgggtgtggc ggaccgctat caggacatag cgttggctac ccgtgatatt    3540
gctgaagagc ttggcggcga atgggctgac cgcttcctcg tgctttacgg tatcgccgct    3600
cccgattcgc agcgcatcgc cttctatcgc cttcttgacg agttcttctg agcgggactc    3660
tggggttcga aatgaccgac caagcgacgc ccaacctgcc atcacgagat ttcgattcca    3720
ccgccgcctt ctatgaaagg ttgggcttcg aatcgttttt ccgggacgcc ggctggatga    3780
tcctccagcg cggggatctc atgctggagt tcttcgccca ccctagggggg aggctaactg    3840 aaacacggaa ggagacaata ccggaaggaa cccgcgctat gacggcaata aaaagacaga    3900
ataaaacgca cggtgttggg tcgtttgttc ataaacgcgg ggttcggtcc cagggctggc    3960
actctgtcga taccccaccg agaccccatt ggggccaata cgcccgcgtt tcttcctttt    4020 cccacccca ccccccaagt tcgggtgaag gcccagggct cgcagccaac gtcggggcgg    4080
```

```
caggccctgc catagcctca ggttactcat atatacttta gattgattta aaacttcatt    4140
tttaatttaa aaggatctag gtgaagatcc tttttgataa tctcatgacc aaaatccctt    4200
aacgtgagtt ttcgttccac tgagcgtcag accccgtaga aaagatcaaa ggatcttctt    4260
gagatccttt ttttctgcgc gtaatctgct gcttgcaaac aaaaaaacca ccgctaccag    4320
cggtggtttg tttgccggat caagagctac caactctttt tccgaaggta actggcttca    4380
gcagagcgca gataccaaat actgtccttc tagtgtagcc gtagttaggc caccacttca    4440
agaactctgt agcaccgcct acatacctcg ctctgctaat cctgttacca gtggctgctg    4500
ccagtggcga taagtcgtgt cttaccgggt tggactcaag acgatagtta ccggataagg    4560
cgcagcggtc gggctgaacg gggggttcgt gcacacagcc cagcttggag cgaacgacct    4620
acaccgaact gagataccta cagcgtgagc tatgagaaag cgccacgctt cccgaaggga    4680
gaaaggcgga caggtatccg gtaagcggca gggtcggaac aggagagcgc acgagggagc    4740
ttccaggggg aaacgcctgg tatctttata gtcctgtcgg gtttcgccac ctctgacttg    4800
agcgtcgatt tttgtgatgc tcgtcagggg gcggagcct atggaaaaac gccagcaacg    4860
cggccttttt acggttcctg gccttttgct ggccttttgc tcacatgttc tttcctgcgt    4920
tatcccctga ttctgtggat aaccgtatta ccgccatgca ttagttat               4968

<210> SEQ ID NO 23
<211> LENGTH: 4985
<212> TYPE: DNA
<213> ORGANISM: Artificial Sequence
<220> FEATURE:
<223> OTHER INFORMATION: p5-3'IL4/d1EGFP-N1

<400> SEQUENCE: 23
taatagtaat caattacggg gtcattagtt catagcccat atatggagtt ccgcgttaca      60
taacttacgg taaatggccc gcctggctga ccgcccaacg accccgccc attgacgtca     120 ataatgacgt atgttcccat agtaacgcca atagggactt ccattgacg tcaatgggtg     180 gagtatttac ggtaaactgc ccacttggca gtacatcaag tgtatcatat gccaagtacg     240 cccctattg acgtcaatga cggtaaatgg cccgcctggc attatgccca gtacatgacc     300
ttatgggact ttcctacttg gcagtacatc tacgtattag tcatcgctat taccatggtg     360
atgcggtttt ggcagtacat caatgggcgt ggatagcggt ttgactcacg gggatttcca     420
agtctccacc ccattgacgt caatgggagt ttgttttggc accaaaatca acgggacttt     480
ccaaaatgtc gtaacaactc cgccccattg acgcaaatgg gcggtaggcg tgtacggtgg     540
gaggtctata taagcagagc tggtttagtg aaccgtcaga tccgctagcg ctaccggact     600
cagatctcga gctcaagctt cgaattctgc agtcgacggt accgcgggcc cgggatccac     660
cggtcgccac catggtgagc aagggcgagg agctgttcac cggggtggtg cccatcctgg     720
tcgagctgga cggcgacgta aacggccaca agttcagcgt gtccggcgag ggcgagggcg     780
atgccaccta cggcaagctg accctgaagt tcatctgcac caccggcaag ctgcccgtgc     840
cctggcccac cctcgtgacc accctgacct acggcgtgca gtgcttcagc cgctaccccg     900
accacatgaa gcagcacgac ttcttcaagt ccgccatgcc cgaaggctac gtccaggagc     960
gcaccatctt cttcaaggac gacggcaact acaagacccg cgccgaggtg aagttcgagg    1020
gcgacaccct ggtgaaccgc atcgagctga agggcatcga cttcaaggag gacggcaaca    1080
tcctggggca caagctggag tacaactaca acagccacaa cgtctatatc atggccgaca    1140
agcagaagaa cggcatcaag gtgaacttca agatccgcca caacatcgag gacggcagcg    1200
```

```
tgcagctcgc cgaccactac cagcagaaca cccccatcgg cgacggcccc gtgctgctgc    1260
ccgacaacca ctacctgagc acccagtccg ccctgagcaa agaccccaac gagaagcgcg    1320
atcacatggt cctgctggag ttcgtgaccg ccgccgggat cactctcggc atggacgagc    1380
tgtacaagaa gcttagccat ggcttcccgc cggcggtggc ggcgcaggat gatggcacgc    1440
tgcccatgtc ttgtgcccag gagagcggga tggaccgtca ccctgcagcc tgtgcttctg    1500
ctaggatcaa tgtgtagatg cgcggccgcc agtgtgatgg atatctgcag aattcggctt    1560
actcgtagta ctgagccacc atgctttaac ttatgaattt ttaatggttt tattttaat    1620 atttatatat ttataattca taaaataaaa tatttgtata atgtaacaga aatgataact    1680
aatgacactt catttgccat aaggtttcta ctgtaagccg aattccagca cactggcggc    1740
cgcgactcta gatcataatc agccatacca catttgtaga gttttactt gctttaaaaa    1800 acctcccaca cctccccctg aacctgaaac ataaaatgaa tgcatgcatt ctagttgtgg    1860
tttgtccaaa ctcatcaatg tatcttaagg cgtaaattgt aagcgttaat attttgttaa    1920
aattcgcgtt aaattttgt taaatcagct cattttttaa ccaataggcc gaaatcggca    1980
aaatccctta taaatcaaaa gaatagaccg atatagggtt gagtgttgtt ccagtttgga    2040
acaagagtcc actattaaag aacgtggact ccaacgtcaa agggcgaaaa accgtctatc    2100
agggcgatgg cccactacgt gaaccatcac cctaatcaag ttttttgggg tcgaggtgcc    2160
gtaaagcact aaatcggaac cctaaaggga gcccccgatt tagagcttga cggggaaagc    2220
cggcgaacgt ggcgagaaag gaagggaaga agcgaaagg agcgggcgct agggcgctgg    2280
caagtgtagc ggtcacgctg cgcgtaacca ccacacccgc cgcgcttaat gcgccgctac    2340
agggcgcgtc aggtggcact tttcggggaa atgtgcgcgg aaccctatt tgtttatttt    2400 tctaaataca ttcaaatatg tatccgctca tgagacaata accctgataa atgcttcaat    2460
aatattgaaa aaggaagagt cctgaggcgg aaagaaccag ctgtggaatg tgtgtcagtt    2520
agggtgtgga aagtccccag gctccccagc aggcagaagt atgcaaagca tgcatctcaa    2580
ttagtcagca accaggtgtg gaaagtcccc aggctcccca gcaggcagaa gtatgcaaag    2640
catgcatctc aattagtcag caaccatagt cccgccccta ctccgcccca tcccgcccct    2700
aactccgccc agttccgccc attctccgcc ccatggctga ctaatttttt ttatttatgc    2760
agaggccgag gccgcctcgg cctctgagct attccagaag tagtgaggag gcttttttgg    2820
aggcctaggc ttttgcaaag atcgatcaag agacaggatg aggatcgttt cgcatgattg    2880
aacaagatgg attgcacgca ggttctccgg ccgcttgggt ggagaggcta ttcggctatg    2940
actgggcaca acagacaatc ggctgctctg atgccgccgt gttccggctg tcagcgcagg    3000
ggcgcccggt tctttttgtc aagaccgacc tgtccggtgc cctgaatgaa ctgcaagacg    3060
aggcagcgcg gctatcgtgg ctggccacga cgggcgttcc ttgcgcagct gtgctcgacg    3120
ttgtcactga agcgggaagg gactggctgc tattgggcga agtgccgggg caggatctcc    3180
tgtcatctca ccttgctcct gccgagaaag tatccatcat ggctgatgca atgcggcggc    3240
tgcatacgct tgatccggct acctgcccat tcgaccacca agcgaaacat cgcatcgagc    3300
gagcacgtac tcggatggaa gccggtcttg tcgatcagga tgatctggac gaagagcatc    3360
aggggctcgc gccagccgaa ctgttcgcca ggctcaaggc gagcatgccc gacggcgagg    3420
atctcgtcgt gacccatggc gatgcctgct tgccgaatat catggtggaa aatggccgct    3480
tttctggatt catcgactgt ggccggctgg gtgtggcgga ccgctatcag gacatagcgt    3540
tggctacccg tgatattgct gaagagcttg gcggcgaatg ggctgaccgc ttcctcgtgc    3600
```

-continued

```
tttacggtat cgccgctccc gattcgcagc gcatcgcctt ctatcgcctt cttgacgagt    3660
tcttctgagc gggactctgg ggttcgaaat gaccgaccaa cgacgccca acctgccatc     3720 acgagatttc gattccaccg ccgccttcta tgaaaggttg ggcttcggaa tcgttttccg    3780
ggacgccggc tggatgatcc tccagcgcgg ggatctcatg ctggagttct tcgcccaccc    3840 taggggagg ctaactgaaa cacggaagga acaataccg aaggaaccc gcgctatgac       3900 ggcaataaaa agacagaata aaacgcacgg tgttgggtcg tttgttcata acgcggggt     3960 tcggtcccag ggctggcact ctgtcgatac cccaccgaga ccccattggg gccaatacgc    4020
ccgcgtttct tccttttccc caccccaccc ccaagttcg ggtgaaggcc cagggctcgc     4080
agccaacgtc ggggcggcag gccctgccat agcctcaggt tactcatata actttagat    4140 tgatttaaaa cttcattttt aatttaaaag gatctaggtg aagatccttt ttgataatct    4200
catgaccaaa atcccttaac gtgagttttc gttccactga gcgtcagacc ccgtagaaaa    4260
gatcaaagga tcttcttgag atcctttttt tctgcgcgta atctgctgct tgcaaacaaa    4320
aaaaccaccg ctaccagcgg tggtttgttt gccggatcaa gagctaccaa ctcttttcc     4380 gaaggtaact ggcttcagca gagcgcagat accaaatact gtccttctag tgtagccgta    4440
gttaggccac cacttcaaga actctgtagc accgcctaca tacctcgctc tgctaatcct    4500
gttaccagtg gctgctgcca gtggcgataa gtcgtgtctt accgggttgg actcaagacg    4560
atagttaccg gataaggcgc agcggtcggg ctgaacgggg ggttcgtgca cacagcccag    4620
cttggagcga acgacctaca ccgaactgag atacctacag cgtgagctat gagaaagcgc    4680
cacgcttccc gaagggagaa aggcggacag gtatccggta agcggcaggg tcggaacagg    4740
agagcgcacg agggagcttc cagggggaaa cgcctggtat ctttatagtc ctgtcgggtt    4800
tcgccacctc tgacttgagc gtcgattttt gtgatgctcg tcagggggc ggagcctatg     4860 gaaaaacgcc agcaacgcgg ccttttacg gttcctggcc ttttgctggc cttttgctca    4920
catgttcttt cctgcgttat cccctgattc tgtggataac cgtattaccg ccatgcatta    4980
gttat                                                               4985
```

<210> SEQ ID NO 24
<211> LENGTH: 4229
<212> TYPE: DNA
<213> ORGANISM: Artificial Sequence
<220> FEATURE:
<223> OTHER INFORMATION: p1-5'IL4/EGFP-1

<400> SEQUENCE: 24

```
agcttggtgt aataaaattt tccaatgtaa actcattttc ccttgccttt cagcaacttt     60
aactctatat atagagagat ctctgccagc attgcattgg actctagagg gcccgggatc    120
caccggtcgc caccatggtg agcaagggcg aggagctgtt caccggggtg gtgcccatcc    180
tggtcgagct ggacggcgac gtaaacggcc acaagttcag cgtgtccggc gagggcgagg    240
gcgatgccac ctacggcaag ctgaccctga agttcatctg caccaccggc aagctgcccg    300
tgccctggcc cacccctgtg accaccctga cctacggcgt gcagtgcttc agccgctacc    360
ccgaccacat gaagcagcac gacttcttca gtccgccat gcccgaaggc tacgtccagg     420
agcgcaccat cttcttcaag gacgacggca actacaagac ccgcgccgag gtgaagttcg    480
agggcgacac cctggtgaac cgcatcgagc tgaagggcat cgacttcaag gaggacggca    540
acatcctggg gcacaagctg gagtacaact acaacagcca caacgtctat atcatggccg    600
acaagcagaa gaacggcatc aaggtgaact tcaagatccg ccacaacatc gaggacggca    660
```

```
gcgtgcagct cgccgaccac taccagcaga acaccccat cggcgacggc ccgtgctgc     720
tgcccgacaa ccactacctg agcacccagt ccgccctgag caaagacccc aacgagaagc    780
gcgatcacat ggtcctgctg gagttcgtga ccgccgccgg gatcactctc ggcatggacg    840
agctgtacaa gtaaagcggc cgcgactcta gatcataatc agccatacca catttgtaga    900
ggttttactt gctttaaaaa acctcccaca cctcccctg aacctgaaac ataaatgaa     960
tgcaattgtt gttgttaact tgtttattgc agcttataat ggttacaaat aaagcaatag   1020
catcacaaat ttcacaaata aagcattttt tcactgcat tctagttgtg gtttgtccaa    1080
actcatcaat gtatcttaag gcgtaaattg taagcgttaa tattttgtta aaattcgcgt   1140
taaattttg ttaaatcagc tcatttttta accataggc cgaaatcggc aaaatccctt     1200
ataaatcaaa agaatagacc gagatagggt tgagtgttgt ccagtttgg aacaagagtc    1260
cactattaaa gaacgtggac tccaacgtca agggcgaaa aaccgtctat cagggcgatg    1320
gcccactacg tgaaccatca ccctaatcaa gttttttggg gtcgaggtgc cgtaaagcac   1380
taaatcggaa ccctaaaggg agcccccgat ttagagcttg acggggaaag ccggcgaacg   1440
tggcgagaaa ggaagggaag aaagcgaaag gagcgggcgc tagggcgctg gcaagtgtag   1500
cggtcacgct gcgcgtaacc accacacccg ccgcgcttaa tgcgccgcta cagggcgcgt   1560
caggtggcac ttttcgggga aatgtgcgcg gaaccccctat ttgtttattt ttctaaatac  1620
attcaaatat gtatccgctc atgagacaat aaccctgata aatgcttcaa taatattgaa   1680
aaaggaagag tcctgaggcg gaaagaacca gctgtggaat gtgtgtcagt tagggtgtgg   1740
aaagtcccca ggctccccag caggcagaag tatgcaaagc atgcatctca attagtcagc   1800
aaccaggtgt ggaaagtccc caggctcccc agcaggcaga agtatgcaaa gcatgcatct   1860
caattagtca gcaaccatag tcccgcccct aactccgccc atcccgcccc taactccgcc   1920
cagttccgcc cattctccgc cccatggctg actaatttt tttatttatg cagaggccga    1980
ggccgcctcg gcctctgagc tattccagaa gtagtgagga ggcttttttg gaggcctagg   2040
cttttgcaaa gatcgatcaa gagacaggat gaggatcgtt tcgcatgatt gaacaagatg   2100
gattgcacgc aggttctccg gccgcttggg tggagaggct attcggctat gactgggcac   2160
aacagacaat cggctgctct gatgccgccg tgttccggct gtcagcgcag ggcgcccgg    2220
ttcttttgt caagaccgac ctgtccggtg ccctgaatga actgcaagac gaggcagcgc    2280
ggctatcgtg gctggccacg acgggcgttc cttgcgcagc tgtgctcgac gttgtcactg   2340
aagcgggaag gactggctg ctattgggcg aagtgccggg gcaggatctc ctgtcatctc    2400
accttgctcc tgccgagaaa gtatccatca tggctgatgc aatgcggcgg ctgcatacgc   2460
ttgatccggc tacctgccca ttcgaccacc aagcgaaaca tcgcatcgag cgagcacgta   2520
ctcggatgga agccggtctt gtcgatcagg atgatctgga cgaagagcat caggggctcg   2580
cgccagccga actgttcgcc aggctcaagg cgagcatgcc cgacggcgag gatctcgtcg   2640
tgacccatgg cgatgcctgc ttgccgaata tcatggtgga aaatggccgc ttttctggat   2700
tcatcgactg tggccggctg ggtgtggcgg accgctatca ggacatagcg ttggctaccc   2760
gtgatattgc tgaagagctt ggcggcgaat gggctgaccg cttcctcgtg ctttacggta   2820
tcgccgctcc cgattcgcag cgcatcgcct tctatcgcct tcttgacgag ttcttctgag   2880
cgggactctg gggttcgaaa tgaccgacca agcgacgccc aacctgccat cacgagattt   2940
cgattccacc gccgccttct atgaaaggtt gggcttcgga atcgttttcc gggacgccgg   3000
ctggatgatc ctccagcgcg gggatctcat gctggagttc ttcgcccacc ctaggggag   3060
```

| | |
|---|---|
| gctaactgaa acacggaagg agacaatacc ggaaggaacc cgcgctatga cggcaataaa | 3120 |
| aagacagaat aaaacgcacg gtgttgggtc gtttgttcat aaacgcgggg ttcggtccca | 3180 |
| gggctggcac tctgtcgata ccccaccgag accccattgg ggccaatacg cccgcgtttc | 3240 |
| ttccttttcc ccaccccacc ccccaagttc gggtgaaggc ccagggctcg cagccaacgt | 3300 |
| cggggcggca ggccctgcca tagcctcagg ttactcatat atactttaga ttgatttaaa | 3360 |
| acttcatttt taatttaaaa ggatctaggt gaagatcctt tttgataatc tcatgaccaa | 3420 |
| aatcccttaa cgtgagtttt cgttccactg agcgtcagac cccgtagaaa agatcaaagg | 3480 |
| atcttcttga tccttttt ttctgcgcgt aatctgctgc ttgcaaacaa aaaaaccacc | 3540 |
| gctaccagcg gtggtttgtt tgccggatca agagctacca actcttttt cgaaggtaac | 3600 |
| tggcttcagc agagcgcaga taccaaatac tgtccttcta gtgtagccgt agttaggcca | 3660 |
| ccacttcaag aactctgtag caccgcctac atacctcgct ctgctaatcc tgttaccagt | 3720 |
| ggctgctgcc agtggcgata gtcgtgtct taccggttg gactcaagac gatagttacc | 3780 |
| ggataaggcg cagcggtcgg gctgaacggg gggttcgtgc acacagccca gcttggagcg | 3840 |
| aacgacctac accgaactga gatacctaca gcgtgagcta tgagaaagcg ccacgcttcc | 3900 |
| cgaagggaga aaggcggaca ggtatccggt aagcggcagg gtcggaacag gagagcgcac | 3960 |
| gagggagctt ccaggggaa acgcctggta tctttatagt cctgtcgggt ttcgccacct | 4020 |
| ctgacttgag cgtcgatttt tgtgatgctc gtcagggggg cggagcctat ggaaaaacgc | 4080 |
| cagcaacgcg gcctttttac ggttcctggc cttttgctgg ccttttgctc acatgttctt | 4140 |
| tcctgcgtta tccctgatt ctgtggataa ccgtattacc gccatgcatt agttattact | 4200 |
| agcgctaccg gactcagatc tcgagctca | 4229 |

<210> SEQ ID NO 25
<211> LENGTH: 5178
<212> TYPE: DNA
<213> ORGANISM: Artificial Sequence
<220> FEATURE:
<223> OTHER INFORMATION: p2-5'IL4/EGFP-1

<400> SEQUENCE: 25

| | |
|---|---|
| tagttattaa tgtgagttag ctcactcatt aggcacccca ggctttacac tttatgcttc | 60 |
| cggctcgtat gttgtgtgga attgtgagcg gataacaatt tcacacagga aacagctatg | 120 |
| accatgatta cgccaagctt ggtaccgagc tcggatccac tagtaacggc cgccagtgtg | 180 |
| ctggaattcg gcttggctcg tatgttgtgt ggaattgtga gcggataaca atttcacaca | 240 |
| ggaaacagct atgaccatga ttacgccaag cttgcatgcc tgcaggtcag cttgtgagtc | 300 |
| tgagttcaag gatccacacg gtgcaaagag agacccggtc tcctgacctc cacactgatg | 360 |
| ctgtagtgca catagataca cacatgctca catgaagtaa tttaaaaaaa attttttta | 420 |
| aatcagccat ttctcaggct tctgtctaag gtaggaaaaa tcttcaacct agcccagaac | 480 |
| ctccatatag ctaaagcctc attccatggt cctgcctgcc ccactccatg tcacctctct | 540 |
| gtctccaaag accacaaact tgtaagatca gctgggctag gatgcgagaa ggtctgcctc | 600 |
| catcatcctt ctatgaggta agaccccaga atcagctttc caagatatc agagtttcca | 660 |
| aggggccccc atagcaggaa gcagctaggc ccaggtgtgc gcaaggcaga ctttcttgat | 720 |
| attactctgt cttttcccag ggcgacacca gcaccctcgg acacctgtga cctctttctt | 780 |
| ctctgcagga ggagagccag tggcaaccct acgctgatta gattagtctt aaaggccgtt | 840 |
| atgggtgtaa tttcctatgc tgaaactttg tagatttaaa aaaaaaagg ggggggaggg | 900 |

```
gtgtttcatt ttccaattgg tctgatttca caggaaaatt tacctgtttc tcttttttct    960
cctggaagag aggtgctgat tggcccagaa taactgacaa tctggtgtaa taaaattttc   1020
caatgtaaac tcattttccc ttggtttcag caactttaac tctatatata gagagatctc   1080
tgccagcatt gcattggact cccgggatcc accggtcgcc accatggtga gcaagggcga   1140
ggagctgttc accggggtgg tgcccatcct ggtcgagctg gacggcgacg taaacggcca   1200
caagttcagc gtgtccggcg agggcgaggg cgatgccacc tacggcaagc tgaccctgaa   1260
gttcatctgc accaccggca agctgcccgt gccctggccc accctcgtga ccaccctgac   1320
ctacggcgtg cagtgcttca gccgctaccc cgaccacatg aagcagcacg acttcttcaa   1380
gtccgccatg cccgaaggct acgtccagga gcgcaccatc ttcttcaagg acgacggcaa   1440
ctacaagacc cgcgccgagg tgaagttcga gggcgacacc ctggtgaacc gcatcgagct   1500
gaagggcatc gacttcaagg aggacggcaa catcctgggg cacaagctgg agtacaacta   1560
caacagccac aacgtctata tcatggccga caagcagaag aacggcatca aggtgaactt   1620
caagatccgc cacaacatcg aggacggcag cgtgcagctc gccgaccact accagcagaa   1680
cacccccatc ggcgacggcc ccgtgctgct gcccgacaac cactacctga gcacccagtc   1740
cgccctgagc aaagacccca acgagaagcg cgatcacatg gtcctgctgg agttcgtgac   1800
cgccgccggg atcactctcg gcatggacga gctgtacaag taaagcggcc gcgactctag   1860
atcataatca gccataccac atttgtagag gttttacttg ctttaaaaaa cctcccacac   1920
ctccccctga acctgaaaca taaaatgaat gcaattgttg ttgttaactt gtttattgca   1980
gcttataatg gttacaaata agcaatagc atcacaaatt tcacaaataa agcatttttt   2040
tcactgcatt ctagttgtgg tttgtccaaa ctcatcaatg tatcttaagg cgtaaattgt   2100
aagcgttaat attttgttaa aattcgcgtt aaatttttgt taaatcagct catttttta   2160
ccaataggcc gaaatcggca aaatccctta taaatcaaaa gaatagaccg agatagggtt   2220
gagtgttgtt ccagtttgga acaagagtcc actattaaag aacgtggact ccaacgtcaa   2280
agggcgaaaa accgtctatc agggcgatgg cccactacgt gaaccatcac cctaatcaag   2340
ttttttgggg tcgaggtgcc gtaaagcact aaatcggaac cctaaaggga gcccccgatt   2400
tagagcttga cggggaaagc cggcgaacgt ggcgagaaag gaagggaaga agcgaaagg   2460
agcgggcgct agggcgctgg caagtgtagc ggtcacgctg cgcgtaacca ccacacccgc   2520
cgcgcttaat gcgccgctac agggcgcgtc aggtggcact tttcgggaa atgtgcgcgg   2580
aacccctatt tgtttatttt tctaaataca ttcaaatatg tatccgctca tgagacaata   2640
accctgataa atgcttcaat aatattgaaa aaggaagagt cctgaggcgg aaagaaccag   2700
ctgtggaatg tgtgtcagtt agggtgtgga agtccccag ctccccagc aggcagaagt   2760
atgcaaagca tgcatctcaa ttagtcagca accaggtgtg gaaagtcccc aggctcccca   2820
gcaggcagaa gtatgcaaag catgcatctc aattagtcag caaccatagt cccgccccta   2880
actccgccca tcccgcccct aactccgccc agttccgccc attctccgcc ccatggctga   2940
ctaattttt ttatttatgc agaggccgag gccgcctcgg cctctgagct attccagaag   3000
tagtgaggag gctttttgg aggcctaggc ttttgcaaag atcgatcaag agacaggatg   3060
aggatcgttt cgcatgattg aacaagatgg attgcacgca ggttctccgg ccgcttgggt   3120
ggagaggcta ttcggctatg actgggcaca acagacaatc ggctgctctg atgccgccgt   3180
gttccggctg tcagcgcagg ggcgcccggt tctttttgtc aagaccgacc tgtccggtgc   3240
cctgaatgaa ctgcaagacg aggcagcgcg gctatcgtgg ctggccacga cgggcgttcc   3300
```

```
ttgcgcagct gtgctcgacg ttgtcactga agcgggaagg gactggctgc tattgggcga   3360
agtgccgggg caggatctcc tgtcatctca ccttgctcct gccgagaaag tatccatcat   3420
ggctgatgca atgcggcggc tgcatacgct tgatccggct acctgcccat tcgaccacca   3480
agcgaaacat cgcatcgagc gagcacgtac tcggatggaa gccggtcttg tcgatcagga   3540
tgatctggac gaagagcatc aggggctcgc gccagccgaa ctgttcgcca ggctcaaggc   3600
gagcatgccc gacggcgagg atctcgtcgt gacccatggc gatgcctgct tgccgaatat   3660
catggtggaa aatggccgct tttctggatt catcgactgt ggccggctgg gtgtggcgga   3720
ccgctatcag gacatagcgt tggctacccg tgatattgct gaagagcttg gcggcgaatg   3780
ggctgaccgc ttcctcgtgc tttacggtat cgccgctccc gattcgcagc gcatcgcctt   3840
ctatcgcctt cttgacgagt tcttctgagc gggactctgg ggttcgaaat gaccgaccaa   3900
gcgacgccca acctgccatc acgagatttc gattccaccg ccgccttcta tgaaaggttg   3960
ggcttcggaa tcgttttccg ggacgccggc tggatgatcc tccagcgcgg gatctcatg    4020
ctggagttct cgcccaccc  taggggagg ctaactgaaa cacggaagga gacaataccg    4080
gaaggaaccc gcgctatgac ggcaataaaa agacagaata aaacgcacgg tgttgggtcg    4140
tttgttcata acgcggggt  tcggtcccag ggctggcact ctgtcgatac cccaccgaga    4200
ccccattggg gccaatacgc ccgcgtttct cctttcccc  caccccaccc cccaagttcg    4260
ggtgaaggcc cagggctcgc agccaacgtc ggggcggcag gccctgccat agcctcaggt   4320
tactcatata tactttagat tgatttaaaa cttcattttt aatttaaaag gatctaggtg   4380
aagatccttt ttgataatct catgaccaaa atcccttaac gtgagttttc gttccactga   4440
gcgtcagacc ccgtagaaaa gatcaaagga tcttcttgag atccttttt  tctgcgcgta   4500
atctgctgct tgcaaacaaa aaaaccaccg ctaccagcgg tggtttgttt gccggatcaa   4560
gagctaccaa ctcttttcc  gaaggtaact ggcttcagca gagcgcagat accaaatact   4620
gtccttctag tgtagccgta gttaggccac cacttcaaga actctgtagc accgcctaca   4680
tacctcgctc tgctaatcct gttaccagtg gctgctgcca gtggcgataa gtcgtgtctt   4740
accgggttgg actcaagacg atagttaccg gataaggcgc agcggtcggg ctgaacgggg   4800
ggttcgtgca cacagcccag cttggagcga acgacctaca ccgaactgag atacctacag   4860
cgtgagctat gagaaagcgc cacgcttccc gaagggagaa aggcggacag gtatccggta   4920
agcggcaggg tcggaacagg agagcgcacg agggagcttc caggggggaaa cgcctggtat   4980
ctttatagtc ctgtcgggtt tcgccacctc tgacttgagc gtcgattttt gtgatgctcg   5040
tcagggggc  ggagcctatg gaaaaacgcc agcaacgcgg cctttttacg gttcctggcc   5100
ttttgctggc cttttgctca catgttcttt cctgcgttat cccctgattc tgtggataac   5160
cgtattaccg ccatgcat                                                 5178
```

<210> SEQ ID NO 26
<211> LENGTH: 4352
<212> TYPE: DNA
<213> ORGANISM: Artificial Sequence
<220> FEATURE:
<223> OTHER INFORMATION: p1-5'IL4/d1EGFP-N1

<400> SEQUENCE: 26

```
agcttggtgt aataaaattt tccaatgtaa actcattttc ccttgccttt cagcaacttt     60
aactctatat atagagagat ctctgccagc attgcattgg actctagagg gcccgggatc    120
caccggtcgc caccatggtg agcaagggcg aggagctgtt caccggggtg gtgcccatcc    180
```

-continued

```
tggtcgagct ggacggcgac gtaaacggcc acaagttcag cgtgtccggc gagggcgagg    240
gcgatgccac ctacgcaag ctgaccctga agttcatctg caccaccggc aagctgcccg     300
tgccctggcc caccctcgtg accaccctga cctacggcgt gcagtgcttc agccgctacc    360
ccgaccacat gaagcagcac gacttcttca gtccgccat gcccgaaggc tacgtccagg     420
agcgcaccat cttcttcaag gacgacggca actacaagac ccgcgccgag gtgaagttcg    480
agggcgacac cctggtgaac cgcatcgagc tgaagggcat cgacttcaag gaggacggca    540
acatcctggg gcacaagctg gagtacaact acaacagcca caacgtctat atcatggccg    600
acaagcagaa gaacggcatc aaggtgaact tcaagatccg ccacaacatc gaggacggca    660
gcgtgcagct cgccgaccac taccagcaga caccccccat cggcgacggc ccgtgctgc    720 tgcccgacaa ccactacctg agcacccagt ccgccctgag caaagacccc aacgagaagc    780
gcgatcacat ggtcctgctg gagttcgtga ccgccgccgg gatcactctc ggcatggacg    840
agctgtacaa gaagcttagc catggcttcc cgccggcggt ggcggcgcag gatgatggca    900
cgctgcccat gtcttgtgcc caggagagcg ggatggaccg tcaccctgca gcctgtgctt    960
ctgctaggat caatgtgtag atgcgcggcc gcgactctag atcataatca gccataccac   1020
atttgtagag gttttacttg ctttaaaaaa cctcccacac ctcccctga acctgaaaca    1080 taaaatgaat gcaattgttg ttgttaactt gttattgca gcttataatg gttacaaata    1140
aagcaatagc atcacaaatt tcacaaataa agcattttt tcactgcatt ctagttgtgg    1200
tttgtccaaa ctcatcaatg tatcttaagg cgtaaattgt aagcgttaat attttgttaa    1260
aattcgcgtt aaattttgt taaatcagct catttttaa ccataggcc gaaatcggca     1320 aaatccctta taaatcaaaa gaatagaccg agatagggtt gagtgttgtt ccagtttgga    1380
acaagagtcc actattaaag aacgtggact ccaacgtcaa agggcgaaaa accgtctatc    1440
agggcgatgg cccactacgt gaaccatcac cctaatcaag ttttttgggg tcgaggtgcc    1500
gtaaagcact aaatcggaac cctaaaggga gccccgatt tagagcttga cggggaaagc    1560
cggcgaacgt ggcgagaaag gaagggaaga aagcgaaagg agcgggcgct agggcgctgg    1620
caagtgtagc ggtcacgctg cgcgtaacca ccacacccgc cgcgcttaat gcgccgctac    1680
agggcgcgtc aggtggcact tttcggggaa atgtgcgcgg aaccctatt tgtttatttt    1740 tctaaataca ttcaaatatg tatccgctca tgagacaata accctgataa atgcttcaat    1800
aatattgaaa aaggaagagt cctgaggcgg aaagaaccag ctgtggaatg tgtgtcagtt    1860
agggtgtgga aagtccccag gctccccagc aggcagaagt atgcaaagca tgcatctcaa    1920
ttagtcagca accaggtgtg gaaagtcccc aggctcccca gcaggcagaa gtatgcaaag    1980
catgcatctc aattagtcag caaccatagt cccgcccta actccgccca tcccgccct    2040 aactccgccc agttccgccc attctccgcc ccatggctga ctaatttttt ttatttatgc    2100
agaggccgag gccgcctcgg cctctgagct attccagaag tagtgaggag gcttttttgg    2160
aggcctaggc ttttgcaaag atcgatcaag agacaggatg aggatcgttt cgcatgattg    2220
aacaagatgg attgcacgca ggttctccgg ccgcttgggt ggagaggcta ttcggctatg    2280
actgggcaca acagacaatc ggctgctctg atgccgccgt gttccggctg tcagcgcagg    2340
ggcgcccggt tctttttgtc aagaccgacc tgtccggtgc cctgaatgaa ctgcaagacg    2400
aggcagcgcg gctatcgtgg ctggccacga cgggcgttcc ttgcgcagct gtgctcgacg    2460
ttgtcactga gcgggaagg gactggctgc tattgggcga agtgccgggg caggatctcc    2520
tgtcatctca ccttgctcct gccgagaaag tatccatcat ggctgatgca atgcggcggc    2580
```

```
tgcatacgct tgatccggct acctgcccat tcgaccacca agcgaaacat cgcatcgagc   2640
gagcacgtac tcggatggaa gccggtcttg tcgatcagga tgatctggac gaagagcatc   2700
aggggctcgc gccagccgaa ctgttcgcca ggctcaaggc gagcatgccc gacggcgagg   2760
atctcgtcgt gacccatggc gatgcctgct tgccgaatat catggtggaa aatggccgct   2820
tttctggatt catcgactgt ggccggctgg gtgtggcgga ccgctatcag gacatagcgt   2880
tggctacccg tgatattgct gaagagcttg gcggcgaatg ggctgaccgc ttcctcgtgc   2940
tttacggtat cgccgctccc gattcgcagc gcatcgcctt ctatcgcctt cttgacgagt   3000
tcttctgagc gggactctgg ggttcgaaat gaccgaccaa gcgacgccca acctgccatc   3060
acgagatttc gattccaccg ccgccttcta tgaaaggttg ggcttcggaa tcgttttccg   3120
ggacgccggc tggatgatcc tccagcgcgg ggatctcatg ctggagttct cgcccaccc   3180 taggggagg ctaactgaaa cacggaagga gacaataccg gaaggaaccc gcgctatgac   3240
ggcaataaaa agacagaata aaacgcacgg tgttgggtcg tttgttcata acgcggggt   3300 tcggtcccag ggctggcact ctgtcgatac cccaccgaga ccccattggg gccaatacgc   3360
ccgcgtttct tccttttccc caccccaccc cccaagttcg ggtgaaggcc cagggctcgc   3420
agccaacgtc ggggcggcag gccctgccat agcctcaggt tactcatata tactttagat   3480
tgatttaaaa cttcattttt aatttaaaag gatctaggtg aagatccttt ttgataatct   3540
catgaccaaa atcccttaac gtgagttttc gttccactga gcgtcagacc ccgtagaaaa   3600
gatcaaagga tcttcttgag atccttttt tctgcgcgta atctgctgct tgcaaacaaa   3660
aaaaccaccg ctaccagcgg tggtttgttt gccggatcaa gagctaccaa ctcttttcc   3720 gaaggtaact ggcttcagca gagcgcagat accaaatact gtccttctag tgtagccgta   3780
gttaggccac cacttcaaga actctgtagc accgcctaca tacctcgctc tgctaatcct   3840
gttaccagtg gctgctgcca gtggcgataa gtcgtgtctt accgggttgg actcaagacg   3900
atagttaccg gataaggcgc agcggtcggg ctgaacgggg ggttcgtgca cacagcccag   3960
cttggagcga acgacctaca ccgaactgag atacctacag cgtgagctat gagaaagcgc   4020
cacgcttccc gaagggagaa aggcggacag gtatccggta agcggcaggg tcggaacagg   4080
agagcgcacg agggagcttc caggggggaaa cgcctggtat ctttatagtc ctgtcgggtt   4140
tcgccacctc tgacttgagc gtcgattttt gtgatgctcg tcaggggggc ggagcctatg   4200
gaaaaacgcc agcaacgcgg cctttttacg gttcctggcc ttttgctggc cttttgctca   4260
catgttcttt cctgcgttat cccctgattc tgtggataac cgtattaccg ccatgcatta   4320
gttatcgcta ccggactcag atctcgagct ca                                 4352
```

<210> SEQ ID NO 27
<211> LENGTH: 5307
<212> TYPE: DNA
<213> ORGANISM: Artificial Sequence
<220> FEATURE:
<223> OTHER INFORMATION: p2-5'IL4/d1EGFP-N1

<400> SEQUENCE: 27

```
agcttggtac cgagctcgga tccactagta acggccgcca gtgtgctgga attcggcttg    60
gctcgtatgt tgtgtggaat tgtgagcgga taacaatttc acacaggaaa cagctatgac   120
catgattacg ccaagcttgc atgcctgcag gtcagcttgt gagtctgagt tcaaggatcc   180
acacggtgca aagagagacc cggtctcctg acctccacac tgatgctgta gtgcacatag   240
atacacacat gctcacatga agtaattaa aaaaaattttt ttttaaatca gccatttctc   300
```

```
aggcttctgt ctaaggtagg aaaaatcttc aacctagccc agaacctcca tatagctaaa    360
gcctcattcc atggtcctgc ctgccccact ccatgtcacc tctctgtctc caaagaccac    420
aaacttgtaa gatcagctgg gctaggatgc gagaaggtct gcctccatca tccttctatg    480
aggtaagacc ccagaatcag ctttcccaag atatcagagt ttccaagggg cccccatagc    540
aggaagcagc taggcccagg tgtgcgcaag gcagactttc ttgatattac tctgtctttc    600
cccagggcga caccagcacc ctcggacacc tgtgacctct ttcttctctg caggaggaga    660
gccagtggca accctacgct gattagatta gtcttaaagg ccgttatggg tgtaatttcc    720
tatgctgaaa ctttgtagat ttaaaaaaaa aaggggggg gagggggtgtt tcattttcca    780
attggtctga tttcacagga aaatttacct gtttctcttt tttctcctgg aagagaggtg    840
ctgattggcc cagaataact gacaatctgg tgtaataaaa ttttccaatg taaactcatt    900
ttcccttggt ttcagcaact ttaactctat atatagagag atctctgcca gcattgcatt    960
ggactcccgg gatccaccgg tcgccaccat ggtgagcaag ggcgaggagc tgttcaccgg   1020
ggtggtgccc atcctggtcg agctggacgg cgacgtaaac ggccacaagt tcagcgtgtc   1080
cggcgagggc gagggcgatg ccacctacgg caagctgacc ctgaagttca tctgcaccac   1140
cggcaagctg cccgtgccct ggcccaccct cgtgaccacc ctgacctacg gcgtgcagtg   1200
cttcagccgc taccccgacc acatgaagca gcacgacttc ttcaagtccg ccatgcccga   1260
aggctacgtc caggagcgca ccatcttctt caaggacgac ggcaactaca agacccgcgc   1320
cgaggtgaag ttcgagggcg acaccctggt gaaccgcatc gagctgaagg gcatcgactt   1380
caaggaggac ggcaacatcc tggggcacaa gctggagtac aactacaaca gccacaacgt   1440
ctatatcatg gccgacaagc agaagaacgg catcaaggtg aacttcaaga tccgccacaa   1500
catcgaggac ggcagcgtgc agctcgccga ccactaccag cagaacaccc ccatcggcga   1560
cggccccgtg ctgctgcccg acaaccacta cctgagcacc cagtccgccc tgagcaaaga   1620
ccccaacgag aagcgcgatc acatggtcct gctggagttc gtgaccgccg ccgggatcac   1680
tctcggcatg gacgagctgt acaagaagct tagccatggc ttcccgccgg cggtggcggc   1740
gcaggatgat ggcacgctgc ccatgtcttg tgcccaggag agcgggatgg accgtcaccc   1800
tgcagcctgt gcttctgcta ggatcaatgt gtagatgcgc ggccgcgact ctagatcata   1860
atcagccata ccacatttgt agaggtttta cttgctttaa aaaacctccc acacctcccc   1920
ctgaacctga acataaaat gaatgcaatt gttgttgtta acttgtttat tgcagcttat   1980
aatggttaca aataaagcaa tagcatcaca aatttcacaa ataaagcatt tttttcactg   2040
cattctagtt gtggtttgtc caaactcatc aatgtatctt aaggcgtaaa ttgtaagcgt   2100
taatattttg ttaaaattcg cgttaaattt tgttaaatc agctcatttt ttaaccaata   2160
ggccgaaatc ggcaaaatcc cttataaatc aaaagaatag accgagatag ggttgagtgt   2220
tgttccagtt tggaacaaga gtccactatt aaagaacgtg gactccaacg tcaaagggcg   2280
aaaaaccgtc tatcagggcg atggcccact acgtgaacca tcaccctaat caagtttttt   2340
ggggtcgagg tgccgtaaag cactaaatcg gaacctaaa gggagccccc gatttagagc   2400
ttgacgggga agccggcga acgtggcgag aaaggaaggg aagaaagcga aggagcggg   2460
cgctagggcg ctggcaagtg tagcggtcac gctgcgcgta accaccacac ccgccgcgct   2520
taatgcgccg ctacagggcg cgtcaggtgg cacttttcgg ggaaatgtgc gcggaacccc   2580
tatttgttta ttttctaaa tacattcaaa tatgtatccg ctcatgagac aataaccctg   2640
ataaatgctt caataatatt gaaaaaggaa gagtcctgag gcggaaagaa ccagctgtgg   2700
```

```
aatgtgtgtc agttagggtg tggaaagtcc ccaggctccc cagcaggcag aagtatgcaa    2760
agcatgcatc tcaattagtc agcaaccagg tgtggaaagt ccccaggctc cccagcaggc    2820
agaagtatgc aaagcatgca tctcaattag tcagcaacca tagtcccgcc cctaactccg    2880
cccatcccgc ccctaactcc gcccagttcc gcccattctc cgccccatgg ctgactaatt    2940
ttttttattt atgcagaggc cgaggccgcc tcggcctctg agctattcca gaagtagtga    3000
ggaggctttt ttggaggcct aggcttttgc aaagatcgat caagacacag gatgaggatc    3060
gtttcgcatg attgaacaag atggattgca cgcaggttct ccggccgctt gggtggagag    3120
gctattcggc tatgactggg cacaacagac aatcggctgc tctgatgccg ccgtgttccg    3180
gctgtcagcg caggggcgcc cggttctttt tgtcaagacc gacctgtccg gtgccctgaa    3240
tgaactgcaa gacgaggcag cgcggctatc gtggctggcc acgacgggcg ttccttgcgc    3300
agctgtgctc gacgttgtca ctgaagcggg aagggactgg ctgctattgg gcgaagtgcc    3360
ggggcaggat ctcctgtcat ctcaccttgc tcctgccgag aaagtatcca tcatggctga    3420
tgcaatgcgg cggctgcata cgcttgatcc ggctacctgc ccattcgacc accaagcgaa    3480
acatcgcatc gagcgagcac gtactcggat ggaagccggt cttgtcgatc aggatgatct    3540
ggacgaagag catcaggggc tcgcgccagc cgaactgttc gccaggctca aggcgagcat    3600
gcccgacggc gaggatctcg tcgtgaccca tggcgatgcc tgcttgccga atatcatggt    3660
ggaaaatggc cgcttttctg gattcatcga ctgtggccgg ctgggtgtgg cggaccgcta    3720
tcaggacata gcgttggcta cccgtgatat tgctgaagag cttggcggcg aatgggctga    3780
ccgcttcctc gtgctttacg gtatcgccgc tcccgattcg cagcgcatcg ccttctatcg    3840
ccttcttgac gagttcttct gagcgggact ctggggttcg aaatgaccga ccaagcgacg    3900
cccaacctgc catcacgaga tttcgattcc accgccgcct tctatgaaag gttgggcttc    3960
ggaatcgttt tccgggacgc cggctggatg atcctccagc gcggggatct catgctggag    4020
ttcttcgccc acccctagggg gaggctaact gaaacacgga aggagacaat accggaagga    4080
acccgcgcta tgacggcaat aaaaagacag aataaaacgc acggtgttgg gtcgtttgtt    4140
cataaacgcg gggttcggtc ccagggctgg cactctgtcg ataccccacc gagacccat    4200
tggggccaat acgcccgcgt ttcttccttt tccccacccc acccccaag ttcgggtgaa    4260
ggcccagggc tcgcagccaa cgtcggggcg cagcgcctg ccatagcctc aggttactca    4320
tatatacttt agattgattt aaaacttcat tttaattta aaaggatcta ggtgaagatc    4380
cttttgata atctcatgac caaaatccct taacgtgagt tttcgttcca ctgagcgtca    4440
gaccccgtag aaaagatcaa aggatcttct tgagatcctt tttttctgcg cgtaatctgc    4500
tgcttgcaaa caaaaaaacc accgctacca gcggtggttt gtttgccgga tcaagagcta    4560
ccaactcttt ttccgaaggt aactggcttc agcagagcgc agataccaaa tactgtcctt    4620
ctagtgtagc cgtagttagg ccaccacttc aagaactctg tagcaccgcc tacatacctc    4680
gctctgctaa tcctgttacc agtggctgct gccagtggcg ataagtcgtg tcttaccggg    4740
ttggactcaa gacgatagtt accggataag gcgcagcggt cgggctgaac ggggggttcg    4800
tgcacacagc ccagcttgga gcgaacgacc tacaccgaac tgagatacct acagcgtgag    4860
ctatgagaaa gcgccacgct tcccgaaggg agaaaggcgg acaggtatcc ggtaagcggc    4920
agggtcggaa caggagagcg cacgagggag cttccagggg gaaacgcctg gtatctttat    4980
agtcctgtcg ggtttcgcca cctctgactt gagcgtcgat ttttgtgatg ctcgtcaggg    5040
ggcggagcc tatggaaaaa cgccagcaac gcggcctttt tacggttcct ggccttttgc    5100
```

| | |
|---|---|
| tggccttttg ctcacatgtt ctttcctgcg ttatcccctg attctgtgga taaccgtatt | 5160 |
| accgccatgc attagttatt aatgtgagtt agctcactca ttaggcaccc caggctttac | 5220 |
| actttatgct tccggctcgt atgttgtgtg gaattgtgag cggataacaa tttcacacag | 5280 |
| gaaacagcta tgaccatgat tacgcca | 5307 |

<210> SEQ ID NO 28
<211> LENGTH: 4566
<212> TYPE: DNA
<213> ORGANISM: Artificial Sequence
<220> FEATURE:
<223> OTHER INFORMATION: p1-5'3'IL4/d1EGFP-N1

<400> SEQUENCE: 28

| | |
|---|---|
| agcttggtgt aataaaattt tccaatgtaa actcattttc ccttgccttt cagcaacttt | 60 |
| aactctatat atagagagat ctctgccagc attgcattgg actctagagg gcccgggatc | 120 |
| caccggtcgc caccatggtg agcaagggcg aggagctgtt caccggggtg gtgcccatcc | 180 |
| tggtcgagct ggacggcgac gtaaacggcc acaagttcag cgtgtccggc gagggcgagg | 240 |
| gcgatgccac ctacggcaag ctgaccctga agttcatctg caccaccggc aagctgcccg | 300 |
| tgccctggcc caccctcgtg accaccctga cctacggcgt gcagtgcttc agccgctacc | 360 |
| ccgaccacat gaagcagcac gacttcttca gtccgccat gcccgaaggc tacgtccagg | 420 |
| agcgcaccat cttcttcaag gacgacggca actacaagac ccgcgccgag gtgaagttcg | 480 |
| agggcgacac cctggtgaac cgcatcgagc tgaagggcat cgacttcaag gaggacggca | 540 |
| acatcctggg gcacaagctg gagtacaact acaacagcca caacgtctat atcatggccg | 600 |
| acaagcagaa gaacggcatc aaggtgaact tcaagatccg ccacaacatc gaggacggca | 660 |
| gcgtgcagct cgccgaccac taccagcaga acacccccat cggcgacggc cccgtgctgc | 720 |
| tgcccgacaa ccactacctg agcacccagt ccgccctgag caaagacccc aacgagaagc | 780 |
| gcgatcacat ggtcctgctg gagttcgtga ccgccgccgg gatcactctc ggcatggacg | 840 |
| agctgtacaa gaagcttagc catggcttcc cgccggcggt ggcggcgcag atgatggca | 900 |
| cgctgcccat gtcttgtgcc caggagagcg ggatggaccg tcaccctgca gcctgtgctt | 960 |
| ctgctaggat caatgtgtag atgcgcggcc gccagtgtga tggatatctg cagaattcgg | 1020 |
| cttactcgta gtactgagcc accatgcttt aacttatgaa ttttttaatgg ttttattttt | 1080 |
| aatatttata tatttataat tcataaaata aaatatttgt ataatgtaac agaaatgata | 1140 |
| actaatgaca cttcatttgc cataaggttt ctactgtaag ccgaattcca gcacactggc | 1200 |
| ggccgcgact ctagatcata atcagccata ccacatttgt agaggtttta cttgctttaa | 1260 |
| aaaacctccc acacctcccc ctgaacctga aacataaaat gaatgcaatt gttgttgtta | 1320 |
| acttgtttat tgcagcttat aatggttaca ataaagcaa tagcatcaca aatttcacaa | 1380 |
| ataaagcatt ttttcactg cattctagtt gtggtttgtc caaactcatc aatgtatctt | 1440 |
| aaggcgtaaa ttgtaagcgt taatattttg ttaaaattcg cgttaaattt tgttaaatc | 1500 |
| agctcatttt ttaaccaata ggccgaaatc ggcaaaatcc cttataaatc aaaagaatag | 1560 |
| accgagatag ggttgagtgt tgttccagtt tggaacaaga gtccactatt aaagaacgtg | 1620 |
| gactccaacg tcaaagggcg aaaaaccgtc tatcagggcg atggcccact acgtgaacca | 1680 |
| tcaccctaat caagttttt ggggtcgagg tgccgtaaag cactaaatcg gaaccctaaa | 1740 |
| gggagccccc gatttagagc ttgacgggga agccggcga acgtggcgag aaaggaaggg | 1800 |
| aagaaagcga aaggagcggg cgctagggcg ctggcaagtg tagcggtcac gctgcgcgta | 1860 |

```
accaccacac ccgccgcgct taatgcgccg ctacagggcg cgtcaggtgg cacttttcgg    1920
ggaaatgtgc gcggaacccc tatttgttta tttttctaaa tacattcaaa tatgtatccg    1980
ctcatgagac aataaccctg ataaatgctt caataatatt gaaaaaggaa gagtcctgag    2040
gcggaaagaa ccagctgtgg aatgtgtgtc agttagggtg tggaaagtcc ccaggctccc    2100
cagcaggcag aagtatgcaa agcatgcatc tcaattagtc agcaaccagg tgtggaaagt    2160
ccccaggctc cccagcaggc agaagtatgc aaagcatgca tctcaattag tcagcaacca    2220
tagtcccgcc cctaactccg cccatcccgc cctaactccg cccagttccg cccattctc    2280
cgccccatgg ctgactaatt ttttttattt atgcagaggc cgaggccgcc tcggcctctg    2340
agctattcca gaagtagtga ggaggctttt ttggaggcct aggcttttgc aaagatcgat    2400
caagagacag gatgaggatc gtttcgcatg attgaacaag atggattgca cgcaggttct    2460
ccggccgctt gggtggagag gctattcggc tatgactggg cacaacagac aatcggctgc    2520
tctgatgccg ccgtgttccg gctgtcagcg caggggcgcc cggttctttt tgtcaagacc    2580
gacctgtccg gtgccctgaa tgaactgcaa gacgaggcag cgcggctatc gtggctggcc    2640
acgacgggcg ttccttgcgc agctgtgctc gacgttgtca ctgaagcggg aagggactgg    2700
ctgctattgg gcgaagtgcc ggggcaggat ctcctgtcat ctcaccttgc tcctgccgag    2760
aaagtatcca tcatggctga tgcaatgcgg cggctgcata cgcttgatcc ggctacctgc    2820
ccattcgacc accaagcgaa acatcgcatc gagcgagcac gtactcggat ggaagccggt    2880
cttgtcgatc aggatgatct ggacgaagag catcaggggc tcgcgccagc cgaactgttc    2940
gccaggctca aggcgagcat gcccgacggc gaggatctcg tcgtgaccca tggcgatgcc    3000
tgcttgccga atatcatggt ggaaaatggc cgcttttctg gattcatcga ctgtggccgg    3060
ctgggtgtgg cggaccgcta tcaggacata gcgttggcta cccgtgatat tgctgaagag    3120
cttggcggcg aatgggctga ccgcttcctc gtgctttacg gtatcgccgc tcccgattcg    3180
cagcgcatcg ccttctatcg ccttcttgac gagttcttct gagcgggact ctggggttcg    3240
aaatgaccga ccaagcgacg cccaacctgc catcacgaga tttcgattcc accgccgcct    3300
tctatgaaag gttgggcttc ggaatcgttt tccgggacgc cggctggatg atcctccagc    3360
gcggggatct catgctggag ttcttcgccc accctagggg gaggctaact gaaacacgga    3420
aggagacaat accggaagga acccgcgcta tgacggcaat aaaaagacag aataaaacgc    3480
acggtgttgg gtcgtttgtt cataaacgcg gggttcggtc ccagggctgg cactctgtcg    3540
ataccccacc gagaccccat tggggccaat acgcccgcgt ttcttccttt tccccacccc    3600
accccccaag ttcgggtgaa ggcccagggc tcgcagccaa cgtcggggcg caggccctg    3660
ccatagcctc aggttactca tatatacttt agattgattt aaaacttcat ttttaattta    3720
aaaggatcta ggtgaagatc cttttttgata atctcatgac caaaatccct aacgtgagt    3780
tttcgttcca ctgagcgtca gaccccgtag aaaagatcaa aggatcttct tgagatcctt    3840
ttttctgcg cgtaatctgc tgcttgcaaa caaaaaaacc accgctacca gcggtggttt    3900
gtttgccgga tcaagagcta ccaactcttt ttccgaaggt aactggcttc agcagagcgc    3960
agataccaaa tactgtcctt ctagtgtagc cgtagttagg ccaccacttc aagaactctg    4020
tagcaccgcc tacatacctc gctctgctaa tcctgttacc agtggctgct gccagtggcg    4080
ataagtcgtg tcttaccggg ttggactcaa gacgatagtt accggataag gcgcagcggt    4140
cgggctgaac ggggggttcg tgcacacagc ccagcttgga gcgaacgacc tacaccgaac    4200
tgagatacct acagcgtgag ctatgagaaa gcgccacgct cccgaaggg agaaaggcgg    4260
```

| | |
|---|---|
| acaggtatcc ggtaagcggc agggtcggaa caggagagcg cacgagggag cttccagggg | 4320 |
| gaaacgcctg gtatctttat agtcctgtcg ggtttcgcca cctctgactt gagcgtcgat | 4380 |
| ttttgtgatg ctcgtcaggg gggcggagcc tatggaaaaa cgccagcaac gcggccttt | 4440 |
| tacggttcct ggccttttgc tggccttttg ctcacatgtt ctttcctgcg ttatcccctg | 4500 |
| attctgtgga taaccgtatt accgccatgc attagttatc gctaccggac tcagatctcg | 4560 |
| agctca | 4566 |

<210> SEQ ID NO 29
<211> LENGTH: 5521
<212> TYPE: DNA
<213> ORGANISM: Artificial Sequence
<220> FEATURE:
<223> OTHER INFORMATION: p2-5'3'IL4/d1EGFP-N1

<400> SEQUENCE: 29

| | |
|---|---|
| agcttggtac cgagctcgga tccactagta acggccgcca gtgtgctgga attcggcttg | 60 |
| gctcgtatgt tgtgtggaat tgtgagcgga taacaatttc acacaggaaa cagctatgac | 120 |
| catgattacg ccaagcttgc atgcctgcag gtcagcttgt gagtctgagt tcaaggatcc | 180 |
| acacggtgca aagagagacc cggtctcctg acctccacac tgatgctgta gtgcacatag | 240 |
| atacacacat gctcacatga agtaatttaa aaaaaatttt ttttaaatca gccatttctc | 300 |
| aggcttctgt ctaaggtagg aaaaatcttc aacctagccc agaacctcca tatagctaaa | 360 |
| gcctcattcc atggtcctgc ctgccccact ccatgtcacc tctctgtctc aaagaccac | 420 |
| aaacttgtaa gatcagctgg gctaggatgc agaaggtct gcctccatca tccttctatg | 480 |
| aggtaagacc ccagaatcag ctttcccaag atatcagagt ttccaagggg cccccatagc | 540 |
| aggaagcagc taggcccagg tgtgcgcaag gcagactttc ttgatattac tctgtctttc | 600 |
| cccagggcga caccagcacc ctcggacacc tgtgacctct tcttctctg caggaggaga | 660 |
| gccagtggca accctacgct gattagatta gtcttaaagg ccgttatggg tgtaatttcc | 720 |
| tatgctgaaa ctttgtagat ttaaaaaaaa aaggggggg gaggggtgtt tcattttcca | 780 |
| attggtctga tttcacagga aaatttacct gtttctcttt tttctcctgg aagagaggtg | 840 |
| ctgattggcc cagaataact gacaatctgg tgtaataaaa ttttccaatg taaactcatt | 900 |
| ttcccttggt ttcagcaact ttaactctat atatagagag atctctgcca gcattgcatt | 960 |
| ggactcccgg gatccaccgg tcgccaccat ggtgagcaag ggcgaggagc tgttcaccgg | 1020 |
| ggtggtgccc atcctggtcg agctggacgg cgacgtaaac ggccacaagt tcagcgtgtc | 1080 |
| cggcgagggc gagggcgatg ccacctacgg caagctgacc ctgaagttca tctgcaccac | 1140 |
| cggcaagctg cccgtgccct ggcccaccct cgtgaccacc ctgacctacg gcgtgcagtg | 1200 |
| cttcagccgc taccccgacc acatgaagca gcacgacttc ttcaagtccg ccatgcccga | 1260 |
| aggctacgtc caggagcgca ccatcttctt caaggacgac ggcaactaca agacccgcgc | 1320 |
| cgaggtgaag ttcgagggcg acaccctggt gaaccgcatc gagctgaagg gcatcgactt | 1380 |
| caaggaggac ggcaacatcc tggggcacaa gctggagtac aactacaaca gccacaacgt | 1440 |
| ctatatcatg gccgacaagc agaagaacgg catcaaggtg aacttcaaga tccgccacaa | 1500 |
| catcgaggac ggcagcgtgc agctcgccga ccactaccag cagaacaccc ccatcggcga | 1560 |
| cggccccgtg ctgctgcccg acaaccacta cctgagcacc cagtccgccc tgagcaaaga | 1620 |
| ccccaacgag aagcgcgatc acatggtcct gctggagttc gtgaccgccg ccgggatcac | 1680 |
| tctcggcatg gacgagctgt acaagaagct tagccatggc ttcccgccgg cggtggcggc | 1740 |

```
gcaggatgat ggcacgctgc ccatgtcttg tgcccaggag agcgggatgg accgtcaccc   1800
tgcagcctgt gcttctgcta ggatcaatgt gtagatgcgc ggccgccagt gtgatggata   1860
tctgcagaat tcggcttact cgtagtactg agccaccatg ctttaactta tgaatttta    1920 atggttttat ttttaatatt tatatattta taattcataa aataaaatat ttgtataatg   1980
taacagaaat gataactaat gacacttcat ttgccataag gtttctactg taagccgaat   2040
tccagcacac tggcggccgc gactctagat cataatcagc cataccacat ttgtagaggt   2100
tttacttgct ttaaaaaacc tcccacacct cccctgaac ctgaaacata aatgaatgc     2160 aattgttgtt gttaacttgt ttattgcagc ttataatggt tacaaataaa gcaatagcat   2220
cacaaatttc acaaataaag catttttttc actgcattct agttgtggtt tgtccaaact   2280
catcaatgta tcttaaggcg taaattgtaa gcgttaatat tttgttaaaa ttcgcgttaa   2340 attttttgtta aatcagctca tttttaacc aataggccga aatcggcaaa atcccttata   2400
aatcaaaaga atagaccgag ataggggttga gtgttgttcc agtttggaac aagagtccac   2460
tattaaagaa cgtggactcc aacgtcaaag ggcgaaaaac cgtctatcag ggcgatggcc   2520
cactacgtga accatcaccc taatcaagtt ttttggggtc gaggtgccgt aaagcactaa   2580
atcggaaccc taagggagc ccccgattta gagcttgacg gggaaagccg cgaacgtgg    2640 cgagaaagga agggaagaaa gcgaaaggag cgggcgctag ggcgctggca agtgtagcgg   2700
tcacgctgcg cgtaaccacc acaccgccg cgcttaatgc gccgctacag ggcgcgtcag   2760
gtggcacttt tcggggaaat gtgcgcggaa ccctatttg tttattttc taaatacatt     2820 caaatatgta tccgctcatg agacaataac cctgataaat gcttcaataa tattgaaaaa   2880
ggaagagtcc tgaggcggaa agaaccagct gtggaatgtg tgtcagttag ggtgtggaaa   2940
gtccccaggc tccccagcag gcagaagtat gcaaagcatg catctcaatt agtcagcaac   3000
caggtgtgga aagtcccag gctccccagc aggcagaagt atgcaaagca tgcatctcaa    3060
ttagtcagca accatagtcc cgcccctaac tccgcccatc ccgcccctaa ctccgcccag   3120
ttccgcccat tctccgcccc atggctgact aatttttttt atttatgcag aggccgaggc   3180
cgcctcggcc tctgagctat tccagaagta gtgaggaggc ttttttggag gcctaggctt   3240
ttgcaaagat cgatcaagag acaggatgag gatcgtttcg catgattgaa caagatggat   3300
tgcacgcagg ttctccggcc gcttgggtgg agaggctatt cggctatgac tgggcacaac   3360
agacaatcgg ctgctctgat gccgccgtgt tccggctgtc agcgcagggg cgcccggttc   3420
tttttgtcaa gaccgacctg tccggtgccc tgaatgaact gcaagacgag gcagcgcggc   3480
tatcgtggct ggccacgacg ggcgttcctt gcgcagctgt gctcgacgtt gtcactgaag   3540
cgggaaggga ctggctgcta ttgggcgaag tgccggggca ggatctcctg tcatctcacc   3600
ttgctcctgc cgagaaagta tccatcatgg ctgatgcaat gcggcggctg catacgcttg   3660
atccggctac ctgcccattc gaccaccaag cgaaacatcg catcgagcga gcacgtactc   3720
ggatggaagc cggtcttgtc gatcaggatg atctggacga agagcatcag ggctcgcgc    3780 cagccgaact gttcgccagg ctcaaggcga gcatgcccga cggcgaggat ctcgtcgtga   3840
cccatggcga tgcctgcttg ccgaatatca tggtggaaaa tggccgcttt tctggattca   3900
tcgactgtgg ccggctgggt gtggcggacc gctatcagga catagcgttg gctacccgtg   3960
atattgctga agagcttggc ggcgaatggg ctgaccgctt cctcgtgctt tacggtatcg   4020
ccgctcccga ttcgcagcgc atcgccttct atcgccttct tgacgagttc ttctgagcgg   4080
gactctgggg ttcgaaatga ccgaccaagc gacgcccaac ctgccatcac gagatttcga   4140
```

-continued

| | |
|---|---|
| ttccaccgcc gccttctatg aaaggttggg cttcggaatc gttttccggg acgccggctg | 4200 |
| gatgatcctc cagcgcgggg atctcatgct ggagttcttc gcccacccta gggggaggct | 4260 |
| aactgaaaca cggaaggaga caataccgga aggaacccgc gctatgacgg caataaaaag | 4320 |
| acagaataaa acgcacggtg ttgggtcgtt tgttcataaa cgcggggttc ggtcccaggg | 4380 |
| ctggcactct gtcgataccc caccgagacc ccattggggc caatacgccc gcgtttcttc | 4440 |
| cttttcccca ccccaccccc caagttcggg tgaaggccca gggctcgcag ccaacgtcgg | 4500 |
| ggcggcaggc cctgccatag cctcaggtta ctcatatata ctttagattg atttaaaact | 4560 |
| tcattttttaa tttaaaagga tctaggtgaa gatcctttt gataatctca tgaccaaaat | 4620 |
| cccttaacgt gagttttcgt tccactgagc gtcagacccc gtagaaaaga tcaaaggatc | 4680 |
| ttcttgagat cctttttttc tgcgcgtaat ctgctgcttg caaacaaaaa aaccaccgct | 4740 |
| accagcggtg gtttgtttgc cggatcaaga gctaccaact cttttttccga aggtaactgg | 4800 |
| cttcagcaga gcgcagatac caaatactgt ccttctagtg tagccgtagt taggccacca | 4860 |
| cttcaagaac tctgtagcac cgcctacata cctcgctctg ctaatcctgt taccagtggc | 4920 |
| tgctgccagt ggcgataagt cgtgtcttac cgggttggac tcaagacgat agttaccgga | 4980 |
| taaggcgcag cggtcgggct gaacggggggg ttcgtgcaca cagcccagct tggagcgaac | 5040 |
| gacctacacc gaactgagat acctacagcg tgagctatga aaagcgcca cgcttcccga | 5100 |
| agggagaaag gcggacaggt atccggtaag cggcagggtc ggaacaggag agcgcacgag | 5160 |
| ggagcttcca gggggaaacg cctggtatct ttatagtcct gtcgggtttc gccacctctg | 5220 |
| acttgagcgt cgatttttgt gatgctcgtc agggggggcgg agcctatgga aaaacgccag | 5280 |
| caacgcggcc ttttacggtt cctggccctt ttgctggcct tttgctcaca tgttctttcc | 5340 |
| tgcgttatcc cctgattctg tggataaccg tattaccgcc atgcattagt tattaatgtg | 5400 |
| agttagctca ctcattaggc accccaggct ttacacttta tgcttccggc tcgtatgttg | 5460 |
| tgtggaattg tgagcggata caatttcac acaggaaaca gctatgacca tgattacgcc | 5520 |
| a | 5521 |

<210> SEQ ID NO 30
<211> LENGTH: 4476
<212> TYPE: DNA
<213> ORGANISM: Artificial Sequence
<220> FEATURE:
<223> OTHER INFORMATION: p1-5'3'IL4/EGFP-1

<400> SEQUENCE: 30

| | |
|---|---|
| agcttggtgt aataaaattt tccaatgtaa actcattttc ccttgccttt cagcaacttt | 60 |
| aactctatat atagagagat ctctgccagc attgcattgg actctagagg gcccgggatc | 120 |
| caccggtcgc caccatggtg agcaagggcg aggagctgtt caccggggtg gtgcccatcc | 180 |
| tggtcgagct ggacggcgac gtaaacggcc acaagttcag cgtgtccggc gagggcgagg | 240 |
| gcgatgccac ctacggcaag ctgaccctga agttcatctg caccaccggc aagctgcccg | 300 |
| tgccctggcc caccctcgtg accaccctga cctacggcgt gcagtgcttc agccgctacc | 360 |
| ccgaccacat gaagcagcac gacttcttca gtccgccat gcccgaaggc tacgtccagg | 420 |
| agcgcaccat cttcttcaag gacgacggca actacaagac ccgcgccgag gtgaagttcg | 480 |
| agggcgacac cctggtgaac cgcatcgagc tgaagggcat cgacttcaag gaggacggca | 540 |
| acatcctggg gcacaagctg gagtacaact acaacagcca caacgtctat atcatggccg | 600 |
| acaagcagaa gaacggcatc aaggtgaact tcaagatccg ccacaacatc gaggacggca | 660 |

```
gcgtgcagct cgccgaccac taccagcaga acacccccat cggcgacggc ccgtgctgc      720
tgcccgacaa ccactacctg agcacccagt ccgccctgag caaagacccc aacgagaagc      780
gcgatcacat ggtcctgctg gagttcgtga ccgccgccgg gatcactctc ggcatggacg      840
agctgtacaa gtaaagcggc cgcgactcta gatcataatc agccatacca catttgtaga      900
ggttttactt gctttatctg cagaattcgg cttactcgta gtactgagcc accatgcttt      960
aacttatgaa ttttaatgg ttttattttt aatatttata tatttataat tcataaaata     1020
aaatatttgt ataatgtaac agaaatgata actaatgaca cttcatttgc cataaggttt     1080
ctactgtaag ccgaattcca gcacactggc ggccgcgact ctagatcata atcagccata     1140
ccacatttgt agaggtttta cttgctttaa aaaacctccc acacctcccc ctgaacctga     1200
aacataaaat gaatgcaatt gttgttgtta acttgtttat tgcagcttat aatggttaca     1260
aataaagcaa tagcatcaca aatttcacaa ataaagcatt ttttcactg cattctagtt     1320
gtggtttgtc caaactcatc aatgtatctt aaggcgtaaa ttgtaagcgt taatattttg     1380
ttaaaattcg cgttaaattt ttgttaaatc agctcatttt ttaaccaata ggccgaaatc     1440
ggcaaaatcc cttataaatc aaaagaatag accgagatag ggttgagtgt tgttccagtt     1500
tggaacaaga gtccactatt aaagaacgtg gactccaacg tcaaagggcg aaaaaccgtc     1560
tatcagggcg atggcccact acgtgaacca tcaccctaat caagtttttt ggggtcgagg     1620
tgccgtaaag cactaaatcg gaaccctaaa gggagccccc gatttagagc ttgacgggga     1680
aagccgcga acgtggcgag aaaggaaggg aagaaagcga aggagcgggg cgctagggcg     1740
ctggcaagtg tagcggtcac gctgcgcgta accaccacac ccgccgcgct taatgcgccg     1800
ctacagggcg cgtcaggtgg cacttttcgg ggaaatgtgc gcggaacccc tatttgttta     1860
tttttctaaa tacattcaaa tatgtatccg ctcatgagac aataaccctg ataaatgctt     1920
caataatatt gaaaaggaa gagtcctgag gcggaaagaa ccagctgtgg aatgtgtgtc     1980
agttagggtg tggaaagtcc ccaggctccc cagcaggcag aagtatgcaa agcatgcatc     2040
tcaattagtc agcaaccagg tgtggaaagt ccccaggctc cccagcaggc agaagtatgc     2100
aaagcatgca tctcaattag tcagcaacca tagtcccgcc cctaactccg cccatcccgc     2160
ccctaactcc gcccagttcc gcccattctc cgccccatgg ctgactaatt ttttttattt     2220
atgcagaggc cgaggccgcc tcggcctctg agctattcca gaagtagtga ggaggctttt     2280
ttggaggcct aggcttttgc aaagatcgat caagagacag gatgaggatc gtttcgcatg     2340
attgaacaag atgattgca cgcaggttct ccggccgctt gggtggagag ctattcggc      2400
tatgactggg cacaacagac aatcggctgc tctgatgccg ccgtgttccg gctgtcagcg     2460
caggggcgcc cggttctttt tgtcaagacc gacctgtccg gtgccctgaa tgaactgcaa     2520
gacgaggcag cgcggctatc gtggctggcc acgacgggcg ttccttgcgc agctgtgctc     2580
gacgttgtca ctgaagcggg aagggactgg ctgctattgg gcgaagtgcc ggggcaggat     2640
ctcctgtcat ctcaccttgc tcctgccgag aaagtatcca tcatggctga tgcaatgcgg     2700
cggctgcata cgcttgatcc ggctacctgc ccattcgacc accaagcgaa acatcgcatc     2760
gagcgagcac gtactcggat ggaagccggt cttgtcgatc aggatgatct ggacgaagag     2820
catcagggc tcgcgccagc cgaactgttc gccaggctca aggcgagcat gcccgacggc     2880
gaggatctcg tcgtgaccca tggcgatgcc tgcttgccga atatcatggt ggaaaatggc     2940
cgcttttctg gattcatcga ctgtggccgg ctgggtgtgg cggaccgcta tcaggacata     3000
gcgttggcta cccgtgatat tgctgaagag cttggcggcg aatgggctga ccgcttcctc     3060
```

```
gtgctttacg gtatcgccgc tcccgattcg cagcgcatcg ccttctatcg ccttcttgac    3120
gagttcttct gagcgggact ctggggttcg aaatgaccga ccaagcgacg cccaacctgc    3180
catcacgaga tttcgattcc accgccgcct tctatgaaag gttgggcttc ggaatcgttt    3240
tccgggacgc cggctggatg atcctccagc gcggggatct catgctggag ttcttcgccc    3300
accctagggg gaggctaact gaaacacgga aggagacaat accggaagga cccgcgcta    3360 tgacggcaat aaaagacag aataaaacgc acggtgttgg gtcgtttgtt cataaacgcg    3420
gggttcggtc ccagggctgg cactctgtcg ataccccacc gagacccat tggggccaat    3480 acgcccgcgt ttcttccttt tccccacccc accccccaag ttcgggtgaa ggcccagggc    3540
tcgcagccaa cgtcggggcg gcaggccctg ccatagcctc aggttactca tatatacttt    3600
agattgattt aaaacttcat ttttaattta aaaggatcta ggtgaagatc cttttgata    3660 atctcatgac caaaatccct taacgtgagt tttcgttcca ctgagcgtca gaccccgtag    3720
aaaagatcaa aggatcttct tgagatcctt ttttctgcg cgtaatctgc tgcttgcaaa    3780
caaaaaaacc accgctacca gcggtggttt gtttgccgga tcaagagcta ccaactcttt    3840
ttccgaaggt aactggcttc agcagagcgc agataccaaa tactgtcctt ctagtgtagc    3900
cgtagttagg ccaccacttc aagaactctg tagcaccgcc tacatacctc gctctgctaa    3960
tcctgttacc agtggctgct gccagtggcg ataagtcgtg tcttaccggg ttggactcaa    4020
gacgatagtt accggataag gcgcagcggt cgggctgaac ggggggttcg tgcacacagc    4080
ccagcttgga gcgaacgacc tacaccgaac tgagatacct acagcgtgag ctatgagaaa    4140
gcgccacgct cccgaagggg agaaaggcgg acaggtatcc ggtaagcggc agggtcggaa    4200
caggagagcg cacgagggag cttccagggg gaaacgcctg gtatctttat agtcctgtcg    4260
ggtttcgcca cctctgactt gagcgtcgat ttttgtgatg ctcgtcaggg gggcggagcc    4320 tatgaaaaa cgccagcaac gcggcctttt tacggttcct ggccttttgc tggccttttg    4380
ctcacatgtt ctttcctgcg ttatcccctg attctgtgga taaccgtatt accgccatgc    4440
attagttatc gctaccggac tcagatctcg agctca                             4476
```

<210> SEQ ID NO 31
<211> LENGTH: 6241
<212> TYPE: DNA
<213> ORGANISM: Artificial Sequence
<220> FEATURE:
<223> OTHER INFORMATION: p1-5'INFgamma/EGFP-1

<400> SEQUENCE: 31

```
ggcggccgcg aattcactag tgatagattg ctggcttctg tcacctgagt gctgggatta     60
aaggtatgag ttaccacgac cctgctagat tttttttta agacagattc tcatgattct    120
taaactggcc ttcaagtctc cagcagcaga aggtgacctc gcactcatga tcatcttacc    180
tctgttccca tctgtatttc atgcctattt taagtcaggg ttttataca agcactctac    240 caaccaagag atgttcctga ctgtcaaaac agagattctt aggtaaacat tcaaatgaat    300
atttgtgtgt gtgtgtgtgt tgtttgtgta taaatcttta tgcttatgta tttgagggaa    360
ataaattgtg tcacagaagc aatgaaacac tttctggttt taaggaaatt agtgggcact    420 gggatgggg taggggcat gcatagttac ctcgtatatg agactgggga aattgagaac    480
ccatgaagca tagaaacaaa gtgctagccc tgcccagagg ataaagtctg atttgaagct    540
ggaggcttgg gggagaacca aaacagagga tggtttgcat ctgggtcaag ataactgggt    600
accactctga gatgctcaga tgagggaaag ggggcacatg gccaaaggaa ctgcacgaac    660
```

```
aagctgcata gcgttgttaa acatctgaca ttgccaaata accatcaagt tttaattgag    720
ccactaggaa tgccgggaag aattctctca actttccatg gagcatttgg ttgagccttt    780
ggctgaagtc cggaagaaaa tgctagtgtt aagctcactg tataaatgtg gaaactgagt    840
cacagatcat aaagatgctg actcaagacc ccgaggctag aatatgaatg gttcaagtct    900
gcacccatag ccactgtgta atgttaatga atacaggaaa ggcagggatg aatacacgtg    960
ggctggcact gaagagcaga gggcctcctg ccccatcctc aaggatcgaa tttcatagat   1020
aggttaccaa agacagagaa ggaaactttt agtgtttgaa cttgatgggg gaaacaattt   1080
tcagttatta atccttatttt gggacaagtg tgtgtctagt gctggactag tcattgggat   1140
agccttagcc acatgtgggt atgagagtta gaaacatggc taatcctgaa gtgatttctg   1200
ctgtgtatat aggatagcca ctaggcttta aatatttagt ggcagaggaa ttgaaactct   1260
tattcatcat aaatcttgat acacattgat accttgggtg tgttgagtga aatacaatat   1320
ctaatgaagt attcttgcat ttttactttt atttcatttt gcattttttt cccttttatt   1380
aatggaggaa ctagatgatt ttattttacc tatgtggtct gccttttctt ctttctgggc   1440
acgttgaccc tgagtgattt gtagtaggta ttttactaat cacctccatt gaagggcttc   1500
ctcaccacat tggcttttta accatacccct ttccttgctt ttctggtcat ttgcaagaaa   1560
agtttgaaaa ggcttccccc attgcatggt ttgagaagcc caagagtttc ctcatggttt   1620
gagaagccca agagtttcct tttattcagc cgtccccaac cacaaacaaa ggctccctgt   1680
gctgtgctct gtggatgaga aattcacatt acaagggcaa aaaggggggag acgtaaaagc   1740 aatttccagc ccccacccca aatggtgtga agtaaaagtg ctttcagaga atcccacaag   1800
aatggcacag gtgggcacag cggggctgtc tcatcgtcag agagcccaag gagtcgaaag   1860
gaaactctaa catgccacaa aaccatagct gtaatgcaaa gtaacttagc tcccccacc   1920 tatctgtcac catcttaaaa aaaaaaaac caaaaaaaaa cttgtgaaaa tacgtaatcc   1980
cgaggagcct tcgatcaggt ataaaactgg aagccagaga ggtgcaggct atagctgcca   2040
tcggctgacc tagagaagaa tcgaattccc gcggccgcca tggcggccgg gagcatgcga   2100
cgtcgggccc gggatccacc ggtcgccacc atggtgagca agggcgagga gctgttcacc   2160
ggggtggtgc ccatcctggt cgagctggac ggcgacgtaa acggccacaa gttcagcgtg   2220
tccggcgagg gcgagggcga tgccacctac ggcaagctga ccctgaagtt catctgcacc   2280
accggcaagc tgcccgtgcc ctggcccacc ctcgtgacca ccctgaccta cggcgtgcag   2340
tgcttcagcc gctaccccga ccacatgaag cagcacgact tcttcaagtc cgccatgccc   2400
gaaggctacg tccaggagcg caccatcttc ttcaaggacg acggcaacta caagacccgc   2460
gccgaggtga agttcgaggg cgacaccctg gtgaaccgca tcgagctgaa gggcatcgac   2520
ttcaaggagg acggcaacat cctggggcac aagctggagt acaactacaa cagccacaac   2580
gtctatatca tggccgacaa gcagaagaac ggcatcaagg tgaacttcaa gatccgccac   2640
aacatcgagg acggcagcgt gcagctcgcc gaccactacc agcagaacac ccccatcggc   2700
gacggccccg tgctgctgcc cgacaaccac tacctgagca cccagtccgc cctgagcaaa   2760
gaccccaacg agaagcgcga tcacatggtc ctgctggagt tcgtgaccgc cgccgggatc   2820
actctcggca tggacgagct gtacaagtaa agcggccgcg actctagatc ataatcagcc   2880
ataccacatt tgtagaggtt ttacttgctt taaaaaacct cccacacctc cccctgaacc   2940
tgaaacataa aatgaatgca attgttgttg ttaacttgtt tattgcagct tataatggtt   3000
acaaataaag caatagcatc acaaatttca caaataaagc attttttttca ctgcattcta   3060
```

```
gttgtggttt gtccaaactc atcaatgtat cttaaggcgt aaattgtaag cgttaatatt    3120
ttgttaaaat tcgcgttaaa ttttgttaa atcagctcat ttttaacca ataggccgaa     3180 atcggcaaaa tcccttataa atcaaaagaa tagaccgaga tagggttgag tgttgttcca    3240
gtttggaaca agagtccact attaaagaac gtggactcca acgtcaaagg gcgaaaaacc   3300
gtctatcagg gcgatggccc actacgtgaa ccatcaccct aatcaagttt ttggggtcg    3360 aggtgccgta aagcactaaa tcggaaccct aaagggagcc cccgatttag agcttgacgg   3420
ggaaagccgg cgaacgtggc gagaaaggaa gggaagaaag cgaaaggagc gggcgctagg   3480
gcgctggcaa gtgtagcggt cacgctgcgc gtaaccacca cacccgccgc gcttaatgcg   3540
ccgctacagg gcgcgtcagg tggcactttt cggggaaatg tgcgcggaac ccctatttgt   3600
ttatttttct aaatacattc aaatatgtat ccgctcatga caataaacc ctgataaatg    3660 cttcaataat attgaaaaag gaagagtcct gaggcggaaa gaaccagctg tggaatgtgt   3720
gtcagttagg gtgtggaaag tccccaggct ccccagcagg cagaagtatg caaagcatgc   3780
atctcaatta gtcagcaacc aggtgtggaa agtccccagg ctccccagca ggcagaagta   3840
tgcaaagcat gcatctcaat tagtcagcaa ccatagtccc gcccctaact ccgcccatcc   3900
cgcccctaac tccgcccagt tccgcccatt ctccgcccca tggctgacta atttttttta   3960
tttatgcaga ggccgaggcc gcctcggcct ctgagctatt ccagaagtag tgaggaggct   4020 ttttttggagg cctaggcttt tgcaaagatc gatcaagaga caggatgagg atcgtttcgc   4080
atgattgaac aagatggatt gcacgcaggt tctccggccg cttgggtgga gaggctattc   4140
ggctatgact gggcacaaca gacaatcggc tgctctgatg ccgccgtgtt ccggctgtca   4200 gcgcagggc gcccggttct ttttgtcaag accgacctgt ccggtgccct gaatgaactg    4260
caagacgagg cagcgcggct atcgtggctg gccacgacgg gcgttccttg cgcagctgtg   4320
ctcgacgttg tcactgaagc gggaagggac tggctgctat tgggcgaagt gccggggcag   4380
gatctcctgt catctcacct tgctcctgcc gagaaagtat ccatcatggc tgatgcaatg   4440
cggcggctgc atacgcttga tccggctacc tgcccattcg accaccaagc gaaacatcgc   4500
atcgagcgag cacgtactcg gatggaagcc ggtcttgtcg atcaggatga tctggacgaa   4560
gagcatcagg ggctcgcgcc agccgaactg ttcgccaggc tcaaggcgag catgcccgac   4620
ggcgaggatc tcgtcgtgac ccatggcgat gcctgcttgc cgaatatcat ggtggaaaat   4680
ggccgctttt ctggattcat cgactgtggc cggctgggtg tggcggaccg ctatcaggac   4740
atagcgttgg ctacccgtga tattgctgaa gagcttggcg gcgaatgggc tgaccgcttc   4800
ctcgtgcttt acggtatcgc cgctcccgat tcgcagcgca tcgccttcta tcgccttctt   4860
gacgagttct tctgagcggg actctggggt tcgaaatgac cgaccaagcg acgcccaacc   4920
tgccatcacg agatttcgat tccaccgccg ccttctatga aggttgggc ttcggaatcg    4980 ttttccggga cgccgctgg atgatcctcc agcgcgggga tctcatgctg gagttcttcg    5040 cccacccta ggggaggcta actgaaacac ggaaggagac aataccggaa ggaacccgcg    5100
ctatgacggc aataaaaaga cagaataaaa cgcacggtgt tgggtcgttt gttcataaac   5160
gcggggttcg gtcccagggc tggcactctg tcgatacccc accgagaccc cattggggcc   5220
aatacgcccg cgtttcttcc ttttcccac cccacccccc aagttcgggt gaaggcccag    5280
ggctcgcagc caacgtcggg gcggcaggcc ctgccatagc ctcaggttac tcatatatac   5340
tttagattga tttaaaactt cattttaat ttaaaaggat ctaggtgaag atccttttg    5400 ataatctcat gaccaaaatc ccttaacgtg agttttcgtt ccactgagcg tcagaccccg   5460
```

-continued

```
tagaaaagat caaaggatct tcttgagatc cttttttct gcgcgtaatc tgctgcttgc    5520
aaacaaaaaa accaccgcta ccagcggtgg tttgtttgcc ggatcaagag ctaccaactc    5580
tttttccgaa ggtaactggc ttcagcagag cgcagatacc aaatactgtc cttctagtgt    5640
agccgtagtt aggccaccac ttcaagaact ctgtagcacc gcctacatac ctcgctctgc    5700
taatcctgtt accagtggct gctgccagtg gcgataagtc gtgtcttacc gggttggact    5760
caagacgata gttaccggat aaggcgcagc ggtcgggctg aacggggggt tcgtgcacac    5820
agcccagctt ggagcgaacg acctacaccg aactgagata cctacagcgt gagctatgag    5880
aaagcgccac gcttcccgaa gggagaaagg cggacaggta tccggtaagc ggcagggtcg    5940
gaacaggaga gcgcacgagg gagcttccag ggggaaacgc ctggtatctt tatagtcctg    6000
tcgggtttcg ccacctctga cttgagcgtc gattttgtg atgctcgtca ggggggcgga    6060
gcctatggaa aaacgccagc aacgcggcct ttttacggtt cctggccttt tgctggcctt    6120
ttgctcacat gttctttcct gcgttatccc ctgattctgt ggataaccgt attaccgcca    6180
tgcattagtt attactagcg ctaccggact cagatctcga gctcaagctt cgaattctgc    6240
a                                                                   6241
```

<210> SEQ ID NO 32
<211> LENGTH: 6370
<212> TYPE: DNA
<213> ORGANISM: Artificial Sequence
<220> FEATURE:
<223> OTHER INFORMATION: p1-5'INFgamma/d2EGFP-1

<400> SEQUENCE: 32

```
tcgagctcaa gcttcgaatt ctgcaggcgg ccgcgaattc actagtgata gattgctggc      60
ttctgtcacc tgagtgctgg gattaaaggt atgagttacc acgaccctgc tagatttttt     120
ttttaagaca gattctcatg attcttaaac tggccttcaa gtctccagca gcagaaggtg     180
acctcgcact catgatcatc ttacctctgt ttccatctgt atttcatgcc tattttaagt     240
cagggttttt atacaagcac tctaccaacc aagagatgtt cctgactgtc aaaacagaga     300
ttcttaggta aacattcaaa tgaatatttg tgtgtgtgtg tgtgttgttt gtgtataaat     360
ctttatgctt atgtatttga gggaaataaa ttgtgtcaca gaagcaatga aacactttct     420
ggttttaagg aaattagtgg gcactgggat ggggtaggg ggcatgcata gttacctcgt     480
atatgagact ggggaaattg agaacccatg aagcatagaa acaaagtgct agccctgccc     540
agaggataaa gtctgatttg aagctggagg cttggggag aaccaaaaca gaggatggtt     600
tgcatctggg tcaagataac tgggtaccac tctgagatgc tcagatgagg gaagggggc     660 acatggccaa aggaactgca cgaacaagct gcatagcgtt gttaaacatc tgacattgcc     720
aaataaccat caagttttaa ttgagccact aggaatgccg ggaagaattc tctcaacttt     780
ccatggagca tttggttgag cctttggctg aagtccggaa gaaatgcta gtgttaagct     840 cactgtataa atgtggaaac tgagtcacag atcataaaga tgctgactca agaccccgag     900
gctagaatat gaatggttca agtctgcacc catagccact gtgtaatgtt aatgaataca     960
ggaaaggcag ggatgaatac acgtgggctg gcactgaaga gcagagggcc tcctgcccca    1020
tcctcaagga tcgaatttca tagataggtt accaaagaca gagaaggaaa cttttagtgt    1080
ttgaacttga tgggggaaac aatttttcagt tattaatcct tatttgggac aagtgtgtgt    1140
ctagtgctgg actagtcatt gggatagcct tagccacatg tgggtatgag agttagaaac    1200
atggctaatc ctgaagtgat ttctgctgtg tatataggat agccactagg ctttaaatat    1260
```

```
ttagtggcag aggaattgaa actcttattc atcataaatc ttgatacaca ttgatacctt    1320
gggtgtgttg agtgaaatac aatatctaat gaagtattct tgcattttta cttttatttc    1380
attttgcatt ttttccctt ttattaatgg aggaactaga tgatttttatt ttacctatgt    1440 ggtctgcctt ttcttctttc tgggcacgtt gaccctgagt gatttgtagt aggtattta     1500 ctaatcacct ccattgaagg gcttcctcac cacattggct ttttaaccat accctttcct    1560
tgcttttctg gtcatttgca agaaaagttt gaaaaggctt cccccattgc atggtttgag    1620
aagcccaaga gtttcctcat ggtttgagaa gcccaagagt ttccttttat tcagccgtcc    1680
ccaaccacaa acaaaggctc cctgtgctgt gctctgtgga tgagaaattc acattacaag    1740
ggcaaaaagg gggagacgta aaagcaattt ccagccccca ccccaaatgg tgtgaagtaa    1800
aagtgctttc agagaatccc acaagaatgg cacaggtggg cacagcgggg ctgtctcatc    1860
gtcagagagc ccaaggagtc gaaaggaaac tctaacatgc cacaaaacca tagctgtaat    1920
gcaaagtaac ttagctcccc ccacctatct gtcaccatct taaaaaaaaa aaaaccaaaa    1980
aaaaacttgt gaaaatacgt aatcccgagg agccttcgat caggtataaa actggaagcc    2040
agagaggtgc aggctatagc tgccatcggc tgacctagag aagaatcgaa ttcccgcggc    2100
cgccatggcg gccgggagca tgcgacgtcg ggcccgggat ccaccggtcg ccaccatggt    2160
gagcaagggc gaggagctgt tcaccggggt ggtgcccatc ctggtcgagc tggacggcga    2220
cgtaaacggc cacaagttca gcgtgtccgg cgagggcgag ggcgatgcca cctacggcaa    2280
gctgaccctg aagttcatct gcaccaccgg caagctgccc gtgccctggc ccaccctcgt    2340
gaccaccctg acctacggcg tgcagtgctt cagccgctac cccgaccaca tgaagcagca    2400
cgacttcttc aagtccgcca tgcccgaagg ctacgtccag gagcgcacca tcttcttcaa    2460
ggacgacggc aactacaaga cccgcgccga ggtgaagttc gagggcgaca ccctggtgaa    2520
ccgcatcgag ctgaagggca tcgacttcaa ggaggacggc aacatcctgg ggcacaagct    2580
ggagtacaac tacaacagcc acaacgtcta tatcatggcc gacaagcaga agaacggcat    2640
caaggtgaac ttcaagatcc gccacaacat cgaggacggc agcgtgcagc tcgccgacca    2700
ctaccagcag aacacccca tcggcgacgg ccccgtgctg ctgcccgaca ccactacct    2760 gagcacccag tccgccctga gcaaagaccc caacgagaag cgcgatcaca tggtcctgct    2820
ggagttcgtg accgccgccg ggatcactct cggcatggac gagctgtaca agaagcttag    2880
ccatggcttc ccgccggagg tggaggagca ggatgatggc acgctgccca tgtcttgtgc    2940
ccaggagagc gggatggacc gtcaccctgc agcctgtgct tctgctagga tcaatgtgta    3000
gatgcgcggc cgcgactcta gatcataatc agccatacca catttgtaga ggttttactt    3060
gctttaaaaa acctcccaca cctcccctg aacctgaaac ataaaatgaa tgcaattgtt    3120
gttgttaact tgtttattgc agcttataat ggttacaaat aaagcaatag catcacaaat    3180
ttcacaaata aagcattttt ttcactgcat tctagttgtg gtttgtccaa actcatcaat    3240
gtatcttaag gcgtaaattg taagcgttaa tattttgtta aaattcgcgt taaattttg     3300 ttaaatcagc tcatttttta accaataggc cgaaatcggc aaaatccctt ataaatcaaa    3360
agaatagacc gagatagggt tgagtgttgt tccagtttgg aacaagagtc cactattaaa    3420
gaacgtggac tccaacgtca aagggcgaaa aaccgtctat cagggcgatg gcccactacg    3480
tgaaccatca ccctaatcaa gttttttggg gtcgaggtgc cgtaaagcac taaatcggaa    3540
ccctaaaggg agcccccgat ttagagcttg acggggaaag ccggcgaacg tggcgagaaa    3600
ggaagggaag aaagcgaaag gagcgggcgc tagggcgctg gcaagtgtag cggtcacgct    3660
```

```
gcgcgtaacc accacacccg ccgcgcttaa tgcgccgcta cagggcgcgt caggtggcac    3720
ttttcgggga aatgtgcgcg gaaccccTAT ttgtttattt ttctaaatac attcaaatat    3780
gtatccgctc atgagacaat aaccctgata aatgcttcaa taatattgaa aaaggaagag    3840
tcctgaggcg gaaagaacca gctgtggaat gtgtgtcagt tagggtgtgg aaagtcccca    3900
ggctccccag caggcagaag tatgcaaagc atgcatctca attagtcagc aaccaggtgt    3960
ggaaagtccc caggctcccc agcaggcaga agtatgcaaa gcatgcatct caattagtca    4020
gcaaccatag tcccgcccct aactccgccc atcccgcccc taactccgcc cagttccgcc    4080
cattctccgc cccatggctg actaattttt tttatttatg cagaggccga ggccgcctcg    4140
gcctctgagc tattccagaa gtagtgagga ggcttttttg gaggcctagg cttttgcaaa    4200
gatcgatcaa gagacaggat gaggatcgtt tcgcatgatt gaacaagatg gattgcacgc    4260
aggttctccg gccgcttggg tggagaggct attcggctat gactgggcac aacagacaat    4320
cggctgctct gatgccgccg tgttccggct gtcagcgcag gggcgcccgg ttcttttgt     4380 caagaccgac ctgtccggtg ccctgaatga actgcaagac gaggcagcgc ggctatcgtg    4440
gctggccacg acgggcgttc cttgcgcagc tgtgctcgac gttgtcactg aagcgggaag    4500
ggactggctg ctattgggcg aagtgccggg gcaggatctc ctgtcatctc accttgctcc    4560
tgccgagaaa gtatccatca tggctgatgc aatgcggcgg ctgcatacgc ttgatccggc    4620
tacctgccca ttcgaccacc aagcgaaaca tcgcatcgag cgagcacgta ctcggatgga    4680
agccggtctt gtcgatcagg atgatctgga cgaagagcat caggggctcg cgccagccga    4740
actgttcgcc aggctcaagg cgagcatgcc cgacggcgag gatctcgtcg tgacccatgg    4800
cgatgcctgc ttgccgaata tcatggtgga aaatggccgc ttttctggat tcatcgactg    4860
tggccggctg ggtgtggcgg accgctatca ggacatagcg ttggctaccc gtgatattgc    4920
tgaagagctt ggcggcgaat gggctgaccg cttcctcgtg ctttacggta tcgccgctcc    4980
cgattcgcag cgcatcgcct tctatcgcct tcttgacgag ttcttctgag cgggactctg    5040
gggttcgaaa tgaccgacca agcgacgccc aacctgccat cacgagattt cgattccacc    5100
gccgccttct atgaaaggtt gggcttcgga atcgttttcc gggacgccgg ctggatgatc    5160
ctccagcgcg ggatctcat gctggagttc ttcgcccacc ctaggggag gctaactgaa     5220 acacggaagg agacaatacc ggaaggaacc cgcgctatga cggcaataaa aagacagaat    5280
aaaacgcacg gtgttgggtc gtttgttcat aaacgcgggg ttcggtccca gggctggcac    5340
tctgtcgata ccccaccgag accccattgg ggccaatacg cccgcgtttc ttccttttcc    5400
ccaccccacc ccccaagttc gggtgaaggc ccagggctcg cagccaacgt cggggcggca    5460
ggccctgcca tagcctcagg ttactcatat atacttTAGA ttgatttaaa acttcatttt    5520
taatttaaaa ggatctaggt gaagatcctt tttgataatc tcatgaccaa aatcccttaa    5580
cgtgagtttt cgttccactg agcgtcagac cccgtagaaa agatcaaagg atcttcttga    5640
gatccttttt ttctgcgcgt aatctgctgc ttgcaaacaa aaaaaccacc gctaccagcg    5700
gtggtttgtt tgccggatca agagctacca actctttttc cgaaggtaac tggcttcagc    5760
agagcgcaga taccaaatac tgtccttcta gtgtagccgt agttaggcca ccacttcaag    5820
aactctgtag caccgcctac atacctcgct ctgctaatcc tgttaccagt ggctgctgcc    5880
agtggcgata agtcgtgtct taccgggttg gactcaagac gatagttacc ggataaggcg    5940
cagcggtcgg gctgaacggg gggttcgtgc acacagccca gcttggagcg aacgacctac    6000
accgaactga gatacctaca gcgtgagcta tgagaaagcg ccacgcttcc cgaagggaga    6060
```

| | |
|---|---:|
| aaggcggaca ggtatccggt aagcggcagg gtcggaacag gagagcgcac gagggagctt | 6120 |
| ccaggggaa acgcctggta tctttatagt cctgtcgggt ttcgccacct ctgacttgag | 6180 |
| cgtcgatttt tgtgatgctc gtcagggggg cggagcctat ggaaaaacgc cagcaacgcg | 6240 |
| gcctttttac ggttcctggc cttttgctgg ccttttgctc acatgttctt tcctgcgtta | 6300 |
| tcccctgatt ctgtggataa ccgtattacc gccatgcatt agttattact agcgctaccg | 6360 |
| gactcagatc | 6370 |

<210> SEQ ID NO 33
<211> LENGTH: 6795
<212> TYPE: DNA
<213> ORGANISM: Artificial Sequence
<220> FEATURE:
<223> OTHER INFORMATION: p1-5'3'INFgamma/d2EGFP-1

<400> SEQUENCE: 33

| | |
|---|---:|
| tcgagctcaa gcttcgaatt ctgcaggcgg ccgcgaattc actagtgata gattgctggc | 60 |
| ttctgtcacc tgagtgctgg gattaaaggt atgagttacc acgaccctgc tagatttttt | 120 |
| ttttaagaca gattctcatg attcttaaac tggccttcaa gtctccagca gcagaaggtg | 180 |
| acctcgcact catgatcatc ttacctctgt ttccatctgt atttcatgcc tattttaagt | 240 |
| cagggttttt atacaagcac tctaccaacc aagagatgtt cctgactgtc aaaacagaga | 300 |
| ttcttaggta acattcaaa tgaatatttg tgtgtgtgtg tgtgttgttt gtgtataaat | 360 |
| ctttatgctt atgtatttga gggaaataaa ttgtgtcaca gaagcaatga acactttct | 420 |
| ggttttaagg aaattagtgg gcactgggat gggggtaggg ggcatgcata gttacctcgt | 480 |
| atatgagact ggggaaattg agaacccatg aagcatagaa acaaagtgct agccctgccc | 540 |
| agaggataaa gtctgatttg aagctggagg cttggggag aaccaaaaca gaggatggtt | 600 |
| tgcatctggg tcaagataac tgggtaccac tctgagatgc tcagatgagg gaaaggggc | 660 |
| acatggccaa aggaactgca cgaacaagct gcatagcgtt gttaaacatc tgacattgcc | 720 |
| aaataaccat caagttttaa ttgagccact aggaatgccg ggaagaattc tctcaacttt | 780 |
| ccatggagca tttggttgag cctttggctg aagtccggaa gaaaatgcta gtgttaagct | 840 |
| cactgtataa atgtggaaac tgagtcacag atcataaaga tgctgactca agaccccgag | 900 |
| gctagaatat gaatggttca agtctgcacc catagccact gtgtaatgtt aatgaataca | 960 |
| ggaaaggcag ggatgaatac acgtgggctg gcactgaaga gcagagggcc tcctgcccca | 1020 |
| tcctcaagga tcgaatttca tagataggtt accaaagaca gagaaggaaa cttttagtgt | 1080 |
| ttgaacttga tgggggaaac aattttcagt tattaatcct tatttgggac aagtgtgtgt | 1140 |
| ctagtgctgg actagtcatt gggatagcct tagccacatg tgggtatgag agttagaaac | 1200 |
| atggctaatc ctgaagtgat ttctgctgtg tatataggat agccactagg ctttaaatat | 1260 |
| ttagtggcag aggaattgaa actcttattc atcataaatc ttgatacaca ttgatacctt | 1320 |
| gggtgtgttg agtgaaatac aatatctaat gaagtattct tgcatttta cttttatttc | 1380 |
| attttgcatt ttttcccctt ttattaatgg aggaactaga tgatttatt ttacctatgt | 1440 |
| ggtctgcctt ttcttctttc tgggcacgtt gaccctgagt gatttgtagt aggtattta | 1500 |
| ctaatcacct ccattgaagg gcttcctcac cacattggct ttttaaccat acccttcct | 1560 |
| tgcttttctg gtcatttgca agaaaagttt gaaaaggctt cccccattgc atggtttgag | 1620 |
| aagcccaaga gtttcctcat ggtttgagaa gcccaagagt ttccttttat tcagccgtcc | 1680 |
| ccaaccacaa acaaaggctc cctgtgctgt gctctgtgga tgagaaattc acattacaag | 1740 |

```
ggcaaaaagg gggagacgta aaagcaattt ccagccccca ccccaaatgg tgtgaagtaa    1800
aagtgctttc agagaatccc acaagaatgg cacaggtggg cacagcgggg ctgtctcatc    1860
gtcagagagc ccaaggagtc gaaaggaaac tctaacatgc cacaaaacca tagctgtaat    1920
gcaaagtaac ttagctcccc ccacctatct gtcaccatct taaaaaaaaa aaaaccaaaa    1980
aaaaacttgt gaaaatacgt aatcccgagg agccttcgat caggtataaa actggaagcc    2040
agagaggtgc aggctatagc tgccatcggc tgacctagag aagaatcgaa ttcccgcggc    2100
cgccatggcg gccgggagca tgcgacgtcg ggcccgggat ccaccggtcg ccaccatggt    2160
gagcaagggc gaggagctgt tcaccggggt ggtgcccatc ctggtcgagc tggacggcga    2220
cgtaaacggc cacaagttca gcgtgtccgg cgagggcgag ggcgatgcca cctacggcaa    2280
gctgaccctg aagttcatct gcaccaccgg caagctgccc gtgccctggc ccaccctcgt    2340
gaccaccctg acctacggcg tgcagtgctt cagccgctac cccgaccaca tgaagcagca    2400
cgacttcttc aagtccgcca tgcccgaagg ctacgtccag gagcgcacca tcttcttcaa    2460
ggacgacggc aactacaaga cccgcgccga ggtgaagttc gagggcgaca ccctggtgaa    2520
ccgcatcgag ctgaagggca tcgacttcaa ggaggacggc aacatcctgg ggcacaagct    2580
ggagtacaac tacaacagcc acaacgtcta tatcatggcc gacaagcaga gaacggcat    2640 caaggtgaac ttcaagatcc gccacaacat cgaggacggc agcgtgcagc tcgccgacca    2700
ctaccagcag aacacccca tcggcgacgg ccccgtgctg ctgcccgaca ccactacct    2760 gagcacccag tccgccctga gcaaagaccc caacgagaag cgcgatcaca tggtcctgct    2820
ggagttcgtg accgccgccg ggatcactct cggcatggac gagctgtaca agaagcttag    2880
ccatggcttc ccgccggagg tggaggagca ggatgatggc acgctgccca tgtcttgtgc    2940
ccaggagagc gggatggacc gtcaccctgc agcctgtgct tctgctagga tcaatgtgta    3000
gatgcgcggc cgcggaatt cgataaagga gtcgctgctg attcggggtg gggaagagat    3060
tgtcccaata agaataattc tgccagcact atttgaattt ttaaatctaa acctatttat    3120
taatatttaa aactatttat atggagaatc tattttagat gcatcaacca agaagtatt    3180 tatagtaaca acttatatgt gataagagtg aattcctatt aatatatgtg ttatttataa    3240
tttctgtctc ctcaactatt tctctttgac caattaatta ttcttctga ctaattagcc    3300 aagactgtga ttgcggggtt gtatctgggg gtggggaca gccaagcggc tgactgaact    3360
cagattgtag cttgtacctt tacttcactg accaataaga aacattcaga gctgcagtga    3420
ccccgggagt gctgctgatg ggaggagatg tctacactcc gggccagcgc tttaacagca    3480
ggccagacag cactcgaatg tgtcaggtag taacaggctg tccctgaaag aaagcagtgt    3540
ctcaagagac ttgacactgg tcttccctat acagctgaaa actgtgacta cacccgaatg    3600
acaaataact cgctcattta tagtttatca ctgtctaatt gcatatgaat aaagtatacc    3660
tttgcaaccc ttaaggcgta aattgtaagc gttaatattt tgttaaaatt cgcgttaaat    3720
ttttgttaaa tcagctcatt ttttaaccaa taggccgaaa tcggcaaaat cccttataaa    3780
tcaaaagaat agaccgagat agggttgagt gttgttccag tttggaacaa gagtccacta    3840
ttaaagaacg tggactccaa cgtcaaaggg cgaaaaaccg tctatcaggg cgatggccca    3900
ctacgtgaac catcacccta atcaagtttt tggggtcga ggtgccgtaa agcactaaat    3960
cggaacccta agggagcccc cgatttaga gcttgacggg gaaagccggc gaacgtggcg    4020
agaaaggaag ggaagaaagc gaaaggagcg ggcgctaggg cgctggcaag tgtagcggtc    4080
acgctgcgcg taaccaccac acccgccgcg cttaatgcgc cgctacaggg cgcgtcaggt    4140
```

```
ggcactttc  ggggaaatgt  gcgcggaacc  cctatttgtt  tatttttcta  aatacattca   4200
aatatgtatc  cgctcatgag  acaataaccc  tgataaatgc  ttcaataata  ttgaaaaagg   4260
aagagtcctg  aggcggaaag  aaccagctgt  ggaatgtgtg  tcagttaggg  tgtggaaagt   4320
ccccaggctc  cccagcaggc  agaagtatgc  aaagcatgca  tctcaattag  tcagcaacca   4380
ggtgtggaaa  gtccccaggc  tccccagcag  gcagaagtat  gcaaagcatg  catctcaatt   4440
agtcagcaac  catagtcccg  ccctaactc   cgcccatccc  gcccctaact  ccgcccagtt   4500
ccgcccattc  tccgcccat   ggctgactaa  ttttttttat  ttatgcagag  gccgaggccg   4560
cctcggcctc  tgagctattc  cagaagtagt  gaggaggctt  ttttggaggc  ctaggctttt   4620
gcaaagatcg  atcaagagac  aggatgagga  tcgtttcgca  tgattgaaca  agatggattg   4680
cacgcaggtt  ctccggccgc  ttgggtggag  aggctattcg  gctatgactg  ggcacaacag   4740
acaatcggct  gctctgatgc  cgccgtgttc  cggctgtcag  cgcaggggcg  cccggttctt   4800
tttgtcaaga  ccgacctgtc  cggtgccctg  aatgaactgc  aagacgaggc  agcgcggcta   4860
tcgtggctgg  ccacgacggg  cgttccttgc  gcagctgtgc  tcgacgttgt  cactgaagcg   4920
ggaagggact  ggctgctatt  gggcgaagtg  ccggggcagg  atctcctgtc  atctcacctt   4980
gctcctgccg  agaaagtatc  catcatggct  gatgcaatgc  ggcggctgca  tacgcttgat   5040
ccggctacct  gcccattcga  ccaccaagcg  aaacatcgca  tcgagcgagc  acgtactcgg   5100
atggaagccg  gtcttgtcga  tcaggatgat  ctggacgaag  agcatcaggg  gctcgcgcca   5160
gccgaactgt  tcgccaggct  caaggcgagc  atgcccgacg  gcgaggatct  cgtcgtgacc   5220
catggcgatg  cctgcttgcc  gaatatcatg  gtggaaaatg  gccgcttttc  tggattcatc   5280
gactgtggcc  ggctgggtgt  ggcggaccgc  tatcaggaca  tagcgttggc  tacccgtgat   5340
attgctgaag  agcttggcgg  cgaatgggct  gaccgcttcc  tcgtgcttta  cggtatcgcc   5400
gctcccgatt  cgcagcgcat  cgccttctat  cgccttcttg  acgagttctt  ctgagcggga   5460
ctctggggtt  cgaaatgacc  gaccaagcga  cgcccaacct  gccatcacga  gatttcgatt   5520
ccaccgccgc  cttctatgaa  aggttgggct  tcggaatcgt  tttccgggac  gccggctgga   5580
tgatcctcca  gcgcggggat  ctcatgctgg  agttcttcgc  ccaccctagg  gggaggctaa   5640
ctgaaacacg  gaaggagaca  ataccggaag  gaacccgcgc  tatgacggca  ataaaaagac   5700
agaataaaac  gcacggtgtt  gggtcgtttg  ttcataaacg  cggggttcgg  tcccagggct   5760
ggcactctgt  cgataccca   ccgagacccc  attggggcca  atacgcccgc  gtttcttcct   5820
tttccccacc  ccaccccca   agttcgggtg  aaggcccagg  gctcgcagcc  aacgtcgggg   5880
cggcaggccc  tgccatagcc  tcaggttact  catatatact  ttagattgat  ttaaaacttc   5940 attttaatt   taaaggatc   taggtgaaga  tcctttttga  taatctcatg  accaaaatcc   6000
cttaacgtga  gttttcgttc  cactgagcgt  cagacccgt   agaaaagatc  aaaggatctt   6060
cttgagatcc  ttttttctg   cgcgtaatct  gctgcttgca  aacaaaaaaa  ccaccgctac   6120
cagcggtggt  ttgtttgccg  gatcaagagc  taccaactct  ttttccgaag  gtaactggct   6180
tcagcagagc  gcagatacca  aatactgtcc  ttctagtgta  gccgtagtta  ggccaccact   6240
tcaagaactc  tgtagcaccg  cctacatacc  tcgctctgct  aatcctgtta  ccagtggctg   6300
ctgccagtgg  cgataagtcg  tgtcttaccg  ggttggactc  aagacgatag  ttaccggata   6360
aggcgcagcg  gtcgggctga  acggggggtt  cgtgcacaca  gcccagcttg  gagcgaacga   6420
cctacaccga  actgagatac  ctacagcgtg  agctatgaga  aagcgccacg  cttcccgaag   6480
ggagaaaggc  ggacaggtat  ccggtaagcg  gcagggtcgg  aacaggagag  cgcacgaggg   6540
```

-continued

```
agcttccagg gggaaacgcc tggtatcttt atagtcctgt cgggtttcgc cacctctgac    6600
ttgagcgtcg atttttgtga tgctcgtcag gggggcggag cctatggaaa aacgccagca    6660
acgcggcctt tttacggttc ctggccttttt gctggccttt tgctcacatg ttctttcctg    6720
cgttatcccc tgattctgtg ataaccgta ttaccgccat gcattagtta ttactagcgc    6780
taccggactc agatc                                                     6795
```

<210> SEQ ID NO 34
<211> LENGTH: 5106
<212> TYPE: DNA
<213> ORGANISM: Artificial Sequence
<220> FEATURE:
<223> OTHER INFORMATION: p1-3'GAPHD/d1EGFP-N1

<400> SEQUENCE: 34

```
taatagtaat caattacggg gtcattagtt catagcccat atatggagtt ccgcgttaca      60
taacttacgg taaatggccc gcctggctga ccgcccaacg accccgccc attgacgtca     120 ataatgacgt atgttcccat agtaacgcca tagggactt ccattgacg tcaatgggtg     180 gagtatttac ggtaaactgc ccacttggca gtacatcaag tgtatcatat gccaagtacg     240
ccccctattg acgtcaatga cggtaaatgg cccgcctggc attatgccca gtacatgacc     300
ttatgggact ttcctacttg gcagtacatc tacgtattag tcatcgctat taccatggtg     360
atgcggtttt ggcagtacat caatgggcgt ggatagcggt ttgactcacg gggatttcca     420
agtctccacc ccattgacgt caatgggagt ttgttttggc accaaaatca acgggacttt     480
ccaaaatgtc gtaacaactc cgccccattg acgcaaatgg gcggtaggcg tgtacggtgg     540
gaggtctata taagcagagc tggtttagtg aaccgtcaga tccgctagcg ctaccggact     600
cagatctcga gctcaagctt cgaattctgc agtcgacggt accgcgggcc cgggatccac     660
cggtcgccac catggtgagc aagggcgagg agctgttcac cggggtggtg cccatcctgg     720
tcgagctgga cggcgacgta aacggccaca agttcagcgt gtccggcgag ggcgagggcg     780
atgccaccta cggcaagctg acctgaagt tcatctgcac caccggcaag ctgcccgtgc     840
cctggcccac cctcgtgacc accctgacct acggcgtgca gtgcttcagc cgctaccccg     900
accacatgaa gcagcacgac ttcttcaagt ccgccatgcc cgaaggctac gtccaggagc     960
gcaccatctt cttcaaggac gacggcaact acaagacccg cgccgaggtg aagttcgagg    1020
gcgacaccct ggtgaaccgc atcgagctga agggcatcga cttcaaggag gacggcaaca    1080
tcctggggca caagctggag tacaactaca acagccacaa cgtctatatc atggccgaca    1140
agcagaagaa cggcatcaag gtgaacttca agatccgcca caacatcgag gacggcagcg    1200
tgcagctcgc cgaccactac cagcagaaca cccccatcgg cgacggcccc gtgctgctgc    1260
ccgacaacca ctacctgagc acccagtccg ccctgagcaa agaccccaac gagaagcgcg    1320
atcacatggt cctgctggag ttcgtgaccg ccgccgggat cactctcggc atggacgagc    1380
tgtacaagaa gcttagccat ggcttcccgc cggcggtggc ggcgcaggat gatggcacgc    1440
tgcccatgtc cttgtgccag agagcgggga tggaccgtca ccctgcagcc tgtgcttctg    1500
ctaggatcaa tgtgtagatg cgcggccgcc agtgtgctgg aattcggcgt aagaaaccct    1560
ggaccaccca ccccagcaag gacactgagc aagagaggcc ctatcccaac tcggccccca    1620
acactgagca tctccctcac aatttccatc ccagacccc ataataacag gaggggccta    1680
gggagccctc cctactctct tgaataccat caataaagtt cgctgcaccc acttaagccg    1740
aattctgcag atatccatca cactggcggc cgcgactcta gatcataatc agccatacca    1800
```

-continued

```
catttgtaga ggttttactt gctttaaaaa acctcccaca cctcccctg aacctgaaac      1860 ataaaatgaa tgcaattgtt gttgttaact tgtttattgc agcttataat ggttacaaat      1920
aaagcaatag catcacaaat ttcacaaata aagcattttt ttcactgcat tctagttgtg      1980
gtttgtccaa actcatcaat gtatcttaag gcgtaaattg taagcgttaa tattttgtta      2040
aaattcgcgt taaattttg ttaaatcagc tcatttttta accaataggc cgaaatcggc      2100
aaaatccctt ataaatcaaa agaatagacc gagatagggt tgagtgttgt tccagtttgg      2160
aacaagagtc cactattaaa gaacgtggac tccaacgtca aagggcgaaa aaccgtctat      2220
cagggcgatg gcccactacg tgaaccatca ccctaatcaa gttttttggg gtcgaggtgc      2280
cgtaaagcac taaatcggaa ccctaaaggg agccccgat ttagagcttg acggggaaag      2340
ccggcgaacg tggcgagaaa ggaagggaag aaagcgaaag gagcgggcgc tagggcgctg      2400
gcaagtgtag cggtcacgct gcgcgtaacc accacacccg ccgcgcttaa tgcgccgcta      2460
cagggcgcgt caggtggcac ttttcgggga aatgtgcgcg gaaccccctat tgtttattt      2520 ttctaaatac attcaaatat gtatccgctc atgagacaat aaccctgata aatgcttcaa      2580
taatattgaa aaaggaagag tcctgaggcg gaaagaacca gctgtggaat gtgtgtcagt      2640
tagggtgtgg aaagtcccca ggctccccag caggcagaag tatgcaaagc atgcatctca      2700
attagtcagc aaccaggtgt ggaaagtccc caggctcccc agcaggcaga agtatgcaaa      2760
gcatgcatct caattagtca gcaaccatag tcccgcccct aactccgccc atcccgcccc      2820
taactccgcc cagttccgcc cattctccgc cccatggctg actaatttt tttatttatg      2880 cagaggccga ggccgcctcg gcctctgagc tattccagaa gtagtgagga ggcttttttg      2940
gaggcctagg cttttgcaaa gatcgatcaa gagacaggat gaggatcgtt tcgcatgatt      3000
gaacaagatg gattgcacgc aggttctccg gccgcttggg tggagaggct attcggctat      3060
gactgggcac aacagacaat cggctgctct gatgccgccg tgttccggct gtcagcgcag      3120
gggcgcccgg ttctttttgt caagaccgac ctgtccggtg ccctgaatga actgcaagac      3180
gaggcagcgc ggctatcgtg gctggccacg acgggcgttc cttgcgcagc tgtgctcgac      3240
gttgtcactg aagcgggaag ggactggctg ctattgggcg aagtgccggg gcaggatctc      3300
ctgtcatctc accttgctcc tgccgagaaa gtatccatca tggctgatgc aatgcggcgg      3360
ctgcatacgc ttgatccggc tacctgccca ttcgaccacc aagcgaaaca tcgcatcgag      3420
cgagcacgta ctcggatgga agccggtctt gtcgatcagg atgatctgga cgaagagcat      3480
caggggctcg cgccagccga actgttcgcc aggctcaagg cgagcatgcc cgacggcgag      3540
gatctcgtcg tgacccatgg cgatgcctgc ttgccgaata tcatggtgga aaatggccgc      3600
ttttctggat tcatcgactg tggccggctg ggtgtggcgg accgctatca ggacatagcg      3660
ttggctaccc gtgatattgc tgaagagctt ggcggcgaat gggctgaccg cttcctcgtg      3720
ctttacggta tcgccgctcc cgattcgcag cgcatcgcct tctatcgcct tcttgacgag      3780
ttcttctgag cgggactctg gggttcgaaa tgaccgacca agcgacgccc aacctgccat      3840
cacgagattt cgattccacc gccgccttct atgaaaggtt gggcttcgga atcgttttcc      3900
gggacgccgg ctgatgatc ctccagcgcg ggatctcat gctggagttc ttcgcccacc      3960 ctaggggag gctaactgaa acacggaagg agacaatacc ggaaggaacc cgcgctatga      4020
cggcaataaa aagacagaat aaaacgcacg gtgttgggtc gtttgttcat aaacgcgggg      4080
ttcggtccca gggctggcac tctgtcgata ccccaccgag accccattgg ggccaatacg      4140
cccgcgtttc ttccttttcc ccaccccacc ccccaagttc gggtgaaggc ccagggctcg      4200
```

| | | | | |
|---|---|---|---|---|
| cagccaacgt | cggggcggca | ggccctgcca | tagcctcagg | ttactcatat atactttaga | 4260 |
| ttgatttaaa | acttcatttt | taatttaaaa | ggatctaggt | gaagatcctt tttgataatc | 4320 |
| tcatgaccaa | aatcccttaa | cgtgagtttt | cgttccactg | agcgtcagac cccgtagaaa | 4380 |
| agatcaaagg | atcttcttga | gatccttttt | ttctgcgcgt | aatctgctgc ttgcaaacaa | 4440 |
| aaaaaccacc | gctaccagcg | gtggtttgtt | tgccggatca | agagctacca actcttttc | 4500 |
| cgaaggtaac | tggcttcagc | agagcgcaga | taccaaatac | tgtccttcta gtgtagccgt | 4560 |
| agttaggcca | ccacttcaag | aactctgtag | caccgcctac | atacctcgct ctgctaatcc | 4620 |
| tgttaccagt | ggctgctgcc | agtggcgata | agtcgtgtct | taccgggttg gactcaagac | 4680 |
| gatagttacc | ggataaggcg | cagcggtcgg | gctgaacggg | gggttcgtgc acacagccca | 4740 |
| gcttggagcg | aacgacctac | accgaactga | gatacctaca | gcgtgagcta tgagaaagcg | 4800 |
| ccacgcttcc | cgaagggaga | aaggcggaca | ggtatccggt | aagcggcagg gtcggaacag | 4860 |
| gagagcgcac | gagggagctt | ccaggggaa | acgcctggta | tctttatagt cctgtcgggt | 4920 |
| ttcgccacct | ctgacttgag | cgtcgatttt | tgtgatgctc | gtcagggggg cggagcctat | 4980 |
| ggaaaaacgc | cagcaacgcg | gccttttac | ggttcctggc | cttttgctgg ccttttgctc | 5040 |
| acatgttctt | tcctgcgtta | tcccctgatt | ctgtggataa | ccgtattacc gccatgcatt | 5100 |
| agttat | | | | | 5106 |

<210> SEQ ID NO 35
<211> LENGTH: 5006
<212> TYPE: DNA
<213> ORGANISM: Artificial Sequence
<220> FEATURE:
<223> OTHER INFORMATION: p2-3'GAPDH/EGFP-F

<400> SEQUENCE: 35

| | | | | |
|---|---|---|---|---|
| tagttattaa | tagtaatcaa | ttacggggtc | attagttcat | agcccatata tggagttccg | 60 |
| cgttacataa | cttacggtaa | atggcccgcc | tggctgaccg | cccaacgacc cccgcccatt | 120 |
| gacgtcaata | atgacgtatg | ttcccatagt | aacgccaata | gggactttcc attgacgtca | 180 |
| atgggtggag | tatttacggt | aaactgccca | cttggcagta | catcaagtgt atcatatgcc | 240 |
| aagtacgccc | cctattgacg | tcaatgacgg | taaatggccc | gcctggcatt atgcccagta | 300 |
| catgacctta | tgggactttc | ctacttggca | gtacatctac | gtattagtca tcgctattac | 360 |
| catggtgatg | cggttttggc | agtacatcaa | tgggcgtgga | tagcggtttg actcacgggg | 420 |
| atttccaagt | ctccacccca | ttgacgtcaa | tgggagtttg | ttttggcacc aaaatcaacg | 480 |
| ggactttcca | aaatgtcgta | acaactccgc | cccattgacg | caaatgggcg gtaggcgtgt | 540 |
| acggtgggag | gtctatataa | gcagagctgg | tttagtgaac | cgtcagatcc gctagcgcta | 600 |
| ccggtcgcca | ccatggtgag | caagggcgag | gagctgttca | ccggggtggt gcccatcctg | 660 |
| gtcgagctgg | acggcgacgt | aaacggccac | aagttcagcg | tgtccggcga gggcgagggc | 720 |
| gatgccacct | acggcaagct | gaccctgaag | ttcatctgca | ccaccggcaa gctgcccgtg | 780 |
| ccctggccca | cctcgtgac | cacccctgacc | tacggcgtgc | agtgcttcag ccgctacccc | 840 |
| gaccacatga | agcagcacga | cttcttcaag | tccgccatgc | ccgaaggcta cgtccaggag | 900 |
| cgcaccatct | tcttcaagga | cgacggcaac | tacaagaccc | gcgccgaggt gaagttcgag | 960 |
| ggcgacaccc | tggtgaaccg | catcgagctg | aagggcatcg | acttcaagga ggacggcaac | 1020 |
| atcctggggc | acaagctgga | gtacaactac | aacagccaca | acgtctatat catggccgac | 1080 |
| aagcagaaga | acggcatcaa | ggtgaacttc | aagatccgcc | acaacatcga ggacggcagc | 1140 |

-continued

```
gtgcagctcg ccgaccacta ccagcagaac accoccatog gogacggocc ogtgctgctg    1200 cccgacaacc actacctgag cacccagtcc gccctgagca aagaccccaa cgagaagcgc    1260
gatcacatgg tcctgctgga gttcgtgacc gccgccggga tcactctcgg catggacgag    1320
ctgtacaagt ccgactcag atctaagctg aaccctcctg atgagagtgg ccccggctgc    1380
atgagctgca agtgtgtgct ctcctgagga tccagatctc gagctcaagc ttcgaattcg    1440
gcgtaagaaa ccctggacca cccacccag caaggacact gagcaagaga ggccctatcc    1500
caactcggcc cccaacactg agcatctccc tcacaatttc catcccagac ccccataata    1560
acaggagggg cctagggagc cctccctact ctcttgaata ccatcaataa agttcgctgc    1620
acccacttaa gccgaattct gcagtcgacg gtaccgcggg cccgggatcc accggatcta    1680
gataactgat cataatcagc cataccacat ttgtagaggt tttacttgct ttaaaaaacc    1740
tcccacacct cccoctgaac ctgaaacata aaatgaatgc aattgttgtt gttaacttgt    1800
ttattgcagc ttataatggt tacaaataaa gcaatagcat cacaaatttc acaaataaag    1860
catttttttc actgcattct agttgtggtt tgtccaaact catcaatgta tcttaacgcg    1920
taaattgtaa gcgttaatat tttgttaaaa ttcgcgttaa attttgtta atcagctca    1980 ttttttaacc aataggccga atcggcaaa atcccttata atcaaaaga atagaccgag    2040 atagggttga gtgttgttcc agtttggaac aagagtccac tattaaagaa cgtggactcc    2100
aacgtcaaag ggcgaaaaac cgtctatcag ggcgatggcc cactacgtga accatcaccc    2160
taatcaagtt ttttggggtc gaggtgccgt aaagcactaa atcggaaccc taaagggagc    2220
ccccgattta gagcttgacg gggaaagccg cgaacgtgg cgagaaagga agggaagaaa    2280
gcgaaaggag cgggcgctag ggcgctggca agtgtagcgg tcacgctgcg cgtaaccacc    2340
acacccgccg cgcttaatgc gccgctacag ggcgcgtcag gtggcactt tcggggaaat    2400 gtgcgcggaa cccctatttg tttattttc taaatacatt caaatatgta tccgctcatg    2460
agacaataac cctgataaat gcttcaataa tattgaaaaa ggaagagtcc tgaggcggaa    2520
agaaccagct gtggaatgtg tgtcagttag ggtgtggaaa gtccccaggc tccccagcag    2580
gcagaagtat gcaaagcatg catctcaatt agtcagcaac caggtgtgga agtccccag    2640 gctccccagc aggcagaagt atgcaaagca tgcatctcaa ttagtcagca accatagtcc    2700
cgcccctaac tccgcccatc ccgccctaa ctccgcccag ttccgcccat tctccgcccc    2760
atggctgact aattttttt atttatgcag aggccgaggc cgcctcggcc tctgagctat    2820
tccagaagta gtgaggaggc ttttttggag gcctaggctt ttgcaaagat cgatcaagag    2880
acaggatgag gatcgtttcg catgattgaa caagatggat tgcacgcagg ttctccggcc    2940
gcttgggtgg agaggctatt cggctatgac tgggcacaac agacaatcgg ctgctctgat    3000
gccgccgtgt tccggctgtc agcgcagggg cgcccggttc tttttgtcaa gaccgacctg    3060
tccggtgccc tgaatgaact gcaagacgag gcagcgcggc tatcgtggct ggccacgacg    3120
ggcgttcctt gcgcagctgt gctcgacgtt gtcactgaag cgggaaggga ctggctgcta    3180
ttgggcgaag tgccggggca ggatctcctg tcatctcacc ttgctcctgc cgagaaagta    3240
tccatcatgg ctgatgcaat gcggcggctg catacgcttg atccggctac ctgcccattc    3300
gaccaccaag cgaaacatcg catcgagcga gcacgtactc ggatggaagc cggtcttgtc    3360
gatcaggatg atctggacga agagcatcag gggctcgcgc cagccgaact gttcgccagg    3420
ctcaaggcga gcatgcccga cggcgaggat ctcgtcgtga cccatggcga tgcctgcttg    3480
ccgaatatca tggtggaaaa tggccgcttt tctggattca tcgactgtgg ccggctgggt    3540
```

```
gtggcggacc gctatcagga catagcgttg gctaccgtg atattgctga agagcttggc    3600
ggcgaatggg ctgaccgctt cctcgtgctt tacggtatcg ccgctcccga ttcgcagcgc    3660
atcgccttct atcgccttct tgacgagttc ttctgagcgg gactctgggg ttcgaaatga    3720
ccgaccaagc gacgcccaac ctgccatcac gagatttcga ttccaccgcc gccttctatg    3780
aaaggttggg cttcggaatc gttttccggg acgccggctg gatgatcctc cagcgcgggg    3840
atctcatgct ggagttcttc gcccacccta ggggaggct aactgaaaca cggaaggaga    3900
caataccgga aggaacccgc gctatgacgg caataaaaag acagaataaa acgcacggtg    3960
ttgggtcgtt tgttcataaa cgcggggttc ggtcccaggg ctggcactct gtcgataccc    4020
caccgagacc ccattggggc caatacgccc gcgtttcttc cttttcccca ccccaccccc    4080
caagttcggg tgaaggccca gggctcgcag ccaacgtcgg ggcggcaggc cctgccatag    4140
cctcaggtta ctcatatata ctttagattg atttaaaact tcatttttaa tttaaaagga    4200
tctaggtgaa gatcctttt gataatctca tgaccaaaat cccttaacgt gagttttcgt    4260
tccactgagc gtcagacccc gtagaaaaga tcaaaggatc ttcttgagat cctttttttc    4320
tgcgcgtaat ctgctgcttg caaacaaaaa aaccaccgct accagcggtg gtttgtttgc    4380
cggatcaaga gctaccaact ctttttccga aggtaactgg cttcagcaga gcgcagatac    4440
caaatactgt ccttctagtg tagccgtagt taggccacca cttcaagaac tctgtagcac    4500
cgcctacata cctcgctctg ctaatcctgt taccagtggc tgctgccagt ggcgataagt    4560
cgtgtcttac cgggttggac tcaagacgat agttaccgga taaggcgcag cggtcgggct    4620
gaacgggggg ttcgtgcaca cagcccagct tggagcgaac gacctacacc gaactgagat    4680
acctacagcg tgagctatga gaaagcgcca cgcttcccga agggagaaag gcggacaggt    4740
atccggtaag cggcagggtc ggaacaggag agcgcacgag ggagcttcca gggggaaacg    4800
cctggtatct ttatagtcct gtcgggtttc gccacctctg acttgagcgt cgatttttgt    4860
gatgctcgtc aggggggcgg agcctatgga aaaacgccag caacgcggcc ttttacggt    4920 tcctggccctt tgctggcctt tttgctcaca tgttctttcc tgcgttatcc cctgattctg    4980
tggataaccg tattaccgcc atgcat                                         5006
```

<210> SEQ ID NO 36
<211> LENGTH: 4810
<212> TYPE: DNA
<213> ORGANISM: Artificial Sequence
<220> FEATURE:
<223> OTHER INFORMATION: p3-3'GAPDH/EGFP-F

<400> SEQUENCE: 36

```
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
atttccaagt ctccacccca ttgacgtcaa tgggagtttg ttttggcacc aaaatcaacg     480
ggactttcca aaatgtcgta acaactccgc cccattgacg caaatgggcg gtaggcgtgt     540
acggtgggag gtctatataa gcagagctgg tttagtgaac cgtcagatcc gctagcgcta     600
```

```
ccggtcgcca ccatggtgag caagggcgag gagctgttca ccggggtggt gcccatcctg   660
gtcgagctgg acggcgacgt aaacggccac aagttcagcg tgtccggcga gggcgagggc   720
gatgccacct acggcaagct gaccctgaag ttcatctgca ccaccggcaa gctgcccgtg   780
ccctggccca ccctcgtgac caccctgacc tacggcgtgc agtgcttcag ccgctacccc   840
gaccacatga agcagcacga cttcttcaag tccgccatgc ccgaaggcta cgtccaggag   900
cgcaccatct tcttcaagga cgacggcaac tacaagaccc gcgccgaggt gaagttcgag   960
ggcgacaccc tggtgaaccg catcgagctg aagggcatcg acttcaagga ggacggcaac  1020
atcctggggc acaagctgga gtacaactac aacagccaca acgtctatat catggccgac  1080
aagcagaaga acggcatcaa ggtgaacttc aagatccgcc acaacatcga ggacggcagc  1140
gtgcagctcg ccgaccacta ccagcagaac acccccatcg gcgacggccc cgtgctgctg  1200
cccgacaacc actacctgag cacccagtcc gccctgagca agaccccaa cgagaagcgc  1260
gatcacatgg tcctgctgga gttcgtgacc gccgccggga tcactctcgg catggacgag  1320
ctgtacaagt ccggactcag atctaagctg aaccctcctg atgagagtgg ccccggctgc  1380
atgagctgca agtgtgtgct ctcctgagga tccagatctc gagctcaagc ttcgaattcg  1440
gcgtaagaaa ccctggacca cccaccccag caaggacact gagcaagaga ggccctatcc  1500
caactcggcc cccaacactg agcatctccc tcacaatttc catcccagac ccccataata  1560
acaggagggg cctagggagc cctccctact ctcttgaata ccatcaataa agttcgctgc  1620
acccacttaa gccgaattct gcagtcgacg gtaccgcggg cccgggatcc accgatcta   1680
gataactgat cataatcagc cataccacat ttgtagaggt tttacttgct ttaagcgtta  1740
atattttgtt aaaattcgcg ttaaattttt gttaaatcag ctcatttttt aaccaatagg  1800
ccgaaatcgg caaaatccct tataaatcaa agaatagacc gagatagggg ttgagtgttg  1860
ttccagtttg gaacaagagt ccactattaa agaacgtgga ctccaacgtc aaagggcgaa  1920
aaaccgtcta tcagggcgat ggcccactac gtgaaccatc accctaatca agttttttgg  1980
ggtcgaggtg ccgtaaagca ctaaatcgga accctaaagg gagcccccga tttagagctt  2040
gacggggaaa gccggcgaac gtggcgagaa aggaagggaa gaaagcgaaa ggagcgggcg  2100
ctagggcgct ggcaagtgta gcggtcacgc tgcgcgtaac caccacaccc gccgcgctta  2160
atgcgccgct acagggcgcg tcaggtggca cttttcgggg aaatgtgcgc ggaaccccta  2220
tttgtttatt tttctaaata cattcaaata tgtatccgct catgagacaa taaccctgat  2280
aaatgcttca ataatattga aaaggaaga gtcctgaggc ggaaagaacc agctgtggaa  2340
tgtgtgtcag ttagggtgtg gaaagtcccc aggctcccca gcaggcagaa gtatgcaaag  2400
catgcatctc aattagtcag caaccaggtg tggaaagtcc caggctccc cagcaggcag  2460
aagtatgcaa agcatgcatc tcaattagtc agcaaccata gtcccgcccc taactccgcc  2520
catcccgccc ctaactccgc ccagttccgc ccattctccg ccccatggct gactaatttt  2580
ttttatttat gcagaggccg aggccgcctc ggcctctgag ctattccaga agtagtgagg  2640
aggcttttt ggaggcctag gcttttgcaa agatcgatca agagacagga tgaggatcgt  2700
ttcgcatgat tgaacaagat ggattgcacg caggttctcc ggccgcttgg gtggagaggc  2760
tattcggcta tgactgggca caacagacaa tcggctgctc tgatgccgcc gtgttccggc  2820
tgtcagcgca ggggcgcccg gttcttttg tcaagaccga cctgtccggt gccctgaatg  2880
aactgcaaga cgaggcagcg cggctatcgt ggctggccac gacggcgtt ccttgcgcag  2940
ctgtgctcga cgttgtcact gaagcgggaa gggactggct gctattgggc gaagtgccgg  3000
```

| | |
|---|---|
| ggcaggatct cctgtcatct caccttgctc ctgccgagaa agtatccatc atggctgatg | 3060 |
| caatgcggcg gctgcatacg cttgatccgg ctacctgccc attcgaccac caagcgaaac | 3120 |
| atcgcatcga gcgagcacgt actcggatgg aagccggtct tgtcgatcag gatgatctgg | 3180 |
| acgaagagca tcaggggctc gcgccagccg aactgttcgc caggctcaag gcgagcatgc | 3240 |
| ccgacggcga ggatctcgtc gtgacccatg gcgatgcctg cttgccgaat atcatggtgg | 3300 |
| aaaatggccg cttttctgga ttcatcgact gtggccggct gggtgtggcg gaccgctatc | 3360 |
| aggacatagc gttggctacc cgtgatattg ctgaagagct tggcggcgaa tgggctgacc | 3420 |
| gcttcctcgt gctttacggt atcgccgctc ccgattcgca gcgcatcgcc ttctatcgcc | 3480 |
| ttcttgacga gttcttctga gcgggactct ggggttcgaa atgaccgacc aagcgacgcc | 3540 |
| caacctgcca tcacgagatt tcgattccac cgccgccttc tatgaaaggt tgggcttcgg | 3600 |
| aatcgttttc cgggacgccg gctggatgat cctccagcgc ggggatctca tgctggagtt | 3660 |
| cttcgcccac cctaggggga ggctaactga aacacgaaag gagacaatac cggaaggaac | 3720 |
| ccgcgctatg acggcaataa aaagacagaa taaaacgcac ggtgttgggt cgtttgttca | 3780 |
| taaacgcggg gttcggtccc agggctggca ctctgtcgat accccaccga dccccattg | 3840 |
| gggccaatac gcccgcgttt cttccttttc cccacccac cccccaagtt cgggtgaagg | 3900 |
| cccagggctc gcagccaacg tcggggcggc aggccctgcc atagcctcag gttactcata | 3960 |
| tatactttag attgatttaa aacttcattt ttaatttaaa aggatctagg tgaagatcct | 4020 |
| ttttgataat ctcatgacca aaatcccta acgtgagttt tcgttccact gagcgtcaga | 4080 |
| ccccgtagaa aagatcaaag gatcttcttg agatcctttt tttctgcgcg taatctgctg | 4140 |
| cttgcaaaca aaaaaaccac cgctaccagc ggtggtttgt ttgccggatc aagagctacc | 4200 |
| aactcttttt ccgaaggtaa ctggcttcag cagagcgcag ataccaaata ctgtccttct | 4260 |
| agtgtagccg tagttaggcc accacttcaa gaactctgta gcaccgccta catacctcgc | 4320 |
| tctgctaatc ctgttaccag tggctgctgc cagtggcgat aagtcgtgtc ttaccgggtt | 4380 |
| ggactcaaga cgatagttac cggataaggc gcagcggtcg gctgaacgg ggggttcgtg | 4440 |
| cacacagccc agcttggagc gaacgaccta caccgaactg agatacctac agcgtgagct | 4500 |
| atgagaaagc gccacgcttc ccgaagggag aaaggcggac aggtatccgg taagcggcag | 4560 |
| ggtcggaaca ggagagcgca cgagggagct tccagggga aacgcctggt atctttatag | 4620 |
| tcctgtcggg tttcgccacc tctgacttga gcgtcgattt ttgtgatgct cgtcaggggg | 4680 |
| gcggagccta tggaaaaacg ccagcaacgc ggcctttta cggttcctgg ccttttgctg | 4740 |
| gccttttgct cacatgttct ttcctgcgtt atcccctgat tctgtggata accgtattac | 4800 |
| cgccatgcat | 4810 |

<210> SEQ ID NO 37
<211> LENGTH: 5737
<212> TYPE: DNA
<213> ORGANISM: Artificial Sequence
<220> FEATURE:
<223> OTHER INFORMATION: p1-5'IL10/EGFP-1

<400> SEQUENCE: 37

| | |
|---|---|
| tcgagcagtc aggagagagg gcagtgaggg tccatgctag ctgggtcttg agcctcttct | 60 |
| ggggttcagt ctctgatcta cagcagtgtg tccacaccta aacatcagc tcagagaggc | 120 |
| agttgcttct gctgttggaa acggacatcc caaaaaaaaa caaaaaacag aaatcaaaag | 180 |
| ggaaggagaa agtgaaaggg atggaggcag cttgtcccct tccctgtgct tgctgctggt | 240 |

```
agaaaactca gcctggaact gaccggagca gcagttcttg agtcaattcc attccaactt    300
ctagaagatt cttttcccgt cgaagagtgt caggaggaga ggccagaccc ccttgatcct    360
gatctgccag ccactgcatc agataagacg agataacccc gagttcctgt tctaccagcc    420
ctggtgtggt aaccctctcc aatggggcag gcttggaacc ctgtgccaac gaagatcctc    480
ccccgtactg atgcaggaag acagcccgg gagtgtaccc tctacatggg tctactttta    540
tttaagcaaa cattccctgg tcaacaggac gtgtagcatt gccccccccc ttgggtcaca    600
cagaaaacag gtaccaggag acaagtagt tgcttgccca gggtacagaa tgaaaggcaa    660 tagggggactc taggcgaatg ttcttcccac ccaaactgag gtagtaggag aagtccctac    720
tgaagggaag gtccagacat aatcaaagga ctaccagaga tctcccaggt atctgtagaa    780
gtactaacat ctccatcctt caacagctac aggttacacg tctccaaggc tgggacattg    840
taaaacaggg ccatggtaag gtctacccga cagcacagag caagcctccc agaagtctga    900
gttccttctc ctaacttctc atgctgggat ctgagcttct tcgtgaaaca cggggcagag    960
gaggcaccag aactctcctc tgaccaactg ccccacagca cacatatcct caaaggatag   1020
tcttgaatac gtgatggaag aattaaagag agtgaggtct gaagaaaatc agccctctcg   1080
gggtttcctt tgggtaactg agtgctaagg tgacttccga gtcagcaaga aatatcggac   1140
gttcaaccca ggttgagtgg aggaaacaat tatttctcaa tcctaatatg ttctggaata   1200
gcccatttat ccacgtcatt atgacctggg agtgcgtgaa tggaatccac agatgagggc   1260
ctctgtacat agaacagctg tctgcctcag gaaatacaac ttttagtatt gagaagctaa   1320
aaagaaaaaa aaattaaaag agaggtagcc catactaaaa atagctgtaa tgcagaagtt   1380
cattccgacc agttctttag cgcttacaat gcaaaaaaaa gggaaaggaa aaaaaaaaag   1440
aaagaaatta aactcaaaaa ttgcatggtt tagaagaggg aggaggagcc tgaataacaa   1500
aaacctttgc caggaaggcc ccactgagcc ttcagtataa aaggggacc aagaacagga   1560 ggtctacatt tagagacttg ctcttgcact accaaagcca caaggcagcc ttgcagaaaa   1620
gagagctcca tcggatccac cggtcgccac catggtgagc aagggcgagg agctgttcac   1680
cggggtggtg cccatcctgg tcgagctgga cggcgacgta acggccaca agttcagcgt   1740 gtccggcgag ggcgagggcg atgccaccta cggcaagctg accctgaagt tcatctgcac   1800
caccggcaag ctgcccgtgc cctggcccac cctcgtgacc accctgacct acggcgtgca   1860
gtgcttcagc cgctaccccg accacatgaa gcagcacgac ttcttcaagt ccgccatgcc   1920
cgaaggctac gtccaggagc gcaccatctt cttcaaggac gacggcaact acaagacccg   1980
cgccgaggtg aagttcgagg gcgacaccct ggtgaaccgc atcgagctga agggcatcga   2040
cttcaaggag gacggcaaca tcctggggca caagctggag tacaactaca acagccacaa   2100
cgtctatatc atggccgaca agcagaagaa cggcatcaag gtgaacttca agatccgcca   2160
caacatcgag gacggcagcg tgcagctcgc cgaccactac cagcagaaca cccccatcgg   2220
cgacggcccc gtgctgctgc ccgacaacca ctacctgagc acccagtccg ccctgagcaa   2280 agacccccaac gagaagcgcg atcacatggt cctgctggag ttcgtgaccg ccgccgggat   2340
cactctcggc atggacgagc tgtacaagta aagcggccgc gactctagat cataatcagc   2400
cataccacat ttgtagaggt tttacttgct ttaaaaaacc tcccacacct ccccctgaac   2460
ctgaaacata aaatgaatgc aattgttgtt gttaacttgt ttattgcagc ttataatggt   2520
tacaaataaa gcaatagcat cacaaatttc acaaataaag cattttttc actgcattct   2580 agttgtggtt tgtccaaact catcaatgta tcttaaggcg taaattgtaa gcgttaatat   2640
```

```
tttgttaaaa ttcgcgttaa attttgtta aatcagctca tttttaacc aataggccga    2700
aatcggcaaa atcccttata aatcaaaaga atagaccgag atagggttga gtgttgttcc    2760
agtttggaac aagagtccac tattaaagaa cgtggactcc aacgtcaaag ggcgaaaaac    2820
cgtctatcag ggcgatggcc cactacgtga accatcaccc taatcaagtt ttttggggtc    2880
gaggtgccgt aaagcactaa atcggaaccc taaagggagc ccccgattta gagcttgacg    2940
gggaaagccg gcgaacgtgg cgagaaagga agggaagaaa gcgaaggag cgggcgctag    3000
ggcgctggca agtgtagcgg tcacgctgcg cgtaaccacc acacccgccg cgcttaatgc    3060
gccgctacag ggcgcgtcag gtggcacttt tcggggaaat gtgcgcggaa ccctatttg    3120
tttatttttc taaatacatt caaatatgta tccgctcatg agacaataac cctgataaat    3180
gcttcaataa tattgaaaaa ggaagagtcc tgaggcggaa agaaccagct gtggaatgtg    3240
tgtcagttag ggtgtggaaa gtccccaggc tccccagcag gcagaagtat gcaaagcatg    3300
catctcaatt agtcagcaac caggtgtgga aagtccccag gctccccagc aggcagaagt    3360
atgcaaagca tgcatctcaa ttagtcagca accatagtcc cgcccctaac tccgcccatc    3420
ccgcccctaa ctccgcccag ttccgcccat tctccgcccc atggctgact aatttttttt    3480
atttatgcag aggccgaggc cgcctcggcc tctgagctat tccagaagta gtgaggaggc    3540
ttttttggag gcctaggctt ttgcaaagat cgatcaagag acaggatgag gatcgtttcg    3600
catgattgaa caagatggat tgcacgcagg ttctccggcc gcttgggtgg agaggctatt    3660
cggctatgac tgggcacaac agacaatcgg ctgctctgat gccgccgtgt tccggctgtc    3720
agcgcagggg cgcccggttc ttttgtcaa gaccgacctg tccggtgccc tgaatgaact    3780
gcaagacgag gcagcgcggc tatcgtggct ggccacgacg ggcgttcctt gcgcagctgt    3840
gctcgacgtt gtcactgaag cgggaaggga ctggctgcta ttgggcgaag tgccggggca    3900
ggatctcctg tcatctcacc ttgctcctgc cgagaaagta tccatcatgg ctgatgcaat    3960
gcggcggctg catacgcttg atccggctac ctgcccattc gaccaccaag cgaaacatcg    4020
catcgagcga gcacgtactc ggatggaagc cggtcttgtc gatcaggatg atctggacga    4080
agagcatcag gggctcgcgc cagccgaact gttcgccagg ctcaaggcga gcatgcccga    4140
cggcgaggat ctcgtcgtga cccatggcga tgcctgcttg ccgaatatca tggtggaaaa    4200
tggccgcttt tctggattca tcgactgtgg ccggctgggt gtggcggacc gctatcagga    4260
catagcgttg gctacccgtg atattgctga agagcttggc ggcgaatggg ctgaccgctt    4320
cctcgtgctt tacggtatcg ccgctcccga ttcgcagcgc atcgccttct atcgccttct    4380
tgacgagttc ttctgagcgg gactctgggg ttcgaaatga ccgaccaagc gacgcccaac    4440
ctgccatcac gagatttcga ttccaccgcc gccttctatg aaaggttggg cttcggaatc    4500
gttttccggg acgccggctg atgatcctc cagcgcgggg atctcatgct ggagttcttc    4560
gcccacccta gggggaggct aactgaaaca cggaaggaga caataccgga aggaacccgc    4620
gctatgacgg caataaaaag acagaataaa acgcacggtg ttgggtcgtt tgttcataaa    4680
cgcggggttc ggtcccaggg ctggcactct gtcgataccc caccgagacc ccattggggc    4740
caatacgccc gcgtttcttc cttttcccca ccccaccccc caagttcggg tgaaggccca    4800
gggctcgcag ccaacgtcgg ggcggcaggc cctgccatag cctcaggtta ctcatatata    4860
ctttagattg atttaaaact tcatttttaa tttaaaagga tctaggtgaa gatcctttt    4920
gataatctca tgaccaaaat cccttaacgt gagttttcgt tccactgagc gtcagacccc    4980
gtagaaaaga tcaaaggatc ttcttgagat cctttttttc tgcgcgtaat ctgctgcttg    5040
```

-continued

| | | | | |
|---|---|---|---|---|
| caaacaaaaa | aaccaccgct | accagcggtg | gtttgtttgc | cggatcaaga gctaccaact | 5100 |
| cttttttccga | aggtaactgg | cttcagcaga | gcgcagatac | caaatactgt ccttctagtg | 5160 |
| tagccgtagt | taggccacca | cttcaagaac | tctgtagcac | cgcctacata cctcgctctg | 5220 |
| ctaatcctgt | taccagtggc | tgctgccagt | ggcgataagt | cgtgtcttac cgggttggac | 5280 |
| tcaagacgat | agttaccgga | taaggcgcag | cggtcgggct | gaacggggg ttcgtgcaca | 5340 |
| cagcccagct | tggagcgaac | gacctacacc | gaactgagat | acctacagcg tgagctatga | 5400 |
| gaaagcgcca | cgcttcccga | agggagaaag | gcggacaggt | atccggtaag cggcagggtc | 5460 |
| ggaacaggag | agcgcacgag | ggagcttcca | gggggaaacg | cctggtatct ttatagtcct | 5520 |
| gtcgggtttc | gccacctctg | acttgagcgt | cgatttttgt | gatgctcgtc aggggggcgg | 5580 |
| agcctatgga | aaaacgccag | caacgcggcc | tttttacggt | tcctggcctt ttgctggcct | 5640 |
| tttgctcaca | tgttctttcc | tgcgttatcc | cctgattctg | tggataaccg tattaccgcc | 5700 |
| atgcattagt | tattactagc | gctaccggac | tcagatc | | 5737 |

<210> SEQ ID NO 38
<211> LENGTH: 5866
<212> TYPE: DNA
<213> ORGANISM: Artificial Sequence
<220> FEATURE:
<223> OTHER INFORMATION: p2-5'IL10/d2EGFP-1

<400> SEQUENCE: 38

| | | | | |
|---|---|---|---|---|
| tcgagcagtc | aggagagagg | gcagtgaggg | tccatgctag | ctgggtcttg agcctcttct | 60 |
| ggggttcagt | ctctgatcta | cagcagtgtg | tccacaccta | aacatcagc tcagagaggc | 120 |
| agttgcttct | gctgttggaa | acggacatcc | caaaaaaaaa | caaaaaacag aaatcaaaag | 180 |
| ggaaggagaa | agtgaaaggg | atggaggcag | cttgtcccct | tccctgtgct tgctgctggt | 240 |
| agaaaactca | gcctggaact | gaccggagca | gcagttcttg | agtcaattcc attccaactt | 300 |
| ctagaagatt | cttttcccgt | cgaagagtgt | caggaggaga | ggccagaccc ccttgatcct | 360 |
| gatctgccag | ccactgcatc | agataagacg | agataacccc | gagttcctgt tctaccagcc | 420 |
| ctggtgtggt | aaccctctcc | aatggggcag | gcttggaacc | ctgtgccaac gaagatcctc | 480 |
| ccccgtactg | atgcaggaag | gacagcccgg | gagtgtaccc | tctacatggg tctactttta | 540 |
| tttaagcaaa | cattccctgg | tcaacaggac | gtgtagcatt | gccccccccc ttgggtcaca | 600 |
| cagaaaacag | gtaccaggag | gacaagtagt | tgcttgccca | gggtacagaa tgaaaggcaa | 660 |
| taggggactc | taggcgaatg | ttcttcccac | ccaaactgag | gtagtaggag aagtccctac | 720 |
| tgaagggaag | gtccagacat | aatcaaagga | ctaccagaga | tctcccaggt atctgtagaa | 780 |
| gtactaacat | ctccatcctt | caacagctac | aggttacacg | tctccaaggc tgggacattg | 840 |
| taaaacaggg | ccatggtaag | gtctacccga | cagcacagag | caagcctccc agaagtctga | 900 |
| gttccttctc | ctaacttctc | atgctgggat | ctgagcttct | tcgtgaaaca cggggcagag | 960 |
| gaggcaccag | aactctcctc | tgaccaactg | ccccacagca | cacatatcct caaaggatag | 1020 |
| tcttgaatac | gtgatggaag | aattaaagag | agtgaggtct | gaagaaaatc agccctctcg | 1080 |
| gggtttcctt | tgggtaactg | agtgctaagg | tgacttccga | gtcagcaaga aatatcggac | 1140 |
| gttcaaccca | ggttgagtgg | aggaaacaat | tatttctcaa | tcctaatatg ttctggaata | 1200 |
| gcccatttat | ccacgtcatt | atgacctggg | agtgcgtgaa | tggaatccac agatgagggc | 1260 |
| ctctgtacat | agaacagctg | tctgcctcag | gaaatacaac | ttttagtatt gagaagctaa | 1320 |
| aaagaaaaaa | aaattaaaag | agaggtagcc | catactaaaa | atagctgtaa tgcagaagtt | 1380 |

```
cattccgacc agttctttag cgcttacaat gcaaaaaaaa gggaaaggaa aaaaaaaaag    1440
aaagaaatta aactcaaaaa ttgcatggtt tagaagaggg aggaggagcc tgaataacaa    1500
aaacctttgc caggaaggcc ccactgagcc ttcagtataa aaggggggacc aagaacagga   1560 ggtctacatt tagagacttg ctcttgcact accaaagcca caaggcagcc ttgcagaaaa    1620
gagagctcca tcggatccac cggtcgccac catggtgagc aagggcgagg agctgttcac    1680
cggggtggtg cccatcctgg tcgagctgga cggcgacgta acggccaca agttcagcgt     1740 gtccggcgag ggcgagggcg atgccaccta cggcaagctg accctgaagt tcatctgcac    1800
caccggcaag ctgcccgtgc cctggcccac cctcgtgacc accctgacct acggcgtgca    1860
gtgcttcagc cgctaccccg accacatgaa gcagcacgac ttcttcaagt ccgccatgcc    1920
cgaaggctac gtccaggagc gcaccatctt cttcaaggac gacggcaact acaagacccg    1980
cgccgaggtg aagttcgagg gcgacaccct ggtgaaccgc atcgagctga agggcatcga    2040
cttcaaggag gacggcaaca tcctggggca caagctggag tacaactaca acagccacaa    2100
cgtctatatc atggccgaca agcagaagaa cggcatcaag gtgaacttca gatccgcca    2160 caacatcgag gacggcagcg tgcagctcgc cgaccactac cagcagaaca cccccatcgg    2220
cgacggcccc gtgctgctgc ccgacaacca ctacctgagc acccagtccg ccctgagcaa    2280
agaccccaac gagaagcgcg atcacatggt cctgctggag ttcgtgaccg ccgccgggat    2340
cactctcggc atggacgagc tgtacaagaa gcttagccat ggcttcccgc cggaggtgga    2400
ggagcaggat gatggcacgc tgcccatgtc ttgtgcccag gagagcggga tggaccgtca    2460
ccctgcagcc tgtgcttctg ctaggatcaa tgtgtagatg cgcggccgcg actctagatc    2520
ataatcagcc ataccacatt tgtagaggtt ttacttgctt taaaaaacct cccacacctc    2580
cccctgaacc tgaaacataa aatgaatgca attgttgttg ttaacttgtt tattgcagct    2640
tataatggtt acaaataaag caatagcatc acaaatttca caaataaagc atttttttca    2700
ctgcattcta gttgtggttt gtccaaactc atcaatgtat cttaaggcgt aaattgtaag    2760
cgttaatatt tgttaaaat cgcgttaaa ttttgttaa atcagctcat ttttaacca      2820 ataggccgaa atcggcaaaa tcccttataa atcaaaagaa tagaccgaga tagggttgag    2880
tgttgttcca gtttggaaca agagtccact attaaagaac gtggactcca acgtcaaagg    2940
gcgaaaaacc gtctatcagg gcgatggccc actacgtgaa ccatcaccct aatcaagttt    3000
tttggggtcg aggtgccgta aagcactaaa tcggaaccct aaagggagcc cccgatttag    3060
agcttgacgg ggaaagccgg cgaacgtggc gagaaaggaa gggaagaaag cgaaaggagc    3120
gggcgctagg gcgctggcaa gtgtagcggt cacgctgcgc gtaaccacca cacccgccgc    3180
gcttaatgcg ccgctacagg gcgcgtcagg tggcacttt cggggaaatg tgcgcggaac    3240
ccctatttgt ttatttttct aaatacattc aaatatgtat ccgctcatga caataaacc     3300 ctgataaatg cttcaataat attgaaaaag gaagagtcct gaggcggaaa gaaccagctg    3360
tggaatgtgt gtcagttagg gtgtggaaag tccccaggct ccccagcagg cagaagtatg    3420
caaagcatgc atctcaatta gtcagcaacc aggtgtggaa agtccccagg ctccccagca    3480
ggcagaagta tgcaaagcat gcatctcaat tagtcagcaa ccatagtccc gcccctaact    3540
ccgcccatcc cgcccctaac tccgcccagt tccgcccatt ctccgcccca tggctgacta    3600
atttttttta tttatgcaga ggccgaggcc gcctcggcct ctgagctatt ccagaagtag    3660
tgaggaggct ttttttggagg cctaggcttt tgcaaagatc gatcaagaga caggatgagg    3720
atcgtttcgc atgattgaac aagatggatt gcacgcaggt tctccggccg cttgggtgga    3780
```

-continued

```
gaggctattc ggctatgact gggcacaaca gacaatcggc tgctctgatg ccgccgtgtt    3840
ccggctgtca gcgcaggggc gcccggttct ttttgtcaag accgaccgt ccggtgccct     3900
gaatgaactg caagacgagg cagcgcggct atcgtggctg ccacgacgg gcgttccttg     3960
cgcagctgtg ctcgacgttg tcactgaagc gggaagggac tggctgctat gggcgaagt    4020
gccggggcag gatctcctgt catctcacct tgctcctgcc gagaaagtat ccatcatggc    4080
tgatgcaatg cggcggctgc atacgcttga tccggctacc tgcccattcg accaccaagc   4140
gaaacatcgc atcgagcgag cacgtactcg gatggaagcc ggtcttgtcg atcaggatga   4200
tctggacgaa gagcatcagg ggctcgcgcc agccgaactg ttcgccaggc tcaaggcgag   4260
catgcccgac ggcgaggatc tcgtcgtgac ccatggcgat gcctgcttgc cgaatatcat   4320
ggtggaaaat ggccgctttt ctggattcat cgactgtggc cggctgggtg tggcggaccg   4380
ctatcaggac atagcgttgg ctacccgtga tattgctgaa gagcttggcg gcgaatgggc   4440
tgaccgcttc ctcgtgcttt acggtatcgc cgctcccgat tcgcagcgca tcgccttcta   4500
tcgccttctt gacgagttct tctgagcggg actctggggt tcgaaatgac cgaccaagcg   4560
acgcccaacc tgccatcacg agatttcgat tccaccgccg ccttctatga aaggttgggc   4620
ttcggaatcg ttttccggga cgccggctgg atgatcctcc agcgcgggga tctcatgctg   4680
gagttcttcg cccaccctag ggggaggcta actgaaacac ggaaggagac aataccggaa   4740
ggaacccgcg ctatgacggc aataaaaaga cagaataaaa cgcacggtgt tgggtcgttt   4800
gttcataaac gcggggttcg gtcccagggc tggcactctg tcgataccccc accgagaccc  4860
cattggggcc aatacgcccg cgtttcttcc ttttccccac cccaccccc aagttcgggt    4920
gaaggcccag ggctcgcagc caacgtcggg gcggcaggcc ctgccatagc ctcaggttac   4980
tcatatatac tttagattga tttaaaactt cattttaat ttaaaggat ctaggtgaag     5040
atccttttg ataatctcat gaccaaaatc ccttaacgtg agttttcgtt ccactgagcg    5100
tcagacccccg tagaaaagat caaaggatct tcttgagatc ctttttttct gcgcgtaatc  5160
tgctgcttgc aaacaaaaaa accaccgcta ccagcggtgg tttgtttgcc ggatcaagag   5220
ctaccaactc tttttccgaa ggtaactggc ttcagcagag cgcagatacc aaatactgtc   5280
cttctagtgt agccgtagtt aggccaccac ttcaagaact ctgtagcacc gcctacatac   5340
ctcgctctgc taatcctgtt accagtggct gctgccagtg gcgataagtc gtgtcttacc   5400
gggttggact caagacgata gttaccggat aaggcgcagc ggtcgggctg aacggggggt   5460
tcgtgcacac agcccagctt ggagcgaacg acctacaccg aactgagata cctacagcgt   5520
gagctatgag aaagcgccac gcttcccgaa gggagaaagg cggacaggta tccggtaagc   5580
ggcagggtcg gaacaggaga gcgcacgagg gagcttccag ggggaaacgc ctggtatctt   5640
tatagtcctg tcgggtttcg ccacctctga cttgagcgtc gatttttgtg atgctcgtca   5700
ggggggcgga gcctatggaa aaacgccagc aacgcggcct ttttacggtt cctggccttt   5760
tgctggcctt tgctcacat gttctttcct gcgttatccc ctgattctgt ggataaccgt    5820
attaccgcca tgcattagtt attactagcg ctaccggact cagatc                  5866
```

<210> SEQ ID NO 39
<211> LENGTH: 6223
<212> TYPE: DNA
<213> ORGANISM: Artificial Sequence
<220> FEATURE:
<223> OTHER INFORMATION: p1-5'3'IL10/EGFP-1

<400> SEQUENCE: 39

```
tcgagcagtc aggagagagg gcagtgaggg tccatgctag ctgggtcttg agcctcttct    60
ggggttcagt ctctgatcta cagcagtgtg tccacaccta aaacatcagc tcagagaggc   120
agttgcttct gctgttggaa acggacatcc caaaaaaaaa caaaaaacag aaatcaaaag   180
ggaaggagaa agtgaaaggg atggaggcag cttgtcccct tccctgtgct tgctgctggt   240
agaaaactca gcctggaact gaccggagca gcagttcttg agtcaattcc attccaactt   300
ctagaagatt cttttcccgt cgaagagtgt caggaggaga ggccagaccc ccttgatcct   360
gatctgccag ccactgcatc agataagacg agataacccc gagttcctgt tctaccagcc   420
ctggtgtggt aaccctctcc aatggggcag gcttggaacc ctgtgccaac gaagatcctc   480
ccccgtactg atgcaggaag acagcccgg gagtgtaccc tctacatggg tctacttta   540
tttaagcaaa cattccctgg tcaacaggac gtgtagcatt gccccccccc ttgggtcaca   600
cagaaaacag gtaccaggag acaagtagt tgcttgccca gggtacagaa tgaaaggcaa   660
taggggactc taggcgaatg ttcttcccac ccaaactgag gtagtaggag aagtccctac   720
tgaagggaag gtccagacat aatcaaagga ctaccagaga tctcccaggt atctgtagaa   780
gtactaacat ctccatcctt caacagctac aggttacacg tctccaaggc tgggacattg   840
taaaacaggg ccatggtaag gtctacccga cagcacagag caagcctccc agaagtctga   900
gttccttctc ctaacttctc atgctgggat ctgagcttct tcgtgaaaca cggggcagag   960
gaggcaccag aactctcctc tgaccaactg ccccacagca cacatatcct caaaggatag  1020
tcttgaatac gtgatggaag aattaaagag agtgaggtct gaagaaaatc agccctctcg  1080
gggtttcctt tgggtaactg agtgctaagg tgacttccga gtcagcaaga aatatcggac  1140
gttcaaccca ggttgagtgg aggaaacaat tatttctcaa tcctaatatg ttctggaata  1200
gcccatttat ccacgtcatt atgacctggg agtgcgtgaa tggaatccac agatgagggc  1260
ctctgtacat agaacagctg tctgcctcag gaaatacaac ttttagtatt gagaagctaa  1320
aaagaaaaaa aaattaaaag agaggtagcc catactaaaa atagctgtaa tgcagaagtt  1380
cattccgacc agttctttag cgcttacaat gcaaaaaaaa gggaaaggaa aaaaaaaaag  1440
aaagaaatta aactcaaaaa ttgcatggtt tagaagaggg aggaggagcc tgaataacaa  1500
aaacctttgc caggaaggcc ccactgagcc ttcagtataa aggggggacc aagaacagga  1560
ggtctacatt tagagacttg ctcttgcact accaaagcca caaggcagcc ttgcagaaaa  1620
gagagctcca tcggatccac cggtcgccac catggtgagc aagggcgagg agctgttcac  1680
cggggtggtg cccatcctgg tcgagctgga cggcgacgta aacggccaca gttcagcgt  1740
gtccggcgag ggcgagggcg atgccaccta cggcaagctg accctgaagt tcatctgcac  1800
caccggcaag ctgcccgtgc cctggcccac cctcgtgacc accctgacct acggcgtgca  1860
gtgcttcagc cgctaccccg accacatgaa gcagcacgac ttcttcaagt ccgccatgcc  1920
cgaaggctac gtccaggagc gcaccatctt cttcaaggac gacggcaact acaagacccg  1980
cgccgaggtg aagttcgagg gcgacaccct ggtgaaccgc atcgagctga agggcatcga  2040
cttcaaggag gacggcaaca tcctggggca caagctggag tacaactaca acagccacaa  2100
cgtctatatc atggccgaca agcagaagaa cggcatcaag gtgaacttca agatccgcca  2160
caacatcgag gacggcagcg tgcagctcgc cgaccactac cagcagaaca cccccatcgg  2220
cgacggcccc gtgctgctgc ccgacaacca ctacctgagc acccagtccg ccctgagcaa  2280
agaccccaac gagaagcgcg atcacatggt cctgctggag ttcgtgaccg ccgcgggat  2340
cactctcggc atggacgagc tgtacaagta aagcggccgc gggaattcga tttaaaacac  2400
```

```
ctgcagtgtg tattgagtct gctggactcc aggacctaga cagagctctc taaatctgat    2460
ccagggatct tagctaacgg aaacaactcc ttggaaaacc tcgtttgtac ctctctccga    2520
aatatttatt acctctgata cctcagttcc cattctattt attcactgag cttctctgtg    2580
aactatttag aaagaagccc aatattataa ttttacagta tttattattt ttaacctgtg    2640
tttaagctgt ttccattggg gacactttat agtatttaaa gggagattat attatatgat    2700
gggaggggtt cttccttggg aagcaattga agcttctatt ctaaggctgg ccacacttga    2760
gagctgcagg gccctttgct atggtgtcct ttcaattgct ctcatccctg agttcagagc    2820
tcctaagaga gttgtgaaga aactcatggg tcttgggaag agaaaccagg agatcctttt    2880
gatgatcatt cctgcagcag ctcagagggt tcccctactg tcatccccca gccgcttcat    2940
ccctgaaaac tgtggccagt ttgttattta taaccaccta aaattagttc taatagaact    3000
catttttaac tagaagtaat gcaattcctc tgggaatggt gtattgtttg tctgcctttg    3060
tagcagactc taattttgaa taaatggatc ttattcgctt aaggcgtaaa ttgtaagcgt    3120
taatatttg ttaaaattcg cgttaaattt ttgttaaatc agctcatttt ttaaccaata    3180
ggccgaaatc ggcaaaatcc cttataaatc aaaagaatag accgagatag ggttgagtgt    3240
tgttccagtt tggaacaaga gtccactatt aaagaacgtg gactccaacg tcaaagggcg    3300
aaaaaccgtc tatcagggcg atggcccact acgtgaacca tcaccctaat caagtttttt    3360
ggggtcgagg tgccgtaaag cactaaatcg gaaccctaaa gggagccccc gatttagagc    3420
ttgacgggga agccggcgaa cgtggcgag aaaggaaggg aagaaagcga aggagcggg     3480
cgctagggcg ctggcaagtg tagcggtcac gctgcgcgta accaccacac ccgccgcgct    3540
taatgcgccg ctacagggcg cgtcaggtgg cactttcgg ggaaatgtgc gcggaacccc     3600
tatttgttta ttttttctaaa tacattcaaa tatgtatccg ctcatgagac aataaccctg    3660
ataaatgctt caataatatt gaaaaggaa gagtcctgag gcggaaagaa ccagctgtgg    3720
aatgtgtgtc agttagggtg tggaaagtcc ccaggctccc cagcaggcag aagtatgcaa    3780
agcatgcatc tcaattagtc agcaaccagg tgtggaaagt ccccaggctc cccagcaggc    3840
agaagtatgc aaagcatgca tctcaattag tcagcaacca tagtcccgcc cctaactccg    3900
cccatcccgc ccctaactcc gcccagttcc gcccattctc cgccccatgg ctgactaatt    3960
tttttattt atgcagaggc cgaggccgcc tcggcctctg agctattcca gaagtagtga    4020
ggaggctttt ttggaggcct aggcttttgc aaagatcgat caagagacag gatgaggatc    4080
gtttcgcatg attgaacaag atggattgca cgcaggttct ccggccgctt gggtggagag    4140
gctattcggc tatgactggg cacaacagac aatcggctgc tctgatgccg ccgtgttccg    4200
gctgtcagcg caggggcgcc cggttctttt tgtcaagacc gacctgtccg gtgccctgaa    4260
tgaactgcaa gacgaggcag cgcggctatc gtggctggcc acgacgggcg ttccttgcgc    4320
agctgtgctc gacgttgtca ctgaagcggg aagggactgg ctgctattgg gcgaagtgcc    4380
ggggcaggat ctcctgtcat ctcaccttgc tcctgccgag aaagtatcca tcatggctga    4440
tgcaatgcgg cggctgcata cgcttgatcc ggctacctgc ccattcgacc accaagcgaa    4500
acatcgcatc gagcgagcac gtactcggat ggaagccggt cttgtcgatc aggatgatct    4560
ggacgaagag catcagggc tcgcgccagc cgaactgttc gccaggctca aggcgagcat    4620
gcccgacggc gaggatctcg tcgtgaccca tggcgatgcc tgcttgccga atatcatggt    4680
ggaaaatggc cgcttttctg gattcatcga ctgtggccgg ctgggtgtgg cggaccgcta    4740
tcaggacata gcgttggcta cccgtgatat tgctgaagag cttggcggcg aatgggctga    4800
```

```
ccgcttcctc gtgctttacg gtatcgccgc tcccgattcg cagcgcatcg ccttctatcg   4860
ccttcttgac gagttcttct gagcgggact ctggggttcg aaatgaccga ccaagcgacg   4920
cccaacctgc catcacgaga tttcgattcc accgccgcct tctatgaaag gttgggcttc   4980
ggaatcgttt tccgggacgc cggctggatg atcctccagc gcgggatct catgctggag    5040
ttcttcgccc accctagggg gaggctaact gaaacacgga aggagacaat accggaagga   5100
acccgcgcta tgacgcaat aaaaagacag aataaaacgc acggtgttgg gtcgtttgtt    5160
cataaacgcg gggttcggtc ccagggctgg cactctgtcg atacccacc gagacccat     5220
tggggccaat acgcccgcgt tcttcctttt tccccacccc acccccaag ttcgggtgaa    5280
ggcccagggc tcgcagccaa cgtcggggcg gcaggccctg ccatagcctc aggttactca   5340
tatatacttt agattgattt aaaacttcat ttttaattta aaaggatcta ggtgaagatc   5400
cttttttgata atctcatgac caaaatccct taacgtgagt tttcgttcca ctgagcgtca  5460
gaccccgtag aaaagatcaa aggatcttct tgagatcctt ttttttctgcg cgtaatctgc  5520
tgcttgcaaa caaaaaaacc accgctacca gcggtggttt gtttgccgga tcaagagcta  5580
ccaactcttt ttccgaaggt aactggcttc agcagagcgc agataccaaa tactgtcctt  5640
ctagtgtagc cgtagttagg ccaccacttc aagaactctg tagcaccgcc tacatacctc  5700
gctctgctaa tcctgttacc agtggctgct gccagtggcg ataagtcgtg tcttaccggg  5760
ttggactcaa gacgatagtt accggataag gcgcagcggt cgggctgaac ggggggttcg  5820
tgcacacagc ccagcttgga gcgaacgacc tacaccgaac tgagatacct acagcgtgag  5880
ctatgagaaa gcgccacgct tcccgaaggg agaaaggcgg acaggtatcc ggtaagcggc  5940
agggtcggaa caggagagcg cacgagggag cttccagggg gaaacgcctg gtatctttat  6000
agtcctgtcg ggtttcgcca cctctgactt gagcgtcgat ttttgtgatg ctcgtcaggg  6060
gggcggagcc tatggaaaaa cgccagcaac gcggcctttt tacggttcct ggccttttgc  6120
tggccttttg ctcacatgtt ctttcctgcg ttatccctg attctgtgga taaccgtatt   6180
accgccatgc attagttatt actagcgcta ccggactcag atc                     6223

<210> SEQ ID NO 40
<211> LENGTH: 6352
<212> TYPE: DNA
<213> ORGANISM: Artificial Sequence
<220> FEATURE:
<223> OTHER INFORMATION: p2-5'3'IL10/d2EGFP-1

<400> SEQUENCE: 40
tcgagcagtc aggagagagg gcagtgaggg tccatgctag ctgggtcttg agcctcttct     60
ggggttcagt tctctgatcta cagcagtgtg tccacaccta aaacatcagc tcagagaggc   120
agttgcttct gctgttggaa acggacatcc caaaaaaaaa caaaaaacag aaatcaaaag   180
ggaaggagaa agtgaaaggg atggaggcag cttgtcccct tccctgtgct tgctgctggt   240
agaaaactca gcctggaact gaccggagca gcagttcttg agtcaattcc attccaactt   300
ctagaagatt cttttcccgt cgaagagtgt caggaggaga ggccagaccc ccttgatcct   360
gatctgccag ccactgcatc agataagacg agataacccc gagttcctgt tctaccagcc   420
ctggtgtggt aaccctctcc aatggggcag gcttggaacc ctgtgccaac gaagatcctc   480
ccccgtactg atgcaggaag acagcccgg gagtgtaccc tctacatggg tctacttta     540
tttaagcaaa cattccctgg tcaacaggac gtgtagcatt gccccccccc ttgggtcaca   600
cagaaaacag gtaccaggag gacaagtagt tgcttgccca gggtacagaa tgaaaggcaa   660
```

```
tagggggactc taggcgaatg ttcttcccac ccaaactgag gtagtaggag aagtccctac    720
tgaagggaag gtccagacat aatcaaagga ctaccagaga tctcccaggt atctgtagaa    780
gtactaacat ctccatcctt caacagctac aggttacacg tctccaaggc tgggacattg    840
taaaacaggg ccatggtaag gtctacccga cagcacagag caagcctccc agaagtctga    900
gttccttctc ctaacttctc atgctgggat ctgagcttct tcgtgaaaca cggggcagag    960
gaggcaccag aactctcctc tgaccaactg ccccacagca cacatatcct caaaggatag   1020
tcttgaatac gtgatggaag aattaaagag agtgaggtct gaagaaaatc agccctctcg   1080
gggtttcctt tgggtaactg agtgctaagg tgacttccga gtcagcaaga aatatcggac   1140
gttcaaccca ggttgagtgg aggaaacaat tatttctcaa tcctaatatg ttctggaata   1200
gcccatttat ccacgtcatt atgacctggg agtgcgtgaa tggaatccac agatgagggc   1260
ctctgtacat agaacagctg tctgcctcag gaaatacaac ttttagtatt gagaagctaa   1320
aaagaaaaaa aaattaaaag agaggtagcc catactaaaa atagctgtaa tgcagaagtt   1380
cattccgacc agttctttag cgcttacaat gcaaaaaaaa gggaaaggaa aaaaaaaaag   1440
aaagaaatta aactcaaaaa ttgcatggtt tagaagaggg aggaggagcc tgaataacaa   1500
aaacctttgc caggaaggcc ccactgagcc ttcagtataa aaggggggacc aagaacagga   1560 ggtctacatt tagagacttg ctcttgcact accaaagcca caaggcagcc ttgcagaaaa   1620
gagagctcca tcggatccac cggtcgccac catggtgagc aagggcgagg agctgttcac   1680
cggggtggtg cccatcctgg tcgagctgga cggcgacgta acggccaca agttcagcgt   1740 gtccggcgag ggcgagggcg atgccaccta cggcaagctg accctgaagt tcatctgcac   1800
caccggcaag ctgcccgtgc cctggcccac cctcgtgacc accctgacct acggcgtgca   1860
gtgcttcagc cgctacccccg accacatgaa gcagcacgac ttcttcaagt ccgccatgcc   1920
cgaaggctac gtccaggagc gcaccatctt cttcaaggac gacggcaact acaagacccg   1980
cgccgaggtg aagttcgagg gcgacaccct ggtgaaccgc atcgagctga agggcatcga   2040
cttcaaggag gacggcaaca tcctggggca caagctggag tacaactaca acagccacaa   2100
cgtctatatc atggccgaca agcagaagaa cggcatcaag gtgaacttca agatccgcca   2160
caacatcgag gacggcagcg tgcagctcgc cgaccactac cagcagaaca cccccatcgg   2220
cgacggcccc gtgctgctgc ccgacaacca ctacctgagc acccagtccg ccctgagcaa   2280
agaccccaac gagaagcgcg atcacatggt cctgctggag ttcgtgaccg ccgccgggat   2340
cactctcggc atgacgagc tgtacaagaa gcttagccat ggcttcccgc cggaggtgga   2400
ggagcaggat gatggcacgc tgcccatgtc ttgtgcccag gagagcggga tggaccgtca   2460
ccctgcagcc tgtgcttctg ctaggatcaa tgtgtagatg cgcggccgcg ggaattcgat   2520
ttaaaacacc tgcagtgtgt attgagtctg ctggactcca ggacctagac agagctctct   2580
aaatctgatc cagggatctt agctaacgga aacaactcct tggaaaacct cgtttgtacc   2640
tctctccgaa atatttatta cctctgatac ctcagttccc attctattta ttcactgagc   2700
ttctctgtga actattaga aagaagccca atattataat tttacagtat ttattatttt   2760
taacctgtgt ttaagctgtt tccattgggg acactttata gtatttaaag ggagattata   2820
ttatatgatg ggaggggttc ttccttggga agcaattgaa gcttctattc taaggctggc   2880
cacacttgag agctgcaggg cccttttgcta tggtgtcctt tcaattgctc tcatccctga   2940
gttcagagct cctaagagag ttgtgaagaa actcatgggt cttgggaaga gaaaccaggg   3000
agatcctttg atgatcattc ctgcagcagc tcagagggtt cccctactgt catccccag   3060
```

-continued

```
ccgcttcatc cctgaaaact gtggccagtt tgttatttat aaccacctaa aattagttct    3120
aatagaactc attttaact agaagtaatg caattcctct gggaatggtg tattgtttgt    3180
ctgcctttgt agcagactct aattttgaat aaatggatct tattcgctta aggcgtaaat    3240
tgtaagcgtt aatattttgt taaaattcgc gttaaatttt tgttaaatca gctcatttt    3300 taaccaatag gccgaaatcg gcaaaatccc ttataaatca aaagaataga ccgagatagg    3360
gttgagtgtt gttccagttt ggaacaagag tccactatta agaacgtgg actccaacgt    3420 caaagggcga aaaccgtct atcagggcga tggcccacta cgtgaaccat caccctaatc    3480 aagtttttg gggtcgaggt gccgtaaagc actaaatcgg aaccctaaag ggagcccccg    3540
atttagagct tgacggggaa agccggcgaa cgtggcgaga aggaaggga agaaagcgaa    3600 aggagcgggc gctagggcgc tggcaagtgt agcggtcacg ctgcgcgtaa ccaccacacc    3660
cgccgcgctt aatgcgccgc tacagggcgc gtcaggtggc acttttcggg gaaatgtgcg    3720 cggaaccct atttgtttat tttctaaat acattcaaat atgtatccgc tcatgagaca    3780
ataaccctga taaatgcttc aataatattg aaaaaggaag agtcctgagg cggaaagaac    3840
cagctgtgga atgtgtgtca gttagggtgt ggaaagtccc caggctcccc agcaggcaga    3900
agtatgcaaa gcatgcatct caattagtca gcaaccaggt gtggaaagtc cccaggctcc    3960
ccagcaggca gaagtatgca aagcatgcat ctcaattagt cagcaaccat agtcccgccc    4020
ctaactccgc ccatcccgcc cctaactccg cccagttccg cccattctcc gccccatggc    4080
tgactaattt ttttattta tgcagaggcc gaggccgcct cggcctctga gctattccag    4140
aagtagtgag gaggcttttt tggaggccta ggcttttgca aagatcgatc aagagacagg    4200
atgaggatcg tttcgcatga ttgaacaaga tggattgcac gcaggttctc cggccgcttg    4260
ggtggagagg ctattcggct atgactgggc acaacagaca atcggctgct ctgatgccgc    4320
cgtgttccgg ctgtcagcgc aggggcgccc ggttcttttt gtcaagaccg acctgtccgg    4380
tgccctgaat gaactgcaag acgaggcagc gcggctatcg tggctggcca cgacgggcgt    4440
tccttgcgca gctgtgctcg acgttgtcac tgaagcggga agggactggc tgctattggg    4500
cgaagtgccg gggcaggatc tcctgtcatc tcaccttgct cctgccgaga agtatccat    4560 catggctgat gcaatgcggc ggctgcatac gcttgatccg gctacctgcc cattcgacca    4620
ccaagcgaaa catcgcatcg agcgagcacg tactcggatg aagccggtc ttgtcgatca    4680 ggatgatctg gacgaagagc atcaggggct cgcgccagcc gaactgttcg ccaggctcaa    4740
ggcgagcatg cccgacggcg aggatctcgt cgtgacccat ggcgatgcct gcttgccgaa    4800
tatcatggtg gaaaatggcc gcttttctgg attcatcgac tgtggccggc tgggtgtggc    4860
ggaccgctat caggacatag cgttggctac ccgtgatatt gctgaagagc ttggcggcga    4920
atgggctgac cgcttcctcg tgctttacgg tatcgccgct cccgattcgc agcgcatcgc    4980
cttctatcgc cttcttgacg agttcttctg agcgggactc tggggttcga atgaccgac    5040 caagcgacgc ccaacctgcc atcacgagat ttcgattcca ccgccgcctt ctatgaaagg    5100
ttgggcttcg gaatcgtttt ccgggacgcc ggctggatga tcctccagcg cggggatctc    5160
atgctggagt tcttcgccca ccctagggg aggctaactg aaacacggaa ggagacaata    5220
ccggaaggaa cccgcgctat gacggcaata aaaagacaga ataaaacgca cggtgttggg    5280
tcgtttgttc ataaacgcgg ggttcggtcc cagggctggc actctgtcga tacccccaccg    5340 agacccatt ggggccaata cgcccgcgtt tcttcctttt ccccaccccca ccccccaagt    5400 tcgggtgaag gcccagggct cgcagccaac gtcggggcgg caggccctgc catagcctca    5460
```

```
ggttactcat atatacttta gattgattta aaacttcatt tttaatttaa aaggatctag    5520
gtgaagatcc tttttgataa tctcatgacc aaaatcccct aacgtgagtt ttcgttccac    5580
tgagcgtcag accccgtaga aaagatcaaa ggatcttctt gagatccttt ttttctgcgc    5640
gtaatctgct gcttgcaaac aaaaaaacca ccgctaccag cggtggtttg tttgccggat    5700
caagagctac caactctttt tccgaaggta actggcttca gcagagcgca gataccaaat    5760
actgtccttc tagtgtagcc gtagttaggc caccacttca agaactctgt agcaccgcct    5820
acatacctcg ctctgctaat cctgttacca gtggctgctg ccagtggcga taagtcgtgt    5880
cttaccgggt tggactcaag acgatagtta ccggataagg cgcagcggtc gggctgaacg    5940
gggggttcgt gcacacagcc cagcttggag cgaacgacct acaccgaact gagataccta    6000
cagcgtgagc tatgagaaag cgccacgctt cccgaaggga gaaaggcgga caggtatccg    6060
gtaagcggca gggtcggaac aggagagcgc acgagggagc ttccaggggg aaacgcctgg    6120
tatctttata gtcctgtcgg gtttcgccac ctctgacttg agcgtcgatt tttgtgatgc    6180
tcgtcagggg ggcggagcct atggaaaaac gccagcaacg cggcctttt acggttcctg    6240 gccttttgct ggccttttgc tcacatgttc tttcctgcgt tatccctga ttctgtggat    6300 aaccgtatta ccgccatgca ttagttatta ctagcgctac cggactcaga tc    6352
```